US006300061B1

(12) United States Patent
Jacobs, Jr. et al.

(10) Patent No.: US 6,300,061 B1
(45) Date of Patent: Oct. 9, 2001

(54) MYCOBACTERIAL SPECIES-SPECIFIC REPORTER MYCOBACTERIOPHAGES

(75) Inventors: William R. Jacobs, Jr., City Island; Barry R. Bloom, Hastings-on-Hudson, both of NY (US); Graham F. Hatfull, Pittsburgh, PA (US)

(73) Assignees: Albert Einstein College of Medicine of Yeshiva University, Bronx, NY (US); University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 08/705,557

(22) Filed: Aug. 29, 1996

Related U.S. Application Data

(63) Continuation of application No. 08/430,314, filed on Apr. 28, 1995, now abandoned, which is a continuation of application No. 08/057,531, filed on Apr. 29, 1993, now abandoned, which is a continuation-in-part of application No. 07/833,431, filed on Feb. 7, 1992, now abandoned.

(51) Int. Cl.[7] ..................... C12Q 1/68
(52) U.S. Cl. ..................... 435/6
(58) Field of Search ..................... 435/6, 69.8, 235.1

(56) References Cited

U.S. PATENT DOCUMENTS 4,581,335 4/1986 Baldwin ..................... 435/172.3
4,861,709 * 8/1989 Ulitzur et al. ..................... 435/6

FOREIGN PATENT DOCUMENTS 9000594 1/1990 (WO) .

OTHER PUBLICATIONS

Sellers (1970) in "Host–Virus Relationships in *Myobacterium, Nocardia & Actinomyces*" ed. Juhasz et al. p. 39–52, C. C. Thomas, Sprigfield Ill.*

Snapper et al. (1988) Proc. Natl. Acad. Sci USA 85, 6987–6991.*

Lee et al. (1991) Proc. Natl. Acad. Sci. U.S.A. 88, 3111–3115.*

Jacobs et. al. (1987). Nature 327, 532–535.*

Stover et. al (1991) Nature 351, 456–460.*

Husson et. al. (1990) J. Bacter. 172(2), 519–524.*

Sood et al. (1980) Antonie Van Leeuwenhoek J. Microbiol. 46(5), 467–473 p. 1 of 2.*

"DNA Sequence, Structure and Gene Expression of Mycobacteriophage L5: a Phage System for Mycobacterial Genetics", by Hatfull et al., in Molecular Microbiology, vol. 7, No. 3, pp. 395–405 (1993).

"Superinfection Immunity of Mycobacteriophage L5: Applications for Genetic Transformation of Mycobacteria", by Donnelly–Wu et al., in *Molecular Microbiology*, vol. 7, No. 3, pp. 407–417 (1993).

* cited by examiner

*Primary Examiner*—James Ketter
(74) *Attorney, Agent, or Firm*—Amster, Rothstein & Ebenstein

(57) ABSTRACT

This invention relates to mycobacterial species-specific reporter mycobacteriophages (reporter mycobacteriophages), methods of producing said reporter mycobacteriophages and the use of said reporter mycobacteriophages for the rapid diagnosis of mycobacterial infection and the assessment of drug susceptibilities of mycobacterial strains in clinical samples. In particular, this invention is directed to the production and use of luciferase reporter mycobacteriophages to diagnose tuberculosis. The mycobacterial species-specific reporter mycobacteriophages comprise mycobacterial species-specific mycobacteriophages which contain reporter genes and transcriptional promoters therein. When the reporter mycobacteriophages are incubated with clinical samples which may contain the mycobacteria of interest, the gene product of the reporter genes will be expressed if the sample contains the mycobacteria of interest, thereby diagnosing mycobacterial infection.

8 Claims, 33 Drawing Sheets

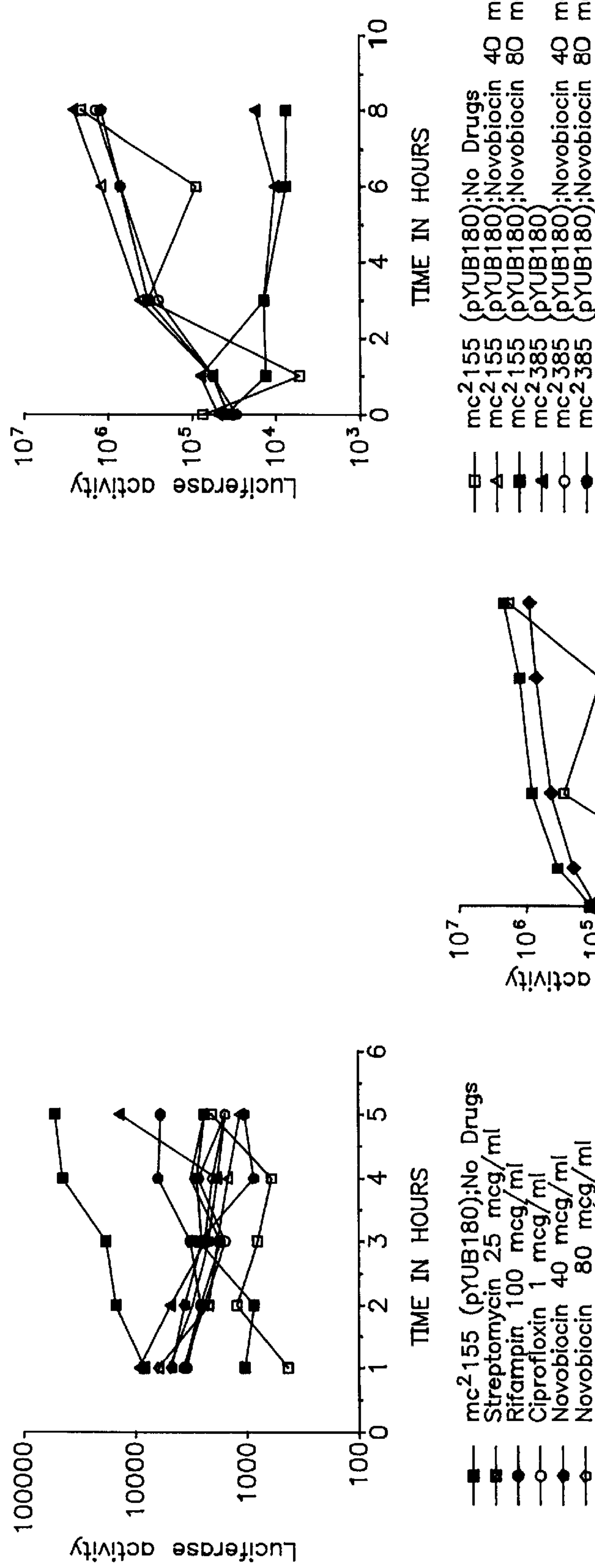
Luciferase activity
100000
10000
1000
100
0
1
2
3
4
5
6
TIME IN HOURS
mc2155 (pYUB180);No Drugs
Streptomycin 25 mcg/ml
Rifampin 100 mcg/ml
Ciprofloxin 1 mcg/ml
Novobiocin 40 mcg/ml
Novobiocin 80 mcg/ml
Isoniazid 50 mcg/ml
Ethambutol 10 mcg/ml
KCN 20 mcg
NaAzide 20 mcg
mc2155 cells alone
FIG. 4A
Luciferase activity
$10^7$
$10^6$
$10^5$
$10^4$
$10^3$
$10^2$
0
2
4
6
8
10
TIME IN HOURS
mc2155 (pYUB180);No Drugs
mc2155 (pYUB180);Streptomycin 25 mcg/ml
mc2733 (pYUB180)
mc2733 (pYUB180);Streptomycin 25 mcg/ml
FIG. 4B
Luciferase activity
$10^7$
$10^6$
$10^5$
$10^4$
$10^3$
0
2
4
6
8
10
TIME IN HOURS
mc2155 (pYUB180);No Drugs
mc2155 (pYUB180);Novobiocin 40 mcg/ml
mc2155 (pYUB180);Novobiocin 80 mcg/ml
mc2385 (pYUB180)
mc2385 (pYUB180);Novobiocin 40 mcg/ml
mc2385 (pYUB180);Novobiocin 80 mcg/ml
FIG. 4C

| | TB | BCG |
|---|---|---|
| phAE39 | + | − |
| phAE40 | + | + |

pGS-12 probe pYUB-216 probe

Mycobacteriophage L5
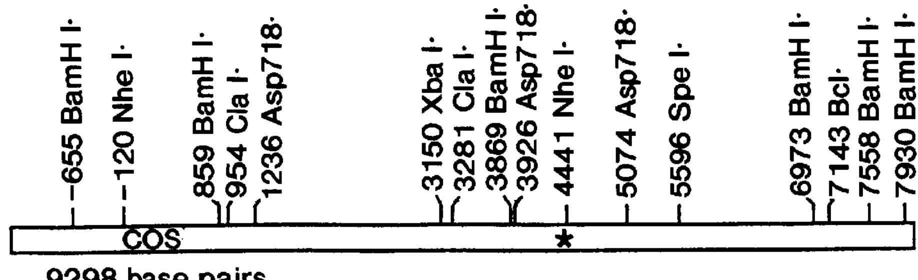
9298 base pairs
Probe
3010 base pairs 3104 base pairs
Labelled BamHI fragments
L5::FFlux Recombinants
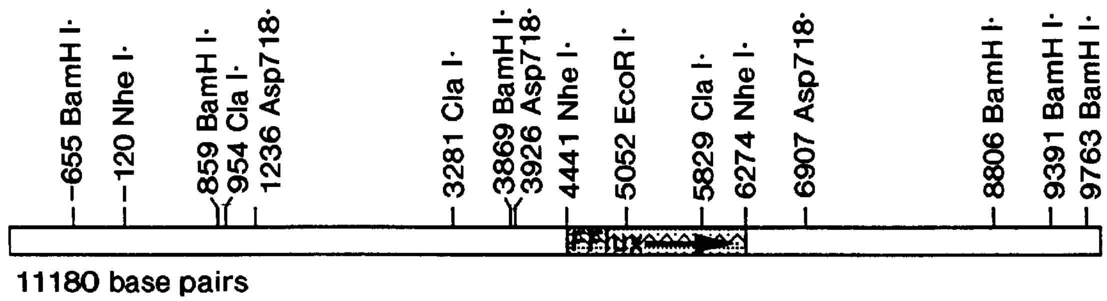
11180 base pairs
3010 base pairs 4937 base pairs
Labelled BamHI fragments
3010 base pairs 1183 base pairs 3754 base pairs
Labelled BamHI/EcoRI fragments
FIG. 21A

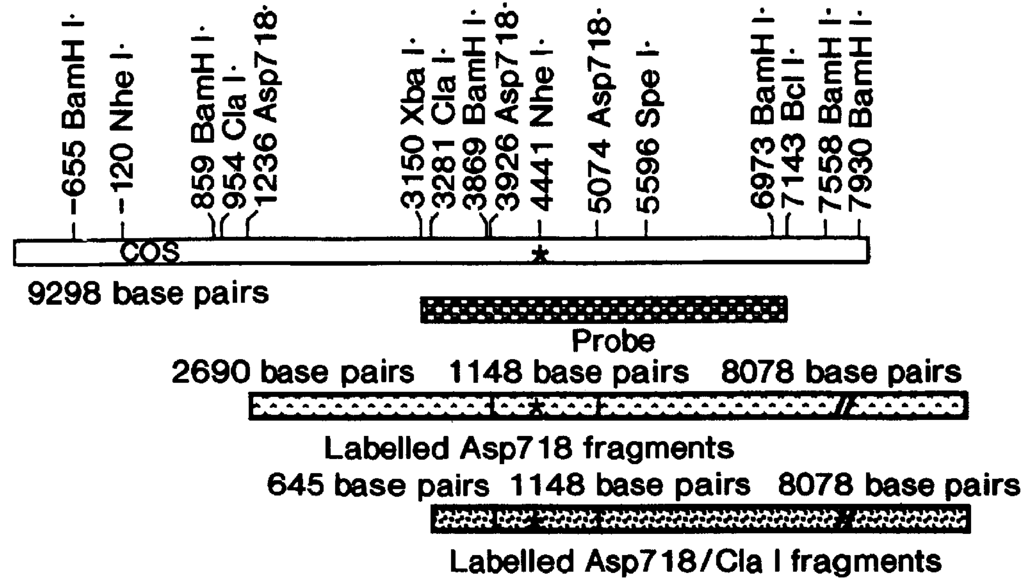
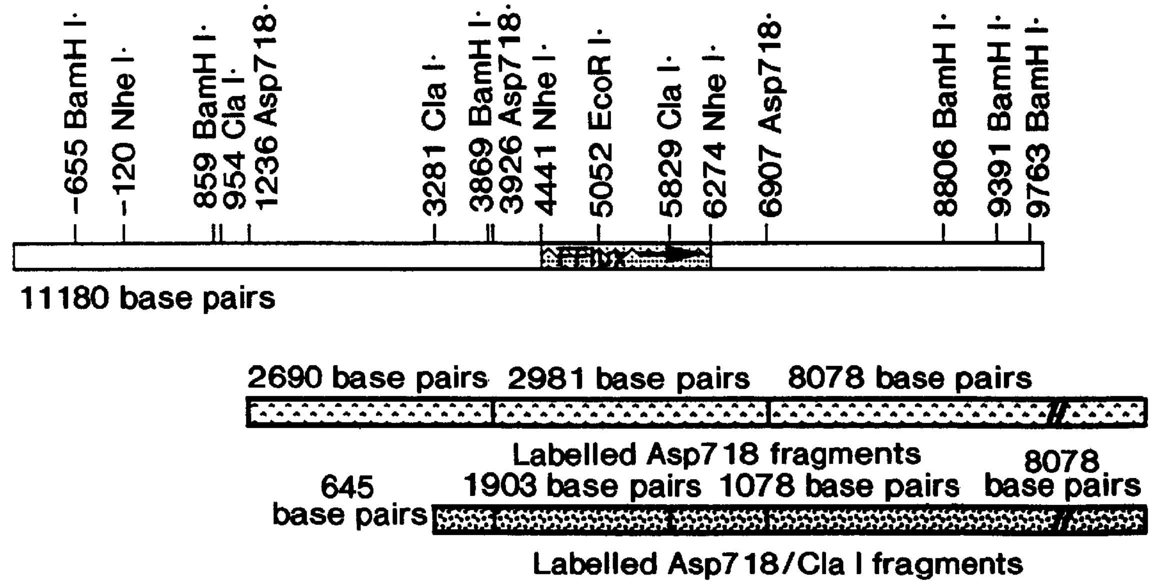
FIG. 21B

| Titer | Cells T=0 | Cells T=20 | RLU | RLU Cell | Cells T=40 | RLU | RLU Cell |
|---|---|---|---|---|---|---|---|
| $5 \times 10^7$ | 6850 | 2125 | 6981 | 3.4 | ND | 49680 | - |
| $5 \times 10^7$ | 685 | 210 | 466 | 2.2 | 2598 | 1943 | 0.8 |
| $5 \times 10^7$ | 69 | 25 | 55 | 2.2 | 305 | 107 | 0.4 |
| $5 \times 10^7$ | 7 | ND | 0 | - | ND | 4 | - |
| $5 \times 10^5$ | 685 | 1300 | 1840 | 1.4 | ND | 21188 | - |
| $5 \times 10^5$ | 69 | 110 | 201.5 | 1.8 | 3175 | 2229 | 0.7 |
| $5 \times 10^5$ | 7 | 22.5 | 37 | 1.7 | 225 | 150 | 0.7 |

FIG. 28B

| Phage | Other name | Characterized | Description | Date isolated |
|---|---|---|---|---|
| phGS1 | ts-phGS-1 | yes | FFlux derivative of L5ts11 | 1/15/93 |
| phGS2 | | no | FFlux derivative of L5ts11 | 1/15/93 |
| phGS3 | | no | FFlux derivative of L5ts11 | 1/15/93 |
| phGS4 | | no | FFlux derivative of L5ts11 | 1/15/93 |
| phGS5 | ts-phGS-5 | yes | FFlux derivative of L5ts11 | 1/15/93 |
| phGS6 | | no | FFlux derivative of L5ts11 | 1/15/93 |
| phGS7 | | no | FFlux derivative of L5ts11 | 1/15/93 |
| phGS8 | | no | FFlux derivative of L5ts11 | 1/15/93 |
| phGS9 | | no | FFlux derivative of L5ts11 | 1/15/93 |
| phGS10 | | no | FFlux derivative of L5ts11 | 1/15/93 |
| phGS11 | | no | FFlux derivative of L5ts11 | 1/15/93 |
| phGS12 | | no | FFlux derivative of L5ts11 | 1/15/93 |
| phGS13 | | no | FFlux derivative of L5ts11 | 1/15/93 |
| phGS14 | | no | FFlux derivative of L5ts11 | 1/15/93 |
| phGS15 | ts+phGS1 | yes | ts+ derivative of phGS1 | 2/10/93 |
| phGS16 | ts+phGS1 | yes | ts+ derivative of phGS1 | 2/10/93 |
| phGS17 | ts+phGS1 | yes | ts+ derivative of phGS1 | 2/10/93 |
| phGS18 | ts+phGS5 | yes | ts+ derivative of phGS5 | 2/10/93 |
| phGS19 | ts+phGS5 | yes | ts+ derivative of phGS5 | 2/10/93 |
| phGS20 | ts+phGS5 | yes | ts+ derivative of phGS5 | 2/10/93 |
| phGS21 | cpm5-1-1 | yes | clear plaque mutant of phGS18 | 3/1/93 |
| phGS22 | cpm5-1-3 | yes | clear plaque mutant of phGS18 | 3/1/93 |
| phGS23 | cpm5-1-4 | yes | clear plaque mutant of phGS18 | 3/1/93 |
| phGS24 | cpm5-2-1 | yes | clear plaque mutant of phGS19 | 3/1/93 |
| phGS25 | cpm5-2-3 | yes | clear plaque mutant of phGS19 | 3/1/93 |
| phGS26 | cpm5-2-4 | yes | clear plaque mutant of phGS19 | 3/1/93 |

FIG. 30

```
                        SEQUENCE LISTING


(1) GENERAL INFORMATION:

   (iii) NUMBER OF SEQUENCES:   1


(2) INFORMATION FOR SEQ ID NO: 1:

     (i) SEQUENCE CHARACTERISTICS:
          (A) LENGTH:         52297
          (B) TYPE:           nucleotide
          (C) STRANDEDNESS:   single
          (D) TOPOLOGY:       linear

    (ii) MOLECULE TYPE:
          (A) DESCRIPTION:   phage genome sequence

   (iii) HYPOTHETICAL:    no

    (iv) ANTI-SENSE:      no

     (v) FRAGMENT TYPE:   not applicable.

    (vi) ORIGINAL SOURCE:
```

(A) ORGANISM: mycobacteriophage L5
(B) STRAIN: not applicable
(C) INDIVIDUAL ISOLATE: L5
(D) DEVELOPMENTAL STAGE: not applicable
(E) HAPLOTYPE: not applicable
(F) TISSUE TYPE: not applicable
(G) CELL TYPE: not applicable
(H) CELL LINE: not applicable
(I) ORGANELLE: not applicable (vii) IMMEDIATE SOURCE: mycobacteriophage L5 particles (viii) POSITION IN GENOME: entire genome (ix) FEATURE:
(A) NAME/KEY:
(B) LOCATION:
(C) IDENTIFICATION METHOD:
(D) OTHER INFORMATION:

(x) PUBLICATION INFORMATION:
(A) AUTHORS: Hatfull and Sarkis
(B) TITLE: DNA Sequence, Structure and Gene Expression of Mycobacteriophage L5: A Phage System for Mycobacterial Genetics
(C) JOURNAL: Molecular Microbiology
(D) VOLUME: 7
(F) PAGES: 395-405
(G) DATE: 1993

(xi) SEQUENCE DESCRIPTION: SEQ ID NO: 1:

```
GGTCGGTTAT GCGGCCGAGC CATCCTGTAC GGGTTTCCAA GTCGATCAGA GGTAGGGGCA     60
GGCACAGAAA CCACTCACAT CAGGGCTGTG CGCCTCCAGG GCGCGTGAAC TCCCACACCC    120
CGGTGTAGTT ACATCCCGGA ATTGTCTCAG CGCCTCTCAG GGCGCTTCTC ATAAACAGTG    180
ATCTACGCCA CTCCTGACGG GTGGCTGTCA AGGATACTCA CCTTCCCTAC TAATGAGGGG    240
CTAAGAGCCC CTCTCTATAG AGCGCCGCAC AGGCGGCGCG ATAAGAGCGC CACCAGGCGC    300
TCATCTAAAG ACCGGCCTTG AAGGGCCGGT CATAGAGATC TATTCGATCC GGCAACCGCC    360
GGATCTCAAG GCCGCGCCAG TGCGCGGCCC TATAGAGGGG TGACTCAACT GTGCATGGCA    420
CTCGCTCGAG TGCCCACTGG AGCACTCAAC CGGGGAAGTT CGACGTTCTC AACCTGCGAA    480
TGACGTTTGA ATCGTCATCC GCGTACGAAA TCCCCGATCT GCGGCCGACC GACTTCGTGC    540
CGGCCTATCT CGCGGCCTGG AATATGCCGC GTCACCGCGA TTACGCCGCC AAGAACGGCG    600
GCGCGCTGCA CTTCTTCCTT GACGATTACC GGTTTGAGAC CGCGTGGTCG TCCCCCGAGC    660
GCCTTCTCGA CCGCGTAAAG CAGGTCGGCG CTGCACTCAC GCCGGATTTC AGCCTCTGGA    720
CGAACATGCC GAAGGCGGCG CAGCTATGGA ACGTCTACCG CTCCCGCTGG TGTGGCGCGT    780
ATTGGCAGTC GGAAGGAATC GAGGTGATTC CGACGGCGTG TTGGGCGACT CCCGACACGT    840
TCGATTTCTG TTTCGACGGG ATCCCGATGG GATCGACCGT CGCAATTTCT TCGATGGGCA    900
TTCGCTCTTC AAAAGTCGAC CAGGAGCTTT TCCGGTACGG ACTACGCGAA CTCATCGATC    960
GCACTCAACC GCAACTGCTT TTGGCATATG GCCAGCTTCG GCATTGCGAC GACATGGATT   1020
TACCAGAGGT CCGCGAATAC CCGACCTACT GGGACAGACG ACGAAAGTGG GTAACGGCCG   1080
ATGGGAGGCC GGGGAAGTAA AGGCGGCCCC GGTCCCGGAA CCGGAGCACG CAACCGCAGA   1140
GGCGCTGGAG CCCCCGGATC GGGCGGCGTA GGCGGCGTCG GAGGCGGGGG TGGAGCTGCA   1200
GGGAGCAGCG GAGGCGGCAA GGGAACGGCA GCGCCGGTAC CGGAGGCGTC ACCGGTGGCG   1260
GCGGAAGTGG AGCCGGCGGC GGTGGCAGCA GCCCCAACAC CCCGGTGCCC CCCACCGAGC   1320
TGGAGAAGAA GCGCGGCGAA TACAACCAGA TCGCCATCGA CGCCCAGAAA CAGCACGCGC   1380
```

-continued

```
CCACCGATGA GAAGCGCGAG GCCAAGCGCA AGCAACTGAT GGATCGAGTC GGAGGAGACT   1440
GGCAGGCTTT GGACCCGGAT CACCACGACG CCATCAAGGT GGCGATGGAT GACGCCATGC   1500
GGAAGATCCT CTCCGAGGAG GAGATCGTCC ACCGCACCAA GCACTTCGGC GACCTACTCG   1560
ACTCCGGTCG ACTCAAGTCG CTGTTCGAGG TCGGCTTCTC AGCCGGTGGC GACACCCCGA   1620
CCGAACGCGC CCTCCTCGAG GACGCCTGGT TCGGCGCAGG CAAGGTTCCC CCGATCTACT   1680
CGGCAATCGA GTTCAACGGC GCTCCGACAG CCGGCCTCGG CATGTACGGC GGCACCAAGC   1740
TCTACATGAA GGACTCGGTC AAGGACCGCG TCACCGTGAC CATCGGCGAC TCGCTGATGT   1800
CGAGCTGGGA CGTATTCCCC GGCCGTCCTG GCGACGGCGT GGGGCTGTGG GCCAGCCTGT   1860
CGAAGATCGA GGGGCTGGTC GATCCGAGCA AGACCCGCGA AGAGAACATG CAGGCGGTGT   1920
ACGACTCGTT CAAGAAGTAC GGCACCCTGG ACGGCTTCAT CGAGGCGCAG ATCCACGGCG   1980
GCGTCCTGGT CGAGGACATC AAGAAGGTCG TGTTCACGCA GCCGCCGAGC CCGATCTTCA   2040
CCGATAAACT GGACGAACTT GGAATCCCGT GGGAGGTGCA GTAATGGCGC AGATGCAGGC   2100
GACACACACA ATCGAGGGGT TCCTGGCTGT CGAGGTGGCC CCTCGGGCGT TCGTCGACGA   2160
GAACGGCCAC GTACTGACCC GGCTGTCGGC CACGAAGTGG GGCGGTGGCG AGGGTCTCGA   2220
GATCCTCAAC TACGAGGGTC CAGGGACCGT CGAGGTCTCC GACGAGAAGC TCGCCGCTGG   2280
CCAGCGGGCC AGCGAGGTCG AGGCTGAACT TCGCCGCGAG GTCGGCAAGG AGTGAGCTGG   2340
GCCGGCTCAG GCCGGCGACA GGAACTACCA GAGGACTGGG AGCTGAATTA CCGGCTCCCG   2400
GTCCTTTCTG CTGCCAACTG GCTTTGCCAG ATCAACGGTC CCGGATGCGT AAGGGCCGCA   2460
ACCGATGTCG ACCACATCAA GCGCGGGAAC GACCACAGCC GGTCCAATCT GCAGGCAGCC   2520
TGCCATGTCT GTCACGGCAA GAAATCAGCC GCCGAGGGCG TAGCCCGACG GCGGGAACTT   2580
AGAGCCCGGA GGAAGCGACC ACCCGAACGC CATCCTGGGC GTCGATAAGC GGGCCATGAA   2640
CCCGCTCCAC CCAGGAGGTG AACAGTGGGC ACGCGAGGCC CAATCGGAAA ACGAGATGAA   2700
GAGCGGGTTC GTCGGAACAC CCCGGACAGT CCAACCGACA CGATCCAGAT GCCCGGTCTG   2760
GTGACGATCC CCGAGATGGG CGATCTAAGC CACGACGGCC GCACGCACCA GCTCGTCAAG   2820
GACATGTACG AGTCGATCAA GCAGTCGGCA GCCGTGAAGT ACTACGAGCC GACCGACTTG   2880
CAGATGGCCC GACTCGCCCT CTACACACTT AACCAGGAAC TCATCGCAGC CGAGAACAAC   2940
GGCAAGCCCG TGGGCGCGAT GAAGCTCACT GCCATCAACC AGATGCTCTC CGCGCTGCTG   3000
CTGACCGAAG GTGACCGACG CCGCGTCCGA CTCGAAGTCG AACGAGCACC CGCTGACCCG   3060
ACAGGCGGGA AGGTCGTTGA CGTGACCGAC GTGCTCAAGC AGCGCCTCGC CAAGGCGAGC   3120
GGCGGGAGCT GATGGTCCCC CGAGGGGTTT CTAGAGCCGC TGCCGCTACC AGCCGCTCCC   3180
CCTCGGGGTA GACATCGAAA GGAACCACAT GGCCGACCTC GGCAACCCAC TCGACCTCGA   3240
GATGCTCTGC CTGGTCACAG GCCGGGACTT CCGCTGGACC ATCGATTACC CGTGGGGTCC   3300
GGGAGAGCTG TTCCTCGAAC TCGAGACCGG CGGCGAACAC AACGCGCTGC ATCAGGTCTA   3360
TGTCACCGGG GCGACCGGAG GCACGTACAC GCTGAACGTC AACGGCACCA ACACCCCGGC   3420
CATCGACTAC AACGACGTGT CGGAGAATCC GCAGGGGCTG GCAGGCGACA TCCAAGACGC   3480
TCTGGACGCA GCCGTCGGAG CCGGAAACGC TGTCGTGCAT CCGGTCTCGC TGTTCCCTGC   3540
GTGGACACTG AACTTCAACC TCAACGCCAG CAAGCCGCTC ACCGAGCAGT TGGTCAACAC   3600
GATCAACAAG GCCGCGAACG ACTTCTTCGA CACGTTCGAC CAACTACTTG GGGTCGACGT   3660
GGAGATGACG GTCACCGACA CCCTGAACTT CAAGCTCAAG GTGACCTCGC GGCGCTCGTT   3720
CGATGAGGTC GGTGTCGTCA CGTTCGCGGT CGACGTGACC AGCCAGGCAG TCATCAACTT   3780
```

-continued

```
CTTCAACTCC GTCGCCGAAC TCACCGGAGC GGTGAACACC GTCAACGTCG ACTTCTACTG   3840
GAACCGGACG TATGACATCG AGTTCACCGG ATCCCTTGGG CTGCAGCCGA TTCCGGCTAC   3900
TACAGCCGAC ATCACCAACC TGGCGGGTAC CAGCAAGGCC GTCTCAGTCA CGGTGGTCGA   3960
GCCAGGAAAG AAGAGGCTGA CCATCTGGCC GTTCACGGTC AACGGTGAAA CCGCAACCAT   4020
CAAGGTCGAG TCCGAAGAGG CCGACAAGAT CCCCAACCGC TGCCGCTGGC AGTTGGTTCA   4080
CATGCCGACC GGCGAGGCAG CCGGCGGCGA TGCAAAGCAG CTCGGCCGCG TTTACCGACA   4140
GCCGAGGTAA CACCGCACCC ATCAGAGATG GTGGGCCAGA CGGCCTTCGG GCCGTCCCCT   4200
GACGTGTAGC TCAATGGCAG AGCGCCCGAC TGTTAATCGG GTGGTTGAAG GTTCGAGTCC   4260
TTCCATGTCA GCGAGGGCTG AACCGGACCC GTGTCCGGTG TAGGCACTTT CCGCAGGCGG   4320
TTCCCCAGAG CGTGGGGAGC CCCTGCCCTG TACACGTAGC TCAATTGGTA GAGCAGCGGT   4380
CTCCAAAGCC GCCGGTTCCA GGTTCGACTC CTGGCGTGTA TGCACACACC CCTGACTCCT   4440
GCTAGCGGAG TGTTCGCCTT TCGGGCCTGG GGTCTTTTTC CCCGTTCGTC TAATCGGTAA   4500
GACACCCGGC TCTGGACCGG GCAATTGAGG TTCGAGTCCT TGGCGGGGAG CCAACTTGAC   4560
ATCCACCCGA AAGGAACAAC ATGACCTTCA CAGTCACCCG CGAGAGAGCG CAGTGGGTCC   4620
ACGACATGGC CCGCGCTCGC GACGGTCTCC CCTACGCGTA CGGCGGGGCG TTCACCAACA   4680
ACCCGAGGGT GTCGACTGAC TGCTCTGGCC TGGTGCTGCA GACCGGGGCT TGGTATGGAG   4740
GTCGCACCGA CTGGGTCGGA AACCGTTACG GCTCAACCGA ATCGTTCCGG CTCGACCACA   4800
AGATCGTCTA CGACCTAGGG TTCAAGCGGA TGCCCCGAGG CGGGCCAGCG GCCTTGCCGA   4860
TCAAGCCGGT GATGCTCGTC GGGCTCCAGC ACGGAGGCGG CGGGGTCTAC TCGCACACCG   4920
CTTGCACGTT GATGACGATG GACCACCCCG GTGGCCCGGT CAAGATGTCC GACCGAGGCG   4980
TCGACTGGGA GTCCCACGGC AACCGCAACG GCGTAGGCGT CGAACTTTAC GAGGGCGCAC   5040
GGGCATGGAA CGACCCTCTG TTCCATGACT TTTGGTACCT GGACGCAGTC CTCGAAGACG   5100
AAGGAGACGA TGACGAATTG GCTGACCCAG TTCTAGGGAA GATGATCCGC GAGATCCACG   5160
CGTGCCTGTT CAATCAGACC GCGTCGACCA GCGATCTGGC GACCCCTGGT GAAGGCGCTA   5220
TCTGGCAGCT ACACCAGAAG ATCCACTCGA TTGACGGCAT GCTCCACCCG ATCCACGCTG   5280
AGCGGCGCGC TCGCGCAGGC GATCTCGGTG AGCTGCACCG AATCGTGTTG GCCGCGAAGG   5340
GCTTGGGCGT GAAGCGCGAC GAGGTGACCA AGCGGGTCTA CCAGAGCATC CTCGCCGACA   5400
TCGAGCGGGA CAACCCCGAA GTACTTCAGC GATACATCGC AGAAAGAGGT GGCCTATGAG   5460
CCCCAAGATC CGACAGACCA TCTACCTGCT CGGCACCGCC GCCCCGGCAC TGCTGGGCAT   5520
CGTCCTGATC TGGGGCGGGC TCGACGCTGA GTCGGCGGCT GACCTCGGTG ACATCATTGC   5580
GGGCGTCGTG TCGATACTAG TCTCCGGTGC GCCGGCCGTA GCGGCAGGCA CCGTACGCAG   5640
CCAGCGCAAG GACGGCACGT TGTCCACCAG CCCGGTGGAT CAGGTCACCA AGGGCCTCGA   5700
GCAGGTGCTC GCGGCCAGGC AGAGTGCCGA GGCTGAAGTC GCGAAGGTCA AGCAGGCGCT   5760
GGAGACCGCC GTCAGCGGTT CTCTCCCCCA GCTCGGCCCG CTGGCCACGC AGATCCTCAA   5820
CGTGGCTGAC GACACCGTCT GGCGTCCATG AGCAAGCCCT GGCTGTTCAC CGTCCACGGC   5880
ACAGGCCAGC CCGACCCGCT CGGGCCTGGT CTGCCTGCCG ATACCGCACG GGACGTACTT   5940
GACATCTACC GGTGGCAGCC CATCGGCAAC TACCCGGCAG CGGCGTTCCC GATGTGGCGG   6000
TCGGTCGAAA AGGGTGTCGC TGAGCTGATC CTGCAGATCG AGCTGAAGCT GGACGCAGAT   6060
CCGTACGCGG ACTTCGCGCT GGCCGGCTAC TCGCAGGGAG CCATCGTGGT GGGCCAGGTG   6120
```

-continued

```
CTCAAGCACC ACATCATCAA CCCGAGAGGT CGACTGCACC GGTTCCTGCA CCGGCTCAGG   6180
AAGGTCATCT TCTGGGGTAA TCCGATGCGG CAGAAGGGCT TTGCCCACAC CGACGAGTGG   6240
ATTCACCAGG TCGCTGCCTC GGACACGATG GGCATCCTCG AGGACCGACT GGAGAACCTC   6300
GAGCAGTACG GCTTTGAGGT CCGCGACTAC GCGCACGACG GCGACATGTA CGCCTCCATC   6360
AAGGAGGACG ACATGCACGA GTACGAGGTG GCCATTGGCC GAATCGTGAT GAGCGCTAGG   6420
CGATTCATCG GAGGTAAGGA CTCCGTCATC GCCCAGCTCA TCGAGCTTGG ACAGCGTCCG   6480
ATCTGGGAGG GAATCGCGAT GGCCAGAGCC ATCATCGACG CCCTCACGTT CTTCGCCAAG   6540
TCGACCCAAG GCCCGAGCTG GCCGCATTTG TACAACCGCT TCCCGGCGGT CGAGTTCCTA   6600
CGACGAATCT GAGAAAGGAG GCGGGGTGAG CCTCAACAAC CACCACCCGG AGCTTGCCCC   6660
GTCTCCCCCT CACATCATCG GCCCGTCCTG GCAGAAGACG GTCGATGGTG AGTGGTATCT   6720
GCCTGAGAAG ACCCTCGGCT GGGGAGTCCT GAAGTGGCTC TCCGAGTACG TGAATACCCC   6780
TGGCGGGCAT GACGATCCGA ACCGTCTGGC GACGTTGATC GCGCTCTCCG AGGCAGGTCT   6840
TCTCGACAAC GAGAACATGT TCATCCCCAC CGACGAGCAG GTACGCCTGG TCCTCTGGTG   6900
GTACGCAGTA GATGACCAGG GCCAGTACAT CTACCGCGAG GGCGTGATCC GCCGGCTCAA   6960
GGGCTGGGGC AAGGATCCGT TCACCGCCGC GCTCTGCTTG GCGGAACTCT GTGGCCCCGT   7020
AGCCTTTTCA CACTTCGACG CCGACGGTAA CCCGGTCGGC AAGCCGCGTT CAGCCGCGTG   7080
GATCACCGTC GCGGCCGTCA GCCAGGACCA GACGAAGAAC ACGTTCTCGC TGTTCCCGGT   7140
GATGATCAGC AAGAAGCTGA AGGCCGAGTA CGGCCTGGAC GTGAACCGCT TCATCATCTA   7200
CTCCGCAGCC GGTGGCCGTA TTGAGGCAGC GACCTCGAGC CCCGCGTCGA TGGAGGGTAA   7260
CCGCCCGACG TTCGTCGTCC AGAACGAGAC GCAGTGGTGG GGCCAAGGCC CCGACGGCAA   7320
GGTCAATGAA GGCCACGCGA TGGCAGAGGT CATCGAAGGC AACATGACCA AGGTCGAGGG   7380
CTCCCGCACC CTGTCGATCT GCAACGCCCA CATCCCCGGC ACCGAGACGG TCGCCGAGAA   7440
GGCATGGGAC GAGTACCAGA AGGTCCAGGC AGGCGACTCT GTCGACACCG GGATGATGTA   7500
CGACGCGCTG GAAGCGCCGG CCGACACCCC GGTCTCCGAG ATCCCCCCGC AGAAGGAGGA   7560
TCCCGAGGGA TTCGAGAAGG GCATCGAGAA GCTCCGCGAG GGCCTGCTCA TCGCCCGAGG   7620
CGACTCCACC TGGCTGCCGA TAGACGACAT CATCAAGTCG ATTCTGTCGA CCAAGAACCC   7680
GATCACCGAG TCGCGGCGCA AGTTCCTGAA TCAGGTAAAC GCCGCTGAGG ACTCGTGGCT   7740
CTCACCGCAG GAATGGAACC GGTGCCAGGT CGACCTGGCC AAGTACCTGG ATAAGCACGG   7800
CAGGGAGTTC GCTCCGCTGC AGCGCGGTGA CCGGATCACC CTCGGGTTCG ACGGGTCGAA   7860
GTCCAACGAC TGGACCGCGC TCGTCGGCTG CCGTGTCAGC GACGGCCTGC TGTTCGTCAT   7920
CGACATCTGG GATCCCCAGA AGTACGGCGG GGAGGTTCCC CGCGAAGACG TTGACGCCAA   7980
GGTCCATTCG GCGTTCGCCC ACTACGACGT GGTGGCGTTC CGCGCCGACG TGAAGGAGTT   8040
CGAGGCGTAC GTCGACCAGT GGGGCCGGAC CTACAAGAAG AAGCTCAAGG TCAACGCCAG   8100
CCCGAACAAC CCGGTGGCGT TCGACATGCG CGGACAGCAG AAGAGGTTCG CGTTCGACTG   8160
CGAGCGACTC GAGGACGCGG TCCTTGAGGG CGAGGTCTGG CACGACGGCA ATCCCGTTCT   8220
GCGCCAACAC GTTCTGAACG CCAAACGACA CCCAACGAAC TACGACGCCA TCGCGATTCG   8280
CAAGGTCACG AAGGACTCCA GCAAGAAAAT CGACGCTGCA GTCTGCGCTG TCCTCGCGTT   8340
CGGGGCGAGA CAGGACTACC TCATGAGCAA GAAGGCCCGT AGCGGCCGGG TGGTGATGGT   8400
TCGATGACAG CACCGCTCCC CGGTATGGAG GAGATCGAAG ACCCCGCAGT CGTACGAGAA   8460
GAGATGATCT CGGCCTTCGA GGATGCTTCC AAGGATCTCG CCAGCAACAC CAGCTACTAC   8520
```

-continued

```
GACGCTGAGC GCCGGCCAGA GGCCATCGGC GTCACCGTCC CGAGAGAGAT GCAGCAACTG   8580
CTGGCTCACG TCGGATACCC CAGGCTCTAC GTCGACTCAG TCGCCGAGCG CCAGGCCGTC   8640
GAGGGTTTCC GCCTCGGCGA TGCCGACGAG GCTGACGAAG AGCTGTGGCA GTGGTGGCAG   8700
GCCAACAACC TCGACATCGA GGCACCACTG GGCTACACCG ACGCTTACGT TCACGGCCGG   8760
TCGTTCATCA CGATCAGCAA GCCAGACCCG CAGCTCGACC TGGGTTGGGA TCAGAACGTC   8820
CCGATCATCC GCGTCGAGCC GCCCACCCGA ATGCACGCCG AGATCGACCC CCGGATCAAC   8880
CGGGTGTCCA AGGCCATCCG AGTCGCATAT GACAAGGAGG GCAACGAGAT TCAGGCTGCC   8940
ACGCTGTACA CGCCGATGGA GACCATCGGC TGGTTCCGCG CTGACGGTGA GTGGGCTGAG   9000
TGGTTCAACG TCCCGCACGG TCTGGGCGTC GTTCCCGTTG TGCCGCTTCC GAACCGGACC   9060
CGGCTCTCGG ACCTGTACGG CACCAGTGAG ATCACGCCCG AGCTTCGGTC GATGACCGAC   9120
GCGGCGGCGC GCATCCTCAT GTTGATGCAG GCGACCGCCG AGCTGATGGG TGTCCCCCAG   9180
CGCCTGATCT TCGGCATCAA GCCCGAAGAG ATCGGCGTCG ACTCCGAGAC CGGCCAGACG   9240
CTGTTCGATG CGTACCTGGC CCGGATCCTG GCGTTCGAGG ACGCTGAGGG CAAGATCCAG   9300
CAGTTCTCTG CAGCCGAGCT GGCCAACTTC ACCAACGCGC TCGATCAGAT CGCCAAACAG   9360
GTCGCTGCGT ACACGGGATT GCCTCCCCAG TACCTGAGTA CCGCCGCAGA CAATCCGGCC   9420
TCCGCTGAGG CGATCAGGGC CGCTGAGAGC CGACTCATCA AGAAGGTCGA GCGGAAGAAC   9480
CTGATGTTCG GCGGCGCATG GAAGAGGCC  ATGCGGATCG CCTACCGGAT CATGAAGGGC   9540
GGCGACGTTC CCCCGGACAT GCTCCGCATG GAGACCGTCT GGCGAGACCC GAGCACTCCC   9600
ACCTACGCGG CCAAGGCCGA CGCAGCCACG AAGCTGTACG GCAACGGCCA GGGTGTCATC   9660
CCGCGTGAAC GTGCTCGCAT CGACATGGGC TACTCCGTCA AGGAGCGCGA AGAGATGCGC   9720
CGATGGGACG AGGAAGAGGC CGCAATGGGT CTCGGCCTGT TGGGCACGAT GGTCGACGCC   9780
GACCCGACGG TCCCAGGCTC CCCGAGCCCC ACGGCACCGC CGAAGCCACA GCCGGCCATC   9840
GAGTCGTCTG GTGGTGATGC GTGACCGCAG AGGAGTACGC GGCGGCTCAA GCCGCGATCA   9900
CTGCGGGTCT TGCCACATAC GTCCAGAGGT TCGCTTCGCT CTTCGTCGGT CCAGCTCTCG   9960
CTGTAGGTGA GTGGCTGCGA CTGCTGCAGG TGCTGTTCCC CGAAATCCAA CGGCGGTATG  10020
CAGATGCTGC CGCCTTGGGC AGGGACTTCT ACGACTCCCA ACGCGCACTA CACCACCCAG  10080
AGCTGCCCCG GAACGAGAGG TTCCGGGGAG AGCTTCGGTG GGAGTGGTTC GTCCAGAACA  10140
TGGAGCCCGC TCGAAAAGAG ATGTCGCAGG CCGACTCTCC GCCGAGTGCG ACCTCTAAGT  10200
TGGCTCTGGC CGCAGTTCGC GAAGTGGAGA TGGCAGCACG CCGACAGATC ATCGGCGCTG  10260
TCAAGAACGA TCCGGCCCCG CAGATCGTGC AGGGCTGGGC GAGGGTCGCC ACCGGGCGCG  10320
AAACATGCGC CTGGTGTCTG ATGCTCATCT CACGGGGTGC CGAGCTGAAT CACAAGGGCA  10380
ACTTCGCCTA CAGCTCAGCG GAAGCCGCAG GGCTCAACCT CGATGACGAG ACCGTGATCG  10440
ACCTCTGGAA CGAGTCCGGT CACGACCTTG AGAAGTTCCG CGAGGAGACC AGAGAGGACT  10500
TCGAGAAGTG GCACGCAGGG TGCGACTGTC TGGTGGTCCC GGTCTTCGAT GTGCAGAACT  10560
GGCCCGGAAG AGACGCTGCC CTACGGGCGC AGCAACTTTG GATCGAAGCC AGCGACGAAG  10620
CTGACGACCT CATTGCGTCA GGCAAGGCCC GCTCCAAGAA CAAGAACACG GAGACGCTCA  10680
ACGCGCTCCG ACGCCGCCTA GCACGCGGCG AAATCACCAT GTCCAACTAC GCCCTCGCTG  10740
CGTAGTCCCT CGAACCCCAG GTGGGTTCTC TCAACATGCC CAGGAGGCGA AAACACATGT  10800
CCGACAACCC CACTCCCGAG AGCACCCCAG AGGCCGAGAC CCCGGAGGTC GAGAAGCCGA  10860
```

-continued

```
TGGAACCGCA GGGCAAGGTC TTCGATGAAG CGTACGTTCA GTCGCTTCGC CAGGAGGCTG  10920
CAGCCGCTCG GGTGGCGAAG AAGGACGCCG TAGAAGCGGC AGAGGCTCGA GTGAAGGCCG  10980
AGTACGAGGC CAAGCTCGCT GAGCGCGACA CCGCTTACAC CGAACTGCAG AACCAGTTGG  11040
GACAGGCGTG GATTGAGCTG GAGAAGGTCT ACCTCTCTCT CGACGCCAAG GTGCCCAACG  11100
ACAAGGTTCG GGCGTTTGTC GAGATCCTCG AAGGCAACGA CAGGGACAGC ATCGCTGAGT  11160
CAGTGAAGTC CCGTCTGGAG CTGGTCGGCG GATTCGGCAA CAAGACCCCG AGTCCTGCGT  11220
TCGACCCGTC TCAGGGTCGC GGCGGTAAGC CGCCGATCCC GCTGAACGGT GACCCGATCC  11280
TCGAGGCCAT CAAGGCCGCT GTCGGGATCA AGAAGTAACC CACCCAACAG ATCTCAAGGA  11340
GAGATAAACA ATGGCAGTCA ACCCTGACCG CACCACGCCG TTCCTCGGCG TGAACGACCA  11400
CAAGGTCGCG CAGACCGGCG ACTCGATGTT CGAGGGCTAC CTCGAGCCCG AGCAGGCCCA  11460
GGACTACTTC GCCGAAGCGG AGAAGATCTC CATCGTCCAG CAGTTCGCCC AGAAGATCCC  11520
GATGGGCACG ACCGGCCAGA AGATCCCGCA CTGGACCGGC GACGTGAGTG CGTCGTGGAT  11580
CGGTGAAGGC GACATGAAGC CCATCACCAA GGGCAACATG ACCTCGCAGA CCATGCCCCC  11640
CCACAAGATC GCGACGATCT TCGTGGCCTC GGCGGAAACC GTCCGTGCGA ACCCGGCCAA  11700
CTACCTGGGC ACCATGCGGA CCAAGGTCGC GACCGCCTTC GCGATGGCGT TCGACAACGC  11760
CGCGATCAAC GGCACCGACA GCCCGTTCCC GACCTTCCTA GCGCAGACCA CCAAGGAGGT  11820
CTCGCTGGTG GACCCGGACG GCACCGGCTC CAACGCCGAC CTCACCGTCT ACGACGCGGT  11880
CGCCGTCAAC GCCCTGTCGC TGTTGGTCAA TGCCGGCAAG AAGTGGACCC ACACTCTGCT  11940
GGACGACATC ACCGAGCCGA TCCTCAACGG CGCGAAGGAC AAGAGCGGTC GCCCGCTGTT  12000
CATCGAGTCG ACCTACACCG AGGAGAACAG CCCGTTCCGC CTCGGTCGGA TTGTGGCCCG  12060
TCCGACCATC CTGAGCGACC ACGTCGCCTC GGGCACGGTC GTCGGCTACC AGGGTGACTT  12120
CCGCCAGCTC GTCTGGGGCC AGGTCGGCGG CCTGTCCTTC GACGTGACGG ATCAGGCGAC  12180
TCTGAACCTG GGCACCCCCC AGGCTCCGAA CTTCGTCTCG CTGTGGCAGC ACAACCTCGT  12240
CGCAGTCCGA GTCGAGGCCG AGTACGCCTT CCACTGCAAC GACAAGGACG CGTTCGTCAA  12300
GCTCACGAAC GTGGACGCCA CCGAAGCCTG ATCCAGGCTT GACATCCACC GGGAGGGGGC  12360
TCCTTCGGGA GCCCTCTCCT GATGTGGAGC AGGAAGGACC ACATGCGAAT CCAGTCCACC  12420
CTCAACGGCG GTTTCGCCGA GGTTTCCGAG GAGTTCGCCA AGCAGTTGAT CGCCACTGGC  12480
GGCTGGAAGG TGCCCCGGAA ACCGCGCAAC ACCAAGACCA AGACCGCTCC TGAGGAGCCC  12540
AAGAACGAGG AGTAACCCGT GGCCTACGCG ACCGCCGAAG ACGTTGTGAC GTTGTGGGCC  12600
AAGGAGCCTG AGCCCGAAGT GATGGCGCTG ATCGAGCGCC GGCTCCAGCA GATCGAGCGC  12660
ATGATCAAGC GCCGGATCCC CGACCTGGAC GTGAAAGCCG CTGCGTCGGC GACGTTCCGG  12720
GCCGATCTGA TCGACATCGA AGCTGATGCT GTTCTGCGCC TCGTGCGTAA CCCGGAGGGC  12780
TACCTCTCGG AGACCGACGG TGCGTACACC TATCAGCTCC AGGCCGACCT GTCGCAAGGC  12840
AAGCTCACCA TCCTCGATGA GGAGTGGGAG ATCCTCGGGG TCAACTCCCA GAAGCGCATG  12900
GCGGTCATCG TCCCGAACGT GGTGATGCCG ACGTGAGCGC GAGCGACCGA CACCGCGCCC  12960
CGATTGTCTA TCCGCCTGGC ACTCAGGCGG TTACGCCGGA TCGGGTCAAC GCGTTTGACT  13020
GCGATCACGA AGCTGATCCT CCGGTGTGCC GGTGCGTCCA CGACTGGCGC ATCGAGTGGG  13080
GAAACGTCAA GAAGGCCACC GCCAGATCAC GGTCGGCGGT GCTCTGATGA GCCTCCTCGA  13140
CACCGGTGCC CGGTACCAGA CCTGCATCGT CTACCCCGAA GAGATGGTCA TCGACTCCGA  13200
TGGCAACAAG CGGACCAGGC CGTCGAATAC CGGCATCCCG GCCATCGCAC GGTTCCAGGT  13260
```

-continued

```
AGCCAACCAG TCTGGTACGT CGGCACGACG TGCTGAGCAG GACAACGAGG GGTTCGAGAC  13320
CGAGAAGGTC TACCGGATGC GGTTTCCCCG CTCGTTCACC AAGGAGCACG GCATCCTCGG  13380
GGCCCAGTCC CAGATCGAGT GGCGAGACCA GCGGTGGGCG CTCTTCGGAG ACGCCACCGT  13440
CTACGACTCA TCCCCTGCGT TGGCGCGGGT CGACTACACG ATCAAGAGGT ACTGARGGCC  13500
AAGGTCTACG CGAACGCGAA CAAGGTCGCG GCCCGGTACG TCGAGACGAG GGACGCCGTC  13560
CGAGACGAGC GGAACAAGGT CACCCGTCGA GCCAAAGCCA ATCTGGCGCG GCAGAACTCG  13620
ACCACCCGCA TCACCGACGA GGGCTACTTC CCGGCCACCA TCACCGAGCA AGACGGCGAT  13680
GTCGACTTCC ACACGATCCT CAACGCGCCC AACGCGTTGG CGCTTGAGTT CGGCCACGCG  13740
CCGTCTGGCT TCTTCGCTGG CACCGACACG AAACCACCGG AGGCCACTTA CATCCTCACC  13800
CGAGCCGCCA TCGGCGGCAC CGTCTCATAA GGAGGTCACA TGGCGCGAAT GCCTCGCGTC  13860
CAGGCAGTAG CGGCCCCGAT CCTCCGGTCA GACCCCCGAC TGGAGGGAGT GACGGTCACG  13920
ACATGGGTTC CAGACGTGGA CTTCCGAGAG TTCCCGATGA TCAACCTCCG CCGCATAGGC  13980
GGGACGAGGA ACCCCAACGC ACCGACGCTG CACACGCTGC CGGTGGTCGA AATGACCGCC  14040
TACACCAGAG ACGGTCTCAT CGAGACTGAG GAGCTGTACG AGACCGCGCT AGAGGTTCTC  14100
TACGACGCGG TGGAGAACGG AACACAAACT CCCGCAGGGT ATTTGACCTC CATCTTCGAG  14160
ACGATGGGCG CCACTCAGTT CAGCTCCCTC TACCAGGACT CCTGGCGCAT CCAGGGTCTG  14220
ATCAGGCTCG GCGTCCGCAG ACCGAGAACC ACCCTCTAAC CGAAAGGTAA AGCCACATGG  14280
CTGAAAACGA CGACGCAGTG TTGACTGCGG CGGTCGGCTA CGTGTACGTC GGTGCTGCAG  14340
GCACCGCTGC TCCTACGCCG GCCTTGCTCA AGACCATCGA CCTCAGCAAG CCCGAGACCT  14400
GGACCGGTGC TACCGGTTGG ACGAGCGTCG GCCACACCAG CCGAGGCACG CTCCCCTGAT  14460
TCGGCTTCGA AGGCGGCGAG TCCGAGGTCA AGGGCTCCTG GCAGAAGAAG AAGCTCCGCG  14520
AGATCACCAC CGAGGATCCC ATCGACTACG TCACGGTCCT ACTGCACCAG TTCGATGAGC  14580
AGTCGCTGGG TCTGTACTAC GGCCCCAACG CCTCTGAGAC TCCTGGTGTG TTCGGTGTGA  14640
AGACCGGCCA GACCAACGAG AAGGCCGTGC TGGTCGTGAT CGAAGACGGC GACATGCGCC  14700
TGGGGCATCA CGCCCACAAG GCTGGAGTTC GCCGCGACGA CGCGATTGAG CTGCCCATCG  14760
ATGACCTGGC TGCGCTGCCC GTCCGGTTCA CCTACCTGGA CCACGAAGAC GAGCTGCCGT  14820
TCTCCTGGAT CAACGAAGAC CTCTTCAACG TGCCCGAGGT TCCCGAGGGC TGATCCCAAC  14880
TTGACAGCCA CCCGGCTGTC TACCCCGGAG GGGGAGGTTT CCTTGGCGGG CCTGGCCTCC  14940
CCCTCCTCCC GCCACTCACA GACCCGCCGA CACTGAAAGG TTCGCCATGA CAAACGTATT  15000
CACCATCGAC GCATTCCGCG AAGAGGTCAA GAAGAAGTAC GCTCCGGTCC TCATCGGCCT  15060
GTCCGACGAT GTGACCGTCG AGCTGAAGCC GCTGCTGAAG CTGGGCCAGA AGGCCCGCGA  15120
AGCGGTGGTC GAGGTGTTCA AGGAGTTCGC GGACATCCCC GACCTCGAAG AGGACGACGA  15180
CGACGAGTTG GTCGATGAGT ACTCGCTCCA GGTCTGCGAC ATCATCGCCA AGGCGTTCCG  15240
GCTGATCGCC ACGAAGCCCA AGAAGCTGAT CGCCGCCTTG GACGAGGAGC CGGATCCCCG  15300
TATCCGCGCA GAGCTGTATG CAGCGGTACT CAACACCTGG AAGCGAGAGA CGCAACTGGG  15360
GGAAGCCGCG CCCTCGCCGA GCTGATCGAC AAGTTCGGCG GGGCGATCCT CGCAGACCTG  15420
CTCCAGTACT ACCGGGTAGA CCTGCGCGAC CTGTTCCGCG ACGAGGATCC GCTTTCGCCG  15480
AGATTCGTTC TGTCCCTGGT GCTCTGCCTT CCCAAAGACG GCGCGTTCTA CGCAGAACGT  15540
CGTGGTGGGC AGCAGTACCG GGGCTGGACC GAGGACCGCT ACGCGCTCGC GGACATCTAC  15600
```

-continued

```
GACGCCATCC AGGCGGGCAA CCACATCCTG CTGCTGGCGA ATCGTGATCC GAAGAAGCCA  15660
AAGCCCAAGG CACCCAAGTC ATACCCGCGT CCCGACGACC TAGAGAAGAC CACACCGAAG  15720
CCGGGTTCGT TCGCCGCAAT GGTCGTGCGA GCGAAGAAGG CGGCTCGAGA GAGAAGGGAA  15780
AGGGAGGAGG AGAGTGCCGA ATAGTGCTGG CGTAGAAGTC GCCCGGATCT CGGTCAAGGT  15840
CAGCCCGAAC ACCAAGGAGT TCCGCCGGGA ACTCAAGACC GAACTCGAGA AGATCGAGCG  15900
GGAGCTTAAG GGCGATGTCG AGATCAACGG TCATCTCGAT GCGGCCCAGG CCAAGGCCGA  15960
CTTCAAGCGC ATGATGATGC AGCTCAAGAC CGAAGCTGCC AAGGGCGTTC ACGTCCCGGT  16020
CGACGTAACC GTCGACAAGA AGAGCAAGAA GGGAGGTCTC CTCGGAGGTC TCCTCGGCGG  16080
CAGCCGGGGG CTCGGAGATC TAGGCGATGA CGCCGAGAAG GCGTCGTCTC AAGTACAACA  16140
CCTTGGCAAG TCGTTCCTGG GCCTCACACG AGCCGCCTGG ATAGGCGTAG GCATCGTCGC  16200
CGTAGCAGCT CCGCTGGTCG GCATCGTGGC CGGTCTGCTG GCCGGTCTGC CGTCGCTGCT  16260
GTCTGCGTTC GGAGCCGGCG CTGGCGTAGT CGCGCTCGGC ATGGACGGCA TCAAGGCAGC  16320
CGCCTCGACG CTGGCCCCGA CGCTGGAGAC GGTCAAGGCC GCTGTCTCCT CGACGTTCCA  16380
GCAGGGACTC ACCCCGGTGT TCCAGCAGCT CGGCCCGATG CTGACCGCGA TCACCCCCAA  16440
CCTGCAGAAC GTGGCCTCGG GCCTCGTGAA CATGGCCGGG TCGATCACCG ACGTGATCAC  16500
CCAGGCTCCT GGTCTGCAGC AGATCCAGAA CATCCTCACC AAGACCGGAG AGTTCTTCAC  16560
GGGCCTCGGC CCTGTGCTCG CTACCGGCAC GCAGGCGTTC CTGACGCTGT CCAACGCCGG  16620
CGCGAACTCG TTCGGCACGC TCCTGGCTCC CCTGCAGGAG TTCACCAACG GCTTCAACGA  16680
CATGGTCAAC CGAGTCACGT CCAACGGCGT GTTCGAGGGT GCCATGCAAG GGCTTTCGCA  16740
GACGCTGGGC AGCGTCCTCA ACCTGTTCAA CCGGCTCATG GAGTCCGGTC TGCAGGCGAT  16800
GGGACAGCTC GGCGGTCCGC TGTCGACGTT CATCAACGGG TTCGGAGATC TCTTCGTCTC  16860
GCTGATGCCG GCGCTGACTT CGGTCTCTGG TCTGATCGGC AACGTCCTCG GGACGCTGGG  16920
CACACAGCTC GCTCCCATCG TCACGGCGCT CACGCCGGCC TTCCAGACGC TGGCGAGCAC  16980
GCTCGGCACG ATGCTCACCG GAGCCCTCCA AGCTCTGGGT CCGATCCTGA CTCAGCCGTC  17040
TACGTTGATC GGCACGACGC TGAACACGGC GCTGCAGGCT CTCCAGCCGA TGCTGCCGTC  17100
GCTCATGCAG AGCTTCCAGC AGATCTCCGA CGTACTGGTG ACCAGTCTGG CCCCGCACAT  17160
CCCGGCGCTG GCGACGGCCC TCGGCCAGGT CGCAGGCGCG GTGCTGCAGC TCGCTCCGAC  17220
GATCATCTCG ACGTTGGTTC CGGCGTTCGT TCAGTTGGTC CCAAAGGTCG CTGAGCTAGT  17280
TCCGACCATC GTCAACCTGG TCCAGTCGTT CGCCAACCTG ATGCCGGTGG TTCTGCCCCT  17340
GGCGCAGGCT CTGGTCAGCG TTGCTGGCGC GGTGATTCAG GTGGGTGTCT CCATCGGCGG  17400
CGCGCTCATC GGCGCGCTGG CGAACCTCAC GGAGATCATC TCCAACGTCA TCAAGAAGGT  17460
GTCCGAGTGG GTCAGCAGCT TCTCCAGCGG AGCCCAGCAG ATCGCTGCGA AGGCAGCGGA  17520
ACTGCCGGGG ATGATCCAGT CGGCTCTCGC CAACCTGATG GCCATCGGCC TGCAGGCCGG  17580
TAAGGATCTC GTCCAGGGCC TGATCAACGG CATCGGCGGG ATGGTCAGCG CAGCGGTCAA  17640
CAAGGCCAAG GAGCTGGCGT CCAGCGTGGC TGGTGCAGTG AAGGGCTTCC TGGGCATCGA  17700
GTCCCCGTCG AAGTTGTTCA CCGAGTACGG CCAGTTCACC GCCGAGGGAT TCGGCAACGG  17760
CATGGAGGCA GGGTTCAAGC CCGTCATCGA ACGGGCCAAG GATCTCGCGG CTGAGCTGTC  17820
CAGGGCGATG GAGTCGGGCA CCGACCCCTC CGGGATTCTC GCTGGGCTGG ATCAGAATGA  17880
GCTGAAGCAG ATGCTGGCGG CTCTCGAAGA GGAGCGCAAG CGACTCAAGG TCGAGAAGAA  17940
CGGTATCCCC AAGGGAGACA AGGCAGGCCG AGAGGCGCTG CAGAACCAGC TCGACCAGAT  18000
```

-continued

```
CCAGGCGCAG AAGGACATCC TGTCCTACCA GCGTGACCGC ATCAAGAACG AGTCTGAGTA  18060
CGGCGACATG GCCGGCGAAG ACCCGTTGGT GAAGGCAGCC TCCGGGCTGA TGAGCGCACC  18120
GGTCGACTTC GCGAAAGCGA CTGGCAAGCA GTTCCTTTCG GACATCGGCA TCAGCGGAGA  18180
TGGGTTCATC TCGAAGGCCA TCACCGAGGG CATCCAGTAC ATCTTCCAGA TCGGCTCTGT  18240
CGATGAGGCG CTGTCGATCA AGGACCGCGA GGAGTCGAAG AACGCGCTGT CCGTCGTTGG  18300
CCGCTGACTT GACATCCACC AGGAGGTAAG CATTGATCAC CGACACCATC GTTGAACTCG  18360
AGGGTGTCAA TGGTGAGCGT TTCAACTTGA CGACCGGTGA CCAGGGTGTG TACCTGGCCA  18420
CAGACGTGGA GGGTTGTTTC TACGACCCTC CCGTCAAGGT CGTTGTTGAA GAGCCGGGGA  18480
ACTACCCCGG CGCTCGCTAC TTGTCCCACC GAGCCCTGAA GCGAGACATC GTCTTTGGGG  18540
TCGTCATCCT CAACGACGCG AAGCAGGGGC CGCGCTCCTG GCTGTCGCGA GACTCCGAGT  18600
GGCGCAAGGC GTGGGCGTTC AACCGCACCT GCAAGCTCTA CGTCACCACC CCGGACTCCG  18660
GTACCCGCTA CCTGAAGCTG GCGCTGTTCG AGTCCCCCAC CGTCAAGATG GACACCGACC  18720
CAAGAGGTAA ACCCCTTGAG GTCACGGTGA TGTCGTGCAT CGCGTACGAC CCGTTCTGGT  18780
ACGAGGACGA CAAGGTCTTC TCGGCCAAGA CCAAGACCGA CACCCGGTTC GACCCGTCGT  18840
TCTGGACGCC GCCGTGGCCG TGGGAGGAAC TGCCCAAGGA GACGCTGCGG ATCAAGGTCG  18900
GCCGCGAGCA GGGTGGGCTA AACCCCACCG ACCAGTACAT CTTCCCGAAG TGGACCGTTC  18960
CCGGCTCCAC CGAGAAGGTG CCGAACTTCC CCTGGCCGTT CCCCCCGAAC GTCCCGATCC  19020
CGTGGGAGAC AGCACCGTTC ACTCAGTTCG TCATCCCGGA CTACTCGTTC GAGGATGAGG  19080
AGTTCCGCAA CCGCCGGCTC AAGACGCCGG GGTTGATCTA CGGCGAGAAC TGCGTCATCG  19140
ACACCGACCG GCGCGAGGAG CAGATCGCTT CCGAGTCGGG CTCCCCGGTG TGGGCTCGGA  19200
TGAACGGTGT CCGGTTCCGC AACTCGATCC CGCCCTACAC CGAAGAGGCT GAGTTCGTCA  19260
TAGACGCATC GGGATGCGCT CCGGGACAGG TAGTTACCCT CCGGCTCACG AGGCCGTGGT  19320
CGCGCTGCTG GGGGCTAGAG TGAGTGGTCT GACGAGCGTT CGTGAGGCCG AAGATCTCTG  19380
GCAGAAGATC CAATTGCGGC GCTGCAAGCG CGAGCAGGAA CGGCTCAAGC ATCCCGACGT  19440
AGAGCTGCGC GATGGCGACT TCCGCCTGCG CGGCCTGGTC GCTGGCGAGC GGGTGCTCGA  19500
GTGGGAGTTC ATCGAGAACG AGACTGGCAC CTGCACCTTG CAGCTCTCAC TGAGCCATTA  19560
CCTGGCGAAG TGGGTGATGG ACCACCGGGG TCGAGCAAAG CGCAACGTCA TCATCAACAT  19620
CGAGAAGCAA GGCGCTCGAT GGACCGGGAT GATGGACCAC TACCGGGTCA TCAAGACCGA  19680
CGCAGGGGAC GCCTACATCG AGATCGTGTT TTTGCACGAC TTCGAGCAGA CCAAGCATAT  19740
CCGGGTATGG TGCAACCCGT TCCTACGCCC CGAGCTGCAG TTCCCCAAGG TGTGGATCAT  19800
CTTCGGGCCG GCCAAGTGGT GTTTGCTGGT GACACTGTTC GTCAACCTGC TCAGGCTCGA  19860
GACGAGCTTG TGGACGCTGC CTGATGACCC CACGGACATC AACGAGTGGA TGGGTCCGAG  19920
CTTCAACCCA GCAAATTGGC GGAACATCGT CAAGCCGTTC CCGTTCCTGG CCGACAACTC  19980
ACCGGTCACG ATGGTGTTCA GCCGGTTCGG GACGTTCTAC GACACCGCCA AGAAGATCCT  20040
CGAAGACCAT CAGCTCACGC TGACGTGTCG TCGGTACATC AAGGACCGCG ACCCGCATCC  20100
GTTCGAAGAT CTCAAGGGGC TCTGGGGAAT TGATCCTGTC GAAGACCTGC TGCAGAAGAT  20160
CCCGCTCCGG GACGGCTGCG TGGTCTGGGA CATCGAGGAC AACTCAGGTT GGGGCACTCA  20220
GACCGCGTTC GGCGGTTCGT GGCTGACCGG GTTCGTCCGA GGGATGGTCC AACTGGCCGG  20280
CGACGGCCAG GTCGAGGGCG TCGATGTGTT CACCGGGGAC TACACGTTCC AGGCGAGTA   20340
```

-continued

```
CTACTCCCCC TGGTTCATGG GCACCAGCCC GATAGCACCC CACGTCGTGT TCGACAGCTT  20400
ACCGCTGACC GGGATCAAGT CGTCGGAGTT CTCGTACTAC GAGGCCACCG ACACGAACAT  20460
CCTGGCTGGT GGACAGAGCG CACCTGGCAT CAACGAGGGC ATCTCGGCCC TGGTGAACAT  20520
CGGTGGCGAC CTGCTGACCT CGTTCATCAA CAGCCAGCTC GCCGCGCTCG GCGCGGTCGG  20580
TGGAGCGATT GACCTCCCGC CTCTGGGCGG TCTGCTCGAT GCGGTGTTGC AGCCTCTGTA  20640
CTCCGATGTG TTCGGCGCGT TCATGGAAGT TCCGACTCTG CGTGCGATGG GCATCTCGCT  20700
CCCGATCTCC GGGCTCGAGG ACATCGTCAC CGGACTGGGC GACTTCCACT ACTTCGAGAA  20760
CATGGCCGAC GGGGCGATGA AGGCGTTCAC GCTGTCAGCG TTCGCAGCCA TCGCATCGCA  20820
GATCCACAAG ACGAGGGCTC GAACGACCCA CACCCTCAAG GTGTCTGACG CCGCTCCGTA  20880
CATCTTCGCG CCAAAGCCCT ACGGGCACTG CTGGATCGGA GATCGCGTCG GCACGTCGGT  20940
CCTCGGCTAC CCGGTCGAGC ACCAGTTGTT CGTGGAGCGC ATCCGCAAGG TGAAGTACCG  21000
CATCGACAAA GACGGCATGA AGCCGTTGGA GATCGAGATC GGTTACCGCG AACCGAAGAA  21060
CCCAGCACTA CACATCCTCG AAGAGATCAA GCGCGTCAAC GGCGCTCTTG GCACTGCGGG  21120
GATTCTCTAA ACCGAAAGGC ACGCCGCATG ATTCCCTCAC AAGAGTCTCA CAATCCGAAC  21180
GACCCGCGAC AGCACGTCAT GTGGGCGCTA CGCAATCTCC CGATGATTGC TGGCGTCGGG  21240
GCGATCACGC ATCCGGGTTA CCTGGCGGAT TGGTCAGAGC ACTTGTGGAA GTGCGGCTTT  21300
CGGCACGTCG ACTGGCTCCG GGAGCTGGCT GATGAGGACG GCAACATCCA CGTCAGTCAG  21360
CTTCCTGACC AGGAGATCAA GTTTCAGCAG CCCTTCCGGG GCCAGCGAAG CGACTACAAC  21420
AACGCAGCTC GATGGGTCGG CAAAGACGAT CCTGACCCAG AGCCCGTGCG TATTCCAGAC  21480
ATTCGCAAGC TCACAGACCA GGAGAACAGA GCGATGATCG CGCAGTACGA ACGAGACGGT  21540
TGGATCAAGG ATGGATCCCC CGGCCCAGCG ATAGCCGAGG TCGTGGAGTG ACCCCGTTCA  21600
ACCCAGACTC CATAGGCGAC TACGTGACAC TGCTCGGCGT TGCGTTCCTG ACCTTCTCGG  21660
TTCCCGCATG GTTCACCGGA CGAGCACGCA AGCACAGCAG TGACATCGGC GAAATCAAGG  21720
AACAGGTATG TAACACCCAC GACACGAACC TGCGCGATGA CCTCGACAGC GTCAAGGCAG  21780
ACATCAGCGA CTTGAAAGAG ATTGTGTTGC AAGGGTTCCA CCAGGTGAAC GAGTCGATCA  21840
ACCTCGAGCG CCGTGAGCGG ATCGAAGGAG ACCGCCGAAA GGAGGTTGCG TGACCTACCC  21900
CACCAACCCA CTAGAGGCCA TCGGCGCTGA CGGCGCATTC GAGATCGGTG GGGGCGACTG  21960
GAGCTTCGGC CAGGACTACA CCGAACAGGC CATCCGGGCT CTGTTCACGA TGCCAGCGGT  22020
CACGATGGAG AACGCTCTCG GCCTGCTCGA AGAGCACCTG CTGAAGCTGC CTCTGGAGGC  22080
GCTGCAGGGC TTCAAAGACA TGATCCCGGA CTGGGTCGAA GGAGCATTCG ACACGGTCAC  22140
CGGCGCTGTG CAGGCGATCA TGAACGCGCT CCAAGACGGC CCGCTGTTCC TGAAGTTCGC  22200
CGAGTTCCAG CTCTTCCTGC AGCGTCTGCT GAACAACCCG GCCGAGGTCA TCGGCGAGAT  22260
CCCCCAGACG TTGATCGACG GCCTACAGGA CGCGCTCAAC ACCGTCAACA ACACCATCCA  22320
GACCATCGTG GACATGCTCC TGCAGGCGCT GGGCATCACC CCGGAGGGGG AGCTGATCGA  22380
CCGGATCTTC GACCTGAGCG ATGAGATGGA GTGGCTGCAG ACCGCAGCCT CGAATGCAGC  22440
TACCGGCATC CAGGACACCT GGAACAAGTT CTGGGGAGCC CTCACCGGGC GCGTCCCAGA  22500
CCAGGACCAG ACCGTCGCTG AGCCCGCCGA GCGTATCGGC GAGCTGGCCG GCACCACGTC  22560
TGCTAACTCG TCTGCCATCG CGGAGCTGCA GCGTCGACTG GACAACCAGC AGAACGCTGG  22620
CGGCGTGGCC GGCGGTGACG ACTTCGAGCG ACTGAACATA TCCGGTTGGG ACATCAGGTA  22680
TTCCAACGGA TCCAGCGGCC GAGGGTACTA CCGTGCCGAC GGCCACCAAC TGGTCTGGAT  22740
```

-continued

```
GGACGAAGGC AACCAGCAGA ACACCGCGAC GTTCGTCCGC ACCAACCCCG CAGACGAGAA  22800
GACAGCCACC GACTACCAGA AGATGACGTT GGTCGTCGGG ACTATCTCCG GTGAGGTACA  22860
GACCGTGTTC CCGCCGCAGG GAGGTTCGCA CACCCGGCTA TGGGTCCGCG TCAACGACAA  22920
CGCTCCGACC GTCGGCATCA CCGACGGCGT GTTCGTAGAG ATCGGCGGCG TATCFAAGGC  22980
CCAGATCGGC TACCGCCGCA ACGGCAATGA CACGTTCGTC GGATCTATGG TCGACTGCAC  23040
CTGGGGTGCT GGATCGATCT TCGCTCTGAC CGCCGGCACG GCCAACGGTG CTGAGAAGTT  23100
CGAGGTCTCG AAGAACGGCC CCGTGCTGGC CACATGGTCG GACGACGGCG TCGTCTCCGC  23160
GATGGGTGCG AACTACCGCC GCTGGGGCTG GGAAGGCCAG GCTCGTAACC GCAACCTCGG  23220
CCAGGGCACT CCGAACTCGG TCACCCGAGT GACGATCACC GACAACGATC CTACCGGCGC  23280
AGGCGGTGGA GCTGTCAACG TCGGAGGAGA TGTCGTAGGT GTACTCCCCA TAGAGAACGG  23340
AGGCACCGGA GCTTCGACAG CTTCGGCAGC CCGTACCGCT CTCGGAATCG ATGACCTGGT  23400
CGAAGATATG TCCGACGTAG TTCGTGGATC CGTCGAAGGA CTCCCGTTGA TACCGAAGAT  23460
CTGGGTAGGA ACAGAAGCTC AGTACACGGC TCTCGCCACC AAGGATCAGT CCACGCTATA  23520
CTTCAGGACC GCTTAATGAC TGGTATCTCG TTGGGTGTCA ACGACATCCG CAACCTCTCG  23580
ATATTCTTAG GCGTCAGCAA CAAGATATTG AAGGTCAGTC TAGGCACAGA AAAGGTCTGG  23640
CCTGCGTTCA CCCCGGTGCT GACCACGTTC GCCACGGTCG GCACGTACAC CTACAACATC  23700
CCCGACGGGG CCAAGTTCAT CGACGTCATC CTCCTCGGAG GAGGCGGCGG GGGTAAAGGC  23760
ATGGCCCTGG CTGACGGCTG GGGCAGAGGT GGAGACGCCG GAAGCTGGGC TATCGTCACT  23820
CTCGAACGCG GGGTACACAT CCCGTTGTCG ACCAAGACGA TCACCGGGCT CGTCGGAGCT  23880
GGAGGCGCAG CGGGAGCTGG CTCTGTATTC TCAGGCAAGG CCGGAGGCCC TGGAGGAAAC  23940
ACCACGGCGT CCGCTGTCGG ATGGTCAGGT TTGACCGCAA CCGGCGGTCC CGGAGGCTCT  24000
GTGATCGACA TCCTCAGCGT CGCCGGAAAG TCGCCTGGAG ATCGGACCTA CAACGACCAG  24060
CTCTACATAG GCGGCGCACA ACAGAACTCA GCTGGCGGGA ACGGCAATGC TCCTGGCGGC  24120
GGCGGGGCTG GTGCCCAGGT CTCCGCACAG AGCGGCGGTG CTGGCGCTCG CGGCCAGGCG  24180
TGGTTCTTCG CGTACTGACA AGAAACCCCC CTCTTTAGGA CTCAGTGTCC TTGGGAGGGG  24240
GGCTTTTTGC GTTTCAGGAG GTCTTGGCCA GCTTGGACAT CGCCTCAGCG ATAGCCTCGT  24300
CGCGGGCCTC AGACGCCATC TGGTACTTCA TCGCCATCCT AGGAGTCGTG TGACCGAGAC  24360
GGGCCATCAG CTCCTTGGTC GTCGCACCTG CCTGAGCGGC GAACGTAGCG CCGACAGCGC  24420
GGAGGTCGTG GATGCGGAGT TCCGGCCGAC CGATCTTGGC GTAGCCACGC TTCAGCGACT  24480
TGGTGAACGC GGACTTCGAC AGCCGGTTGC CCTGCGTCGT GGTCACCAGG AATGCCTCGG  24540
GGCCCTTGTT CATCTTCGTA CGGTCCTTCA TGTGCGCTCG GATCATCTCC GCGACGTGAG  24600
GCGGAACCGT CACAGGACGC TTCGACCGGA CGGTCTTGGC GTTGCCAACG ACGATCTTGT  24660
TCCCCACGCG GGAAGCGCCA CGGCGCACCC GGAGCTTCAT CGTCATGCCG TCGTCCACGA  24720
TGTCCTTGCG GCGAAGCTCG ATCAGCTCTC CGAACCGGAG GCTCGTCCAC GCCAGGATCT  24780
ATGCCGCGAT CCGGTAGTGC TCGAAGATCT CAGCGGCGAC GATGTCCAGC TCCTCAGGCG  24840
TCAGCGCCTC TACGTCGCGC TCATCGGCTG CCTTCTGCTC GATCCGGCAC GGGTTCTCTG  24900
CGATCAGCTT GTCCTCGACC GCTGTGTTCA TCACCGCCCG GAGGACGTTG TAGGCATGCC  24960
GGCGGGCAGT CGGGTGCTTC CTACCCATCC CGGCCCACCA CGCACGCACC AGAGCTGGCG  25020
TCATCTCTGT GACCGCCACT TCACCTAGCA CCGGGTAGAT GCGGCGCTCC GCGTGCCCGC  25080
```

-continued

```
TGTACAGATC CCTGGTGCCG TCTGCGAGGT CGCGCTCCAC GAGCCACTTC CGGGTGTACT  25140
CCTCCAGCGT GATGGCGCTG GCGGCTGCCT TCTTCGCCCG GTCCTGTGGA GGGGTCCAGG  25200
TCTCCATCTC GATGAGCCGC TTCTCGCCCG CGAGCCAGGC TTCGGCGTCC ATCTTGTTGT  25260
CGTAGGTCTG CAGCGCGTAG TACCTCACAC CGTCCTGCGG GTTGACGTAT GAGGCTTGGA  25320
TCCTCCCGCT GCGCTGAGTC TTCAGCGATC CCCATCCGCG ACGTGCCAAC TAGGTCTCCT  25380
CTCGTCGTGA ACAAGGCTAC CGGGTTGCAA CTCCTGTGCA ACTCTCAGGC TTCAACGCGC  25440
TTCTACGACC TGCAATTTCT TTCCACTTAG AGGATGCAGC CGAGAGGGGG TAAAAACCTA  25500
TCTTGACCGG CCCATATGTG GTCGGCAGAC ACCCATTCTT CCAAACTAGC TACGCGGGTT  25560
CGATTCCCGT CGCCCGCTCC GCTGGTCAGA GGGTGTTTTC GCCCTCTGGC CATTTTTCTT  25620
TCCAGGGGTC TGCAACTCTT GTGCGACTCT TCTGACCTGG GCATACGCGG TTGCAACGCA  25680
TCCCTGATCT GGCTACTTTC GATGCTGACA AACGAATAGA GCCCCCCGCC TGCGCGAACA  25740
GACGAGGGGC ATTCACACCA GATTGGAGCT GGTGCAGTGA AGAGAATAGA CCGGGACAAG  25800
GTTGCACCGG GAGTTGCAGC GGTCGGAACC CTCGCCGTCG GCGGGCTGGC GTTCGCCCTG  25860
TCGTTCACGG CTCTCAGCGA GCTGGCTGCG GCCAACGGGG TGGCCCAAGC AGAGATGGTG  25920
CCCTTGGTGG TCGACGGCCT GACGCTCGTC GCCACGGTCG CCACAGTGGC CCTCAAGCAG  25980
AACAGTTGGT ACGCGTGGTC GCTGCTGATC CTGTCCACCG TCGTATCGGT GGCCGGCAAC  26040
GTGGCACACG CCTACCCCCA CGGCATCATC GCGATGGTGA TCGCTGCGAT CCCTCCGCTC  26100
TGGCTACTGG CGTCGACCCA CCTAACCGTG ATGCTGGCGA AGCAGCACTC GGAGGCTTGA  26160
GAAGTACCTG TCTCGCGGCC AGAACCCGCG CCTCGGGGCC TGGAGCCCGC TGCCGCTTGA  26220
CTGCGCCCGA CCGGGACAGA AATACATAGA GAACCTATGG ATGTAGGAGG CACAAAAAAA  26280
TACCCCCCGA GCCAGCCCGA AGGCCAGCCC AGGGGGCATG GTTCTGCTTC AGTAGACCTT  26340
GCGAGTCCGA CCCGAGTTGA TCATCGCCAT GATGACCCAG ACGGGCAACC ACATTCCGCA  26400
GGTGATGAGC GAAAGCAACA GGTGCATCGC GTGGTTCGTC CTGACAGGCA TGACAGTGGG  26460
CTGCGGCATC GGAGGAGGCG CGACCGGGTA CGGCGAGCCC GCGTACCACT GAGGTCGATC  26520
TTGTTGGGGC GGATACTGAT TGGTCATCCC GACAGCCTAC TTGCCGATGG GTCGCATCAG  26580
CTCCTCGACC GACTCGCGCT CCACGCGGAT CAGCCGGGGA CCGAGCCGAA CGGCCTTGAG  26640
CCGGCCGTCG GCGATGTAGT TGCGGACGGT CTTGGTGCTG ACACCGAGGT AGTCAGCGGT  26700
CTCCTGGATG GATGCTCTCG GGGGCATCAG CGCGGTCCTC CGTGCTTCAT CGGTTGTCTC  26760
CCGAACCCTG GATCACGCCA CGATCCTTGC GGCTCTGGAG CTTGTTGAGG TTCCTCTGGG  26820
TGACGGTGCT CAACCAGACA TCGAGCTGGT TGGCTAGCTG GGCGACGTAC CACATCACGT  26880
CTCCGAGTTC CGCCTGGAGG TCGTCTCGGT TCTCCTGGGT GATGACACCG TCTTTATCCC  26940
GGAGGATTTT CTTGACCTTG TTGGCGATCT CGCCGGCTTC GCCTACGAGA CCCATCGTCA  27000
CGTAGGAGAG ACCCTCGATG CTGTCGCAGT CGCCTGCACC GGGGTAGATC GCTGTGTCGC  27060
TCGCGGCGAT CTGGTAGATG TCGACGTGCA TCAGATCATC ACCGGGAACA ACTGGCCACC  27120
GGGCATCTGG ATGAACACCG GGACGCTGGG GGTGTAGTCC GACGAACCCG TGCCGCCCTC  27180
ACAGGCGGAC AGGCTCAGGG TGGCGGCAAG GCCGATGATG GCTGCTGCGA TGGTCTTCTT  27240
CATCTGTTGC TCCAGTAGCT AAGTTCGGAC TCCAGTTCGC GGATACGCTC CTGTAGCCCT  27300
TGGTTTTCCA GGTACGCCTC GGCGAGGTTG GCCTCGGCGC GGTCACGGGC CTCGTCCTTC  27360
GACGTGGCCT CATCGATTGC CTCGTGTAGC CGGCGGATCA GATCTGGGAT GGCACCGTGC  27420
AGACCGCATA TGAAGTCGGC GTCTGCCTCG GAGAGGTGGG ACGCCACCAG ATCCTTGTCC  27480
```

-continued

```
TGGGTCTCCT GGTTGACCGC CCAGATGACG TGATCCTCTA GCCCGTGGTC GGTCTCGCAG  27540
ATAGAAGGCG GTTCTACCTC CTCTGGCATC CAGTAAGTCT TCTCAGCCCC GGTGGACTTC  27600
GCCCACTGCT GGTAGAGGAT GTCGAAGAAC TCGTGGTCCT GTTCGTCGGC GGTAATCACA  27660
GATCGTCCTC TTCATCCCAT TCGTCGTAGT AACACGTACA GCCGCAGCAG GTGCAGCAGC  27720
CGCACTCGTA GGTGCCGTAG TCGTAGTCAT CCCAGTCGTC TTCGTCCATC TAGCTGTACT  27780
CCTTCATGAT TCGGTCGAAC GCACGCGTCT GCACGCGCAT CTCCAGGTCG ACCGTTCGCT  27840
TCAACCACGC CCATTCGCCG TCGTGGTTGA TCTCCCACTG GCTCTTGAAT GTCGCTGTCT  27900
CAACGAGGAA CTCGACAGTC AACGTGTGCA GTCCGTTGTT GCTGGGCTGG AATCCGATAC  27960
CGTCCTCAGC GATGTACCAG GGCAACTCCT GGCCGTCGAA GTAGACGGCC TTGTCGGTCA  28020
CCAGTACTTC AGGGAAGGTG TGCTCGGTCA ACGGCGTCCC AGGTATGGGA TGACGCTGGC  28080
CCGGAACTCA AGGAACACCA TGTTGTCCGG GCAGTCCTCG GGGACGTTGT CGGGGCGTTC  28140
GGCGGTGTAG ACGCCGATCT CGTTGCCCTC CAGGGTTCCA AGCTCGTTGA GCTTGTAGAT  28200
CGCCAGACCC ATCAGCTCTT CATCGAGACC GTTCGGTGCT GGCAGTACAA CTTTGGCTTG  28260
TGGCATTAGC CCTCCCTCGG AATTACGTAT GCGCTGAACT CGACGGCCGT AATGCCGTCT  28320
GGCAGTTGGA ATCCGAACCG CTCTTCGAAC TCCTCGTTGG TGATGGGGCC GTACTCGAAG  28380
GTTCCGGGCA CTACCTCGCC CTCCCCCTCG ATCAGGAGGT ACGCACCGGC GGCGTACACC  28440
TCCTCGTCGT TCGGCCATCC GACTACGGTC CCGAGGACCG TGAACTTCCT CGGCTCCATC  28500
AGGGCACGTC CACTTCGTTG ATGAGGAACC GCATCGGAGG TGGAGTGAGC ATTGCCTCGG  28560
CTATGGCGAT GAGGGCGTTC AACTGACCCT TCAGCAGCTT CTCCTCGTCG CCTGCGGGAA  28620
GGTGGCGCAC TCGGCGCTCC ATCTCCTTGG CGCGTTCCAG ATATTCGGTG GCTGTCAAGT  28680
TGTCCTCCTT AGTAATCAGC GCCGTAGAGC GAACCCCACG AACGCTTTCC GACCTCGGGG  28740
TCGGTGCCAA CCAGCACCGG ACCCATCTGT TCTTGCATCA GGTGGCCAAT GTGTGCAGCG  28800
GCTCTCTCAG CCTCTGAGGC GGGCAGAGAC GCGACGATCT CGTCGTGGAT AGGCAACCGT  28860
AGGTACGGGG TGTATCCGGC CTCGTGGAGG CGAATCAGAG CCCGACAGGT CACGTCCCGC  28920
GACGACGACT GGATCATGTA GTTCAGCGCG GAGTATGTCC GCGAGCTGTC CACCGGCAGC  28980
CGCCGGCCCA TCGCGTTGAC GATGTAGCCG TTGCGGCCAG CTTCCATCGC CAGCTTCTTG  29040
CTCAGCCGCT CCACACCGGG GTATGTCGCA GAGAACGCCT CATGAACTCG CTTGGCCACA  29100
GGGATCGAGA TCCCCACTGC CTCAGCGAGA GCCTTCGCCC CACCGCCGTA GACCTTCTGA  29160
AAGTTGGCGG TCTTCCCAAC CTTTCGCGGC ACCTGGGCTG CGTCAGCGGT CATCTGGTGG  29220
AGGTCCGCAC CGTTCTCGAA TGCCTCGATC ATGTTGCGGT CGCCCGACAG CGCCGCCAGG  29280
ACGCGAAGCT CCTGCGCCTG GTAGTCGACT GAGGCCATCA CATCGCCTGG CTCAGCGATG  29340
AAGCATCGCC GCACGATCCA GTCCGACGAC GGCAGCGTCT GCGCCGGGAT GCCGGTGATC  29400
GACATGCGCG AGGTCCGCGC CTGCAGTGGG TTGATGAACG TGTGGCAGCG GTCCTCAGAG  29460
TCCCTGGTGT CGATGAACTT CTGGACCCAG GTCTTCCGCC ACTTCCCCAG CTTCTTAGCC  29520
TCCTGAGCGA TGGCGGCAAG CTCGTTGCCA TCTTCGACCA GCTTGTCGAG CAGAGCCGCG  29580
TTGACCTGGC GCTTGCCAGT CTCGGTGCGA CCGGTGATCT TGACGCCCAT CTCCTCAAGC  29640
CCCTCGGCCA GATCCTCGGT CGAGTTGACC TTCTCCACGC CGTACTCGGT GAAAGCGATT  29700
GCCTCCCAGA CCTCCTGATC GGCCAACCAC TTCTCGGCGA GCGACCGCGA GTACTCCACA  29760
TCGAGCAGGA AGCCCTGCCT GTCGATGTAG CTGCAGATCT CACTGATCTT GTGCTCGTAC  29820
```

-continued

```
GGCACCAGCG ACCGACTCAC GTCGGGCACC AACGGTGTCA GGCTCTTGCA GACCCTCGCG  29880
GTGAAGATCG TGTCCATCCC GGCGTACAGC AGGTACTCCG GGTGGAACAG GTCGATGGTC  29940
GACCAGATCT TGGCCTTGGT CGTCTTGTGC TCGGCGGCTA GCTTGGCCAT GAGCTTCTTG  30000
ACGTTCTCGG CCTGGTCCTC GGAGATGAAC TTCGCGATCA GCTCTTCGAG CGAGTGCCCG  30060
AACCCGCCGG CCTCGAAGGG CCGGGGGTCC ACCAGCTTCG CCAGGATCTG CGTGTCAAGC  30120
ACGCGGGGCC ACAGACCCTC CATCTCGATC CCGAAGCACT GGTCGAGCAC CTGGAGGTCG  30180
AAGGAGGCGT TCTGGAGCAC CATGCGCTTG AGAGCGCCGA TGGCGATCCG CACGTCCTCG  30240
ATGAACACGT CTCCCAGCTC CACCGGCACC ACCCAGGCTT CGTCCTGAGT ACCGAACTGG  30300
ACGAGGCGGC ACTCGAAGGT GTCGCTGTAG ATGTCCAGCC CGGTGGTCTC AGTGTCGACG  30360
GCGAGGCAGT TCAGGTGAGC CCGGATGAAG TTGCGGAAGC CTTCCAGATC CTCTGGGGTT  30420
TCAACGACGT TGACGGTGAC GAGGTCTCCC TGAACCTCAT GCCGCAGCTC GATCAAAATG  30480
CTCTCCTACT GGAAGTACTG AGGCGGAATC CAGGTGGCTG AGGCCATCTC CTTGATGGCC  30540
TGCTGCATGG CCGCTTCGAA CGGACAGTCC GGGTCGATGT CCGGCTTGTA ATGGGTGACG  30600
ATGATCCGGC TGTTGCCGCC GAAGTCGTGG CTGACCAAGC CCTTTGGGGG CAGCTTCTTC  30660
AGCGCCTTGA TCAGTTCCTC AACCGTGGTC CCGGTAGGGG CCTTGCCGTC AGGCAATGCC  30720
TCCCCTCCGT ACGGCACGTC CAATGGGATC GTGTACCGCT CAACGTCTTT GATCTTCATC  30780
GAGCCTCTTC CTCTTCGACT ACCTCGTCTA CCCGGCGGAA TAACTCCGCT AGTTCTGCGG  30840
GTAGCAATAC TGGGTACTTC TCTCGGGCTT CCTGCATCGC TACCGCGATC CCAATCAGGG  30900
CAGCGAGCAG TTCATTGACG GAGTACGCCA ACAGCTCTTC GCGGATCTCT TCTCGGGTCA  30960
TTAGTGGTAG ATCCCCCGGA CGGTGCGCGA GATCGTGGCA GGGTTCACGC CGTAGTTCTC  31020
GGCGAGATCC TTCTGCTTCA TACCGCCCAG GTACGCCTGG CGGATGTCCT TGACCTCGCG  31080
CTCGGTGAGC TTCTTGCGGT TCGGCCGGCT CGGGCCGGTC TCAGGCTTGA CCTGAGCCAG  31140
CGCCTTGCCG AACAGCTCGT TCTGCGTCCG CTGCTTGATC GCGTACCGAC GGTTCGCTGC  31200
AAGCACCTCG TTGAGCCGCT GGGACAACTT GACATTGGCC TCACGCACTA CCTCGACCTC  31260
TCCGAGCAAG TTCGTGATCC GGTAGTCCTT GTCCTGGTTC TCGATGGCCA ACCGGTTGTT  31320
CTCCTCGGAA AGCATCGAGA CCTTGTATTG CGCCTCTCCC AGCGCAGCTT TCAGGTGCTT  31380
CTTCCTCATT CAGCGCCCCT CTCTCGGCGG AACTGTTCGT ACTCGTCTTC GGTCATGTAG  31440
TAGTAGTAGT CAACGACCTT GTCCCAGTTG AAGGTTCGGG ACGTGCCGTC ATCGAACGCG  31500
ATGATCAGGA CACCCTCTTG GGTGTCTAGG ATCGGCTCGC CAGCCACGAC GTGGAAGCGG  31560
TCCTCGAGGG TCACCGCAGT CGCTCTGCGT GCCATGTCAG TTCCTCTCAG TAGCTGTAGG  31620
GGACATCCGG GATGTCCTGG TAGGTGTTGG GTGCGATCTG TCGGAGCTGC CGAAGCAATT  31680
CCCCTGCCAG CTCACGGATC TCGGCATCCG CGGCCTCGTG CCAGCGGGCC TTGATGACGT  31740
ACCGCCACGC CCGATGGTTG CCCGTGACGA CCATCGGTGA GTTCGTCATG TTCGGCAGGA  31800
CAGCTCGCGC TGCCTCGCGG GCCTGCTTGC GCGGCAAGCC CCGGTCAGCC AGCCGGTTGA  31860
CGATGTGTTC GTAGACAGCG TCAATCTCAG AGCTGACGGA CTCCATGATG TGGACGAGGT  31920
CGTCTCGGTC GTCGGGGTGG AGCTTGAACA GAGCCGGGGG CAGATGGATG CCAAGGTCGG  31980
TCGGATCCAC ATATCGCTGA GACACCACCG AGAAGCTCAA GTGACGGTGA CGCTCCAGCT  32040
CGGTCAGCAC CGACCTGCTG GCCTCGATGT AGAACGTCGC CGAGGCGTGC TCGAACACGC  32100
TCTCGTGGCC CAGATCGATG ATGTGGTTGA GGTAGTCCTC GTTCTCGGCA GTTGCCGGGT  32160
TCGGTCGGTG GAACGACCGG TAGCAGTTCC GGCCCGCGAA CTCGGCCAGC TCGTCGGCAT  32220
```

-continued

```
CGAAGTCGCC GAAGTAGGGA TCTTCGTCCT TGGATTCTTC GAAGTCATCG ACCTCGAATC  32280
CGATGTCCCG CAACGCACCC GGATCGATCT CGGTGGCAGC GATCAGTTTG GCTTTCATAC  32340
TCTCCGCTCA GAGTTGGTGG AACGAGGTCA GCCAGGGGGC AGCGAAGCCC TTCTACAGCT  32400
CCCCTTGGCT CGTTACCGGC TTCTCGACCT CGGTGGATGT CAAGTAGTCG AGATGACTAC  32460
TTCTTGTCGG GCCATTGCGC GTCACACTGC TGATCGCGAG GTGCGGTGCA GGAGAACAGC  32520
GCGTACGGCT TGCCCGTCTT CTTCGAGACG CCCGACTTGT AGACCATCTC GCCGTGCTGG  32580
CAGTACCGCT TCTCGCCACC AGGCGCTTCC TGAGCTGCCT GCGGGGCGCG AGACTGCTGC  32640
TGGCCACCGC CGCCGCCGTT GGCCGGCGCG GATCCACCGG AGCCTGCGTA GTGGCCTGCG  32700
ATCTGCTGGA CCTTGTCCAT CAGCGCCTTG AACTCGGCGG TGTTGACCTT GGCCAGCACG  32760
TCGGCCGGGT CCGCACCCTT CACGACCACC CACGGGTCGC TGTACTGACC GGCGAACTTG  32820
AACGTGGCCG ACACCCCATC GGTGGAGTGC TGGACCGCCA TCGAGTCGCG CACAGCAGCC  32880
GAGGCCGTCG TCACCGTCGC CGACGGCGCG GTCTCAGGCT CAGGAGCCGG GGCCGGCTCG  32940
GGCTGGGCAG GGGCGGTGCT CCACGGATCG TCGTAGGACA ACTGGTTACC TTTCACTTAA  33000
TGGGGCATGC GCCGTTGGCG CACTCTTCAT CGACACCGTC TTCGACGGCT TTGGCCGCAG  33060
CAGATTCGTA CTGCTGCTTG GTGATTCGCT CGTACGGAGC CTGCGGGAAG CTGGACTCCG  33120
GGAAGATCGT GGAGCCCTTG ATGAGCCCCG CGAACCTCTT GAGATCGGCT GCGACATCCT  33180
CGGCCTCGTA GGCGTCTGGA TGGACGTTGG CGGTGAACGA CACCGCGTTG TCAGCCCAGC  33240
ACATCTGGTA GAGCGCCTGG AACGCCAGGA GCTGGTGGAG GGTCAACTCG TCGGCTGACT  33300
CAACGATCTC CTCGTCCCAA CCGAGTTCCT CGACAGCCTG GACCAACGTG TCCTTGGTCG  33360
GGATCGAAAC CACCTCGGTG TTCGGAGCGA AGAGATCCTT CTCGATCTCG TAACCCTCGG  33420
CTGCCAACCT CCGCAGCTCG GCCATGTCGC TGTTGAGGTT GAACCGCACA CGCCGGATGA  33480
AGTACCGCGA GAAGATCGGG TGGATCCCCT CGGAGACTCC TGGCATCTTC GCCACCGTGC  33540
CTGTGGGAGC GATGGTTCGC TTCTTCACCG GGACAGGGAT CCTCAGATCA TGGGGCTTAT  33600
GTTCGGCCTC TGAGTCGACC TCAGCGGCCA TCTCCCGCAA GAACTGGGTG AACCGCTTAT  33660
CTCCGGGTGC CTCGGAGTAC CTGCTACCTG TGAGGGCCAA ATAGGAGGCA ACTCCGAGAT  33720
GACCCACGCC GATGCGACGG TTTCGGTCCA GAACCTCCCG GCTCTTCGGG TCGGCCACTT  33780
CCGAGAACGT CGCCCGGATC AGGAATCTCG TCATCAGACG ATGCGCCCGG ATCAGGTCGA  33840
GGTAGTCGGT CTTGCCGGCC GGCGTCACGA ACGCCGCCAG GTTGATGTGG CCGAGGTTGC  33900
ACGGCTCCCA CGGTTCGAGA GTGATCTCGC CGCATGGGTT GGTGCAGACC ACCCGGTTGG  33960
GCTCACCGAC GTTGGACAGT GACGAGTCCC ACATCCCCGG CTCTCCGTTG CGTACGGCTC  34020
CCTCGGAGAG TGCCTTGAGC ACTCGGTGGG CTCGCTTCTG CTTGGGCATG TCCTCGCGGG  34080
CGACCGCGAA GCTGCCGTAG CCCTCCTTGG CCAGACGCCA GAACTCGTCG TCAACCTCGA  34140
CCGAGATGTT CGTCGTCCAG TGCTCGCCCG TGCTCGCCTT GATGTTGATG AACTTGTCGA  34200
TCTGGTAGTC GTCCCAGTGC ATCATCGACA TCCGCGCCGA CCGGCGCACA CCGCCGGCCA  34260
CAACACACTG AGCGATGGCG TGGTCGACCT CCATCGCGGC GATGCCGTCG AGCGTGATCC  34320
CTGCGTACTC CGAGAAGATG TTGGCGACCT TCTGCAGCAT CACAGCGAAC GGCAGCGGGC  34380
CGCTGGCCAC TCCACCGAAC GTCTTGAGCT TGGCCCCTTG CGGCCGGATG CGGCTCACGT  34440
CGTACACCCG CTGGTAGTGG ACCGTGCCGG GTCGGTAGTG CGTGTCGATC AGATCGACCA  34500
GCGCAGCAGC CCAGCCCTCT CGTGAGTCCT CGATGGCGTA GGCACCGGCC CAGTCGTGGC  34560
```

-continued

```
TGTAGTGCTC CGACAGAATG CCTACATCCT TCATCGCCTG GTAGTCGACA TGCTCTGGAT  34620
CACAGACGAT CTCGACCCGC AGGGGGTTTA CGACCTCGGG GTAGCCTTCG AGGTAGTGGT  34680
TCGAGTAGTT CGCCCCGACT CCCCCGCCCT CCATCAGGCG CATGAACGTG AACTGGAAGT  34740
GGTCCGAGAT CTTCTCGGGC CAGCCAGCTA CCCAGCAGTT GAAGAGGTGC TGCGCGTTCT  34800
TGACCCCCGA GGCCCACAGA TGCCGACCTG CCGGCAGCAC CTTGAACTTG GTCATCAGAC  34860
GAACGAGATC TTCTCGCTCT CCTTCCAACA TATGTCGCCG GTCGACAAGA GCAAGATTGC  34920
CGTCCACGAC CCTCTCGACC GTTTCCGGCC AGGTTTCCTT CGAGCCGTCA GGCTTGGTCC  34980
TGGCGTAGGT TCGGTTGTAA ACGAGTTCAC CGGTTGGTCC CCAAGGGATT TCGTCAGTCA  35040
ACTACTTCCT CTCAGTCAGT TCGTATCGCT TGAAATAGGC GTCGGCAGAG TCGCCGCCAG  35100
AGAACGAGAC CCCGTACTCG ACCGGGCCTG CACCACGCAC CTCGCAGGTA ACGACGCCCT  35160
TCCTTCCCCG GAACATCGGC CAGGTTCCCT TGGAGGGGTG CTTGGTCTCG TCCCGCTGGA  35220
CGATGACCTT GGTGCCCTTC TTCATGCCGA CTTCCGTTCT CCGTAGCCGG GAGTGAAGCA  35280
ACCCCCGACG TACAGCTCGA GATCTTCTTG CGACCAGTTC TCCAGTCGCA TCGGCGGCTG  35340
GTGCGGGAAC AGCTCCGGGA ACACCTCGGC CCGGTACAGC TCCGAACCGG GCATCCCGTT  35400
GAACGTCGGA TCAAGAATGT TGTGCATGGC ACCTCCCTCC CAAGAACTCG GAGATCGGCG  35460
GCTCGTAGAG GTAGCCATCG CGCAGCTCGG GGTTCTCGAT GAGCATGATC GCGATGTTCG  35520
CTGTGGGGTC AGAGTGCCCA TCCCCCTGCG ACTTTCGGAT GTCTGGGAAG ATAGCGTGCT  35580
TGCTGCCCGG ACCATCCTTG ACGATGACCT TGCCCTTGTC GTCCTTCTCC ACGCCAGCCG  35640
TGATCGCGAT GATGTTGACG TGCTCGGTCA GCGACTTGTG AGCGCGGAAC AACCGGTTCT  35700
GCCCGCTCTT ATCCTTCGGG GAGATCCCGT CGGTGTAGCG GCTCCTGATC GCCTCTGCAT  35760
AGCCCCCGTT CTGAGCGTCC AGAGCCTTCA TCGCCAGCGG GAGGATGTCG ACCAGGTACC  35820
GATTGGTCGA CTCCCCCTGC AGAGCCTCTT TGACGTTCTC GGACGAGTAG TGGCTGCGCT  35880
CCTGGAACAA GTCGCGGGCC TTGGCCGCTC CCGACAGGAT GTTGCGAACC TGATTGCGTA  35940
CGTAGTGAAC TGCCTCACCA CGGTGCAAGC TCTCCAGCGT CTTCTGGATG TACGGGCTCT  36000
CGAGGTACCA GACCCACAGC TCTTGGATGA TCTCCTCGGC TGTCAGGTTG GTCTCCCAAC  36060
CGATCAGCGC CTTCCGGGTG GCCCTGCTGA ACAGCTTGCT GATGTCGTCG GTCAAGGCAT  36120
CACCTTTCGT AGGTACTCCT CCCGGTCCAA TCGGCGGTCG AGGTGTCGAG TGACCTCCTC  36180
CGCGAAGACC TCGCGGACTT CGCTGGAGGT GATCTGGCGC GAACGTGCGT TCTTGTGCAG  36240
GTACGGCAGC TTGGTGGCTG TCAAGTTCTA GACCTCCCAG ACTCGGCCGT CGACCGAGAA  36300
CCGGCCTCCG ACAATCGGAA CAAGCTCAGG CTTGACGTGC TGGCCGTCGA CCGTCAGCAG  36360
AGCAAAACCA CTCTGCCAGT TGGCTGTTGC ACCCTTGAGG TACTGAGCTA GCTTCATGTT  36420
CATCAGGTTG CCGACCTCCA TCGACCACAG CACCTTCTGG TTGCCGCCGT AGCCCAGCGT  36480
GTGTGGCTTG ATGCCCTGGC GGTGGGTGTG TCCGATGATC ACCGACGTGC CGAACCGCAT  36540
CATCGCGTTG TACGCGGTGT CAGCGGACTT CTGCGTCACC CGGACCCCAC CACGGTGGCC  36600
GTGGGTGGAG ATCCAGCCTG GAGCGATCTT GTAGAACTCA GGCAGCACGT CAACACCGAA  36660
CCCGTCGAAG TCCAGCAGGT TCTGGAACTG GAACGAGCTG ACGTACTCGA CCAGCGCCGG  36720
GGCGAACTGG TGCAGGTAGT CGACTGGCCG GCGGTCGTGG TTGCCCTCGT GGACACCAAC  36780
CGGGCCGTCG TAGACCTGGC GCAGCGGCTC CAGGAACCGC CGCTTGCACT GCTCGGAGTC  36840
GGGCTTGATC CGCTGAGCGA ACTCTTCCTT GGTGCCCTTG GTCCACCGAG ACGGGCTCGG  36900
GTAGTCCATC AGGTCACCGA TGTGGACGAC CTCGTCAGGC TGGGTGTCCC CGATGTAGCC  36960
```

-continued

```
GATGACCGCC TTCAACTGCT TGCGATCATC GAACGGAATC TGGGTGTCCG AGATGACGAC  37020
GATGCGCTTG CTCACTCAGC GACCTCGGTG AAGGGGCCCC GCATACGTTC CTCGTGGGAG  37080
CTGGCGTTGC CTCCTGACCA GCGTCGCTTG CCCACCTTGG TGTGGTGCAA CCCGTTGGGG  37140
TAGTAGATCC ACTTCACTCC TGTGGCGTTG GTGACGGTCT TCACATCGGC AGGAACGTCC  37200
AGCAAGGTGT CCCACTGGCG AGGCCCCTTG GGATACCGCT CGTCCTCGGG GAGCTGCATC  37260
TTCTCCAGAA CGCCTGCGTA ACCGGCGATG TCGACCACCG TGTCCTGGTG GTAGCCGTTC  37320
TCCATGAACC GGGCGATCTT CAGCAGGATC ATCATGACGG CCACGTCCTC CGGGGTGAAC  37380
TCGACGCCGC GCTTGTACGC GCCCCACAGG GTCGCGATGC GTTCGTGGTT CTCCTTGGCG  37440
TCCCCGTAGT CCTGGGCTCG CTGTCCGTTG ATGATCTCTT CGGCGGTGGT CAGAATGCTC  37500
ACAGTCCAGT CTCCGATGCG GTGTAGTAGT CGATCAGCTC ATCGAGCTGG TCCGGTTGAT  37560
AGCCGAGGAT CGGCTTGTGG GTGTCAGTGA CGACGACGGG AACCGACATC GCGTTGAGCA  37620
CCTTGGTGAC GTAGTCGTAC GCCTCCGAGT TGGCCGTGAC ATCGACTGCG TCGAAGTCGA  37680
TCCCGGCAGC CGTCAGCTTG TCTTTGACTC GCTCGCATGG CTTGCAGCCG GGACGGGTGT  37740
ACACCGTGAC CGGCGCGAAC AGCGTTCTCA CGTGAGCACC ATCCCAGTCG ATGTATCGGT  37800
CTCCATACAT CAGATCCTTT CCAGCAGAGC AGCTTTGCCC TGCGATGTGA CTAGTGAGTT  37860
GACATCCTCG CCTTCTGGCA TCGGGATGAT TCGGGCGTTC GGCAGCGTCT TCGCCACCGA  37920
CCGGGCGAAC TCCATACCGG CGTCGTCGCC GTCGGCCAGG ATGTTCACGT TGCGGTAGCC  37980
CAGGAACAGC TCTCGGAAGT ACGGCTTCCA CTTCTGGGCT CCGCTGAGCC CCACCGTCGG  38040
CAGCCCACAC AGCTCGGCGG TGATCGTGTC GAGTTCTCCC TCGCAGATCG CCATGTCCTT  38100
GCTGTATTTG GTCAGCGCGT AGGTGTTGTA GAGCCGGTCC TTCTCCCCTG GCATCGACAG  38160
GTACTTCGGT GTGCCACCGT CGATTCGGCG ATACCGGATC GCAGCTACCG TCCAGTGACG  38220
CCAGGGCGAC CACCGCATAT ACGGAATCGC CAGGCAGCCC CGGTACATCT CATGTCCAGG  38280
GAGTGGGTCG TCCACGAATC CCAGACCGAA CCGGCTTAGT TCCGCTCGGC CGGCCAGCCC  38340
GCGACTCGCC AAATACTCGT CGGCTGGGCT TCCGGGCAGG CTTTCTCTGT ACCGGGACGT  38400
TGCCTCCCAC AGATAGGTTC TCTGCGATTC GCTTAGCCTC TGCAAATGTC ACCTCTTCTT  38460
CGTGACGAAT GATCGAGATC ACGTCTCCAC GGACCCCGCA GGCCATGCAG TTGTAGCCCT  38520
GTAGGTCGTA ACTGACTGCG GCAGACGGCG TTTCGTCGCC GTGGAAGGGG CACAGGCACT  38580
TGTTCCACTC GTGGTGGTCA GGTGGTGGTT CCCAATCCGG GTGGTAGCGA AGAATCGCCC  38640
TCGCGATGGG CGAGTCGTTC ATTCGTCCTC GTCAAGCTCC TCGGGAGAGA GCCCTTCGAA  38700
GATCCCGTTC AGGACGGCGG CGAAGCCCTC GCCGGTCTCC GCTGCGTCGA GCATCTCTGC  38760
AATCGTCTTT GCCATGTTTC CTCCTGGTGG ATGTCAAGTT CGAGACAGCT TGTCAGCCTC  38820
GACTGGAGCG ATGCGCTCCC CGATGACTTG GACGGCCGGC GGGTTCAGCA GGTACTCGAT  38880
GGCCCGTTTG AAGAACTCGA TGCAGTCCCT CGCCCAGCCC AGCGTGTACT TGTTGCACAT  38940
CGTGCAGAGC AACCCTCGGA CGATGCCTGT CTTGTGATCG TGGTCGACCG ACAGGCGCTT  39000
CTTCTTACCG TTGGCTCGCT GGCAGATGTA GCACCGACCA CCTTGGAACT CGTAGATCTG  39060
CCAATACTCA TCGCCGGTGA TGCCGTAGGT GGCCAGGATC CGGGTCTCCC AGCTCGTAGA  39120
GCTGCGAGCC GTCCTGAACT CTCGGTGATG AGTAGCGCAT CGTGGCCCTG GATACTTGGC  39180
GTCTCGCGTG AGCGGGAGCC CCTGTGCGAC ACAGTCTTTG CAAGGCTTCC GCTTGTGCTT  39240
ACGGTTCTGC ACCCGGTACC CCGGAGACCT CTTCGCCGCC CTCGGCACGC GCGTCCTCCT  39300
```

-continued

```
CCCGGTTCTC CATCACCATG CAGAACCACG ACAGCAGCCC TGCCAGGGAG ATGTAGAAGG  39360
CCACCAGAAC TTGGCCGCTC ACTTCACCAT TCCTCGAACC CACCAGCGAG ACAGCGCCTT  39420
ACGCCCTTTG TCGAGCGGGG TCAGCTCGCG CTCATCGTCC TCACCGAAGT CGAACTCGAT  39480
GCTGGCGATC TCGTAGCCGA GGATCTTGAA CGACACGTTC ATAGGCGGTC TCCGAAGTTG  39540
ATGACGGGAA TGCCGGCCCT TTCGGCCTCT CGCATGCAGT GCCGGGTGCC GACTGAGTTG  39600
CCGAGGGGGA ACGCCAGACA GATGTCCGCA CCGGCCCTGA CCATCTCGAT GTTGCGGAGG  39660
ATGCCAGCCC GCTTGCCGTA GCGTTCCCAG TCGGCTCGGT GCAGCTCGGG GAGCACGTCC  39720
CATCCCTCCT GCTTCATCCC CCAGGCCCAG CGGTCTGCGA TGTCGTCAGC GCCGCGAGCG  39780
CCGCCGTGGA CGACCGTGAG ACCGGAGAAG GACCGGTGGT ACTCAGTGGC CAACGCTTCC  39840
CAGACCGTGG TGCGGTCCTT CCAGATCCGA GATCCGGTGA TCAGTACTCG CCGCATCAGA  39900
TCGCCTCCCA CTGCAGGCCG TCGTGCGACG TGACCAGCTC CGCTTCGTAG ACGCCGTAGC  39960
GGGTGGCCAG GAACTGGATC ATCTGCGCCT GCTTGTACCC GAAGGGACAT TCGTGGACGC  40020
CGCTGATCGG GTATCTGACT CCGTATTTCA CTTGATCCAC CGCTTCGCGA TTCGGTCGAC  40080
GTTCTCCTCG GAGACGTTGC GGGCGAGGCC GGTGAACTCC TGGCCGTGGA CCTTGGTCTC  40140
GATCACGCGA GGCTTGCGGG GATCCGGGCT CTCCGGGTCG ATCCGCTTGT GGGTCCAGAC  40200
GGTCGGCTTC GTCTTGATCA GAGCGCCCAG CACCTGCTGG CGCAGTGGGT TGGTCTTGCG  40260
GGGCATAGCG TTTGGAGTGG TCATCTGGAT CCTTTCCTCG GTGGCTGTCA AGTCGGTGTG  40320
CGTAGTGAAG CCCCCCCAGG CATGCGCGCC CCGCCTGGGG AGAGTTGATC AGCGCAGTTC  40380
GATGTCGGGC AGGATCGCCT GCGGCTTGAA GTTGACCTGG TAGAAGTCGG TCGAGACGTT  40440
TGCGCCATCG ACCTGCTCCA TGAAGTAGGA GACGTTGTCC GACAGGCCCA GGAAGTGCTT  40500
CTTGATCCCG TCCTTGGTCT TGCAGGTCAC GTCGAGCTTC TTCGACGCGG TGTCCGCGTT  40560
GATTGAGCAC CGGCCCTGGA TCTCGAGCAG GTACTTGTCC GTGATCCCGT TGAAGAACAC  40620
GATCCGGCGA TTGATCTCGA AGTTGTCAGC GGCCTTGCTG ACGTTCTCCG ATGCGACGTC  40680
GGCGTCGGAG GTACACGCGG AGAGGCCCAG GATCGCCGAT CCGGCGATGA GTGCGGTGGC  40740
GATGATCTTC TTCATGTTCG CTACTTTCTG TTTGGTGGAT GTCAAGTTAG TGACCGAAGT  40800
CGTTGATCTG CATAGTGTCT CCGACGAACT CCAAGGAAGC GAAGTCTTGT CCCGACGGGT  40860
CCGACTTCCC CCCTCGGTTC TTGACCGTGG AGACGTTGAG CATGTCCGGG CCGAACCCGT  40920
CCGATACTCG GTGGAGAGTG AGGATCATCT CAGGAACACG CCCGATCTGA CCTTTGATGC  40980
CCGACAACGG GATCGGCTTG TCGCCGTCGT TGTGCGGGCC GGTGACGTGG TGGAGCCCGA  41040
CGACGCATGA GCCTGTCTCA CGGCCCATCT CGTGTAGGTA GTCCATCAGC GACTCCAGAC  41100
CCGAGAACGG GTCGTCTCCC TCGCTTGAAT CGGTGCGGAC GTTGGTGATG TTGTCCACGA  41160
CGATCAACGC TGGGAAGTCC TCGTACAGCG CGTCATACGC GGCCAGAGCG TTCTCGATCT  41220
CGTCCAACGA CGGTGATGCC TTGTAGTTGA ACCGGATCGG GATCTCGTCT AGTGAGTCAG  41280
CTACCGCGTC CTCGATGTTC TGCTCGCGAA CAGCCCGCGT AGCTCGTTCG AGCGACCATC  41340
CGCTGAGGAT GGACACCGAA CGGGAGAGCT GGGTGAACGC ATCAGAGTCG GCCGAGAAGT  41400
ACAACGTCGG CACCTTCGAC TTGAGCGCGT AGGCGAGGAC GAACGCCGAC TTCCCGGTGC  41460
CGGGGCCGGC GCAGACCAGG ACTAGCTGGC CTCGTCGGAG ATGTGTACCT TTCTGGTCAA  41520
GCGCGGCCCA GACCGGGGGT AGCGGATCCC CCGCCGACCC TCGGATGTAG AGCGATTGTC  41580
TAGGTGTGTA CACCTTCCTC CTCGTGGATG TGATTGACCA GGTCATAGAT CTCGTCGCGA  41640
GAGACCAGCC GGCCCCAGGC GTCGATCCCC ACGTGGATCT GTCTCCGGTG GATGTGTCGG  41700
```

-continued

```
GACAGGATCA TCGGCGAATG CGTGTGCCCG TGGATCAGGA TCTTGCCATC GTCACGGAGC  41760
CTCCACTGGG TGTGTCGGTC CTCGCTGGTG TGGTCCCCGA CGTATGGGAA GTGGCTCAGC  41820
AGAACATCTG TGTGCCCGCC AGCGTCCCCG TACAGCGGCA CCCGGATACG AGCTGCCGTC  41880
GACACATGCT CGAACACCAT CCAGTACGCA CCAACCAGCT TGTGAGCATC GCGGTTCATC  41940
GGGTGGGGCC CATCGTGGTT GCCCAGGATC AGCCGTTTGC GGCCTGGCCG ATCCGAGATC  42000
CACCCGAGGG CATGTATCTG CCCCTTGGTG GAGCCAGAGG AGATGTCACC TAGGATCCAG  42060
ACCGTGTCGT CCTTGCCGAC GACCGAGTCC CACGCCTTCG CCAGGGTGGC GTCGTGCTCT  42120
TCGACATCAT CCGCCAGGTT GCGGATCTCC ATCAGCCGCT TGTGTCCGAT GTGTAGATCG  42180
GACGTGAACC AGGTGTTGCT CATGGCTTCC TTTCAGAACG GCGGGCCGTA CAGCTCGATC  42240
ACCAGCGCGT GCAGCTCCTC TGCCGCGTCG TCACGCTCGA ATCCGCAGCA GGAATCGTGC  42300
CGGTCGAGGA TTGCGACGAT CTGGTCGTAG AGGCTGGGCC TCACTTCACC TTCTTCGGAT  42360
CGATCAAGGC GTCGTGAATC GGCCGACCGG CGCGAGCCGC GTGCGTCTCG GCGTCCAAGG  42420
CTCGCTGCAT CTGGTTCATC AGCCGGGTGC CGCGCAGCTT GAGGATCTTC ATGGTCGCCC  42480
GACCCTTGTA TCCAGCGCGG TGCATCCGTA GGACGCAGGC TGTCTCGTGC GGGGCTATAG  42540
GTGACCTCAG CGACGGGTGG TTTGGATCCC AGTTCGTCAT GTCTTCCTCT CGGTGGCTGT  42600
CAAGTTGGTC ACAGACCGAA CTCTTCCTGG TACTGCGGGA TGAAGTGGCC GGCCGTTCAT  42660
GTTCGGCTCG ATACCTCTCG CGTCACGAAC TCCTGCCCGT TCCATCTCCG ACCGTCCTCG  42720
AACTCGATCA CGATCTCTCG TCCGGGATGA CGCACGGCCT CCGCTTGGGC AAACCTGCGT  42780
GCAGCCTCTG GGGTCGGGAA CGGAAACTTC TGCGAGGCGT ACAGCTCCTG GTGCCACTTC  42840
GGCTTGTCAG GAATCGGCCC CATTTCCACG TACGTGTAAC CCGCGTCGGG GTCGAGTTCG  42900
AGCGTTTTCT TGTATTCCTT CGTGCCTGCC TTAGAGGGAA GGTGAGTATC GGTGGCTGTC  42960
AAGGTGACCT CACTTAAAAA CAGGGCAGCT GTAATTCACA TCACAGAAGC CGCATTTGTC  43020
AGGTTCAGGC AGAGGCTCGA AGTCACCAGC CTGGATCCGA GCCTCGACCT CATGGAACCT  43080
CTCGGTGATC CGCTCCCGCG TCCAATCGGT CAGGTCGTAG GGCGCAGTGG GCTTCGCCTT  43140
GATGCCCTTC TTCCCCGCCA TGAAGTAGTC GCCCGTCTTC GGAGCCTCCA CGTCATAGGT  43200
CATCGCGACC GCGAGCGCGT ACACGCCGAG CTGGAAGTCG TCACCCGGCG AGTTGCCGGT  43260
CTTGTAGTCC CGGACTCGAA GCTCACCGTT GACCACGACG ACCGCGTCGA TGAACCCTCG  43320
GACGCGGATG CCGTCCAGCT CGATGTTGAA CGGAAGCTCG ATGGCCGGCT TGGGCTGTTC  43380
ACACTCCTTG CAGTTGGTGT CTTTCCACGC CTCCGTAGAG CAGATCCCTC GCCCAGGGGT  43440
AGTCCAGATC TGCTGGCCCT TGTCCTTCCG CCACGCGATG AACTTCTCTA CCTGCTCCAG  43500
TCCAAGGTGG AACCGGCGCT CGATGTCACG CTCACCGTTG TACGGCCCGG ACCAAAACCA  43560
CCACTCGAAG TTCGGGGTTT CGTCGCACAG TGCTCCGATG TCCTTGGCGT ACTCCTCGCG  43620
GAAGATCTCT TGTGCCCGTT CGAGGCTCAT CTCGCGGCCC TCGGCCAGAG CCTTCTCGTA  43680
GACCTCAGCG ACGGTGTGAA ACGCGGTGCC CTGCGGCAAC CACGCCGCAG GACGAGCCCA  43740
TACCTTGTCG ATGCGAGCCA GCTTGTACGC CTGCGGGCAA CGTGTGTATT GGTTCAACTG  43800
GCTGACGCTT CGCAGCGGCA GCAATGTCTT GGTGTCTGTC ACGCAGCGGC CATCCTTCCC  43860
TTGCCTATCG TCTCGTTCAG CGCCCCGTCG ACAGCGACAC TGAGCAGTTT TGCGACCTCC  43920
GACATGTCAA TCGGATCCTT GGGGAATTGG TCAGCCTGAG TCATCCTGAG CACCATCCAC  43980
TCGGTGCCCT TGTCGCAGTG GATCATGGTC GGATCAAAGC GAGTTCCCCG TGCTACGTAC  44040
```

-continued

TCGACTTTGT TCGCGGAAAG AATCAAATTC GACACAGGCC GATAAAGTCG TGAGGTGTCT 44100

TTTACACGAG GACTGCGGTA GACGAGCAGA ACTGAGACTG GGTCTTCGTC CAGTTGGCCC 44160

TTCCACCACG CCTCACACCT CTGCGCGAAC AGCCACCCTG GATGATCGGC GATGACTTGC 44220

GGTGAGGTGT GGACGAGGTT GTCTGCGAAC AGCTTTGCGA GCCGAGTGAG GGGCACGGGG 44280

TTTCCTTTCG TTGCGCGGCC TGGGTTGGCT CACACAACCG GTCGTGACTT TTAGGGCTCC 44340

GAGAGAAGCT CCTCGATGTC GTCTGGCCAC GACCAGAGGA GTTCACCCTC GGCGGTGAGG 44400

TTGGTGTGCT CGTTCACCCG GATCAGGAGA TCGTCATCCT CGATGCCTCG GGGGACGTAC 44460

CTGAACCCGC CGCCGGCCAT ACCTTCGTAG GGCTCGATGG ATGGGTCGAA CTCGAGCACT 44520

AAGTCGTCGT CGCGGAGCAT CTTCCACCAC GACAATAGGC GCTTCTTCTT GTCTTCGGAC 44580

ATCGTGCGGA AGCTACCCAC TCGCATGTAC TCGCCGTGAT CCCGGAGCCT CTGAAAAGCC 44640

TTCGACTTAT CGTGAGGTTT CCGCGTGTCC CACGGCCAGT TCTGCTGGAC GATCTGCCTG 44700

GTGGTCAACC GTCCTCCGTA GGTCTTCTTG TGCCACGACA CCGCTTGTCG AGTCACGCCA 44760

TACAGCTCTG CGATTTCGGT CTGATTAAAC CCCTTCCTGC GAAGATCTTC GATCTCGCTG 44820

AGAGTGAGTG GTATTCGGCT AGGGGCCGGA ACCACTGCTT TGTGTTGGAT TTTGCCGCTC 44880

ATGTTTCCCT CCATGAGAAA GGTGCGTGCG TCTCCGCCGA TTACGGAGAC ATGTTGGTGC 44940

CTGTCAAGGA TACCCCTAAT TTAGTTGCGT CTGCGGAACC ATATTCAGTT GTGTTCCCCG 45000

ACGCCGTGGC CGTCTCCCAC TGGGCGTGGG ATCGACTGGC GTTACGCGGT CGTAAATGTA 45060

GCGGCCTGCC CCACTCGGTA GCAAACCTTG TGACAGGTAT CACTTAGGTC GCCTTCTGTT 45120

ACACGTTGAC CTCGGGTTTC ATCGTCACGA CTCTCCTTTC TTAGACAGCC TCAAGATCGT 45180

TACACCGGCT TGCGAAGATG TACCTTCGCC TTGAATCCGG CCCTTGCCAG CTCGAACTCG 45240

ACCACCTGGC GGGCGGTCTC CTTCAGGTCG GACTTCGCCG ACAGCGGCCC GACGAACCCG 45300

TAGCTCTTGA TGTACTCCTC GAGGTCGATG TCGACGTACA GCGTGACAGG GACCACCGAC 45360

AAGTCACACC TCCAATTCGT GGGGCTTGAT CTCGTTGGTC ACGTCGTAGT CGTTCAGCAG 45420

CGACTGGAAG TCGGAGTCTG TCAAGTCGTC CAACTCATCC TGCTCGAACG GCGCGGGCTC 45480

GTCATGCCAC GTCTTCCACT GGTCGTGGTC GGCGCGGAAC CACTTCCGCA GATCCTTGAT 45540

GGCCTCGTCC TCGGTGGCGA AGACGTAGGT CTCGAGCACG TCCTCGTACT CGACGGTCAG 45600

CGACCAGACG GTGATCTTCA CTCCCCGTTC ACCTCCGCTT TGTAGTTCAT CTCGGCGGTC 45660

TCCTCCTAGT TGGGTAGCAG TCGGTTGTAC TCGTCGTGGC TGATCTCGCC AACGATGAAC 45720

TGGCGCATCA GATTTGCGAC CGAAGCCGCG TCCATCCCTT CGGGAATGGG CTTGGCGTGG 45780

CCGAACTGCC AGTCTCGTGA GCGCCAGCGG AACCAGAGTT GGACCTTGTC CAGTGAGGTC 45840

AGGTGCAGGC ACTGAAACGT CATGCCTCCG AACGGGAACT CCATCACACC TCCTGTTTGA 45900

CCTTGACGGT GTGGCCTGTC ATTACTTCGT GGATTCGGAT GCTGGTGCCG AACGTCTTTC 45960

GCGTCTCGGC CTTGAACTCG GTGGAGCACC CCGAGCACTT CGCTTTGAAT CGCACTAGCA 46020

GTACCAACGC TTTCTGCAGA ATCGGGACTT GCCGCCGTCC CGGTTGTCGT TGTCCCGGCG 46080

GGCTTCGCCC TTCGGTGATT CGTCACATGA CGGAAGCTCG CCATGCTTGA TGTGCCATGC 46140

GTCGTCGGCG ACTTTTCCGC CGTGCTCGGC GATGTGCGCT GCGCTCCGGT ACTCACAGAG 46200

CGGGGAAGCC GATGCCTCGG CGATGATCCC AGGCAGGTTG CCTAGAACCA CCGCCAAGCA 46260

CATCAGCAGA ACGACGTGCC ACGCCTTCAT CAGCCCGCCA GCGCGTGGTT CATCGCCGCG 46320

TTGCGGCCGT CGCGCTGACC GTGGGCATAG CCGCTGAGGT CGTACCGGGT CCGAGGCTTG 46380

ACGTTCTTGG TGCGAGGATG CGCCTGGCGC AGAGCCAGCG CAGCTCGTTC CTTGTCGCCT 46440

-continued

```
CGGTAGAGCA CCAACGCTCC CCCGCCGGCC GATTCCACGG CCTTGTTCTC CTCGGCGGTC  46500
AGGCGTTCCT TGACGGCCTG GGCGAAGCCT GCGATCCACG ACCGGCGGTA GCTCTTGAGC  46560
TGGCCAGCGG TGCTCTTCGG CTTGTACTCC CCGGTGTTGT AGTCGTACTT GTACCGAGGC  46620
TCGAAAGCCT GCTCCGGGCG GACATTCTCA ACCAGGCGCA TCATCTGCGG CTGCATGATC  46680
GACCAGAGGA ATTGGAGCCT CTCGATGTGG CGGGGCACGC CGTAGACGTA GATCCGCTGA  46740
CCGCCCGTGA GGCTGGCGTA CACCGTCTTG CAGTGCAGGG CCTGAGCCAT GCCGTGCAGC  46800
AACAACGCTT GTGCGGCAAC GTACTTGCCG GTGACGTAGG TGACCCACTG GATGGCGTCG  46860
GGCAGGTCGG TGGTGTCCAA CCCTTGCTTG CTCGCCTCGA CCTGGGCCAT CTCCAGCCCG  46920
TACTTGGCCA TCAGCTCGAA CGCTTTCGCC TGGAACACAG CCTCTTCCGG CGTACCGGCC  46980
ACGTCTTCGG CCTGGCGCAG CAGCTTGGCG ACCTTGTCCT GCATCTTCTT CGTCTTGCCG  47040
TCGATCATGG TCAGTACTCC TTCTTCCAGT TGTTCCGGTT GCCCTTGCCG GGGCGCTTCA  47100
TCTCTCGCTT GCGGTTACGG TGCGGCTGCG CCGCGTTGGA GAGACGCAAC TCGAGCCGTG  47160
CCTTGAGCTG GTCGCTCATC TTCTTCACCT CTTCTGGTTC AGCGGATCTG GTCGACGTGG  47220
ATGCAGCCGA CGCGGTCTGG CCCGAACTCG GGAGCGAAGC CCAAGACTTC GTCCTCCTCG  47280
CATGGGAACG CTCGCTGGTC GAACGTGATT GGGTCGGCCG AAGCCTCGTA TGGATCGGCC  47340
AAGGCCATCG CTCCGACCGC TGTAGCGAAT GCAACGACGA CGGTGATCAG GTGCTTCTTC  47400
ACTCTTCTTC CCTCCACTTT TGGTCTGCGA GAAGCCTTCT GGCGATCTCG ATAGGTTCGA  47460
TCTCAGGAGT CACTCATCGC CCTCCAAGAT CTTCAGGTTG GCCAGCAGTG CATTGGCCAC  47520
AGCTCCGATG TGGCCACCGC CCTTACCTCC ACGGCGGGAG TACTCGCGGT TCGCGGCCTG  47580
CATGAAGTGG AACCTCGGTG AGCCGTCCTC GTGAACCCAC GAGGCTTTCT CGGCGGGCAG  47640
AGCCCGGTTC ATCTCCACCG ACATCGTGAC GATGATGTGG TCCCTCTGGA GCCGAGCCTC  47700
GGTCTCGGCG TAGTGGGCAG CTTGGATTAC TGCGCCTCGT GTGGTCATGT CTTCTCCTTC  47760
GGTAGATGTC AAGCTGTCGT CACCACTCTT CGACCGGTAT CGGTTTGTCA CAGCCAGCAA  47820
GGATCGCGGC GTTGCTGCGG TGATGCCCGT CCCACAGCGT CTTTCGGTCC CTCGAAACCT  47880
CGAGGGGTTC GAACGGCCAC TCGTTCGATG AGTTGAGGAT GTCCACGACT TCGTGGACCT  47940
TGGCCCAGAA CTTGCCGGTC ACGCCTCCCT GGTAGTTGTA GCGGGGCGTG GTCTGGTAGA  48000
ACTCTTCGAG CACTGGTCCG CTGTCGGCGA CGGTGCAGTC GACACCAGCG CAGGACATGC  48060
AGTCGCTGGC GCGGAGCTGG GCAACTTCAT CGGTGGTCAT GAACGCCGTG GTCACATCGA  48120
GCCTTTCAGG TGTATGTCAA GCGGCGCGGA CGCCGGAATC GGAGAGGTAG ACGCGGTCAG  48180
CTCCCAGGAA CGGAGCCTGT GTGTTGGCGT GGACGAACGT GTCGTTCTCG TAGGGGTTGT  48240
AGGCGATCTT CGATCCCACG AAGTCTTGCG GGAGAAGCGA GATCAGCTCG CCTACGATGC  48300
CAGCGTGGAC CACCTTGCGG CGCTCGCGCC GTACCTTGTC GCGGCCGGCC GGCCGAACCA  48360
CACCCTTGGC GTGGGCCAGC AGGACGTGGC CGCTGCGGTG GATGACTCGA CCCTTGAAGT  48420
CTCCCTCCAA GGCTTGCACC GAGTACCACG GCTTGCCCTC GCGGTGCGTG CGGTGCAGGT  48480
TCTTGTAGAC GAAGACTCGG ATCGGCTTGG GAGTCATGAG ACCTCCAGTG TGCGAACGGC  48540
CTTGTAGGCA CTGATGAGTG ACGCCCCCGA CAGCTCGTTA CCGTGCAGGT GATACCTGTA  48600
TTTCAGATAC ACGGCTTGGT CGACCGGCTT GTACTCGACC GAAGTGACCT CGACAACCAT  48660
CCCGTCGATG ATCGCGAAGT CTCCAGCGCG GAGATGGGTG GGGAATTTGA TCTCGGTGTT  48720
GACTACGGTC ACAGCTTCGA AACCTCCCAG GTACCAACGA ACTTGCCGTT GCGCTTGATG  48780
```

-continued

```
TATCCGCTCT CACCGGGCTC GTACCAATCG ACCTCGAACC CGTAGCGGGC GGCGCAAGCC  48840
TCGAGGTGGT CGAGCAGGAC GCGGCGACCG GACGCGGTAG CTTCTCCGGT CAGCCCGCTG  48900
TCGTTCTTGC GGACGATGAG CTTGAACACT TGGTGCCTAC CCTTCTGCGA TGTCTCGGGA  48960
GATCTCGGCG AAGACTTTCT TTGCCCACGC CACGCCGTCC CAGGTGATGT CGAACAGTGC  49020
CTCGTAGAAC TGGTCTCGCA AGGCTTCGTT GCCGTCGGCC AGCGTTGTGA CGAGCCGGTC  49080
GATGCGGTCC TCGTGGAACT TGTAGACCGA GTGGTTGTAC GGCTCAGCCA TATTGGCGTT  49140
GGCTCGTTTC ACGTTCTCAA CCACGATGGC TTCGAATAGG TGGTTAACCA GCTCCTCGGT  49200
CATGTTCTAT CTCTCCTCAG TAGTCGCTGT GCTGGGTCTC GAAGCCTTCG AGGTCACCGA  49260
CCTCGTCGTC GTACGCGCTC GGGTTGCCGC GCCAGTCGTC GCGGAGCCTT TGACCGCTGG  49320
CGTTGTAGCA GGCACCACAG TTCGGGCAGT CCACATCGCT CTGGCCGTAG TAGCGGCAAA  49380
CCTCGCCGCC GCAGCGTTGG CAGTCCCACG CGCTGTAACC AGGGATCAGG AAACCTTGGT  49440
CGTCGGTCTG ATCAGGGATG CGTCGGAAGT TCTTGGCAGG CATAGCTACT CCTCATAGAA  49500
ACTCGTGGTT GATGGCTCGG TGGGCAGCCT CGCGGAAGGT CAGCCCGTCG TCGTACGCGT  49560
CCCGGTACGT CCAGTCCGCG ATGTCTTGGT AACCAAGACC AAAGGTCTCG GTCATGTAGC  49620
CGTCCAGCGC GGCCATCCAG GTCTCGAAGC TCATGTCTTC CCTCACTTCT TTGTGGTCGA  49680
GAACAGCACG TTCCTGCGGC CGTTGACGCA CAGACCGCAA CGGGCACAAG CCGATCCCTT  49740
GTCGTTGATC AGGTCGATGG CTTTGTTGTT CTCCGGGCAG CGCACCGCCG TCGGAAACTC  49800
GGCCTTGCCT TTGGCGAACG TGGTGTCGAC GTAGGCGATG TTGATGCCCT TGTCTTCCAA  49860
GAAGCGCGCC ACGTCGATGT TGTCCGGGTC TGCGCTGAAG TACAGCGCCA GGTTGTCGAG  49920
CCTCTGCGAG TGCAGGTAGA CAGCCGCCGT CTGAACCCTT GTGTAGGCCC AGAACTGGAC  49980
ATCCGGGTTG TCGCGGATGA CTCGACCCCA AGCGGCCACA TAGGTGGGGC TGAAGAAGTC  50040
TCCATCCCAG TGGATGCGGA ACAGCTTCGG AGCCTTGCGA CGGTCGCAAT CCTTGACGAA  50100
CTCGGCGACC ATCTCGGACA GCAGCGTCAC GGTGTCTGTC AAGTCAGCGT CACGCAACAG  50160
TTCCCAGTTG TGCAGCAGGA CCGAGCTGAC AGCCTTGCGA ACTTTCTCCA GCTTGCCGGC  50220
GTAGCACACC TTGGCACAGA AGGCCGTCGC GTCCGGGCAG GAGAAGCCTT GACCGGAGGG  50280
CAGGCCGATG CTGTTGGCGA TACCTACGGT GGCGTTGCCG CCCTTGGTGA CGTGGACGTA  50340
GTTGGTGACC TTGCGGTCGT TCGAACGCTT CAGCTTGGCC ATACCTAGCC TTCCTTCGGT  50400
GGCTGTCAAG TTGTTGGATA CAAAGCGCCC CGAGAGGGAG TCGAACCCTC ACACCGCGAA  50460
CCGTCGCGGG GCCACCGTGC CTAGTCGATA GAGGTCACTC GACTCTCGTG GACGTAGACC  50520
ACGGTGTTGC CTACGTTCAC CGCGTAGTAC AGGCCATCGG CACCTCGTAG CTTGTGCCGA  50580
ACCGTGCCCG ACGTGGCCGT CATGTCTTCG CCCCAGTCGG CGTTAGGTGC CCAGGTGACT  50640
CGCATGGTGA TCCCTTCAGT AGTCGGTGGC TGTCAAGTCA GCGGATACGG ACGTACCCGT  50700
TGCCTCGAGC GACGTAGATC TTGCCGTCGA TGTAAACGCG CTGCTGCTGG TTCATAATCC  50760
TATTCCTTTC GGTGGCTGTC AAGTCTCAGG CCCAGCGACG AGTCGTCGGC CGGGGGCGGC  50820
GCACCTTGGG CGCGTTGGCT CGCGGTGCCT TACGGATGGC GGTGCCTACC GTGATCTCTT  50880
CCAACTGGCG TTCAGCCAGG CCGACAGGCC GGGCGTCACC GGGCAGTTCG ATCTTGTAAT  50940
CGAAGTCAGT CCACCCCTTC AGACCCTTCT CCAGCTCGCG ATCCAACAGA CGCGGAGCCG  51000
ACAGCTCAGG CGCAACAAAC GGTGTCTTGA CGCTCTCGCG GGCAGTAACC CGAACCTCAC  51060
GGTGCTCAGC GAAGACTGGC ATAGTTCACC CCTTTGGTGG ATGTCAAGCC TGAGCACCAA  51120
AGCTCAGGCG TAGTGGGTAG TCGGGAATCG AACCCGATAG CTTCATAGCC ACGTTCTACG  51180
```

-continued

```
GCTCAGCCAT AGCTCAGCGA TCATTCCATC GCGCCAAGAG CTACCCTCCC GAATGCCGAA  51240

CCAAAGCTCA GCATTCGTAA GTGTGTATTC TCCCCGTGGC TCAGACAGTA TCTATCAGAA  51300

CCTAACCACA GGTCTACATT TAGTTATCCG CAGTGCTCGC ACTTTAACGG CATCGAGCTT  51360

CCGCCGACCC TCAGTCCTCT GGCAGCGAAC TAAAGGTTTG AGTCGGGCTG CGGCCCTTCT  51420

CGGTCTTGCG TGATTCTCAC TCTACCGGAT GTTTCGGTGG CTGTCAAGCG GGCCGTTTTG  51480

GTGTTGCAAC GATGCCCTCG TTTAGCGCCG CTGGCGTAAT GCGCTACCCG CCTGATCTCA  51540

CCGGTCCAAG TTGGTGATGC TTGCAGCTTA CCCGATAACC GGGTGGCTGT CAAACCGGAG  51600

AATCTTGCCG CCGGATTTTC ACCGGCACCG GCACGATCCT CTCGGATCCG CCTACCGCCT  51660

TGCTGCTGCG GTGACACAAG AATGCACTAC TGGCCGGGTG GCTGTCAAGC CCTAATCGCA  51720

AATTGGTGCC CTAGCTGCAG ATATGGCGCG TTCTCGGTGG CTGTAAAGGG CACTACGTGC  51780

CGCTATCCGC TGGTCACGCT GGACAGTCCC GGCAGCCCGT GCCGCGCATA GGCTGCTCAC  51840

TACGTGCCCG GTATCGGCGT TGTCGTGCCG CTGTCGTGGT CGTCGCCCCG TCGCTGTCGC  51900

TGGTCTCGGT GGCATCGCTT GACAGTCGCC CCGCTATCCC CCGTTGCCGC TGGTCAGACG  51960

CTAATCCGCT TATTTCGCAT AGGCTGCTCA CTATCGCATC GGTATGCGTA TGCGCTGGTC  52020

ACATATGCGT GTGGTGGTGG TGTGGTGTGC GTGTGTTTGC GCTGGTCAGC CGTGTGCGTA  52080

CCGTATCCGC ACACTGTGCT TGTGCGTTTG CTGTGTGTCG AGGCCGGCTC TCGCATCGTC  52140

GCATGTCAGC GCGGGTATGG GCGTGTATCG CACGCTTTGC TAGCCGCGTG CCGCGGCGCT  52200

CTCGCATCGC ATCGAGTGTT TGCTGTGTCT CTCATCGTCG CAGGTCAGAA GGGGTAGGGG  52260

GGTTCCCCCT AGGGGTCGGT CCTTGACCGG TCGGTTA                           52297
```

MYCOBACTERIAL SPECIES-SPECIFIC REPORTER MYCOBACTERIOPHAGES

CROSS-REFERENCE TO RELATED APPLICATIONS

This Application is a continuation of application Ser. No. 08/430,314, filed Apr. 28, 1995, now abandoned, which is a continuation of application Ser. No. 08/057,531, now abandoned, filed Apr. 29, 1993, which is a continuation-in-part of application Ser. No. 07/833,431, filed Feb. 7, 1992, now abandoned.

Statement of Government Interest

This invention was made with government support under NIH Grant Nos. A127235, A126170, A128927 and A123545, and with government support under the Special Program for Tropical Diseases and Program for Vaccine Development of the World Health Organization. As such, the government has certain rights in the invention.

FIELD OF THE INVENTION

This invention relates to mycobacterial species-specific reporter mycobacteriophages (reporter mycobacteriophages), methods of making such reporter mycobacteriophages, and the use of such reporter mycobacteriophages, for example, to rapidly diagnose mycobacterial infection and to assess drug susceptibilities of mycobacterial strains in clinical samples. Specifically, this invention relates to the use of mycobacterial species-specific luciferase reporter mycobacteriophages to diagnose tuberculosis and to assess the drug susceptibilities of the various strains of *Mycobacterium tuberculosis* (*M. tuberculosis*).

To produce the mycobacterial species-specific reporter mycobacteriophages of the invention, transcriptional promoters and reporter genes are introduced into the genomes of mycobacterial species-specific mycobacteriophages. These reporter genes may be the genes for luciferase or the β-galactosidase gene, and provide the DNA which encodes the production of a gene product.

The reporter mycobacteriophages may be used for diagnosing mycobacterial infections by incubating same with samples which may contain the specific mycobacteria of interest. If the mycobacteria of interest is present, then the reporter mycobacteriophages introduce the recombinant nucleic acids which encode expression of the gene product into the mycobacteria of interest, and the mycobacteria then express the gene product. The expressed reporter gene product may be detected by a suitable assay, for example, through the detection of photons or the conversion of an easily assayable chemical reaction. The presence of such gene product indicates that the sample contains the mycobacteria of interest, and hence the mycobacterial species-specific reporter mycobacteriophages may be used to detect and thereby diagnose the specific mycobacterial infection.

Since signals may not be generated by cells which are not metabolically active in the presence of antibiotics, the mycobacteria species-specific reporter mycobacteriophages of this invention may be used to assess the drug susceptibilities of various strains of mycobacteria. If antibiotic drugs are added to the sample containing the reporter mycobacteriophages and the gene product is detected, the mycobacteria is metabolically active and hence resistant to the antibiotic drug.

BACKGROUND OF THE INVENTION

In 1990, there was a 10% increase in the incidence of tuberculosis in the United States. In addition, there has been an increase in the appearance of clinical isolates of tuberculosis that are resistant to antibiotics used to treat the disease. This problem is exacerbated by the length of time that is currently needed both to diagnose tuberculosis, and to determine the drug susceptibilities of various strains of *M. tuberculosis*. As a result, patients with *M. tuberculosis* may remain infectious for long periods of time without being treated, or may be treated with a drug to which the bacterial strain is resistant. Therefore, a need has arisen in the field for a method of diagnosis of *M. tuberculosis* (and other mycobacterial infections) which is rapid, sensitive and specific, which method is also capable of assessing the drug susceptibilities of the various strains of *M. tuberculosis* and other mycobacterial strains. It is critical that a mycobacterial strain be assessed for drug resistance rapidly because a patient infected with a strain of *M. tuberculosis* or another mycobacteria must be treated immediately with the particular antibiotic drug(s) to which the strain is not resistant, and not with antibiotic drug(s) to which the strain is resistant, or the patient may die.

Currently, the most rapid test available for the diagnosis of *M. tuberculosis* is the staining of sputum samples for acid-fast bacilli, which is a tedious procedure, and which procedure has low sensitivity. Alternative methods for diagnosis require cultivation of the bacilli for approximately two to six weeks followed by classification of the cultured organism. Typical diagnostic tools include biochemical tests, analysis of mycolic acids and serotyping. All of these tests are time-consuming. More recently, the use of oligonucleotide probes and Polymerase Chain Reaction have been suggested for the identification of *M. tuberculosis* species. Although these methods may be useful approaches, their uses in a clinical setting have not yet been determined. Further, these methods do not distinguish between live and dead organisms, and are therefore of limited use in the determination of drug sensitivities of clinical isolates.

In addition, *Mycobacterium avium* (*M. avium*) is a mycobacteria which is often found in immunosuppressed patients. This mycobacteria is typically disseminated throughout the bodies of immunosuppressed patients, such as AIDS patients, and causes *M. avium* infection. Because this mycobacteria often causes death in immunosuppressed patients, it is necessary to be able to diagnose and assess the drug susceptibilities of the various strains of *M. avium*.

It is therefore an object of this invention to construct broad mycobacterial host range and mycobacterial species-specific reporter mycobacteriophages.

It is another object of this invention to provide mycobacterial species-specific reporter mycobacteriophages which may be used to rapidly diagnose mycobacterial infections.

It is still another object of this invention to provide mycobacterial species-specific reporter mycobacteriophages which may be used to rapidly assess the drug susceptibilities of different strains of mycobacteria in clinical samples.

It is yet another object of this invention to provide mycobacterial species-specific reporter mycobacteriophages wherein the reporter genes are luciferase genes, which mycobacterial species-specific reporter mycobacteriophages may be used to rapidly diagnose mycobacterial infections and to rapidly assess the drug susceptibilities of various strains of mycobacteria.

It is a further object of this invention to provide mycobacterial species-specific luciferase gene reporter mycobacteriophages which may be used to rapidly diagnose tuberculosis and assess the drug susceptibilities of the various strains of *M. tuberculosis*.

SUMMARY OF THE INVENTION

This invention relates to broad host range and mycobacterial species-specific reporter mycobacteriophages, (reporter mycobacteriophages), methods of producing such reporter mycobacteriophages, and the use of such reporter mycobacteriophages to rapidly diagnose mycobacterial infection, such as *M. tuberculosis*, and to distinguish which strains of the mycobacteria are drug-resistant.

To produce these reporter mycobacteriophages, reporter genes and transcriptional promoters are introduced into the genomes of mycobacterial species-specific mycobacteriophages. The promoter and reporter gene-containing mycobacteriophages (reporter mycobacteriophages) are then incubated with a clinical sample which may contain the mycobacteria of interest, such as *M. tuberculosis*. The reporter mycobacteriophages are specific for the mycobacteria which is sought to be detected. The reporter mycobacteriophages efficiently introduce the recombinant nucleic acids which encode the expression of the reporter gene's gene product into the mycobacteria of interest, and the mycobacteria then express the gene product. A substrate or other means capable of allowing for the detection of the gene product is then added to the sample. If the gene product or the signal generated by the gene product is detected, the presence of the infectious mycobacteria is known, thereby diagnosing the disease.

To assess drug susceptibility of mycobacteria, drugs such as antibiotics may be added to a sample containing the reporter mycobacteriophages of this invention. If the mycobacteria are susceptible to a drug after exposure to the drug, the mycobacteria will be killed. However, drug-resistant mycobacteria will continue to be metabolically active in the presence of the drug, and will continue to express the detectable gene product of the reporter genes. Preferably, the reporter mycobacteriophages of the invention are temperate, and have increased sensitivity for use in drug screening.

The preferred reporter genes of the present invention are the Firefly luciferase lux gene (FFlux), the luciferase lux genes of *Vibrio fischeri*, the luciferase lux genes of *Xenorhabdus luminescens* and the *E. coli* β-galactosidase gene (lacZ). Some preferred promoters of the present invention are hsp60 and gene 71-70-69 promoters, and the preferred mycobacteriophages are L5, TM4 and DS6A. These reporter mycobacteriophages are preferably used for the rapid diagnosis of tuberculosis and *M. avium* infection, and the accurate assessment of drug susceptibilities of the various strains of *M. tuberculosis* and *M. avium.*

BRIEF DESCRIPTION OF THE DRAWING

The above brief description, as well as further objects and features of the present invention, will be more fully understood by reference to the following detailed description of the presently preferred, albeit illustrative, embodiment of the present invention when taken in conjunction with the accompanying drawing wherein:

FIG. 4 represents the effect of various antibiotic drugs on the metabolic activity of control mycobacteria and drug resistant mycobacteria in the presence of reporter mycobacteriophages which contain luciferase reporter genes;

FIG. 21 represents a map of expected DNA fragments resulting from a pair of homologous recombination events in common flanking sequences when FFlux is inserted into the L5 genome in a corresponding location to that in pGS24;

FIG. 28B represents the light produced (RLU);

FIG. 30 represents a list of L5 reporter mycobacteriophages of the invention which have been developed.

DETAILED DESCRIPTION OF THE INVENTION

Figure 1:
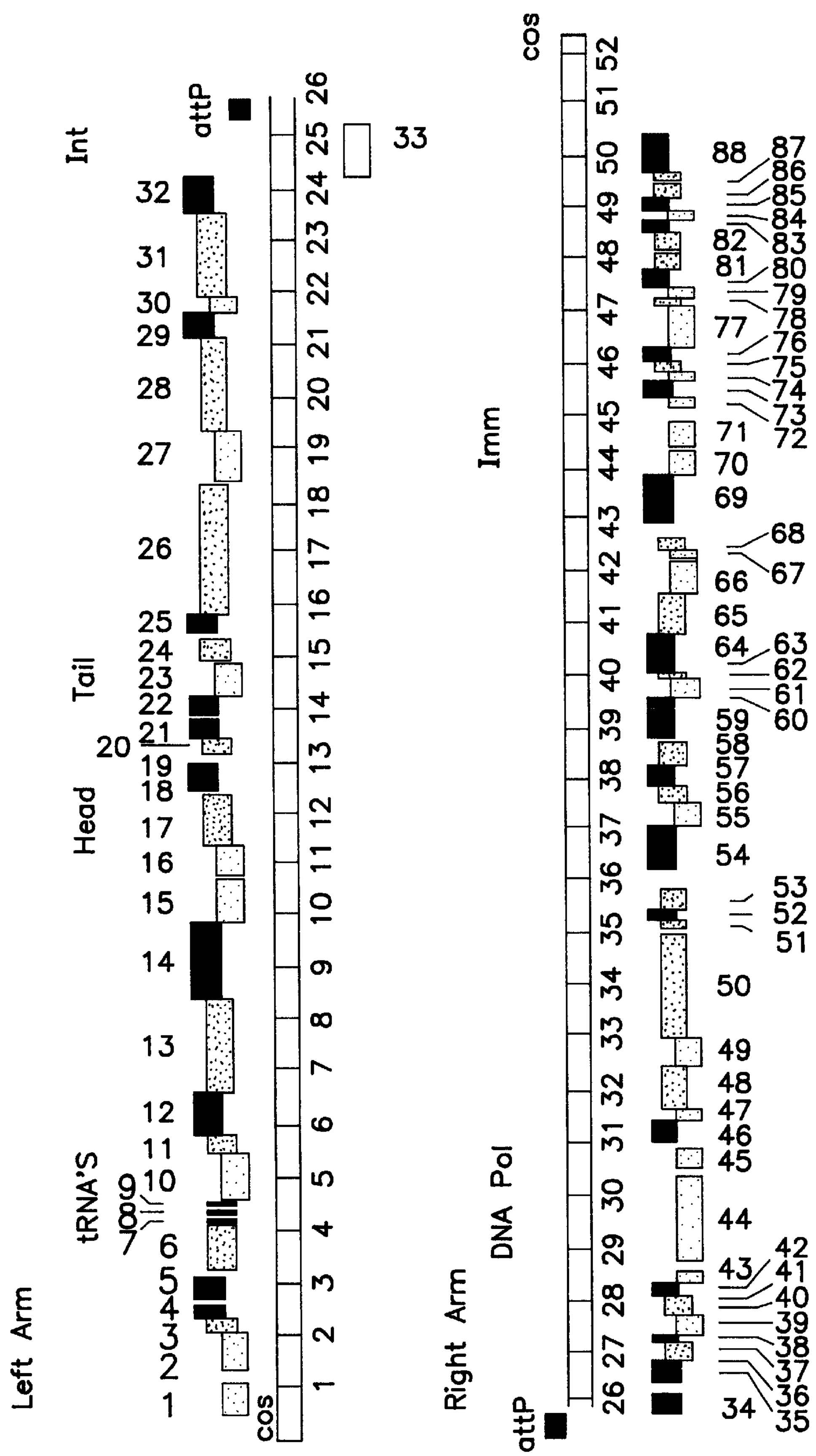
FIG. 1 represents the genome organization of mycobacteriophage L5.

This invention is directed to mycobacterial species-specific reporter mycobacteriophages, (reporter mycobacteriophages), methods of producing such reporter mycobacteriophages and the use of such reporter mycobacteriophages for the rapid diagnosis of mycobacterial infections and the accurate assessment of mycobacterial drug susceptibilities.

In order to produce such reporter mycobacteriophages, mycobacterial species-specific mycobacteriophage genomes are modified by introducing therein transcriptional promoters and reporter genes whose gene product can be sensitively detected. The reporter mycobacteriophages may then be incubated with clinical samples suspected of containing the mycobacteria of interest, either directly of after culture, and the samples tested for the presence of the reporter gene product, thereby diagnosing mycobacterial infection.

The method of this invention allows for rapid diagnosis because only the amount of time necessary for the reporter mycobacteriophages to infect their host cells and the amount of time necessary for the host cells to synthesize the reporter gene product are required to allow for diagnosis. Typically, the amount of time required for the reporter mycobacteriophages to infect their host cells and for the host cells to synthesize the reporter gene product is between ten minutes and sixteen hours.

The assessment of drug susceptibilities with the reporter mycobacteriophages of this invention is accurate because the reporter mycobacteriophages only allow for the detection of metabolically active mycobacterial organisms, the presence of which metabolic activity indicates that a drug has not killed the mycobacteria and that the mycobacteria is resistant to the drug.

The L5 reporter mycobacteriophages of this invention are temperate, i.e., they are able to exist in bacterial cells as prophages integrated into mycobacterial genomes without causing cell lysis. Because the L5 reporter mycobacteriophages do not cause cell lysis, they replicate as part of the bacterial genomes in bacterial cells. The integrated reporter phages express high levels of luciferase activity, since the luciferase reporter phages can be stably maintained. This growth causes amplification of photon signal. Because temperate phages possess the ability to site specifically integrate into mycobacterial genomes, they are replicated as part of the mycobacterial chromosome. In addition, the integrated luciferase reporter phages confer to the infected cell the ability to produce amounts of luciferase activity comparable to plasmid transformed cells and 100 to 1000 times more luciferase activity than phage-infected cells. The luciferase lysogens can be readily used to screen for drug activity by simply observing the inhibition of growth measured by proportional luciferase activity. Hence, the use of temperate L5 reporter mycobacteriophages results in a more sensitive assay for drug screening, as compared to the use of lytic reporter mycobacteriophages.

Mycobacteriophage L5, a temperate virus with a broad host-range among mycobacteria, is the most thoroughly characterized of the mycobacteriophages. L5 particles are morphologically similar to the family of phages that includes phage λ and contain a linear dsDNA genome with cohesive ends. The inventors have determined the DNA sequence of the entire genome of L5, as well as several gene functions. The DNA sequence of the L5 mycobacteriophage is as follows:

```
GGTCGGTTAT GCGGCCGAGC CATCCTGTAC GGGTTTCCAA GTCGATCAGA GGTAGGGGCC      60 SEQ ID NO: 1:
GGCACAGAAA CCACTCACAT CAGGGCTGTG CGCCTCCAGG GCGCGTGAAC TCCCACACCC     120
CGGTGTAGTT ACATCCCGGA ATTGTCTCAG CGCCTCTCAG GGCGCTTCTC ATAAACAGTG     180
ATCTACGCCA CTCCTGACGG GTGGCTGTCA AGGATACTCA CCTTCCCTAC TAATGAGGGG     240
CTAAGAGCCC CTCTCTATAG AGCGCCGCAC AGGCGGCGCG ATAAGAGCGC CACCAGGCGC     300
TCATCTAAAG ACCGGCCTTG AAGGGCCGGT CATAGAGATC TATTCGATCC GGCAACCGCC     360
GGATCTCAAG GCCGCGCCAG TGCGCGGCCC TATAGAGGGG TGACTCAACT GTGCATGGCA     420
CTCGCTCGAG TGCdCACTGG AGCACTCAAC CGGGGAAGTT CGACGTTCTC AACCTGCGAA     480
TGACGTTTGA ATCGTCATCC GCGTACGAAA TCCCCGATCT GCGGCCGACC GACTTCGTGC     540
CGGCCTATCT CGCGGCCTGG AATATGCCGC GTCACCGCGA TTACGCCGCC AAGAACGGCG     600
GCGCGCTGCA CTTCTTCCTT GACGATTACC GGTTTGAGAC CGCGTGGTCG TCCCCCGAGC     660
GCCTTCTCGA CCGCGTAAAG CAGGTCGGCG CTGCACTCAC GCCGGATTTC AGCCTCTGGA     720
CGAACATGCC GAAGGCGGCG CAGCTATGGA ACGTCTACCG CTCCCGCTGG TGTGGCGCGT     780
ATTGGCAGTC GGAAGGAATC GAGGTGATTC CGACGGCGTG TTGGGCGACT CCCGACACGT     840
TCGATTTCTG TTTCGACGGG ATCCCGATGG GATCGACCGT CGCAATTTCT TCGATGGGCA     900
TTCGCTCTTC AAAAGTCGAC CAGGAGCTTT TCCGGTACGG ACTACGCGAA CTCATCGATC     960
GCACTCAACC GCAACTGCTT TTGGdATATG GCCAGCTTCG GCATTGCGAC GACATGGATT    1020
TACCAGAGGT CCGCGAATAC CCGACCTACT GGGACAGACG ACGAAAGTGG GTAACTGCCG    1080
ATGGGAGGCC GGGGAAGTAA AGGCGGCCCC GGTCCCGGAA CCGGAGCACG CAACCGCAGA    1140
GGCGCTGGAG CCCCCGGATC GGGCGGCGTA GGCGGCGTCG GAGGCGGGGG TGGAGCTGCA    1200
GGGAGCAGCG GAGGCGGCAA GGGAACGGCA GCGCCGGTAC CGGAGGCGTC ACCGGTGGCG    1260
GCGGAAGTGG AGCCGGCGGC GGTGGCAGCA GCCCCAACAC CCCGGTGCCC CCCACCGAGC    1320
TGGAGAAGAA GCGCGGCGAA TACAACCAGA TCGCCATCGA CGCCCAGAAA CAGCACGCGC    1380
CCACCGATGA GAAGCGCGAG GCCAAGCGCA AGCAACTGAT GGATCGAGTC GGAGGAGACT    1440
GGCAGGCTTT GGACCCGGAT CACCACGACG CCATCAAGGT GGCGATGGAT GACGCCATGC    1500
GGAAGATCCT CTCCGAGGAG GAGATCGTCC ACCGCACCAA GCACTTCGGC GACCTACTCG    1560
ACTCCGGTCG ACTCAAGTCG CTGTTCGAGG TCGGCTTCTC AGCCGGTGGC GACACCCCGA    1620
CCGAACGCGC CCTCCTCGAG GACGCCTGGT TCGGCGCAGG CAAGGTTCCC CCGATCTACT    1680
```

-continued

```
CGGCAATCGA GTTCAACGGC GCTCCGACAG CCGGCCTCGG CATGTACGGC GGCACCAAGC 1740
TCTACATGAA GGACTCGGTC AAGGACCGCG TCACCGTGAC CATCGGCGAC TCGCTGATGT 1800
CGAGCTGGGA CGTATTCCCC GGCCGTCCTG GCGACGGCGT GGGGCTGTGG GCCAGCCTGT 1860
CGAAGATCGA GGGGCTGGTC GATCCGAGCA AGACCCGCGA AGAGAACATG CAGGCGGTGT 1920
ACGACTCGTT CAAGAAGTAC GGCACCCTGG ACGGCTTCAT CGAGGCGCAG ATCCACGGCG 1980
GCGTCCTGGT CGAGGACATC AAGAAGGTCG TGTTCACGCA GCCGCCGAGC CCGATCTTCA 2040
CCGATAAACT GGACGAACTT GGAATCCCGT GGGAGGTGCA GTAATGGCGC AGATGCAGGC 2100
GACACACACA ATCGAGGGGT TCCTGGCTGT CGAGGTGGCC CCTCGGGCGT TCGTCGCAGA 2160
GAACGGCCAC GTACTGACCC GGCTGTCGGC CACGAAGTGG GGCGGTGGCG AGGGTCTCGA 2220
GATCCTCAAC TACGAGGGTC CAGGGACCGT CGAGGTCTCC GACGAGAAGC TCGCCGAAGC 2280
CCAGCGGGCC AGCGAGGTCG AGGCTGAACT TCGCCGCGAG GTCGGCAAGG AGTGAGCTGG 2340
GCCGGCTCAG GCCGGCGACA GGAACTACCA GAGGACTGGG AGCTGAATTA CCGGCTCCCG 2400
GTCCTTTCTG CTGCCAACTG GCTTTGCCAG ATCAACGGTC CCGGATGCGT AAGGGCCGCA 2460
ACCGATGTCG ACCACATCAA GCGCGGGAAC GACCACAGCG GGTCCAATCT GCAGGCAGCC 2520
TGCCATGTCT GTCACGGCAA GAAATCAGCC GCCGAGGGCG TAGCCCGACG GCGGGAACTT 2580
AGAGCCCGGA GGAAGCGACC ACCCGAACGC CATCCTGGGC GTCGATAAGC GGGCCAGGTG 2640
CCCGCTCCAC CCAGGAGGTG AACAGTGGGC ACGCGAGGCC CAATCGGAAA ACGAGATGAA 2700
GAGCGGGTTC GTCGGAACAC CCCGGACAGT CCAACCGACA CGATCCAGAT GCCCGGTCTG 2760
GTGACGATCC CCGAGATGGG CGATCTAAGC CACGACGGCC GCACGCACCA GCTCGTCAAG 2820
GACATGTACG AGTCGATCAA GCAGTCGGCA GCCGTGAAGT ACTACGAGCC GACCGACTGG 2880
CAGATGGCCC GACTCGCCCT CTACACACTT AACCAGGAAC TCATCGCAGC CGAGAACAAC 2940
GGCAAGCCCG TGGGCGCGAT GAAGCTCACT GCCATCAACC AGATGCTCTC CGCGCTGCTG 3000
CTGACCGAAG GTGACCGACG CCGCGTCCGA CTCGAAGTCG AACGAGCACC CGCTGACCCG 3060
ACAGGCGGGA AGGTCGTTGA CGTGACCGAC GTGCTCAAGC AGCGCCTCGC CAAGGCGAGC 3120
GGCGGGAGCT GATGGTCCCC CGAGGGGTTT CTAGAGCCGC TGCCGCTACC AGCCGCTCCC 3180
CCTCGGGGTA GACATCGAAA GGAACCACAT GGCCGACCTC GGCAACCCAC TCGACCTCGA 3240
GATGCTCTGC CTGGTCACAG GCCGGGACTT CCGCTGGACC ATCGATTACC CGTGGGGTCC 3300
GGGAGAGCTG TTCCTCGAAC TCGAGACCGG CGGCGAACAC AACGCGCTGC ATCAGGTCTA 3360
TGTCACCGGG GCGACCGGAG GCACGTACAC GCTGAACGTC AACGGCACCA ACACCCCGGC 3420
CATCGACTAC AACGACGTGT CGGAGAATCC GCAGGGGCTG GCAGGCGACA TCCAAGACGC 3480
TCTGGACGCA GCCGTCGGAG CCGGAAACGC TGTCGTGCAT CCGGTCTCGC TGTTCCCTGC 3540
GTGGACACTG AACTTCAACC TCAACGCCAG CAAGCCGCTC ACCGAGCAGT TGGTCAACAC 3600
GATCAACAAG GCCGCGAACG ACTTCTTCGA CACGTTCGAC CAACTACTTG GGGTCGACGT 3660
GGAGATGACG GTCACCGACA CCCTGAACTT CAAGCTCAAG GTGACCTCGC GGCGCTCGTT 3720
CGATGAGGTC GGTGTCGTCA CGTTCGCGGT CGACGTGACC AGCCAGGCAG TCATCAACTT 3780
CTTCAACTCC GTCGCCGAAC TCACCGGAGC GGTGAACACC GTCAACGTCG ACTTCTACTG 3840
GAACCGGACG TATGACATCG AGTTCACCGG ATCCCTTGGG CTGCAGCCGA TTCCGGCTAC 3900
TACAGCCGAC ATCACCAACC TGGCGGGTAC CAGCAAGGCC GTCTCAGTCA CGGTGGTCGA 3960
GCCAGGAAAG AAGAGGCTGA CCATCTGGCC GTTCACGGTC AACGGTGAAA CCGCAACCAT 4020
CAAGGTCGAG TCCGAAGAGG CCGACAAGAT CCCCAACCGC TGCCGCTGGC AGTTGGTTCA 4080
CATGCCGACC GGCGAOGCAG CCGGCGGCGA TGCAAAGCAG CTCGGCCGCG TTTACCGACA 4140
GCCGAGGTAA CACCGCACCC ATCAGAGATG GTGGGCCAGA CGGCCTTCGG GCCGTCCCCT 4200
GACGTGTAGC TCAATGGCAG AGCGCCCGAC TGTTAATCGG GTGGTTGAAG GTTCGAGTCC 4260
TTCCATGTCA GCGAGGGCTG AACCGGACCC GTGTCCGGTG TAGGCACTTT CCGCAGGCGG 4320
TTCCCCAGAG CGTGGGGAGC CCCTGCCCTG TACACGTAGC TCAATTGGTA GAGCAGCGGT 4380
CTCCAAAGCC GCCGGTTCCA GGTTCGACTC CTGGCGTGTA TGCACACACC CCTGACTCCT 4440
GCTAGCGGAG TGTTCGCCTT TCGGGCCTGG GGTCTTTTTC CCCGTTCGTC TAATCGGTAA 4500
GACACCCGGC TCTGGACCGG GCAATTGAGG TTCGAGTCCT TGGCGGGGAG CCAACTTGAC 4560
ATCCACCCGA AAGGAACAAC ATGACCTTCA CAGTCACCCG CGAGAGAGCG CAGTGGGTCC 4620
ACGACATGGC CCGCGCTCGC GACGGTCTCC CCTACGCGTA CGGCGGGGCG TTCACCAACA 4680
ACCCGAGGGT GTCGACTGAC TGCTCTGGCC TGGTGCTGCA GACCGGGGCT TGGTATGGAG 4740
GTCGCACCGA CTGGGTCGGA AACCGTTACG GCTCAACCGA ATCGTTCCGG CTCGACCACA 4800
AGATCGTCTA CGACCTAGGG TTCAAGCGGA TGCCCCGAGG CGGGCCAGCG GCCTTGCCGA 4860
TCAAGCCGGT GATGCTCGTC GGGCTCCAGC ACGGAGGCGG CGGGGTCTAC TCGCACACCG 4920
CTTGCACGTT GATGACGATG GACCACCCCG GTGGCCCGGT CAAGATGTCC GACCGAGGCG 4980
TCGACTGGGA GTCCCACGGC AACCGCAACG GCGTAGGCGT CGAACTTTAC GAGGGCGCAC 5040
GGGCATGGAA CGACCCTCTG TTCCATGACT TTTGGTACCT GGACGCAGTC CTCGAAGACG 5100
AAGGAGACGA TGACGAATTG GCTGACCCAG TTCTAGGGAA GATGATCCGC GAGATCCACG 5160
CGTGCCTGTT CAATCAGACC GCGTCGACCA GCGATCTGGC GACCCCTGGT GAAGGCGCTA 5220
TCTGGCAGCT ACACCAGAAG ATCCACTCGA TTGACGGCAT GCTCCACCCG ATCCACGCTG 5280
AGCGGCGCGC TCGCGCAGGC GATCTCGGTG AGCTGCACCG AATCGTGTTG GCCGCGAAGG 5340
GCTTGGGCGT GAAGCGCGAC GAGGTGACCA AGCGGGTCTA CCAGAGCATC CTCGCCGACA 5400
TCGAGCGGGA CAACCCCGAA GTACTTCAGC GATACATCGC AGAAAGAGGT GGCCTATGAG 5460
CCCCAAGATC CGACAGACCA TCTACCTGCT CGGCACCGCC GCCCCGGCAC TGCTGGGCAT 5520
CGTCCTGATC TGGGGCGGGC TCGACGCTGA GTCGGCGGCT GACCTCGGTG ACATCATTGC 5580
GGGCGTCGTG TCGATACTAG TCTCCGGTGC GCCGGCCGTA GCGGCAGGCA CCGTACGCAG 5640
CCAGCGCAAG GACGGCACGT TGTCCACCAG CCCGGTGGAT CAGGTCACCA AGGGCGTCGA 5700
GCAGGTGCTC GCGGCCAGGC AGAGTGCCGA GGCTGAAGTC GCGAAGGTCA AGCAGGCGCT 5760
GGAGACCGCC GTCAGCGGTT CTCTCCCCCA GCTCGGCCCG CTGGCCACGC AGATCCTCAA 5820
CGTGGCTGAC GACACCGTCT GGCGTCCATG AGCAAGCCCT GGCTGTTCAC CGTCCACGGC 5880
ACAGGCCAGC CCGACCCGCT CGGGCCTGGT CTGCCTGCCG ATACCGCACG GGACGTACTT 5940
GACATCTACC GGTGGCAGCC CATCGGCAAC TACCCGGCAG CGGCGTTCCC GATGTGGCCG 6000
TCGGTCGAAA AGGGTGTCGC TGAGCTGATC CTGCAGATCG AGCTGAAGCT GGACGCAGAT 6060
CCGTACGCGG ACTTCGCGCT GGCCGGCTAC TCGCAGGGAG CCATCGTGGT GGGCCAGGTG 6120
CTCAAGCACC ACATCATCAA CCCGAGAGGT CGACTGCACC GGTTCCTGCA CCGGCTCAGG 6180
AAGGTCATCT TCTGGGGTAA TCCGATGCGG CAGAAGGGCT TTGCCCACAC CGACGAGTGG 6240
ATTCACCAGG TCGCTGCCTC GGACACGATG GGCATCCTCG AGGACCGACT GGAGAACCTC 6300
GAGCAGTACG GCTTTGAGGT CCGCGACTAC GCGCACGACG GCGACATGTA CGCCTCCATC 6360
AAGGAGGACG ACATGCACGA GTACGAGGTG GCCATTGGCC GAATCGTGAT GAGCGCTAGG 6420
CGATTCATCG GAGGTAAGGA CTCCGTCATC GCCCAGCTCA TCGAGCTTGG ACAGCGTCCG 6480
```

-continued

```
ATCTGGGAGG GAATCGCGAT GGCCAGAGCC ATCATCGACG CCCTCACGTT CTTCGCCAAG    6540
TCGACCCAAG GCCCGAGCTG GCCGCATTTG TACAACCGCT TCCCGGCGGT CGAGTTCCTA    6600
CGACGAATCT GAGAAAGGAG GCGGGGTGAG CCTCAACAAC CACCACCCGG AGCTTGCCCC    6660
GTCTCCCCCT CACATCATCG GCCCGTCCTG GCAGAAGACG GTCGATGGTG AGTGGTATCT    6720
GCCTGAGAAG ACCCTCGGCT GGGGAGTCCT GAAGTGGCTC TCCGAGTACG TGAATACCCC    6780
TGGCGGGCAT GACGATCCGA ACCGTCTGGC GACGTTGATC GCGCTCTCCG AGGCAGGTCT    6840
TCTCGACAAC GAGAACATGT TCATCCCCAC CGACGAGCAG GTACGCCTGG TCCTCTGGTG    6900
GTACGCAGTA GATGACCAGG GCCAGTACAT CTACCGCGAG GGCGTGATCC GCCGGCTCAA    6960
GGGCTGGGGC AAGGATCCGT TCACCGCCGC GCTCTGCTTG GCGGAACTCT GTGGCCCCGT    7020
AGCCTTTTCA CACTTCGACG CCGACGGTAA CCCGGTCGGC AAGCCGCGTT CAGCCGCGTG    7080
GATCACCGTC GCGGCCGTCA GCCAGGACCA GACGAAGAAC ACGTTCTCGC TGTTCCCGGT    7140
GATGATCAGC AAGAAGCTGA AGGCCGAGTA CGGCCTGGAC GTGAACCGCT TCATCATCTA    7200
CTCCGCAGCC GGTGGCCGTA TTGAGGCAGC GACCTCGAGC CCCGCGTCGA TGGAGGGTAA    7260
CCGCCCGACG TTCGTCGTCC AGAACGAGAC GCAGTGGTGG GGCCAAGGCC CCGACGGCAA    7320
GGTCAATGAA GGCCACGCGA TGGCAGAGGT CATCGAAGGC AACATGACCA AGGTCGAGGG    7380
CTCCCGCACC CTGTCGATCT GCAACGCCCA CATCCCCGGC ACCGAGACGG TCGCCGAGAA    7440
GGCATGGGAC GAGTACCAGA AGGTCCAGGC AGGCGACTCT GTCGACACCG GGATGATGTA    7500
CGACGCGCTG GAAGCGCCGG CCGACACCCC GGTCTCCGAG ATCCCCCCGC AGAAGGAGGA    7560
TCCCGAGGGA TTCGAGAAGG GCATCGAGAA GCTCCGCGAG GGCCTGCTCA TCGCCCGAGG    7620
CGACTCCACC TGGCTGCCGA TAGACGACAT CATCAAGTCG ATTCTGTCGA CCAAGAACCC    7680
GATCACCGAG TCGCGGCGCA AGTTCCTGAA TCAGGTAAAC GCCGCTGAGG ACTCGTGGCT    7740
CTCACCGCAG GAATGGAACC GGTGCCAGGT CGACCTGGCC AAGTACCTGG ATAAGCACGG    7800
CAGGGAGTTC GCTCCGCTGC AGCGCGGTGA CCGGATCACC CTCGGGTTCG ACGGGTCGAA    7860
GTCCAACGAC TGGACCGCGC TCGTCGGCTG CCGTGTCAGC GACGGCCTGC TGTTCGTCAT    7920
CGACATCTGG GATCCCCAGA AGTACGGCGG GGAGGTTCCC CGCGAAGACG TTGACGCCAA    7980
GGTCCATTCG GCGTTCGCCC ACTACGACGT GGTGGCGTTC CGCGCCGACG TGAAGGAGTT    8040
CGAGGCGTAC GTCGACCAGT GGGGCCGGAC CTACAAGAAG AAGCTCAAGG TCAACGCCAG    8100
CCCGAACAAC CCGGTGGCGT TCGACATGCG CGGACAGCAG AAGAGGTTCG CGTTCGACTG    8160
CGAGCGACTC GAGGACGCGG TCCTTGAGGG CGAGGTCTGG CACGACGGCA ATCCCGTTCT    8220
GCGCCAACAC GTTCTGAACG CCAAACGACA CCCAACGAAC TACGACGCCA TCGCGATTCG    8280
CAAGGTCACG AAGGACTCCA GCAAGAAAAT CGACGCTGCA GTCTGCGCTG TCCTCGCGTT    8340
CGGGGCGAGA CAGGACTACC TCATGAGCAA GAAGGCCCGT AGCGGCCGGG TGGTGATGGT    8400
TCGATGACAG CACCGCTCCC CGGTATGGAG GAGATCGAAG ACCCCGCAGT CGTACGAGAA    8460
GAGATGATCT CGGCCTTCGA GGATGCTTCC AAGGATCTCG CCAGCAACAC CAGCTACTAC    8520
GACGCTGAGC GCCGGCCAGA GGCCATCGGC GTCACCGTCC CGAGAGAGAT GCAGCAACTG    8580
CTGGCTCACG TCGGATACCC CAGGCTCTAC GTCGACTCAG TCGCCGAGCG CCAGGCCGTC    8640
GAGGGTTTCC GCCTCGGCGA TGCCGACGAG GCTGACGAAG AGCTGTGGCA GTGGTGGCAG    8700
GCCAACAACC TCGACATCGA GGCACCACTG GGCTACACCG ACGCTTACGT TCACGGCCGG    8760
TCGTTCATCA CGATCAGCAA GCCAGACCCG CAGCTCGACC TGGGTTGGGA TCAGAACGTC    8820
CCGATCATCC GCGTCGAGCC GCCCACCCGA ATGCACGCCG AGATCGACCC CCGGATCAAC    8880
CGGGTGTCCA AGGCCATCCG AGTCGCATAT GACAAGGAGG GCAACGAGAT TCAGGCTGCC    8940
ACGCTGTACA CGCCGATGGA GACCATCGGC TGGTTCCGCG CTGACGGTGA GTGGGCTGAG    9000
TGGTTCAACG TCCCGCACGG TCTGGGCGTC GTTCCCGTTG TGCCGCTTCC GAACCGGACC    9060
CGGCTCTCGG ACCTGTACGG CACCAGTGAG ATCACGCCCG AGCTTCGGTC GATGACCGAC    9120
GCGGCGGCGC GCATCCTCAT GTTGATGCAG GCGACCGCCG AGCTGATGGG TGTCCCCCAG    9180
CGCCTGATCT TCGGCATCAA GCCCGAAGAG ATCGGCGTCG ACTCCGAGAC CGGCCAGACG    9240
CTGTTCGATG CGTACCTGGC CCGGATCCTG GCGTTCGAGG ACGCTGAGGG CAAGATCCAG    9300
CAGTTCTCTG CAGCCGAGCT GGCCAACTTC ACCAACGCGC TCGATCAGAT CGCCAAACAG    9360
GTCGCTGCGT ACACGGGATT GCCTCCCCAG TACCTGAGTA CCGCCGCAGA CAATCCGGCC    9420
TCCGCTGAGG CGATCAGGGC CGCTGAGAGC CGACTCATCA AGAAGGTCGA GCGGAAGAAC    9480
CTGATGTTCG GCGGCGCATG GAAGAGGCC ATGCGGATCG CCTACCGGAT CATGAAGGGC    9540
GGCGACGTTC CCCCGGACAT GCTCCGCATG GAGACCGTCT GGCGAGACCC GAGCACTCCC    9600
ACCTACGCGG CCAAGGCCGA CGCAGCCACG AAGCTGTACG GCAACGGCCA GGGTGTCATC    9660
CCGCGTGAAC GTGCTCGCAT CGACATGGGC TACTCCGTCA AGGAGCGCGA AGAGATGCGC    9720
CGATGGGACG AGGAAGAGGC CGCAATGGGT CTCGGCCTGT TGGGCACGAT GGTCGACGCC    9780
GACCCGACGG TCCCAGGCTC CCCGAGCCCC ACGGCACCGC CGAAGCCACA GCCGGCCATC    9840
GAGTCGTCTG GTGGTGATGC GTGACCGCAG AGGAGTACGC GGCGGCTCAA GCCGCGATCA    9900
CTGCGGGTCT TGCCACATAC GTCCAGAGGT TCGCTTCGCT CTTCGTCGGT CCAGCTCTCG    9960
CTGTAGGTGA GTGGCTGCGA CTGCTGCAGG TGCTGTTCCC CGAAATCCAA CGGCGGTATG    10020
CAGATGCTGC CGCCTTGGGC AGGGACTTCT ACGACTCCCA ACGCGCACTA CACCACCCAG    10080
AGCTGCCCCG GAACGAGAGG TTCCGGGGAG AGCTTCGGTG GGAGTGGTTC GTCCAGAACA    10140
TGGAGCCCGC TCGAAAAGAG ATGTCGCAGG CCGACTCTCC GCCGAGTGCG ACCTCTAAGT    10200
TGGCTCTGGC CGCAGTTCGC GAAGTGGAGA TGGCAGCACG CCGACAGATC ATCGGCGCTG    10260
TCAAGAACGA TCCGGCCCCG CAGATCGTGC AGGGCTGGGC GAGGGTCGCC ACCGGGCGCG    10320
AAACATGCGC CTGGTGTCTG ATGCTCATCT CACGGGGTGC CGAGCTGAAT CACAAGGGCA    10380
ACTTCGCCTA CAGCTCAGCG GAAGCCGCAG GGCTCAACCT CGATGACGAG ACCGTGATCG    10440
ACCTCTGGAA CGAGTCCGGT CACGACCTTG AGAAGTTCCG CGAGGAGACC AdAGAGGACT    10500
TCGAGAAGTG GCACGCAGGG TGCGACTGTC TGGTGGTCCC GGTCTTCGAT GTGCAGAACT    10560
GGCCCGGAAG AGACGCTGCC CTACGGGCGC AGCAACTTTG GATCGAAGCC AGCGACGAAG    10620
CTGACGACCT CATTGCGTCA GGCAAGGCCC GCTCCAAGAA CAAGAACACG GAGACGCTCA    10680
ACGCGCTCCG ACGCCGCCTA GCACGCGGCG AAATCACCAT GTCCAACTAC GCCCTCGCTG    10740
CGTAGTCCCT CGAACCCCAG GTGGGTTCTC TCAACATGCC CAGGAGGCGA AAACACATGT    10800
CCGACAACCC CACTCCCGAG AGCACCCCAG AGGCCGAGAC CCCGGAGGTC GAGAAGCCGA    10860
TGGAACCGCA GGGCAAGGTC TTCGATGAAG CGTACGTTCA GTCGCTTCGC CAGGAGGCTG    10920
CAGCCCCTCG GGTGGCGAAG AAGGACGCCG TAGAAGCGGC AGAGGCTCGA GTGAAGGCCG    10980
AGTACGAGGC CAAGCTCGCT GAGCGCGACA CCGCTTACAC CGAACTGCAG AACCAGTTGG    11040
GACAGGCGTG GATTGAGCTG GAGAAGGTCT ACCTCTCTCT CGACGCCAAG GTGCCCAACG    11100
ACAAGGTTCG GGCGTTTGTC GAGATCCTCG AAGGCAACGA CAGGGACAGC ATCGCTGAGT    11160
CAGTGAAGTC CCGTCTGGAG CTGGTCGGCG GATTCGGCAA CAAGACCCCG AGTCCTGCGT    11220
TCGACCCGTC TCAGGGTCGC GGCGGTAAGC CGCCGATCCC GCTGAACGGT GACCCGATCC    11280
```

-continued

```
TCGAGGCCAT CAAGGCCGCT GTCGGGATCA AGAAGTAACC CACCCAACAG ATCTCAAGGA   11340
GAGATAAACA ATGGCAGTCA ACCCTGACCG CACCACGCCG TTCCTCGGCG TGAACGACCC   11400
CAAGGTCGCG CAGACCGGCG ACTCGATGTT CGAGGGCTAC CTCGAGCCCG AGCAGGCCCA   11460
GGACTACTTC GCCGAAGCGG AGAAGATCTC CATCGTCCAG CAGTTCGCCC AGAAGATCCC   11520
GATGGGCACG ACCGGCCAGA AGATCCCGCA CTGGACCGGC GACGTGAGTG CGTCGTGGAT   11580
CGGTGAAGGC GACATGAAGC CCATCACCAA GGGCAACATG ACCTCGCAGA CCATCGCCCC   11640
CCACAAGATC GCGACGATCT TCGTGGCCTC GGCGGAAACC GTCCGTGCGA ACCCGGCCAA   11700
CTACCTGGGC ACCATGCGGA CCAAGGTCGC GACCGCCTTC GCGATGGCGT TCGACAACGC   11760
CGCGATCAAC GGCACCGACA GCCCGTTCCC GACCTTCCTA GCGCAGACCA CCAAGGAGGT   11820
CTCGCTGGTG GACCCGGACG GCACCGGCTC CAACGCCGAC CTCACCGTCT ACGACGCGGT   11880
CGCCGTCAAC GCCCTGTCGC TGTTGGTCAA TGCCGGCAAG AAGTGGACCC ACACTCTGCT   11940
GGACGACATC ACCGAGCCGA TCCTCAACGG CGCGAAGGAC AAGAGCGGTC GCCCGCTGTT   12000
CATCGAGTCG ACCTACACCG AGGAGAACAG CCCGTTCCGC CTCGGTCGGA TTGTGGCCCG   12060
TCCGACCATC CTGAGCGACC ACGTCGCCTC GGGCACGGTC GTCGGCTACC AGGGTGACTT   12120
CCGCCAGCTC GTCTGGGGCC AGGTCGGCGG CCTGTCCTTC GACGTGACGG ATCAGGCGAC   12180
TCTGAACCTG GGCACCCCCC AGGCTCCGAA CTTCGTCTCG CTGTGGCAGC ACAACCTCGT   12240
CGCAGTCCGA GTCGAGGCCG AGTACGCCTT CCACTGCAAC GACAAGGACG CGTTCGTCAA   12300
GCTCACGAAC GTGGACGCCA CCGAAGCCTG ATCCAGGCTT GACATCCACC GGGAGGGGGC   12360
TCCTTCGGGA GCCCTCTCCT GATGTGGAGC AGGAAGGACC ACATGCGAAT CCAGTCCACC   12420
CTCAACGGCG GTTTCGCCGA GGTTTCCGAG GAGTTCGCCA AGCAGTTGAT CGCCACTGGC   12480
GGCTGGAAGG TGCCCCGGAA ACCGCGCAAC ACCAAGACCA AGACCGCTCC TGAGGAGCCC   12540
AAGAACGAGG AGTAACCCGT GGCCTACGCG ACCGCCGAAG ACGTTGTGAC GTTGTGGGCC   12600
AAGGAGCCTG AGCCCGAAGT GATGGCGCTG ATCGAGCGCC GGCTCCAGCA GATCGAGCGC   12660
ATGATCAAGC GCCGGATCCC CGACCTGGAC GTGAAAGCCG CTGCGTCGGC GACGTTCCGG   12720
GCCGATCTGA TCGACATCGA AGCTGATGCT GTTCTGCGCC TCGTGCGTAA CCCGGAGGGC   12780
TACCTCTCGG AGACCGACGG TGCGTACACC TATCAGCTCC AGGCCGACCT GTCGCAAGGC   12840
AAGCTCACCA TCCTCGATGA GGAGTGGGAG ATCCTCGGGG TCAACTCCCA GAAGCGCATG   12900
GCGGTCATCG TCCCGAACGT GGTGATGCCG ACGTGAGCGC GAGCGACCGA CACCGCGCCC   12960
CGATTGTCTA TCCGCCTGGC ACTCAGGCGG TTACGCCGGA TCGGGTCAAC GCGTTTGACT   13020
GCGATCACGA AGCTGATCCT CCGGTGTGCC GGTGCGTCCA CGACTGGCGC ATCGAGTGGG   13080
GAAACGTCAA GAAGGCCACC GCCAGATCAC GGTCGGCGGT GCTCTGATGA GCCTCCTCGA   13140
CACCGGTGCC CGGTACCAGA CCTGCATCGT CTACCCCGAA GAGATGGTCA TCGACTCCGA   13200
TGGCAACAAG CGGACCAGGC CGTCGAATAC CGGCATCCCG GCCATCGCAC GGTTCCAGGT   13260
AGCCAACCAG TCTGGTACGT CGGCACGACG TGCTGAGCAG GACAACGAGG GGTTCGAGAC   13320
CGAGAAGGTC TACCGGATGC GGTTTCCCCG CTCGTTCACC AAGGAGCACG GCATCCTCGG   13380
GGCCCAGTCC CAGATCGAGT GGCGAGACCA GCGGTGGGCG CTCTTCGGAG ACGCCACCGT   13440
CTACGACTCA TCCCCTGCGT TGGCGCGGGT CGACTACACG ATCAAGAGGT ACTGATGGCC   13500
AAGGTCTACG CGAACGCGAA CAAGGTCGCG GCCCGGTACG TCGAGACGAG GGACGCCGTC   13560
CGAGACGAGC GGAACAAGGT CACCCGTCGA GCCAAAGCCA ATCTGGCGCG GCAGAACTCG   13620
ACCACCCGCA TCACCGACGA GGGCTACTTC CCGGCCACCA TCACCGAGCA AGACGGCGAT   13680
GTCGACTTCC ACACGATCCT CAACGCGCCC AACGCGTTGG CGCTTGAGTT CGGCCACGCG   13740
CCGTCTGGCT TCTTCGCTGG CACCGACACG AAACCACCGG AGGCCACTTA CATCCTCACC   13800
CGAGCCGCCA TCGGCGGCAC CGTCTCATAA GGAGGTCACA TGGCGCGAAT GCCTCGCGTC   13860
CAGGCAGTAG CGGCCCCGAT CCTCCGGTCA GACCCCCGAC TGGAGGGAGT GACGGTCACG   13920
ACATGGGTTC CAGACGTGGA CTTCCGAGAG TTCCCGATGA TCAACCTCCG CCGCATAGGC   13980
GGGACGAGGA ACCCCAACGC ACCGACGCTG CACACGCTGC CGGTGGTCGA AATGACCGCC   14040
TACACCAGAG ACGGTCTCAT CGAGACTGAG GAGCTGTACG AGACCGCGCT AGAGGTTCTC   14100
TACGACGCGG TGGAGAACGG AACACAAACT CCCGCAGGGT ATTTGACCTC CATCTTCGAG   14160
ACGATGGGCG CCACTCAGTT CAGCTCCCTC TACCAGGACT CCTGGCGCAT CCAGGGTCTG   14220
ATCAGGCTCG GCGTCCGCAG ACCGAGAACC ACCCTCTAAC CGAAAGGTAA AGCCACATGG   14280
CTGAAAACGA CGACGCAGTG TTGACTGCGG CGGTCGGCTA CGTGTACGTC GGTGCTGCAG   14340
GCACCGCTGC TCCTACGCCG GCCTTGCTCA AGACCATCGA CCTCAGCAAG CCCGAGACCT   14400
GGACCGGTGC TACCGGTTGG ACGAGCGTCG GCCACACCAG CCGAGGCACG CTCCCTGAGT   14460
TCGGCTTCGA AGGCGGCGAG TCCGAGGTCA AGGGCTCCTG GCAGAAGAAG AAGCTCCGCG   14520
AGATCACCAC CGAGGATCCC ATCGACTACG TCACGGTCCT ACTGCACCAG TTCGATGAGC   14580
AGTCGCTGGG TCTGTACTAC GGCCCCAACG CCTCTGAGAC TCCTGGTGTG TTCGGTGTGA   14640
AGACCGGCCA GACCAACGAG AAGGCCGTGC TGGTCGTGAT CGAAGACGGC GACATGCGCC   14700
TGGGGCATCA CGCCCACAAG GCTGGAGTTC GCCGCGACGA CGCGATTGAG CTGCCCATCG   14760
ATGACCTGGC TGCGCTGCCC GTCCGGTTCA CCTACCTGGA CCACGAAGAC GAGCTGCCGT   14820
TCTCCTGGAT CAACGAAGAC CTCTTCAACG TGCCCGAGGT TCCCGAGGGC TGATCCCAAC   14880
TTGACAGCCA CCCGGCTGTC TACCCCGGAG GGGGAGGTTT CCTTGGCGGG CCTGGCCTCC   14940
CCCTCCTCCC GCCACTCACA GACCCGCCGA CACTGAAAGG TTCGCCATGA CAAACGTATT   15000
CACCATCGAC GCATTCCGCG AAGAGGTCAA GAAGAAGTAC GCTCCGGTCC TCATCGGCCT   15060
GTCCGACGAT GTGACCGTCG AGCTGAAGCC GCTGCTGAAG CTGGGCCAGA AGGCCCGCGA   15120
AGCGGTGGTC GAGGTGTTCA AGGAGTTCGC GGACATCCCC GACCTCGAAG AGGACGACGA   15180
CGACGAGTTG GTCGATGAGT ACTCGCTCCA GGTCTGCGAC ATCATCGCCA AGGCGTTCCG   15240
GCTGATCGCC ACGAAGCCCA AGAAGCTGAT CGCCGCCTTG GACGAGGAGC CGGATCCCCG   15300
TATCCGCGCA GAGCTGTATG CAGCGGTACT CAACACCTGG AAGCGAGAGA CGCAACTGGG   15360
GGAAGCCGCG CCCTCGCCGA GCTGATCGAC AAGTTCGGCG GGGCGATCCT CGCAGACCTG   15420
CTCCAGTACT ACCGGGTAGA CCTGCGCGAC CTGTTCCGCG ACGAGGATCC GCTTTCGCCG   15480
AGATTCGTTC TGTCCCTGGT GCTCTGCCTT CCCAAAGACG GCGCGTTCTA CGCAGAACGT   15540
CGTGGTGGGC AGCAGTACCG GGGCTGGACC GAGGACCGCT ACGCGCTCGC GGACATCTAC   15600
GACGCCATCC AGGCGGGCAA CCACATCCTG CTGCTGGCGA ATCGTGATCC GAAGAAGCCA   15660
AAGCCCAAGG CACCCAAGTC ATACCCGCGT CCCGACGACC TAGAGAAGAC CACACCGAAG   15720
CCGGGTTCGT TCGCCGCAAT GGTCGTGCGA GCGAAGAAGG CGGCTCGAGA GAGAAGGGAA   15780
AGGGAGGAGG AGAGTGCCGA ATAGTGCTGG CGTAGAAGTC GCCCGGATCT CGGTCAAGGT   15840
CAGCCCGAAC ACCAAGGAGT TCCGCCGGGA ACTCAAGACC GAACTCGAGA AGATCGAGCG   15900
GGAGCTTAAG GGCGATGTCG AGATCAACGG TCATCTCGAT GCGGCCCAGG CCAAGGCCGA   15960
CTTCAAGCGC ATGATGATGC AGCTCAAGAC CGAAGCTGCC AAGGGCGTTC ACGTCCCGGT   16020
CGACGTAACC GTCGACAAGA AGAGCAAGAA GGGAGGTCTC CTCGGAGGTC TCCTCGGCGG   16080
```

-continued

```
CAGCCGGGGG CTCGGAGATC TAGGCGATGA CGCCGAGAAG GCGTCGTCTC AAGTACAACA 16140
CCTTGGCAAG TCGTTCCTGG GCCTCACACG AGCCGCCTGG ATAGGCGTAG GCATCGTCGC 16200
CGTAGCAGCT CCGCTGGTCG GCATCGTGGC CGGTCTGCTG GCCGGTCTGC CGTCGCTGCT 16260
GTCTGCGTTC GGAGCCGGCG CTGGCGTAGT CGCGCTCGGC ATGGACGGCA TCAAGGCAGC 16320
CGCCTCGACG CTGGCCCCGA CGCTGGAGAC GGTCAAGGCC GCTGTCTCCT CGACGTTCCA 16380
GCAGGGACTC ACCCCGGTGT TCCAGCAGCT CGGCCCGATG CTGACCGCGA TCACCCCCAA 16440
CCTGCAGAAC GTGGCCTCGG GCCTCGTGAA CATGGCCGGG TCGATCACCG ACGTGATCAC 16500
CCAGGCTCCT GGTCTGCAGC AGATCCAGAA CATCCTCACC AAGACCGGAG AGTTCTTCAC 16560
GGGCCTCGGC CCTGTGCTCG CTACCGGCAC GCAGGCGTTC CTGACGCTGT CCAACGCCGG 16620
CGCGAACTCG TTCGGCACGC TCCTGGCTCC CCTGCAGGAG TTCACCAACG GCTTCAACGA 16680
CATGGTCAAC CGAGTCACGT CCAACGGCGT GTTCGAGGGT GCCATGCAAG GGCTTTCGCA 16740
GACGCTGGGC AGCGTCCTCA ACCTGTTCAA CCGGCTCATG GAGTCCGGTC TGCAGGCGAT 16800
GGGACAGCTC GGCGGTCCGC TGTCGACGTT CATCAACGGG TTCGGAGATC TCTTCGTCTC 16860
GCTGATGCCG GCGCTGACTT CGGTCTCTGG TCTGATCGGC AACGTCCTCG GGACGCTGGG 16920
CACACAGCTC GCTCCCATCG TCACGGCGCT CACGCCGGCC TTCCAGACGC TGGCGAGCAC 16980
GCTCGGCACG ATGCTCACCG GAGCCCTCCA AGCTCTGGGT CCGATCCTGA CTCAGGTCGC 17040
TACGTTGATC GGCACGACGC TGAACACGGC GCTGCAGGCT CTCCAGCCGA TGCTGCCGTC 17100
GCTCATGCAG AGCTTCCAGC AGATCTCCGA CGTACTGGTG ACCAGTCTGG CCCCGCACAT 17160
CCCGGCGCTG GCGACGGCCC TCGGCCAGGT CGCAGGCGCG GTGCTGCAGC TCGCTCCGAC 17220
GATCATCTCG ACGTTGGTTC CGGCGTTCGT TCAGTTGGTC CCAAAGGTCG CTGAGCTAGT 17280
TCCGACCATC GTCAACCTGG TCCAGTCGTT CGCCAACCTG ATGCCGGTGG TTCTGCCCCT 17340
GGCGCAGGCT CTGGTCAGCG TTGCTGGCGC GGTGATTCAG GTGGGTGTCT CCATCGGCGG 17400
CGCGCTCATC GGCGCGCTGG CGAACCTCAC GGAGATCATC TCCAACGTCA TCAAGAAGGT 17460
GTCCGAGTGG GTCAGCAGCT TCTCCAGCGG AGCCCAGCAG ATCGCTGCGA AGGCAGCGGA 17520
ACTGCCGGGG ATGATCCAGT CGGCTCTCGC CAACCTGATG GCCATCGGCC TGCAGGCCGG 17580
TAAGGATCTC GTCCAGGGCC TGATCAACGG CATCGGCGGG ATGGTCAGCG CAGCGGTCAA 17640
CAAGGCCAAG GAGCTGGCGT CCAGCGTGGC TGGTGCAGTG AAGGGCTTCC TGGGCATCGA 17700
GTCCCCGTCG AAGTTGTTCA CCGAGTACGG CCAGTTCACC GCCGAGGGAT TCGGCAACGG 17760
CATGGAGGCA GGGTTCAAGC CCGTCATCGA ACGGGCCAAG GATCTCGCGG CTGAGCTGTC 17820
CAGGGCGATG GAGTCGGGCA CCGACCCCTC CGGGATTCTC GCTGGGCTGG ATCAGAATGA 17880
GCTGAAGCAG ATGCTGGCGG CTCTCGAAGA GGAGCGCAAG CGACTCAAGG TCGAGAAGAA 17940
CGGTATCCCC AAGGGAGACA AGGCAGGCCG AGAGGCGCTG CAGAACCAGC TCGACCAGAT 18000
CCAGGCGCAG AAGGACATCC TGTCCTACCA GCGTGACCGC ATCAAGAACG AGTCTGAGTA 18060
CGGCGACATG GCCGGCGAAG ACCCGTTGGT GAAGGCAGCC TCCGGGCTGA TGAGCGCACC 18120
GGTCGACTTC GCGAAAGCGA CTGGCAAGCA GTTCCTTTCG GACATCGGCA TCAGCGGAGA 18180
TGGGTTCATC TCGAAGGCCA TCACCGAGGG CATCCAGTAC ATCTTCCAGA TCGGCTCTGT 18240
CGATGAGGCG CTGTCGATCA AGGACCGCGA GGAGTCGAAG AACGCGCTGT CCGTCGTTGG 18300
CCGCTGACTT GACATCCACC AGGAGGTAAG CATTGATCAC CGACACCATC GTTGAACTCG 18360
AGGGTGTCAA TGGTGAGCGT TTCAACTTGA CGACCGGTGA CCAGGGTGTG TACCTGGCCA 18420
CAGACGTGGA GGGTTGTTTC TACGACCCTC CCGTCAAGGT CGTTGTTGAA GAGCCGGGGA 18480
ACTACCCCGG CGCTCGCTAC TTGTCCCACC GAGCCCTGAA GCGAGACATC GTCTTTGGGG 18540
TCGTCATCCT CAACGACGCG AAGCAGGGGC CGCGCTCCTG GCTGTCGCGA GACTCCGAGT 18600
GGCGCAAGGC GTGGGCGTTC AACCGCACCT GCAAGCTCTA CGTCACCACC CCGGACTCCG 18660
GTACCCGCTA CCTGAAGCTG GCGCTGTTCG AGTCCCCCAC CGTCAAGATG GACACCGACC 18720
CAAGAGGTAA ACCCCTTGAG GTCACGGTGA TGTCGTGCAT CGCGTACGAC CCGTTCTGGT 18780
ACGAGGACGA CAAGGTCTTC TCGGCCAAGA CCAAGACCGA CACCCGGTTC GACCCGTCGT 18840
TCTGGACGCC GCCGTGGCCG TGGGAGGAAC TGCCCAAGGA GACGCTGCGG ATCAAGGTCG 18900
GCCGCGAGCA GGGTGGGCTA AACCCCACCG ACCAGTACAT CTTCCCGAAG TGGACCGTTC 18960
CCGGCTCCAC CGAGAAGGTG CCGAACTTCC CCTGGCCGTT CCCCCCGAAC GTCCCGATCC 19020
CGTGGGAGAC AGCACCGTTC ACTCAGTTCG TCATCCCGGA CTACTCGTTC GAGGATGAGG 19080
AGTTCCGCAA CCGCCGGCTC AAGACGCCGG GGTTGATCTA CGGCGAGAAC TGCGTCATCG 19140
ACACCGACCG GCGCGAGGAG CAGATCGCTT CCGAGTCGGG CTCCCCGGTG TGGGCTCGGA 19200
TGAACGGTGT CCGGTTCCGC AACTCGATCC CGCCCTACAC CGAAGAGGCT GAGTTCGTCA 19260
TAGACGCATC GGGATGCGCT CCGGGACAGG TAGTTACCCT CCGGCTCACG AGGCCGTGGT 19320
CGCGCTGCTG GGGGCTAGAG TGAGTGGTCT GACGAGCGTT CGTGAGGCCG AAGATCTCTG 19380
GCAGAAGATC CAATTGCGGC GCTGCAAGCG CGAGCAGGAA CGGCTCAAGC ATCCCGACGT 19440
AGAGCTGCGC GATGGCGACT TCCGCCTGCG CGGCCTGGTC GCTGGCGAGC GGGTGCTCGA 19500
GTGGGAGTTC ATCGAGAACG AGACTGGCAC CTGCACCTTG CAGCTCTCAC TGAGCCATTA 19560
CCTGGCGAAG TGGGTGATGG ACCACCGGGG TCGAGCAAAG CGCAACGTCA TCATCAACAT 19620
CGAGAAGCAA GGCGCTCGAT GGACCGGGAT GATGGACCAC TACCGGGTCA TCAAGACCGA 19680
CGCAGGGGAC GCCTACATCG AGATCGTGTT TTTGCACGAC TTCGAGCAGA CCAAGCATAT 19740
CCGGGTATGG TGCAACCCGT TCCTACGCCC CGAGCTGCAG TTCCCCAAGG TGTGGATCAT 19800
CTTCGGGCCG GCCAAGTGGT GTTTGCTGGT GACACTGTTC GTCAACCTGC TCAGGCTCGA 19860
GACGAGCTTG TGGACGCTGC CTGATGACCC CACGGACATC AACGAGTGGA TGGGTCCGAG 19920
CTTCAACCCA GCAAATTGGC GGAACATCGT CAAGCCGTTC CCGTTCCTGG CCGACAACTC 19980
ACCGGTCACG ATGGTGTTCA GCCGGTTCGG GACGTTCTAC GACACCGCCA AGAAGATCCT 20040
CGAAGACCAT CAGCTCACGC TGACGTGTCG TCGGTACATC AAGGACCGCG ACCCGCATCC 20100
GTTCGAAGAT CTCAAGGGGC TCTGGGGAAT TGATCCTGTC GAAGACCTGC TGCAGAAGAT 20160
CCCGCTCCGG GACGGCTGCG TGGTCTGGGA CATCGAGGAC AACTCAGGTT GGGGCACTCA 20220
GACCGCGTTC GGCGGTTCGT GGCTGACCGG GTTCGTCCGA GGGATGGTCC AACTGGCCGG 20280
CGACGGCCAG GTCGAGGGCG TCGATGTGTT CACCGGGGAC TACACGTTCC CAGGCGAGTA 20340
CTACTCCCCC TGGTTCATGG GCACCAGCCC GATAGCACCC CACGTCGTGT TCGAAGAAGG 20400
ACCGCTGACC GGGATCAAGT CGTCGGAGTT CTCGTACTAC GAGGCCACCG ACACCAGCTT 20460
CCTGGCTGGT GGACAGAGCG CACCTGGCAT CAACGAGGGC ATCTCGGCCC TGGTGAACAT 20520
CGGTGGCGAC CTGCTGACCT CGTTCATCAA CAGCCAGCTC GCCGCGCTCG GCGCGGTCGG 20580
TGGAGCGATT GACCTCCCGC CTCTGGGCGG TCTGCTCGAT GCGGTGTTGC AGCCTCTGTA 20640
CTCCGATGTG TTCGGCGCGT TCATGGAAGT TCCGACTCTG CGTGCGATGG GCATCTCGCT 20700
CCCGATCTCC GGGCTCGAGG ACATCGTCAC CGGACTGGGC GACTTCCACT ACTTCGAGAA 20760
CATGGCCGAC GGGGCGATGA AGGCGTTCAC GCTGTCAGCG TTCGCAGCCA TCGCATCGCA 20820
GATCCACAAG ACGAGGGCTC GAACGACCCA CACCCTCAAG GTGTCTGACG CCGCTCCGTA 20880
```

-continued

```
CATCTTCGCG CCAAAGCCCT ACGGGCACTG CTGGATCGGA GATCGCGTCG GCACGTCGGT   20940
CCTCGGCTAC CCGGTCGAGC ACCAGTTGTT CGTGGAGCGC ATCCGCAAGG TGAAGTACCG   21000
CATCGACAAA GACGGCATGA AGCCGTTGGA GATCGAGATC GGTTACCGCG AACCGAAGAA   21060
CCCAGCACTA CACATCCTCG AAGAGATCAA GCGCGTCAAC GGCGCTCTTG GCACTGCGGG   21120
GATTCTCTAA ACCGAAAGGC ACGCCGCATG ATTCCCTCAC AAGAGTCTCA CAATCCGAAC   21180
GACCCGCGAC AGCACGTCAT GTGGGCGCTA CGCAATCTCC CGATGATTGC TGGCGTCGGG   21240
GCGATCACGC ATCCGGGTTA CCTGGCGGAT TGGTCAGAGC ACTTGTGGAA GTGCGGCTTT   21300
CGGCACGTCG ACTGGCTCCG GGAGCTGGCT GATGAGGACG GCAACATCCA CGTCAGTCAG   21360
CTTCCTGACC AGGAGATCAA GTTTCAGCAG CCCTTCCGGG GCCAGCGAAG CGACTACAAC   21420
AACGCAGCTC GATGGGTCGG CAAAGACGAT CCTGACCCAG AGCCCGTGCG TATTCCAGAC   21480
ATTCGCAAGC TCACAGACCA GGAGAACAGA GCGATGATCG CGCAGTACGA ACGAGACGGT   21540
TGGATCAAGG ATGGATCCCC CGGCCCAGCG ATAGCCGAGG TCGTGGAGTG ACCCCGTTCA   21600
ACCCAGACTC CATAGGCGAC TACGTGACAC TGCTCGGCGT TGCGTTCCTG ACCTTCTCGG   21660
TTCCCGCATG GTTCACCGGA CGAGCACGCA AGCACAGCAG TGACATCGGC GAAATCAAGG   21720
AACAGGTATG TAACACCCAC GACACGAACC TGCGCGATGA CCTCGACAGC GTCAAGGCAG   21780
ACATCAGCGA CTTGAAAGAG ATTGTGTTGC AAGGGTTCCA CCAGGTGAAC GAGTCGATCA   21840
ACCTCGAGCG CCGTGAGCGG ATCGAAGGAG ACCGCCGAAA GGAGGTTGCG TGACCTACCC   21900
CACCAACCCA CTAGAGGCCA TCGGCGCTGA CGGCGCATTC GAGATCGGTG GGGGCGACTG   21960
GAGCTTCGGC CAGGACTACA CCGAACAGGC CATCCGGGCT CTGTTCACGA TGCCAGCGGT   22020
CACGATGGAG AACGCTCTCG GCCTGCTCGA AGAGCACCTG CTGAAGCTGC CTCTGGAGGC   22080
GCTGCAGGGC TTCAAAGACA TGATCCCGGA CTGGGTCGAA GGAGCATTCG ACACGGTCAC   22140
CGGCGCTGTG CAGGCGATCA TGAACGCGCT CCAAGACGGC CCGCTGTTCC TGAAGTTCGC   22200
CGAGTTCCAG CTCTTCCTGC AGCGTCTGCT GAACAACCCG GCCGAGGTCA TCGGCGAGAT   22260
CCCCCAGACG TTGATCGACG GCCTACAGGA CGCGCTCAAC ACCGTCAACA ACACCATCCA   22320
GACCATCGTG GACATGCTCC TGCAGGCGCT GGGCATCACC CCGGAGGGGG AGCTGATCGA   22380
CCGGATCTTC GACCTGAGCG ATGAGATGGA GTGGCTGCAG ACCGCAGCCT CGAATGCAGC   22440
TACCGGCATC CAGGACACCT GGAACAAGTT CTGGGGAGCC CTCACCGGGC GCGTCCCAGA   22500
CCAGGACCAG ACCGTCGCTG AGCCCGCCGA GCGTATCGGC GAGCTGGCCG GCACCACGTC   22560
TGCTAACTCG TCTGCCATCG CGGAGCTGCA GCGTCGACTG GACAACCAGC AGAACGCTGG   22620
CGGCGTGGCC GGCGGTGACG ACTTCGAGCG ACTGAACATA TCCGGTTGGG ACATCAGGTA   22680
TTCCAACGGA TCCAGCGGCC GAGGGTACTA CCGTGCCGAC GGCCACCAAC TGGTCTGGAT   22740
GGACGAAGGC AACCAGCAGA ACACCGCGAC GTTCGTCCGC ACCAACCCCG CAGACGAGAA   22800
GACAGCCACC GACTACCAGA AGATGACGTT GGTCGTCGGG ACTATCTCCG GTGAGGTACA   22860
GACCGTGTTC CCGCCGCAGG GAGGTTCGCA CACCCGGCTA TGGGTCCGCG TCAACGACAA   22920
CGCTCCGACC GTCGGCATCA CCGACGGCGT GTTCGTAGAG ATCGGCGGCG TATCGAAGGC   22980
CCAGATCGGC TACCGCCGCA ACGGCAATGA CACGTTCGTC GGATCTATGG TCGACTGCAC   23040
CTGGGGTGCT GGATCGATCT TCGCTCTGAC CGCCGGCACG GCCAACGGTG CTGAGAAGTT   23100
CGAGGTCTCG AAGAACGGCC CCGTGCTGGC CACATGGTCG GACGACGGCG TCGTCTCCGC   23160
GATGGGTGCG AACTACCGCC GCTGGGGCTG GGAAGGCCAG GCTCGTAACC GCAACCTCGG   23220
CCAGGGCACT CCGAACTCGG TCACCCGAGT GACGATCACC GACAACGATC CTACCGGCGC   23280
AGGCGGTGGA GCTGTCAACG TCGGAGGAGA TGTCGTAGGT GTACTCCCCA TAGAGAACGG   23340
AGGCACCGGA GCTTCGACAG CTTCGGCAGC CCGTACCGCT CTCGGAATCG ATGACCTGGT   23400
CGAAGATATG TCCGACGTAG TTCGTGGATC CGTCGAAGGA CTCCCGTTGA TACCGAAGAT   23460
CTGGGTAGGA ACAGAAGCTC AGTACACGGC TCTCGCCACC AAGGATCAGT CCACGCTATA   23520
CTTCAGGACC GCTTAATGAC TGGTATCTCG TTGGGTGTCA ACGACATCCG CAACCTCTCG   23580
ATATTCTTAG GCGTCAGCAA CAAGATATTG AAGGTCAGTC TAGGCACAGA AAAGGTCTGG   23640
CCTGCGTTCA CCCCGGTGCT GACCACGTTC GCCACGGTCG GCACGTACAC CTACAACATC   23700
CCCGACGGGG CCAAGTTCAT CGACGTCATC CTCCTCGGAG GAGGCGGCGG GGGTAAAGGC   23760
ATGGCCCTGG CTGACGGCTG GGGCAGAGGT GGAGACGCCG GAAGCTGGGC TATCGTCACT   23820
CTCGAACGCG GGGTACACAT CCCGTTGTCG ACCAAGACGA TCACCGGGCT CGTCGGAGCT   23880
GGAGGCGCAG CGGGAGCTGG CTCTGTATTC TCAGGCAAGG CCGGAGGCCC TGGAGGAAAC   23940
ACCACGGCGT CCGCTGTCGG ATGGTCAGGT TTGACCGCAA CCGGCGGTCC CGGAGGCTCT   24000
GTGATCGACA TCCTCAGCGT CGCCGGAAAG TCGCCTGGAG ATCGGACCTA CAACGACCAG   24060
CTCTACATAG GCGGCGCACA ACAGAACTCA GCTGGCGGGA ACGGCAATGC TCCTGGCGGC   24120
GGCGGGGCTG GTGCCCAGGT CTCCGCACAG AGCGGCGGTG CTGGCGCTCG CGGCCAGGCG   24180
TGGTTCTTCG CGTACTGACA AGAAACCCCC CTCTTTAGGA CTCAGTGTCC TTGGGAGGGG   24240
GGCTTTTTGC GTTTCAGGAG GTCTTGGCCA GCTTGGACAT CGCCTCAGCG ATAGCCTCGT   24300
CGCGGGCCTC AGACGCCATC TGGTACTTCA TCGCCATCCT AGGAGTCGTG TGACCGAGAC   24360
GGGCCATCAG CTCCTTGGTC GTCGCACCTG CCTGAGCGGC GAACGTAGCG CCGACAGCGC   24420
GGAGGTCGTG GATGCGGAGT TCCGGCCGAC CGATCTTGGC GTAGCCACGC TTCAGCGACT   24480
TGGTGAACGC GGACTTCGAC AGCCGGTTGC CCTGCGTCGT GGTCACCAGG AATGCCTCGG   24540
GGCCCTTGTT CATCTTCGTA CGGTCCTTCA TGTGCGCTCG GATCATCTCC GCGACGTGAG   24600
GCGGAACCGT CACAGGACGC TTCGACCGGA CGGTCTTGGC GTTGCCAACG ACGATCTTGT   24660
TCCCCACGCG GGAAGCGCCA CGGCGCACCC GGAGCTTCAT CGTCATGCCG TCGTCCACGA   24720
TGTCCTTGCG GCGAAGCTCG ATCAGCTCTC CGAACCGGAG GCTCGTCCAC GCCAGGATGT   24780
ATGCCGCGAT CCGGTAGTGC TCGAAGATCT CAGCGGCGAC GATGTCCAGC TCCTCAGGCG   24840
TCAGCGCCTC TACGTCGCGC TCATCGGCTG CCTTCTGCTC GATCCGGCAC GGGTTCTCTG   24900
CGATCAGCTT GTCCTCGACC GCTGTGTTCA TCACCGCCCG GAGGACGTTG TAGGCATGCC   24960
GGCGGGCAGT CGGGTGCTTC CTACCCATCC CGGCCCACCA CGCACGCACC AGAGCTGGCG   25020
TCATCTCTGT GACCGCCACT TCACCTAGCA CCGGGTAGAT GCGGCGCTCC GCGTGCCCGC   25080
TGTACAGATC CCTGGTGCCG TCTGCGAGGT CGCGCTCCAC GAGCCACTTC CGGGTGTACT   25140
CCTCCAGCGT GATGGCGCTG GCGGCTGCCT TCTTCGCCCG GTCCTGTGGA GGGGTCCAGG   25200
TCTCCATCTC GATGAGCCGC TTCTCGCCCG CGAGCCAGGC TTCGGCGTCC ATCTTGTTGT   25260
CGTAGGTCTG CAGCGCGTAG TACCTCACAC CGTCCTGCGG GTTGACGTAT GAGGCTTGGA   25320
TCCTCCCGCT GCGCTGAGTC TTCAGCGATC CCCATCCGCG ACGTGCCAAC TAGGTCTCCT   25380
CTCGTCGTGA ACAAGGCTAC CGGGTTGCAA CTCCTGTGCA ACTCTCAGGC TTCAACGCGC   25440
TTCTACGACC TGCAATTTCT TTCCACTTAG AGGATGCAGC CGAGAGGGGG TAAAAACCTA   25500
TCTTGACCGG CCCATATGTG GTCGGCAGAC ACCCATTCTT CCAAACTAGC TACGCGGGTT   25560
CGATTCCCGT CGCCCGCTCC GCTGGTCAGA GGGTGTTTTC GCCCTCTGGC CATTTTTCTT   25620
TCCAGGGGTC TGCAACTCTT GTGCGACTCT TCTGACCTGG GCATACGCGG TTGCAACGCA   25680
```

-continued

TCCCTGATCT GGCTACTTTC GATGCTGACA AACGAATAGA GCCCCCCGCC TGCGCGAACA 25740
GACGAGGGGC ATTCACACCA GATTGGAGCT GGTGCAGTGA AGAGAATAGA CCGGGACAAG 25800
GTTGCACCGG GAGTTGCAGC GGTCGGAACC CTCGCCGTCG GCGGGCTGGC GTTCGCCCTG 25860
TCGTTCACGG CTCTCAGCGA GCTGGCTGCG GCCAACGGGG TGGCCCAAGC AGAGATGGTG 25920
CCCTTGGTGG TCGACGGCCT GACGCTCGTC GCCACGGTCG CCACAGTGGC CCTCAAGCAG 25980
AACAGTTGGT ACGCGTGGTC GCTGCTGATC CTGTCCACCG TCGTATCGGT GGCCGGCAAC 26040
GTGGCACACG CCTACCCCCA CGGCATCATC GCGATGGTGA TCGCTGCGAT CCCTCCGCTC 26100
TGGCTACTGG CGTCGACCCA CCTAACCGTG ATGCTGGCGA AGCAGCACTC GGAGCACGCC 26160
GAAGTACCTG TCTCGCGGCC AGAACCCGCG CCTCGGGGCC TGGAGCCCGC TGCCGCTTGA 26220
CTGCGCCCGA CCGGGACAGA AATACATAGA GAACCTATGG ATGTAGGAGG CACAAAAAAA 26280
TACCCCCCGA GCCAGCCCGA AGGCCAGCCC AGGGGGCATG GTTCTGCTTC AGTAGACCTT 26340
GCGAGTCCGA CCCGAGTTGA TCATCGCCAT GATGACCCAG ACGGGCAACC ACATTCCGCA 26400
GGTGATGAGC GAAAGCAACA GGTGCATCGC GTGGTTCGTC CTGACAGGCA TGACAGTGGG 26460
CT6CGGCATC GGAGGAGGCG CGACCGGGTA CGGCGAGCCC GCGTACCACT GAGGTCGATC 26520
TTGTTGGGGC GGATACTGAT TGGTCATCCC GACAGCCTAC TTGCCGATGG GTCGCATCAG 26580
CTCCTCGACC GACTCGCGCT CCACGCGGAT CAGCCGGGGA CCGAGCCGAA CGGCCTTGAG 26640
CCGGCCGTCG GCGATGTAGT TGCGGACGGT CTTGGTGCTG ACACCGAGGT AGTCAGCGGT 26700
CTCCTGGATG GATGCTCTCG GGGGCATCAG CGCGGTCCTC CGTGCTTCAT CGGTTGTCTC 26760
CCGAACCCTG GATCACGCCA CGATCCTTGC GGCTCTGGAG CTTGTTGAGG TTCCTCTGGG 26820
TGACGGTGCT CAACCAGACA TCGAGCTGGT TGGCTAGCTG GGCGACGTAC CACATCACGT 26880
CTCCGAGTTC CGCCTGGAGG TCGTCTCGGT TCTCCTGGGT GATGACACCG TCTTTATCCC 26940
GGAGGATTTT CTTGACCTTG TTGGCGATCT CGCCGGCTTC GCCTACGAGA CCCATCGTCA 27000
CGTAGGAGAG ACCCTCGATG CTGTCGCAGT CGCCTGCACC GGGGTAGATC GCTGTGTCGC 27060
TCGCGGCGAT CTGGTAGATG TCGACGTGCA TCAGATCATC ACCGGGAACA ACTGGCCACC 27120
GGGCATCTGG ATGAACACCG GGACGCTGGG GGTGTAGTCC GACGAACCCG TGCCGCCCTC 27180
ACAGGCGGAC AGGCTCAGGG TGGCGGCAAG GCCGATGATG GCTGCTGCGA TGGTCTTCTT 27240
CATCTGTTGC TCCAGTAGCT AAGTTCGGAC TCCAGTTCGC GGATACGCTC CTGTAGCCCT 27300
TGGTTTTCCA GGTACGCCTC GGCGAGGTTG GCCTCGGCGC GGTCACGGGC CTCGTCCTTC 27360
GACGTGGCCT CATCGATTGC CTCGTGTAGC CGGCGGATCA GATCTGGGAT GGCACCGTGC 27420
AGACCGCATA TGAAGTCGGC GTCTGCCTCG GAGAGGTGGG ACGCCACCAG ATCCTTGTCC 27480
TGGGTCTCCT GGTTGACCGC CCAGATGACG TGATCCTCTA GCCCGTGGTC GGTCTCGCAG 27540
ATAGAAGGCG GTTCTACCTC CTCTGGCATC CAGTAAGTCT TCTCAGCCCC GGTGGACTTC 27600
GCCCACTGCT GGTAGAGGAT GTCGAAGAAC TCGTGGTCCT GTTCGTCGGC GGTAATCACA 27660
GATCGTCCTC TTCATCCCAT TCGTCGTAGT AACACGTACA GCCGCAGCAG GTGCAGCAGC 27720
CGCACTCGTA GGTGCCGTAG TCGTAGTCAT CCCAGTCGTC TTCGTCCATC TAGCTGTACT 27780
CCTTCATGAT TCGGTCGAAC GCACGCGTCT GCACGCGCAT CTCCAGGTCG ACCGTTCGCT 27840
TCAACCACGC CCATTCGCCG TCGTGGTTGA TCTCCCACTG GCTCTTGAAT GTCGCTGTCT 27900
CAACGAGGAA CTCGACAGTC AACGTGTGCA GTCCGTTGTT GCTGGGCTGG AATCCGATAC 27960
CGTCCTCAGC GATGTACCAG GGCAACTCCT GGCCGTCGAA GTAGACGGCC TTGTCGGTCA 28020
CCAGTACTTC AGGGAAGGTG TGCTCGGTCA ACGGCGTCCC AGGTATGGGA TGACGCTGGC 28080
CCGGAACTCA AGGAACACCA TGTTGTCCGG GCAGTCCTCG GGGACGTTGT CGGGGCGTTC 28140
GGCGGTGTAG ACGCCGATCT CGTTGCCCTC CAGGGTTCCA AGCTCGTTGA GCTTGTAGAT 28200
CGCCAGACCC ATCAGCTCTT CATCGAGACC GTTCGGTGCT GGCAGTACAA CTTTGGCTTG 28260
TGGCATTAGC CCTCCCTCGG AATTACGTAT GCGCTGAACT CGACGGCCGT AATGCCGTCT 28320
GGCAGTTGGA ATCCGAACCG CTCTTCGAAC TCCTCGTTGG TGATGGGGCC GTACTCGAAG 28380
GTTCCGGGCA CTACCTCGCC CTCCCCCTCG ATCAGGAGGT ACGCACCGGC GGCGTACACC 28440
TCCTCGTCGT TCGGCCATCC GACTACGGTC CCGAGGACCG TGAACTTCCT CGGCTCCATC 28500
AGGGCACGTC CACTTCGTTG ATGAGGAACC GCATCGGAGG TGGAGTGAGC ATTGCCTCGG 28560
CTATGGCGAT GAGGGCGTTC AACTGACCCT TCAGCAGCTT CTCCTCGTCG CCTGCGGGAA 28620
GGTGGCGCAC TCGGCGCTCC ATCTCCTTGG CGCGTTCCAG ATATTCGGTG GCTGTCAAGT 28680
TGTCCTCCTT AGTAATCAGC GCCGTAGAGC GAACCCCACG AACGCTTTCC GACCTCGGGG 28740
TCGGTGCCAA CCAGCACCGG ACCCATCTGT TCTTGCATCA GGTGGCCAAT GTGTGCAGCG 28800
GCTCTCTCAG CCTCTGAGGC GGGCAGAGAC GCGACGATCT CGTCGTGGAT AGGCAACCGT 28860
AGGTACGGGG TGTATCCGGC CTCGTGGAGG CGAATCAGAG CCCGACAGGT CACGTCCCGC 28920
GACGACGACT GGATCATGTA GTTCAGCGCG GAGTATGTCC GCGAGCTGTC CACCGGCAGC 28980
CGCCGGCCCA TCGCGTTGAC GATGTAGCCG TTGCGGCCAG CTTCCATCGC CAGCTTCTTG 29040
CTCAGCCGCT CCACACCGGG GTATGTCGCA GAGAACGCCT CATGAACTCG CTTGGCCACA 29100
GGGATCGAGA TCCCCACTGC CTCAGCGAGA GCCTTCGCCC CACCGCCGTA GACCTTCTGA 29160
AAGTTGGCGG TCTTCCCAAC CTTTCGCGGC ACCTGGGCTG CGTCAGCGGT CATCTGGTGG 29220
AGGTCCGCAC CGTTCTCGAA TGCCTCGATC ATGTTGCGGT CGCCCGACAG CGCCGCCAGG 29280
ACGCGAAGCT CCTGCGCCTG GTAGTCGACT GAGGCCATCA CATCGCCTGG CTCAGCGATG 29340
AAGCATCGCC GCACGATCCA GTCCGACGAC GGCAGCGTCT GCGCCGGGAT GCCGGTGATC 29400
GACATGCGCG AGGTCCGCGC CTGCAGTGGG TTGATGAACG TGTGGCAGCG GTCCTCAGAG 29460
TCCCTGGTGT CGATGAACTT CTGGACCCAG GTCTTCCGCC ACTTCCCCAG CTTCTTAGCC 29520
TCCTGAGCGA TGGCGGCAAG CTCGTTGCCA TCTTCGACCA GCTTGTCGAG CAGAGCCGCG 29580
TTGACCTGGC GCTTGCCAGT CTCGGTGCGA CCGGTGATCT TGACGCCCAT CTCCTCAAGC 29640
CCCTCGGCCA GATCCTCGGT CGAGTTGACC TTCTCCACGC CGTACTCGGT GAAAGCGATT 29700
GCCTCCCAGA CCTCCTGATC GGCCAACCAC TTCTCGGCGA GCGACCGCGA GTACTCCACA 29760
TCGAGCAGGA AGCCCTGCCT GTCGATGTAG CTGCAGATCT CACTGATCTT GTGCTCGTAC 29820
GGCACCAGCG ACCGACTCAC GTCGGGCACC AACGGTGTCA GGCTCTTGCA GACCCTCGCG 29880
GTGAAGATCG TGTCCATCCC GGCGTACAGC AGGTACTCCG GGTGGAACAG GTCGATGGTC 29940
GACCAGATCT TGGCCTTGGT CGTCTTGTGC TCGGCGGCTA GCTTGGCCAT GAGCTTCTTG 30000
ACGTTCTCGG CCTGGTCCTC GGAGATGAAC TTCGCGATCA GCTCTTCGAG CGAGTGCCCG 30060
AACCCGCCGG CCTCGAAGGG CCGGGGGTCC ACCAGCTTCG CCAGGATCTG CGTGTCAAGC 30120
ACGCGGGGCC ACAGACCCTC CATCTCGATC CCGAAGCACT GGTCGAGCAC CTGGAGGTCG 30180
AAGGAGGCGT TCTGGAGCAC CATGCGCTTG AGAGCGCCGA TGGCGATCCG CACGTCCTCG 30240
ATGAACACGT CTCCCAGCTC CACCGGCACC ACCCAGGCTT CGTCCTGAGT ACCGAACTGG 30300
ACGAGGCGGC ACTCGAAGGT GTCGCTGTAG ATGTCCAGCC CGGTGGTCTC AGTGTCGACG 30360
GCGAGGCAGT TCAGGTGAGC CCGGATGAAG TTGCGGAAGC CTTCCAGATC CTCTGGGGTT 30420
TCAACGACGT TGACGGTGAC GAGGTCTCCC TGAACCTCAT GCCGCAGCTC GATCAAAATG 30480

-continued

```
CTCTCCTACT GGAAGTACTG AGGCGGAATC CAGGTGGCTG AGGCCATCTC CTTGATGGCC    30540
TGCTGCATGG CCGCTTCGAA CGGACAGTCC GGGTCGATGT CCGGCTTGTA ATGGGTGACG    30600
ATGATCCGGC TGTTGCCGCC GAAGTCGTGG CTGACCAAGC CCTTTGGGGG CAGCTTCTTC    30660
AGCGCCTTGA TCAGTTCCTC AACCGTGGTC CCGGTAGGGG CCTTGCCGTC AGGCAATGCC    30720
TCCCCTCCGT ACGGCACGTC CAATGGGATC GTGTACCGCT CAACGTCTTT GATCTTCATC    30780
GAGCCTCTTC CTCTTCGACT ACCTCGTCTA CCCGGCGGAA TAACTCCGCT AGTTCTGCGG    30840
GTAGCAATAC TGGGTACTTC TCTCGGGCTT CCTGCATCGC TACCGCGATC CCAATCAGGG    30900
CAGCGAGCAG TTCATTGACG GAGTACGCCA ACAGCTCTTC GCGGATCTCT TCTCGGGTCA    30960
TTAGTGGTAG ATCCCCCGGA CGGTGCGCGA GATCGTGGCA GGGTTCACGC CGTAGTTCTC    31020
GGCGAGATCC TTCTGCTTCA TACCGCCCAG GTACGCCTGG CGGATGTCCT TGACCTCGCG    31080
CTCGGTGAGC TTCTTGCGGT TCGGCCGGCT CGGGCCGGTC TCAGGCTTGA CCTGAGCCAG    31140
CGCCTTGCCG AACAGCTCGT TCTGCGTCCG CTGCTTGATC GCGTACCGAC GGTTCGCTGC    31200
AAGCACCTCG TTGAGCCGCT GGGACAACTT GACATTGGCC TCACGCACTA CCTCGACCTC    31260
TCCGAGCAAG TTCGTGATCC GGTAGTCCTT GTCCTGGTTC TCGATGGCCA ACCGGTTGTT    31320
CTCCTCGGAA AGCATCGAGA CCTTGTATTG CGCCTCTCCC AGCGCAGCTT TCAGGTGCTT    31380
CTTCCTCATT CAGCGCCCCT CTCTCGGCGG AACTGTTCGT ACTCGTCTTC GGTCATGTAG    31440
TAGTAGTAGT CAACGACCTT GTCCCAGTTG AAGGTTCGGG ACGTGCCGTC ATCGAACGCG    31500
ATGATCAGGA CACCCTCTTG GGTGTCTAGG ATCGGCTCGC CAGCCACGAC GTGGAAGCGG    31560
TCCTCGAGGG TCACCGCAGT CGCTCTGCGT GCCATGTCAG TTCCTCTCAG TAGCTGTAGG    31620
GGACATCCGG GATGTCCTGG TAGGTGTTGG GTGCGATCTG TCGGAGCTGC CGAAGCAATT    31680
CCCCTGCCAG CTCACGGATC TCGGCATCCG CGGCCTCGTG CCAGCGGGCC TTGATGACGT    31740
ACCGCCACGC CCGATGGTTG CCCGTGACGA CCATCGGTGA GTTCGTCATG TTCGGCAGGA    31800
CAGCTCGCGC TGCCTCGCGG GCCTGCTTGC GCGGCAAGCC CCGGTCAGCC AGCCGGTTGA    31860
CGATGTGTTC GTAGACAGCG TCAATCTCAG AGCTGACGGA CTCCATGATG TGGACGAGGT    31920
CGTCTCGGTC GTCGGGGTGG AGCTTGAACA GAGCCGGGGG CAGATGGATG CCAAGGTCGG    31980
TCGGATCCAC ATATCGCTGA GACACCACCG AGAAGCTCAA GTGACGGTGA CGCTCCAGCT    32040
CGGTCAGCAC CGACCTGCTG GCCTCGATGT AGAACGTCGC CGAGGCGTGC TCGAACACGC    32100
TCTCGTGGCC CAGATCGATG ATGTGGTTGA GGTAGTCCTC GTTCTCGGCA GTTGCCGGGT    32160
TCGGTCGGTG GAACGACCGG TAGCAGTTCC GGCCCGCGAA CTCGGCCAGC TCGTCGGCAT    32220
CGAAGTCGCC GAAGTAGGGA TCTTCGTCCT TGGATTCTTC GAAGTCATCG ACCTCGAATC    32280
CGATGTCCCG CAACGCACCC GGATCGATCT CGGTGGCAGC GATCAGTTTG GCTTTCATAC    32340
TCTCCGCTCA GAGTTGGTGG AACGAGGTCA GCCAGGGGGC AGCGAAGCCC TTCTACAGCT    32400
CCCCTTGGCT CGTTACCGGC TTCTCGACCT CGGTGGATGT CAAGTAGTCG AGATGACTAC    32460
TTCTTGTCGG GCCATTGCGC GTCACACTGC TGATCGCGAG GTGCGGTGCA GGAGAACAGC    32520
GCGTACGGCT TGCCCGTCTT CTTCGAGACG CCCGACTTGT AGACCATCTC GCCGTGCTGG    32580
CAGTACCGCT TCTCGCCACC AGGCGCTTCC TGAGCTGCCT GCGGGGCGCG AGACTGCTGC    32640
TGGCCACCGC CGCCGCCGTT GGCCGGCGCG GATCCACCGG AGCCTGCGTA GTGGCCTGCG    32700
ATCTGCTGGA CCTTGTCCAT CAGCGCCTTG AACTCGGCGG TGTTGACCTT GGCCAGCACG    32760
TCGGCCGGGT CCGCACCCTT CACGACCACC CACGGGTCGC TGTACTGACC GGCGAACTTG    32820
AACGTGGCCG ACACCCCATC GGTGGAGTGC TGGACCGCCA TCGAGTCGCG CACAGCAGCC    32880
GAGGCCGTCG TCACCGTCGC CGACGGCGCG GTCTCAGGCT CAGGAGCCGG GGCCGGCTCG    32940
GGCTGGGCAG GGGCGGTGCT CCACGGATCG TCGTAGGACA ACTGGTTACC TTTCACTTAA    33000
TGGGGCATGC GCCGTTGGCG CACTCTTCAT CGACACCGTC TTCGACGGCT TTGGCCGCAG    33060
CAGATTCGTA CTGCTGCTTG GTGATTCGCT CGTACGGAGC CTGCGGGAAG CTGGACTCCG    33120
GGAAGATCGT GGAGCCCTTG ATGAGCCCCG CGAACCTCTT GAGATCGGCT GCGACATCCT    33180
CGGCCTCGTA GGCGTCTGGA TGGACGTTGG CGGTGAACGA CACCGCGTTG TCAGCCCAGC    33240
ACATCTGGTA GAGCGCCTGG AACGCCAGGA GCTGGTGGAG GGTCAACTCG TCGGCTGACT    33300
CAACGATCTC CTCGTCCCAA CCGAGTTCCT CGACAGCCTG GACCAACGTG TCCTTGGTCG    33360
GGATCGAAAC CACCTCGGTG TTCGGAGCGA AGAGATCCTT CTCGATCTCG TAACCCTCGG    33420
CTGCCAACCT CCGCAGCTCG GCCATGTCGC TGTTGAGGTT GAACCGCACA CGCCGGATGA    33480
AGTACCGCGA GAAGATCGGG TGGATCCCCT CGGAGACTCC TGGCATCTTC GCCACCGTGC    33540
CTGTGGGAGC GATGGTTCGC TTCTTCACCG GGACAGGGAT CCTCAGATCA TGGGCGAACC    33600
GTTCGGCCTC TGAGTCGACC TCAGCGGCCA TCTCCCGCAA GAACTGGGTG AACCGCTTAT    33660
CTCCGGGTGC CTCGGAGTAC CTGCTACCTG TGAGGGCCAA ATAGGAGGCA ACTCCGAGAT    33720
GACCCACGCC GATGCGACGG TTTCGGTCCA GAACCTCCCG GCTCTTCGGG TCGGCCACTT    33780
CCGAGAACGT CGCCCGGATC AGGAATCTCG TCATCAGACG ATGCGCCCGG ATCAGGTCGA    33840
GGTAGTCGGT CTTGCCGGCC GGCGTCACGA ACGCCGCCAG GTTGATGTGG CCGAGGTTGC    33900
ACGGCTCCCA CGGTTCGAGA GTGATCTCGC CGCATGGGTT GGTGCAGACC ACCCGGTTGG    33960
GCTCACCGAC GTTGGACAGT GACGAGTCCC ACATCCCCGG CTCTCCGTTG CGTACGGCTC    34020
CCTCGGAGAG TGCCTTGAGC ACTCGGTGGG CTCGCTTCTG CTTGGGCATG TCCTCGCGGG    34080
CGACCGCGAA GCTGCCGTAG CCCTCCTTGG CCAGACGCCA GAACTCGTCG TCAACCTCGA    34140
CCGAGATGTT CGTCGTCCAG TGCTCGCCCG TGCTCGCCTT GATGTTGATG AACTTGTCGA    34200
TCTGGTAGTC GTCCCAGTGC ATCATCGACA TCCGCGCCGA CCGGCGCACA CCGCCGGCCA    34260
CAACACACTG AGCGATGGCG TGGTCGACCT CCATCGCGGC GATGCCGTCG AGCGTGATCC    34320
CTGCGTACTC CGAGAAGATG TTGGCGACCT TCTGCAGCAT CACAGCGAAC GGCAGCGGGC    34380
CGCTGGCCAC TCCACCGAAC GTCTTGAGCT TGGCCCCTTG CGGCCGGATG CGGCTCACGT    34440
CGTACACCCG CTGGTAGTGG ACCGTGCCGG GTCGGTAGTG CGTGTCGATC AGATCGACCA    34500
GCGCAGCAGC CCAGCCCTCT CGTGAGTCCT CGATGGCGTA GGCACCGGCC CAGTCGTGGC    34560
TGTAGTGCTC CCACAGAATG CCTACATCCT TCATCGCCTG GTAGTCGACA TGCTCTGGAT    34620
CACAGACGAT CTCGACCCGC AGGGGGTTTA CGACCTCGGG GTAGCCTTCG AGGTAGTGGT    34680
TCGAGTAGTT CGCCCCGACT CCCCCGCCCT CCATCAGGCG CATGAACGTG AACTGGAAGT    34740
GGTCCGAGAT CTTCTCGGGC CAGCCAGCTA CCCAGCAGTT GAAGAGGTGC TGCGCGTTCT    34800
TGACCCCCGA GGCCCACAGA TGCCGACCTG CCGGCAGCAC CTTGAACTTG GTCATCAGAC    34860
GAACGAGATC TTCTCGCTCT CCTTCCAACA TATGTCGCCG GTCGACAAGA GCAAGATTGC    34920
CGTCCACGAC CCTCTCGACC GTTTCCGGCC AGGTTTCCTT CGAGCCGTCA GGCTTGGTCC    34980
TGGCGTAGGT TCGGTTGTAA ACGAGTTCAC CGGTTGGTCC CCAAGGGATT TCGTCAGTCA    35040
ACTACTTCCT TCAGTCAGT  TCGTATCGCT TGAAATAGGC GTCGGCAGAG TCGCCGCCAG    35100
AGAACGAGAC CCCGTACTCG ACCGGGCCTG CACCACGCAC CTCGCAGGTA ACGACGCCCT    35160
TCCTTCCCCG GAACATCGGC CAGGTTCCCT TGGAGGGGTG CTTGGTCTCG TCCCGCTGGA    35220
CGATGACCTT GGTGCCCTTC TTCATGCCGA CTTCCGTTCT CCGTAGCCGG GAGTGAAGCA    35280
```

-continued

```
ACCCCCGACG TACAGCTCGA GATCTTCTTG CGACCAGTTC TCCAGTCGCA TCGGCGGCTG    35340
GTGCGGGAAC AGCTCCGGGA ACACCTCGGC CCGGTACAGC TCCGAACCGG GCATCCCGTT    35400
GAACGTCGGA TCAAGAATGT TGTGCATGGC ACCTCCCTCC CAAGAACTCG GAGATCGGCG    35460
GCTCGTAGAG GTAGCCATCG CGCAGTTCGG GGTTCTCGAT GAGCATGATC GCGATGTTCG    35520
CTGTGGGGTC AGAGTGCCCA TCCCCCTGCG ACTTTCGGAT GTCTGGGAAG ATAGCGTGCT    35580
TGCTGCCCGG ACCATCCTTG ACGATGACCT TGCCCTTGTC GTCCTTCTCC ACGCCAGCCG    35640
TGATCGCGAT GATGTTGACG TGCTCGGTCA GCGACTTGTG AGCGCGGAAC AACCGGTTCT    35700
GCCCGCTCTT ATCCTTCGGG GAGATCCCGT CGGTGTAGCG GCTCCTGATC GCCTCTGCAT    35760
AGCCCCCGTT CTGAGCGTCC AGAGCCTTCA TCGCCAGCGG GAGGATGTCG ACCAGGTACC    35820
GATTGGTCGA CTCCCCCTGC AGAGCCTCTT TGACGTTCTC GGACGAGTAG TGGCTGCGCT    35880
CCTGGAACAA GTCGCGGGCC TTGGCCGCTC CCGACAGGAT GTTGCGAACC TGATTGCGTA    35940
CGTAGTGAAC TGCCTCACCA CGGTGCAAGC TCTCCAGCGT CTTCTGGATG TACGGGCTCT    36000
CGAGGTACCA GACCCACAGC TCTTGGATGA TCTCCTCGGC TGTCAGGTTG GTCTCCCAAC    36060
CGATCAGCGC CTTCCGGGTG GCCCTGCTGA ACAGCTTGCT GATGTCGTCG GTCAAGGCAT    36120
CACCTTTCGT AGGTACTCCT CCCGGTCCAA TCGGCGGTCG AGGTGTCGAG TGACCTCCTC    36180
CGCGAAGACC TCGCGGACTT CGCTGGAGGT GATCTGGCGC GAACGTGCGT TCTTGTGCAG    36240
GTACGGCAGC TTGGTGGCTG TCAAGTTCTA GACCTCCCAG ACTCGGCCGT CGACCGAGAA    36300
CCGGCCTCCG ACAATCGGAA CAAGCTCAGG CTTGACGTGC TGGCCGTCGA CCGTCAGCAG    36360
AGCAAAACCA CTCTGCCAGT TGGCTGTTGC ACCCTTGAGG TACTGAGCTA GCTTCATGTT    36420
CATCAGGTTG CCGACCTCCA TCGACCACAG CACCTTCTGG TTGCCGCCGT AGCCCAGCGT    36480
GTGTGGCTTG ATGCCCTGGC GGTGGGTGTG TCCGATGATC ACCGACGTGC CGAACCGCAT    36540
CATCGCGTTG TACGCGGTGT CAGCGGACTT CTGCGTCACC CGGACCCCAC CACGGTGGCC    36600
GTGGGTGGAG ATCCAGCCTG GAGCGATCTT GTAGAACTCA GGCAGCACGT CAACACCGAA    36660
CCCGTCGAAG TCCAGCAGGT TCTGGAACTG GAACGAGCTG ACGTACTCGA CCAGCGCCGG    36720
GGCGAACTGG TGCAGGTAGT CGACTGGCCG GCGGTCGTGG TTGCCCTCGT GGACACCAAC    36780
CGGGCCGTCG TAGACCTGGC GCAGCGGCTC CAGGAACCGC CGCTTGCACT GCTCGGAGTC    36840
GGGCTTGATC CGCTGAGCGA ACTCTTCCTT GGTGCCCTTG GTCCACCGAG ACGGGCTCGG    36900
GTAGTCCATC AGGTCACCGA TGTGGACGAC CTCGTCAGGC TGGGTGTCCC CGATGTAGCC    36960
GATGACCGCC TTCAACTGCT TGCGATCATC GAACGGAATC TGGGTGTCCG AGATGACGAC    37020
GATGCGCTTG CTCACTCAGC GACCTCGGTG AAGGGGCCCC GCATACGTTC CTCGTGGGAG    37080
CTGGCGTTGC CTCCTGACCA GCGTCGCTTG CCCACCTTGG TGTGGTGCAA CCCGTTGGGG    37140
TAGTAGATCC ACTTCACTCC TGTGGCGTTG GTGACGGTCT TCACATCGGC AGGAACGTCC    37200
AGCAAGGTGT CCCACTGGCG AGGCCCCTTG GGATACCGCT CGTCCTCGGG GAGCTGCATC    37260
TTCTCCAGAA CGCCTGCGTA ACCGGCGATG TCGACCACCG TGTCCTGGTG GTAGCCGTTC    37320
TCCATGAACC GGGCGATCTT CAGCAGGATC ATCATGACGG CCACGTCCTC CGGGGTGAAC    37380
TCGACGCCGC GCTTGTACGC GCCCCACAGG GTCGCGATGC GTTCGTGGTT CTCCTTGGCG    37440
TCCCCGTAGT CCTGGGCTCG CTGTCCGTTG ATGATCTCTT CGGCGGTGGT CAGAATGCTC    37500
ACAGTCCAGT CTCCGATGCG GTGTAGTAGT CGATCAGCTC ATCGAGCTGG TCCGGTTGAT    37560
AGCCGAGGAT CGGCTTGTGG GTGTCAGTGA CGACGACGGG AACCGACATC GCGTTGAGCA    37620
CCTTGGTGAC GTAGTCGTAC GCCTCCGAGT TGGCCGTGAC ATCGACTGCG TCGAAGTCGA    37680
TCCCGGCAGC CGTCAGCTTG TCTTTGACTC GCTCGCATGG CTTGCAGCCG GGACGGGTGT    37740
ACACCGTGAC CGGCGCGAAC AGCGTTCTCA CGTGAGCACC ATCCCAGTCG ATGTATCGGT    37800
CTCCATACAT CAGATCCTTT CCAGCAGAGC AGCTTTGCCC TGCGATGTGA CTAGTGAGTT    37860
GACATCCTCG CCTTCTGGCA TCGGGATGAT TCGGGCGTTC GGCAGCGTCT TCGCCACCGA    37920
CCGGGCGAAC TCCATACCGG CGTCGTCGCC GTCGGCCAGG ATGTTCACGT TGCGGTAGCC    37980
CAGGAACAGC TCTCGGAAGT ACGGCTTCCA CTTCTGGGCT CCGCTGAGCC CCACCGTCGG    38040
CAGCCCACAC AGCTCGGCGG TGATCGTGTC GAGTTCTCCC TCGCAGATCG CCATGTCCTT    38100
GCTGTATTTG GTCAGCGCGT AGGTGTTGTA GAGCCGGTCC TTCTCCCCTG GCATCGACAG    38160
GTACTTCGGT GTGCCACCGT CGATTCGGCG ATACCGGATC GCAGCTACCG TCCAGTGACG    38220
CCAGGGCGAC CACCGCATAT ACGGAATCGC CAGGCAGCCC CGGTACATCT CATGTCCAGG    38280
GAGTGGGTCG TCCACGAATC CCAGACCGAA CCGGCTTAGT TCCGCTCGGC CGGCCAGCCC    38340
GCGACTCGCC AAATACTCGT CGGCTGGGCT TCCGGGCAGG CTTTCTCTGT ACCGGGACGT    38400
TGCCTCCCAC AGATAGGTTC TCTGCGATTC GCTTAGCCTC TGCAAATGTC ACCTCCTCTT    38460
CGTGACGAAT GATCGAGATC ACGTCTCCAC GGACCCCGCA GGCCATGCAG TTGTAGCCCT    38520
GTAGGTCGTA ACTGACTGCG GCAGACGGCG TTTCGTCGCC GTGGAAGGGG CACAGGCACT    38580
TGTTCCACTC GTGGTGGTCA GGTGGTGGTT CCCAATCCGG GTGGTAGCGA AGAATCGCCC    38640
TCGCGATGGG CGAGTCGTTC ATTCGTCCTC GTCAAGCTCC TCGGGAGAGA GCCCTTCGAA    38700
GATCCCGTTC AGGACGGCGG CGAAGCCCTC GCCGGTCTCC GCTGCGTCGA GCATCTCTGC    38760
AATCGTCTTT GCCATGTTTC CTCCTGGTGG ATGTCAAGTT CGAGACAGCT TGTCAGCCTC    38820
GACTGGAGCG ATGCGCTCCC CGATGACTTG GACGGCCGGC GGGTTCAGCA GGTACTCGAT    38880
GGCCCGTTTG AAGAACTCGA TGCAGTCCCT CGCCCAGCCC AGCGTGTACT TGTTGCACAT    38940
CGTGCAGAGC AACCCTCGGA CGATGCCTGT CTTGTGATCG TGGTCGACCG ACAGGCGCTT    39000
CTTCTTACCG TTGGCTCGCT GGCAGATGTA GCACCGACCA CCTTGGAACT CGTAGATCTG    39060
CCAATACTCA TCGCCGGTGA TGCCGTAGGT GGCCAGGATC CGGGTCTCCC AGCTCGTAGA    39120
GCTGCGAGCC GTCCTGAACT CTCGGTGATG AGTAGCGCAT CGTGGCCCTG GATACTTGGC    39180
GTCTCGCGTG AGCGGGAGCC CCTGTGCGAC ACAGTCTTTG CAAGGCTTCC GCTTGTGCTT    39240
ACGGTTCTGC ACCCGGTACC CCGGAGACCT CTTCGCCGCC CTCGGCACGC GCGTCCTCCT    39300
CCCGGTTCTC CATCACCATG CAGAACCACG ACAGCAGCCC TGCCAGGGAG ATGTAGAAGG    39360
CCACCAGAAC TTGGCCGCTC ACTTCACCAT TCCTCGAACC CACCAGCGAG ACAGCGCCTT    39420
ACGCCCTTTG TCGAGCGGGG TCAGCTCGCG CTCATCGTCC TCACCGAAGT CGAACTCGAT    39480
GCTGGCGATC TCGTAGCCGA GGATCTTGAA CGACACGTTC ATAGGCGGTC TCCGAAGTTG    39540
ATGACGGGAA TGCCGGCCCT TTCGGCCTCT CGCATGCAGT GCCGGGTGCC GACTGAGTTG    39600
CCGAGGGGGA ACGCCAGACA GATGTCCGCA CCGGCCCTGA CCATCTCGAT GTTGCGGAGG    39660
ATGCCAGCCC GCTTGCCGTA GCGTTCCCAG TCGGCTCGGT GCAGCTCGGG GAGCACGTCC    39720
CATCCCTCCT GCTTCATCCC CCAGGCCCAG CGGTCTGCGA TGTCGTCAGC GCCGCGAGCG    39780
CCGCCGTGGA CGACCGTGAG ACCGGAGAAG GACCGGTGGT ACTCAGTGGC CAACGCTTCC    39840
CAGACCGTGG TGCGGTCCTT CCAGATCCGA GATCCGGTGA TCAGTACTCG CCGCATCAGA    39900
TCGCCTCCCA CTGCAGGCCG TCGTGCGACG TGACCAGCTC CGCTTCGTAG ACGCCGTAGC    39960
GGGTGGCCAG GAACTGGATC ATCTGCGCCT GCTTGTACCC GAAGGGACAT TCGTGGACGC    40020
CGCTGATCGG GTATCTGACT CCGTATTTCA CTTGATCCAC CGCTTCGCGA TTCGGTCGAC    40080
```

-continued

```
GTTCTCCTCG GAGACGTTGC GGGCGAGGCC GGTGAACTCC TGGCCGTGGA CCTTGGTCTC    40140
GATCACGCGA GGCTTGCGGG GATCCGGGCT CTCCGGGTCG ATCCGCTTGT GGGTCCAGAC    40200
GGTCGGCTTC GTCTTGATCA GAGCGCCCAG CACCTGCTGG CGCAGTGGGT TGGTCTTGCG    40260
GGGCATAGCG TTTGGAGTGG TCATCTGGAT CCTTTCCTCG GTGGCTGTCA AGTCGGTGTG    40320
CGTAGTGAAG CCCCCCCAGG CATGCGCGCC CCGCCTGGGG AGAGTTGATC AGCGCAGTTC    40380
GATGTCGGGC AGGATCGCCT GCGGCTTGAA GTTGACCTGG TAGAAGTCGG TCGAGACGTT    40440
TGCGCCATCG ACCTGCTCCA TGAAGTAGGA GACGTTGTCC GACAGGCCCA GGAAGTGCTT    40500
CTTGATCCCG TCCTTGGTCT TGCAGGTCAC GTCGAGCTTC TTCGACGCGG TGTCCGCGTT    40560
GATTGAGCAC CGGCCCTGGA TCTCGAGCAG GTACTTGTCC GTGATCCCGT TGAAGAACAC    40620
GATCCGGCGA TTGATCTCGA AGTTGTCAGC GGCCTTGCTG ACGTTCTCCG ATGCGACGTC    40680
GGCGTCGGAG GTACACGCGG AGAGGCCCAG GATCGCCGAT CCGGCGATGA GTGCGGTGGC    40740
GATGATCTTC TTCATGTTCG CTACTTTCTG TTTGGTGGAT GTCAAGTTAG TGACCGAAGT    40800
CGTTGATCTG CATAGTGTCT CCGACGAACT CCAAGGAAGC GAAGTCTTGT CCCGACGGGT    40860
CCGACTTCCC CCCTCGGTTC TTGACCGTGG AGACGTTGAG CATGTCCGGG CCGAACCCGT    40920
CCGATACTCG GTGGAGAGTG AGGATCATCT CAGGAACACG CCCGATCTGA CCTTTGATGC    40980
CCGACAACGG GATCGGCTTG TCGCCGTCGT TGTGCGGGCC GGTGACGTGG TGGAGCCCGA    41040
CGACGCATGA GCCTGTCTCA CGGCCCATCT CGTGTAGGTA GTCCATCAGC GACTCCAGAC    41100
CCGAGAACGG GTCGTCTCCC TCGCTTGAAT CGGTGCGGAC GTTGGTGATG TTGTCCACGA    41160
CGATCAACGC TGGGAAGTCC TCGTACAGCG CGTCATACGC GGCCAGAGCG TTCTCGATCT    41220
CGTCCAACGA CGGTGATGCC TTGTAGTTGA ACCGGATCGG GATCTCGTCT AGTGAGTCAG    41280
CTACCGCGTC CTCGATGTTC TGCTCGCGAA CAGCCCGCGT AGCTCGTTCG AGCGACCATC    41340
CGCTGAGGAT GGACACCGAA CGGGAGAGCT GGGTGAACGC ATCAGAGTCG GCCGAGAAGT    41400
ACAACGTCGG CACCTTCGAC TTGAGCGCGT AGGCGAGGAC GAACGCCGAC TTCCCGGTGC    41460
CGGGGCCGGC GCAGACCAGG ACTAGCTGGC CTCGTCGGAG ATGTGTACCT TTCTGGTCAA    41520
GCGCGGCCCA GACCGGGGGT AGCGGATCCC CCGCCGACCC TCGGATGTAG AGCGATTGTC    41580
TAGGTGTGTA CACCTTCCTC CTCGTGGATG TGATTGACCA GGTCATAGAT CTCGTCGCGA    41640
GAGACCAGCC GGCCCCAGGC GTCGATCCCC ACGTGGATCT GTCTCCGGTG GATGTGTCGG    41700
GACAGGATCA TCGGCGAATG CGTGTGCCCG TGGATCAGGA TCTTGCCATC GTCACGGAGC    41760
CTCCACTGGG TGTGTCGGTC CTCGCTGGTG TGGTCCCCGA CGTATGGGAA GTGGCTCAGC    41820
AGAACATCTG TGTGCCCGCC AGCGTCCCCG TACAGCGGCA CCCGGATACG AGCTGCCGTC    41880
GACACATGCT CGAACACCAT CCAGTACGCA CCAACCAGCT TGTGAGCATC GCGGTTCATC    41940
GGGTGGGGCC CATCGTGGTT GCCCAGGATC AGCCGTTTGC GGCCTGGCCG ATCCGAGATC    42000
CACCCGAGGG CATGTATCTG CCCCTTGGTG GAGCCAGAGG AGATGTCACC TAGGATCCAG    42060
ACCGTGTCGT CCTTGCCGAC GACCGAGTCC CACGCCTTCG CCAGGGTGGC GTCGTGCTCT    42120
TCGACATCAT CCGCCAGGTT GCGGATCTCC ATCAGCCGCT TGTGTCCGAT GTGTAGATCG    42180
GACGTGAACC AGGTGTTGCT CATGGCTTCC TTTCAGAACG GCGGGCCGTA CAGCTCGATC    42240
ACCAGCGCGT GCAGCTCCTC TGCCGCGTCG TCACGCTCGA ATCCGCAGCA GGAATCGTGC    42300
CGGTCGAGGA TTGCGACGAT CTGGTCGTAG AGGCTGGGCC TCACTTCACC TTCTTCGGAT    42360
CGATCAAGGC GTCGTGAATC GGCCGACCGG CGCGAGCCGC GTGCGTCTCG GCGTCCAAGG    42420
CTCGCTGCAT CTGGTTCATC AGCCGGGTGC CGCGCAGCTT GAGGATCTTC ATGGTCGCCC    42480
GACCCTTGTA TCCAGCGCGG TGCATCCGTA GGACGCAGGC TGTCTCGTGC GGGGCTATAG    42540
GTGACCTCAG CGACGGGTGG TTTGGATCCC AGTTCGTCAT GTCTTCCTCT CGGTGGCTGT    42600
CAAGTTGGTC ACAGACCGAA CTCTTCCTGG TACTGCGGGA TGAAGTGGCC GGCCGTTCAT    42660
GTTCGGCTCG ATACCTCTCG CGTCACGAAC TCCTGCCCGT TCCATCTCCG ACCGTCCTCG    42720
AACTCGATCA CGATCTCTCG TCCGGGATGA CGCACGGCCT CCGCTTGGGC AAACCTGCGT    42780
GCAGCCTCTG GGGTCGGGAA CGGAAACTTC TGCGAGGCGT ACAGCTCCTG GTGCCACTTC    42840
GGCTTGTCAG GAATCGGCCC CATTTCCACG TACGTGTAAC CCGCGTCGGG GTCGAGTTCG    42900
AGCGTTTTCT TGTATTCCTT CGTGCCTGCC TTAGAGGGAA GGTGAGTATC GGTGGCTGTC    42960
AAGGTGACCT CACTTAAAAA CAGGGCAGCT GTAATTCACA TCACAGAAGC CGCATTTGTC    43020
AGGTTCAGGC AGAGGCTCGA AGTCACCAGC CTGGATCCGA GCCTCGACCT CATGGAACCT    43080
CTCGGTGATC CGCTCCCGCG TCCAATCGGT CAGGTCGTAG GGCGCAGTGG GCTTCGCCTT    43140
GATGCCCTTC TTCCCCGCCA TGAAGTAGTC GCCCGTCTTC GGAGCCTCCA CGTCATAGGT    43200
CATCGCGACC GCGAGCGCGT ACACGCCGAG CTGGAAGTCG TCACCCGGCG AGTTGCCGGT    43260
CTTGTAGTCC CGGACTCGAA GCTCACCGTT GACCACGACG ACCGCGTCGA TGAACCCTCG    43320
GACGCGGATG CCGTCCAGCT CGATGTTGAA CGGAAGCTCG ATGGCCGGCT TGGGCTGTTC    43380
ACACTCCTTG CAGTTGGTGT CTTTCCACGC CTCCGTAGAG CAGATCCCTC GCCCAGGGGT    43440
AGTCCAGATC TGCTGGCCCT TGTCCTTCCG CCACGCGATG AACTTCTCTA CCTGCTCCAG    43500
TCCAAGGTGG AACCGGCGCT CGATGTCACG CTCACCGTTG TACGGCCCGG ACCAAAACCA    43560
CCACTCGAAG TTCGGGGTTT CGTCGCAdAG TGCTCCGATG TCCTTGGdGT ACTCCTCGCG    43620
GAAGATCTCT TGTGCCCGTT CGAGGCTCAT CTCGCGGCCC TCGGCCAGAG CCTTCTCGTA    43680
GACCTCAGCG ACGGTGTGAA ACGCGGTGCC CTGCGGCAAC CACGCCGCAG GACGAGCCCA    43740
TACCTTGTCG ATGCGAGCCA GCTTGTACGC CTGCGGGCAA CGTGTGTATT GGTTCAACTG    43800
GCTGACGCTT CGCAGCGGCA GCAATGTCTT GGTGTCTGTC ACGCAGCGGC CATCCTTCCC    43860
TTGCCTATCG TCTCGTTCAG CGCCCCGTCG ACAGCGACAC TGAGCAGTTT TGCGACCTCC    43920
GACATGTCAA TCGGATCCTT GGGGAATTGG TCAGCCTGAG TCATCCTGAG CACCATCCAC    43980
TCGGTGCCCT TGTCGCAGTG GATCATGGTC GGATCAAAGC GAGTTCCCCG TGCTACGTAC    44040
TCGACTTTGT TCGCGGAAAG AATCAAATTC GACACAGGCC GATAAAGTCG TGAGGTGTCT    44100
TTTACACGAG GACTGCGGTA GACGAGCAGA ACTGAGACTG GGTCTTCGTC CAGTTGGCCC    44160
TTCCACCACG CCTCACACCT CTGCGCGAAC AGCCACCCTG GATGATCGGC GATGACTTGC    44220
GGTGAGGTGT GGACGAGGTT GTCTGCGAAC AGCTTTGCGA GCCGAGTGAG GGGCACGGGG    44280
TTTCCTTTCG TTGCGCGGCC TGGGTTGGCT CACACAACCG GTCGTGACTT TTAGGGCTCC    44340
GAGAGAAGCT CCTCGATGTC GTCTGGCCAC GACCAGAGGA GTTCACCCTC GGCGGTGAGG    44400
TTGGTGTGCT CGTTCACCCG GATCAGGAGA TCGTCATCCT CGATGCCTCG GGGGACGTAC    44460
CTGAACCCGC CGCCGGCCAT ACCTTCGTAG GGCTCGATGG ATGGGTCGAA CTCGAGCACT    44520
AAGTCGTCGT CGCGGAGCAT CTTCCACCAC GACAATAGGC GCTTCTTCTT GTCTTCGGAC    44580
ATCGTGCGGA AGCTACCCAC TCGCATGTAC TCGCCGTGAT CCCGGAGCCT CTGAAAAGCC    44640
TTCGACTTAT CGTGAGGTTT CCGCGTGTCC CACGGCCAGT TCTGCTGGAC GATCTGCCTG    44700
GTGGTCAACC GTCCTCCGTA GGTCTTCTTG TGCCACGACA CCGCTTGTCG AGTCACGCCA    44760
TACAGCTCTG CGATTTCGGT CTGATTAAAC CCCTTCCTGC GAAGATCTTC GATCTCGCTG    44820
AGAGTGAGTG GTATTCGGCT AGGGGCCGGA ACCACTGCTT TGTGTTGGAT TTTGCCGCTC    44880
```

-continued

```
ATGTTTCCCT CCATGAGAAA GGTGCGTGCG TCTCCGCCGA TTACGGAGAC ATGTTGGTGC 44940
CTGTCAAGGA TACCCCTAAT TTAGTTGCGT CTGCGGAACC ATATTCAGTT GTGTTCCCCG 45000
ACGCCGTGGC CGTCTCCCAC TGGGCGTGGG ATCGACTGGC GTTACGCGGT CGTAAATGTA 45060
GCGGCCTGCC CCACTCGGTA GCAAACCTTG TGACAGGTAT CACTTAGGTC GCCTTCTGTT 45120
ACACGTTGAC CTCGGGTTTC ATCGTCACGA CTCTCCTTTC TTAGACAGCC TCAAGATCGT 45180
TACACCGGCT TGCGAAGATG TACCTTCGCC TTGAATCCGG CCCTTGCCAG CTCGAACTCG 45240
ACCACCTGGC GGGCGGTCTC CTTCAGGTCG GACTTCGCCG ACAGCGGCCC GACGAACCCG 45300
TAGCTCTTGA TGTACTCCTC GAGGTCGATG TCGACGTACA GCGTGACAGG GACCACCGAC 45360
AAGTCACACC TCCAATTCGT GGGGCTTGAT CTCGTTGGTC ACGTCGTAGT CGTTCAGCAG 45420
CGACTGGAAG TCGGAGTCTG TCAAGTCGTC CAACTCATCC TGCTCGAACG GCGCGGGCTC 45480
GTCATGCCAC GTCTTCCACT GGTCGTGGTC GGCGCGGAAC CACTTCCGCA GATCCTTGAT 45540
GGCCTCGTCC TCGGTGGCGA AGACGTAGGT CTCGAGCACG TCCTCGTACT CGACGGTCAG 45600
CGACCAGACG GTGATCTTCA CTCCCCGTTC ACCTCCGCTT TGTAGTTCAT CTCGGCGGTC 45660
TCCTCCTAGT TGGGTAGCAG TCGGTTGTAC TCGTCGTGGC TGATCTCGCC AACGATGAAC 45720
TGGCGCATCA GATTTGCGAC CGAAGCCGCG TCCATCCCTT CGGGAATGGG CTTGGCGTGG 45780
CCGAACTGCC AGTCTCGTGA GCGCCAGCGG AACCAGAGTT GGACCTTGTC CAGTGAGGTC 45840
AGGTGCAGGC ACTGAAACGT CATGCCTCCG AACGGGAACT CCATCACACC TCCTGTTTGA 45900
CCTTGACGGT GTGGCCTGTC ATTACTTCGT GGATTCGGAT GCTGGTGCCG AACGTCTTTC 45960
GCGTCTCGGC CTTGAACTCG GTGGAGCACC CCGAGCACTT CGCTTTGAAT CGCACTAGCA 46020
GTACCAACGC TTTCTGCAGA ATCGGGACTT GCCGCCGTCC CGGTTGTCGT TGTCCCGGCG 46080
GGCTTCGCCC TTCGGTGATT CGTCACATGA CGGAAGCTCG CCATGCTTGA TGTGCCATGC 46140
GTCGTCGGCG ACTTTTCCGC CGTGCTCGGC GATGTGCGCT GCGCTCCGGT ACTCACAGAG 46200
CGGGGAAGCC GATGCCTCGG CGATGATCCC AGGCAGGTTG CCTAGAACCA CCGCCAAGCA 46260
CATCAGCAGA ACGACGTGCC ACGCCTTCAT CAGCCCGCCA GCGCGTGGTT CATCGCCGCG 46320
TTGCGGCCGT CGCGCTGACC GTGGGCATAG CCGCTGAGGT CGTACCGGGT CCGAGGCTTG 46380
ACGTTCTTGG TGCGAGGATG CGCCTGGCGC AGAGCCAGCG CAGCTCGTTC CTTGTCGCCT 46440
CGGTAGAGCA CCAACGCTCC CCCGCCGGCC GATTCCACGG CCTTGTTCTC CTCGGCGGTC 46500
AGGCGTTCCT TGACGGCCTG GGCGAAGCCT GCGATCCACG ACCGGCGGTA GCTCTTGAGC 46560
TGGCCAGCGG TGCTCTTCGG CTTGTACTCC CCGGTGTTGT AGTCGTACTT GTACCGAGGC 46620
TCGAAAGCCT GCTCCGGGCG GACATTCTCA ACCAGGCGCA TCATCTGCGG CTGCATGATC 46680
GACCAGAGGA ATTGGAGCCT CTCGATGTGG CGGGGCACGC CGTAGACGTA GATCCGCTGA 46740
CCGCCCGTGA GGCTGGCGTA CACCGTCTTG CAGTGCAGGG CCTGAGCCAT GCCGTGCAGC 46800
AACAACGCTT GTGCGGCAAC GTACTTGCCG GTGACGTAGG TGACCCACTG GATGGCGTCG 46860
GGCAGGTCGG TGGTGTCCAA CCCTTGCTTG CTCGCCTCGA CCTGGGCCAT CTCCAGCCCG 46920
TACTTGGCCA TCAGCTCGAA CGCTTTCGCC TGGAACACAG CCTCTTCCGG CGTACCGGCC 46980
ACGTCTTCGG CCTGGCGCAG CAGCTTGGCG ACCTTGTCCT GCATCTTCTT CGTCTTGCCG 47040
TCGATCATGG TCAGTACTCC TTCTTCCAGT TGTTCCGGTT GCCCTTGCCG GGGCGCTTCA 47100
TCTCTCGCTT GCGGTTACGG TGCGGCTGCG CCGCGTTGGA GAGACGCAAC TCGAGCCGTG 47160
CCTTGAGCTG GTCGCTCATC TTCTTCACCT CTTCTGGTTC AGCGGATCTG GTCGACGTGG 47220
ATGCAGCCGA CGCGGTCTGG CCCGAACTCG GGAGCGAAGC CCAAGACTTC GTCCTCCTCG 47280
CATGGGAACG CTCGCTGGTC GAACGTGATT GGGTCGGCCG AAGCCTCGTA TGGATCGGCC 47340
AAGGCCATCG CTCCGACCGC TGTAGCGAAT GCAACGACGA CGGTGATCAG GTGCTTCTTC 47400
ACTCTTCTTC CCTCCACTTT TGGTCTGCGA GAAGCCTTCT GGCGATCTCG ATAGGTTCGA 47460
TCTCAGGAGT CACTCATCGC CCTCCAAGAT CTTCAGGTTG GCCAGCAGTG CATTGGCCAC 47520
AGCTCCGATG TGGCCACCGC CCTTACCTCC ACGGCGGGAG TACTCGCGGT TCGCGGCCTG 47580
CATGAAGTGG AACCTCGGTG AGCCGTCCTC GTGAACCCAC GAGGCTTTCT CGGCGGGCAG 47640
AGCCCGGTTC ATCTCCACCG ACATCGTGAC GATGATGTGG TCCCTCTGGA GCCGAGCCTC 47700
GGTCTCGGCG TAGTGGGCAG CTTGGATTAC TGCGCCTCGT GTGGTCATGT CTTCTCCTTC 47760
GGTAGATGTC AAGCTGTCGT CACCACTCTT CGACCGGTAT CGGTTTGTCA CAGCCAGCAA 47820
GGATCGCGGC GTTGCTGCGG TGATGCCCGT CCCACAGCGT CTTTCGGTCC CTCGAAACCT 47880
CGAGGGGTTC GAACGGCCAC TCGTTCGATG AGTTGAGGAT GTCCACGACT TCGTGGACCT 47940
TGGCCCAGAA CTTGCCGGTC ACGCCTCCCT GGTAGTTGTA GCGGGGCGTG GTCTGGTAGA 48000
ACTCTTCGAG CACTGGTCCG CTGTCGGCGA CGGTGCAGTC GACACCAGCG CAGGACATGC 48060
AGTCGCTGGC GCGGAGCTGG GCAACTTCAT CGGTGGTCAT GAACGCCGTG GTCACATCGA 48120
GCCTTTCAGG TGTATGTCAA GCGGCGCGGA CGCCGGAATC GGAGAGGTAG ACGCGGTCAG 48180
CTCCCAGGAA CGGAGCCTGT GTGTTGGCGT GGACGAACGT GTCGTTCTCG TAGGGGTTGT 48240
AGGCGATCTT CGATCCCACG AAGTCTTGCG GGAGAAGCGA GATCAGCTCG CCTACGATGC 48300
CAGCGTGGAC CACCTTGCGG CGCTCGCGCC GTACCTTGTC GCGGCCGGCC GGCCGAACCA 48360
CACCCTTGGC GTGGGCCAdC AGGACGTGGC CGCTGCGGTG GATGACTCGA CCCTTGAAGT 48420
CTCCCTCCAA GGCTTGCACC GAGTACCACG GCTTGCCCTC GCGGTGCGTG CGGTGCAGGT 48480
TCTTGTAGAC GAAGACTCGG ATCGGCTTGG GAGTCATGAG ACCTCCAGTG TGCGAACGGC 48540
CTT6TAGGCA CTGATGAGTG ACGCCCCCGA CAGCTCGTTA CCGTGCAGGT GATACCTGTA 48600
TTTCAGATAC ACGGCTTGGT CGACCGGCTT GTACTCGACC GAAGTGACCT CGACAACCAT 48660
CCCGTCGATG ATCGCGAAGT CTCCAGCGCG GAGATGGGTG GGGAATTTGA TCTCGGTGTT 48720
GACTACGGTC ACAGCTTCGA AACCTCCCAG GTACCAACGA ACTTGCCGTT GCGCTTGATG 48780
TATCCGCTCT CACCGGGCTC GTACCAATCG ACCTCGAACC CGTAGCGGGC GGCGCAAGCC 48840
TCGAGGTGGT CGAGCAGGAC GCGGCGACCG GACGCGGTAG CTTCTCCGGT CAGCCCGCTG 48900
TCGTTCTTGC GGACGATGAG CTTGAACACT TGGTGCCTAC CCTTCTGCGA TGTCTCGGGA 48960
GATCTCGGCG AAGACTTTCT TTGCCCACGC CACGCCGTCC CAGGTGATGT CGAACAGTGC 49020
CTCGTAGAAC TGGTCTCGCA AGGCTTCGTT GCCGTCGGCC AGCGTTGTGA CGAGCCGGTC 49080
GATGCGGTCC TCGTGGAACT TGTAGACCGA GTGGTTGTAC GGCTCAGCCA TATTGGCGTT 49140
GGCTCGTTTC ACGTTCTCAA CCACGATGGC TTCGAATAGG TGGTTAACCA GCTCCTCGGT 49200
CATGTTCTAT CTCTCCTCAG TAGTCGCTGT GCTGGGTCTC GAAGCCTTCG AGGTCACCGA 49260
CCTCGTCGTC GTACGCGCTC GGGTTGCCGC GCCAGTCGTC GCGGAGCCTT TGACCGCTGG 49320
CGTTGTAGCA GGCACCACAG TTCGGGCAGT CCACATCGCT CTGGCCGTAG TAGCGGCAAA 49380
CCTCGCCGCC GCAGCGTTGG CAGTCCCACG CGCTGTAACC AGGGATCAGG AAACCTTGGT 49440
CGTCGGTCTG ATCAGGGATG CGTCGGAAGT TCTTGGCAGG CATAGCTACT CCTCATAGAA 49500
ACTCGTGGTT GATGGCTCGG TGGGCAGCCT CGCGGAAGGT CAGCCCGTCG TCGTACGCGT 49560
CCCGGTACGT CCAGTCCGCG ATGTCTTGGT AACCAAGACC AAAGGTCTCG GTCATGTAGC 49620
CGTCCAGCGC GGCCATCCAG GTCTCGAAGC TCATGTCTTC CCTCACTTCT TTGTGGTCGA 49680
```

-continued

```
GAACAGCACG TTCCTGCGGC CGTTGACGCA CAGACCGCAA CGGGCACAAG CCGATCCCTT    49740
GTCGTTGATC AGGTCGATGG CTTTGTTGTT CTCCGGGCAG CGCACCGCCG TCGGAAACTC    49800
GGCCTTGCCT TTGGCGAACG TGGTGTCGAC GTAGGCGATG TTGATGCCCT TGTCTTCCAA    49860
GAAGCGCGCC ACGTCGATGT TGTCCGGGTC TGCGCTGAAG TACAGCGCCA GGTTGTCGAG    49920
CCTCTGCGAG TGCAGGTAGA CAGCCGCCGT CTGAACCCTT GTGTAGGCCC AGAACTGGAC    49980
ATCCGGGTTG TCGCGGATGA CTCGACCCCA AGCGGCCACA TAGGTGGGGC TGAAGAAGTC    50040
TCCATCCCAG TGGATGCGGA ACAGCTTCGG AGCCTTGCGA CGGTCGCAAT CCTTGACGAA    50100
CTCGGCGACC ATCTCGGACA GCAGCGTCAC GGTGTCTGTC AAGTCAGCGT CACGCAACAG    50160
TTCCCAGTTG TGCAGCAGGA CCGAGCTGAC AGCCTTGCGA ACTTTCTCCA GCTTGCCGGC    50220
GTAGCACACC TTGGCACAGA AGGCCGTCGC GTCCGGGCAG GAGAAGCCTT GACCGGAGGG    50280
CAGGCCGATG CTGTTGGCGA TACCTACGGT GGCGTTGCCG CCCTTGGTGA CGTGGACGTA    50340
GTTGGTGACC TTGCGGTCGT TCGAACGCTT CAGCTTGGCC ATACCTAGCC TTCCTTCGGT    50400
GGCTGTCAAG TTGTTGGATA CAAAGCGCCC CGAGAGGGAG TCGAACCCTC ACACCGCGAA    50460
CCGTCGCGGG GCCACCGTGC CTAGTCGATA GAGGTCACTC GACTCTCGTG GACGTAGACC    50520
ACGGTGTTGC CTACGTTCAC CGCGTAGTAC AGGCCATCGG CACCTCGTAG CTTGTGCCGA    50580
ACCGTGCCCG ACGTGGCCGT CATGTCTTCG CCCCAGTCGG CGTTAGGTGC CCAGGTGACT    50640
CGCATGGTGA TCCCTTCAGT AGTCGGTGGC TGTCAAGTCA GCGGATACGG ACGTACCCGT    50700
TGCCTCGAGC GACGTAGATC TTGCCGTCGA TGTAAACGCG CTGCTGCTGG TTCATAATCC    50760
TATTCCTTTC GGTGGCTGTC AAGTCTCAGG CCCAGCGACG AGTCGTCGGC CGGGGGCGGC    50820
GCACCTTGGG CGCGTTGGCT CGCGGTGCCT TACGGATGGC GGTGCCTACC GTGATCTCTT    50880
CCAACTGGCG TTCAGCCAGG CCGACAGGCC GGGCGTCACC GGGCAGTTCG ATCTTGTAAT    50940
CGAAGTCAGT CCACCCCTTC AGACCCTTCT CCAGCTCGCG ATCCAACAGA CGCGGAGCCG    51000
ACAGCTCAGG CGCAACAAAC GGTGTCTTGA CGCTCTCGCG GGCAGTAACC CGAACCTCAC    51060
GGTGCTCAGC GAAGACTGGC ATAGTTCACC CCTTTGGTGG ATGTCAAGCC TGAGCACCAA    51120
AGCTCAGGCG TAGTGGGTAG TCGGGAATCG AACCCGATAG CTTCATAGCC ACGTTCTACG    51180
GCTCAGCCAT AGCTCAGCGA TCATTCCATC GCGCCAAGAG CTACCCTCCC GAATGCCGAA    51240
CCAAAGCTCA GCATTCGTAA GTGTGTATTC TCCCCGTGGC TCAGACAGTA TCTATCAGAA    51300
CCTAACCACA GGTCTACATT TAGTTATCCG CAGTGCTCGC ACTTTAACGG CATCGAGCTT    51360
CCGCCGACCC TCAGTCCTCT GGCAGCGAAC TAAAGGTTTG AGTCGGGCTG CGGCCCTTCT    51420
CGGTCTTGCG TGATTCTCAC TCTACCGGAT GTTTCGGTGG CTGTCAAGCG GGCCGTTTTG    51480
GTGTTGCAAC GATGCCCTCG TTTAGCGCCG CTGGCGTAAT GCGCTACCCG CCTGATCTCA    51540
CCGGTCCAAG TTGGTGATGC TTGCAGCTTA CCCGATAACC GGGTGGCTGT CAAACCGGAG    51600
AATCTTGCCG CCGGATTTTC ACCGGCACCG GCACGATCCT CTCGGATCCG CCTACCGCCT    51660
TGCTGCTGCG GTGACACAAG AATGCACTAC TGGCCGGGTG GCTGTCAAGC CCTAATCGCA    51720
AATTGGTGCC CTAGCTGCAG ATATGGCGCG TTCTCGGTGG CTGTAAAGGG CACTACGTGC    51780
CGCTATCCGC TGGTCACGCT GGACAGTCCC GGCAGCCCGT GCCGCGCATA GGCTGCTCAC    51840
TACGTGCCCG GTATCGGCGT TGTCGTGCCG CTGTCGTGGT CGTCGCCCCG TCGCTGTCGC    51900
TGGTCTCGGT GGCATCGCTT GACAGTCGCC CCGCTATCCC CCGTTGCCGC TGGTCAGACG    51960
CTAATCCGCT TATTTCGCAT AGGCTGCTCA CTATCGCATC GGTATGCGTA TGCGCTGGTC    52020
ACATATGCGT GTGGTGGTGG TGTGGTGTGC GTGTGTTTGC GCTGGTCAGC CGTGTGCGTA    52080
CCGTATCCGC ACACTGTGCT TGTGCGTTTG CTGTGTGTCG AGGCCGGCTC TCGCATCGTC    52140
GCATGTCAGC GCGGGTATGG GCGTGTATCG CACGCTTTGC TAGCCGCGTG CCGCGGCGCT    52200
CTCGCATCGC ATCGAGTGTT TGCTGTGTCT CTCATCGTCG CAGGTCAGAA GGGGTAGGGG    52260
GGTTCCCCCT AGGGGTCGGT CCTTGACCGG TCGGTTA                             52297
```

It is known that during the establishment of lysogeny, the L5 genome becomes integrated into the mycobacterial chromosome via the phage attachment site (attP). Integration-proficient plasmid vectors have been constructed which efficiently transform both fast-growing and slow-growing mycobacteria through stable integration of the plasmid sequences into the bacterial chromosomal attachment site (attB).

Because the L5 sequence is now known, and because L5 has been previously characterized, the use of transcriptional promoters with this mycobacteriophage may be evaluated efficiently, and host synthesis inhibition may also be evaluated efficiently.

FIG. 1 represents the genome organization of the entire L5 genome. DNA analysis has indicated that the L5 genome is organized into a right and left arm with the attachment site at the center of the genome. The integration functions have been successfully employed to construct integration-proficient vectors for mycobacteria.

Part of the L5 genome is not essential for mycobacteriophage growth. By way of example, gene 71-70-69 may be deleted without affecting the lytic cycle of the L5 phage. Therefore, it may be a suitable region in the L5 mycobacteriophage for the insertion of reporter genes. As a general role, it is critical that reporter genes be inserted into non-essential regions of the mycobacteriophage. Otherwise, the mycobacteriophage will be unable to survive and replicate.

For example, the L5 mycobacteriophage may have introduced therein promoter gene 71 fused to reporter gene lacZ, and this reporter mycobacteriophage would be capable of rapid diagnosis of mycobacterial infection and accurate assessment of mycobacterial strain drug susceptibilities.

Another mycobacteriophage which may be successfully used to produce the reporter mycobacteriophages is the mycobacteriophage TM4. TM4 has been used to construct a first generation reporter mycobacteriophage, and has the ability to discriminate between *M. tuberculosis* and BCG. A shuttle plasmid may be employed with TM4, and may be useful in the construction of recombinant and other mycobacteriophages. Unlike L5, which is a broad host-range mycobacteriophage, TM4 is a species-specific mycobacteriophage. However, TM4 is not as well characterized as the L5 mycobacteriophage, and therefore it is more difficult to analyze its functions.

DS6A is a mycobacteriophage that has been found to be specific for the *M. tuberculosis* complex of mycobacteria. It has been shown to infect both *M. tuberculosis* and BCG. It has been demonstrated that DS6A can infect over 3,000 different types of *M. tuberculosis* strains. Current efforts are under way to develop DS6A shuttle phasmids containing Firefly luciferase genes as the reporter molecule.

Figure 31:
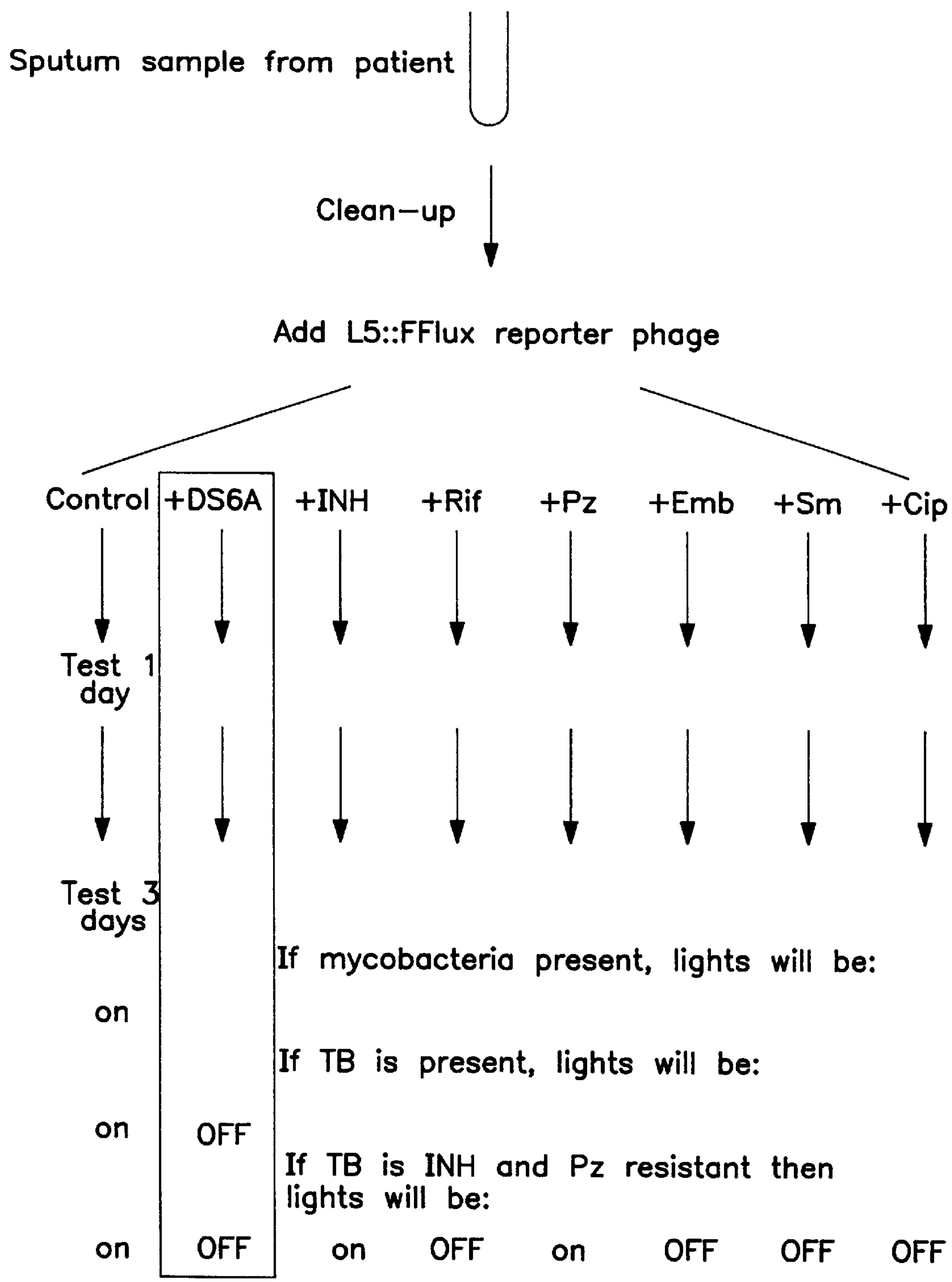
FIG. 31 represents an outline of a method which can be used to diagnose tuberculosis and determine drug susceptibility using reporter mycobacteriophage DS6A.

Different mycobacteriophages have varying host specificities. For example, DS6A mycobacteriophage is specific for only *M. tuberculosis* strains. In contrast, L5 and TM4 mycobacteriophages are specific for several mycobacteria, including *M. tuberculosis* and *M. smegmatis*. In order to diagnose tuberculosis according to the invention, it is necessary to use mycobacteriophages which are specific for *M. tuberculosis* strains only. Because DS6A mycobacteriophage is specific for *M. tuberculosis* strains only, it can be used to narrow the host specificity of L5 and TM4 mycobacteriophages so that L5 and TM4 mycobacteriophages can be used to accurately diagnose tuberculosis. For example, a clinical sample (control) can be infected with L5 reporter mycobacteriophages. Another clinical sample from the same source (experimental) can be co-infected with both L5 reporter mycobacteriophages and DS6A reporter mycobacteriophages. If the photon signal generated by the experimental sample is lower than the signal generated by the control sample, a diagnosis of tuberculosis is confirmed. If, however, there is no decrease in photon signal, then the diagnosis for tuberculosis is negative. Hence, DS6A mycobacteriophages can be used to confer specificity for *M. tuberculosis* onto L5 mycobacteriophages. FIG. 31 represents an outline of a method which can be used to diagnose tuberculosis and determine drug susceptibility using reporter mycobacteriophage DS6A.

In anticipation of the need for a diverse set of mycobacteriophages that can effect a broad or limited range of mycobacterial cells, a total of more than 50 unique mycobacteriophages have been collected and isolated by the inventors. 21 new mycobacteriophages have been isolated from soil samples from India, France, England, Israel, Tunisia, Carville, LA and New York. In addition, another 30 mycobacteriophages from both the Centers for Disease Control in Atlanta and the World Health Organization Phage Reference Laboratory in Amsterdam were collected. The characterization of the nucleic acid content of the phage particles of 30 of these mycobacteriophages have revealed that all of the mycobacteriophages contain double stranded DNA whose genome sizes range from 45 to 100 kb as sized on pulsed field gels. Restriction analysis has shown that all of these mycobacteriophages are different, except that one of the mycobacteriophages from France had a considerable similarity to the L5 mycobacteriophage, which was originally isolated in Japan. The host range of the mycobacteriophages varies greatly, some being able to infect only *M. smegmatis* and others being able to infect *M. smegmatis*, BCG and *M. tuberculosis*, but not *M. avium*. These mycobacteriophages may be developed into reporter mycobacteriophages and cosmid cloning systems, and may provide a source of useful transcriptional translation initiating sequences, transcriptional terminators, or host-range specificity genes.

In addition, the choice of reporter gene and its method of expression are critical. It is necessary to choose a reporter gene whose product would not normally be found in clinical samples, but whose product is also easily detectable.

Luciferase reporter genes have been used in many diversified biological systems, including *E. coli*, cyanobacteria, phytopathogenic bacteria and Bacillus. The presence of luciferase reporter genes can be detected by the emission of photons in the presence of a substrate, such as luciferin or decanal. Luciferin and decanal can permeate mycobacteria, and thereby allow for the detection of gene products, such as photons. Since one molecule of the luciferase gene product can yield 0.85 photons of light, it is the most sensitive biological reporter molecule known. The preferred reporter genes of this invention are luciferase reporter genes, such as the Firefly lux gene (FFlux), the *Vibrio fischeri* lux genes and the *Xenorhabdus luminescens* lux genes, as well as the *E. coli* β-galactosidase (lacZ) genes. Luciferase genes, especially the Firefly lux gene, generate a high amount of luminescence activity. They generate photons, the detection of which is simple and sensitive, using commercially available luminometers that can detect 100–1000 molecules of luciferase with a linear relationship to enzyme concentration. In addition, it is unlikely that clinical samples will contain significant levels of endogenous luciferase activity.

In choosing transcriptional promoters to be introduced into the mycobacteriophages, it is desirable to use strong promoters since this will increase the sensitivity of the system. In addition, it is important that the promoter be active following mycobacteriophage infection. Promoter candidates currently available are the BCG hsp60 promoter and the L5 gene 71 promoter, which are of comparable strength. The hsp60 promoter gives good levels of luciferase expression from plasmid recombinants, but lower levels of luciferase expression where the mycobacteriophage is TM4. It is possible that the reason for this is that the hsp60 promoter is shut off by the TM4 enzymes following infection, thus producing only a modest level of luciferase. The gene 71 promoter may behave in a similar manner with the TM4 phage since the gene 71 product is a good candidate for the L5 repressor and is expressed at high levels in the absence of other mycobacteriophage functions. Knowing the sequence of the mycobacteriophage used will help in identifying, characterizing and cloning the appropriate promoter to be used in the reporter mycobacteriophages of this invention.

There are several methods which can be utilized to introduce the reporter genes and transcriptional promoters into mycobacterial species-specific mycobacteriophages. One method is the utilization of shuttle phasmids. When utilizing shuttle phasmid technology, it is necessary to know the sequence of the mycobacteriophage so that the reporter genes are inserted into non-essential regions of the mycobacteriophage. Insertion of reporter genes into non-essential regions permits the mycobacteriophage to survive and replicate. In order to use the shuttle phasmid methodology, it is necessary to first generate a cosmid library of large double-stranded recombinant DNA fragments of mycobacteriophage. This can be done using cosmid cloning in *E. coli*. Next, the cosmid library is introduced into the mycobacteria of interest to select for cosmids which have been inserted into non-essential regions of the mycobacteriophage. The shuttle phasmids, which consist of the *E. coli* cosmid, the reporter genes and mycobacteriophage promoters, may then be characterized. Shuttle phasmids can be propagated in *E. coli* as plasmids, and propagated in mycobacteria as mycobacteriophages.

A second method of introducing the reporter genes and transcriptional promoters into mycobacteriophages is by homologous recombination. First, non-essential regions of a mycobacteriophage must be determined. Again, in order to do this, it is necessary to know the sequence of the mycobacteriophage. Consequently, L5 is an ideal phage to use with this method as its genome has already been sequenced and characterized by the inventors. Next, plasmids are constructed wherein reporter genes hooked to transcriptional promoters are flanked by mycobacteriophage non-essential region sequences in mycobacterial plasmids. Then, homologous recombination systems may be utilized in *M. smegmatis* or *E. coli* to perform gene replacement whereby the plasmid constructs containing the reporter genes are put into mycobacteriophages.

A third method of introducing reporter genes and transcriptional promoters into mycobacteriophages is by use of transposons. For example, transposon IS1096 may be utilized. In order to use this methodology, reporter genes and transcriptional promoters are put into transposons, and the transposons containing the reporter genes and transcriptional promoters are delivered on plasmids in mycobacteria. Next, it is necessary to grow up the mycobacteriophages on a strain such as *M. smegmatis*, which strain contains the transposons. At certain frequencies, the transposons will hop into non-essential regions of the mycobacteriophages, thereby introducing themselves therein. The mycobacteriophages are still viable, and contain the reporter genes and transcriptional promoters.

A fourth method of introducing reporter genes and transcriptional promoters into mycobacteriophages is by debilitated phages packaged into phage heads and tails (phage particles). To utilize this methodology, it is necessary to develop helper phage systems which allow for pieces of DNA containing pac sites to be packaged. These helper phages allow for the synthesis of head and tail genes at will in mycobacteria, prevent themselves from being packaged into phage heads and tails, and facilitate packaging of pacmids into phage heads and tails. Helper phage systems may be generated from the L5 mycobacteriophage. The genome of the helper phage is put into the mycobacterial chromosome, at which time the mycobacteria are grown up. Next, pacmids which comprise phages which have pac sites, reporter genes, transcriptional promoters and mycobacterial replicons are transformed onto the mycobacterial strain. The production of head and tail proteins may be induced, for example, through an increase in temperature, and the pacmids are then packaged into phage heads and tails. The L5 genome has cohesive (cos) termini. This suggests the possibility of constructing L5 cosmid vectors, which could be packaged through the cos sites into L5 particles either in vivo or in vitro. Then, a large number of genes could be easily and efficiently delivered to mycobacteria.

Packaging into phage heads and tails may also be utilized in a fifth methodology wherein the pacmid is a plasmid. The methodology is similar to the methodology wherein a debilitated phage is used, however, instead of using phage pacmids, the pacmids comprise plasmids which have pac sites, reporter genes, transcriptional promoters, and plasmid replicons.

Finally, direct cloning using recombinant DNA techniques in vitro may be used to introduce reporter genes and transcriptional promoters into mycobacteriophages. This methodology consists of ligating a mycobacteriophage, identifying or introducing unique restriction enzyme sites in non-essential regions of the mycobacteriophage, cleaving the mycobacteriophage with the restriction enzyme sites, and cleaving DNA which encodes the promoter and the reporter gene so that it has the unique sites flanking it on either side. Next, ligation is set up in vitro between the cleaved mycobacteriophage with the unique restriction enzyme sites and the reporter gene cassette. The result is a circular DNA molecule which consists of the mycobacteriophage, the reporter genes and the transcriptional promoters. The circular DNA may then be electroporated directly into mycobacteria.

EXAMPLES

Expression of Reporter Gene lacZ and FFlux in Mycobacteria

A promoter probe vector was constructed which incorporated a truncated *E. coli* β-galactosidase (lacZ) gene as a reporter probe into a shuttle plasmid vector that replicated in either mycobacteria or *E. coli*. Random DNA fragments from the three mycobacteriophages L1, TM4 and Bxb1 were cloned into a unique BamHl site immediately upstream of the lacZ gene and screened for their ability to produce β-galactosidase. This established that lacZ could be used as a reporter gene in the mycobacteria, and identified the DNA sequences which could effectively express foreign genes in both *M. smegmatis* and *M. tuberculosis*. β-galactosidase activity could be detected from lysed cells using OMPG, or from unlysed cells using either X-gal or a fluorescent methylumbelliferyl β-galactosidase derivative. The promoter hsp60 gene highly expressed the lacZ gene in both *M. smegmatis* and BCG.

Figure 2:
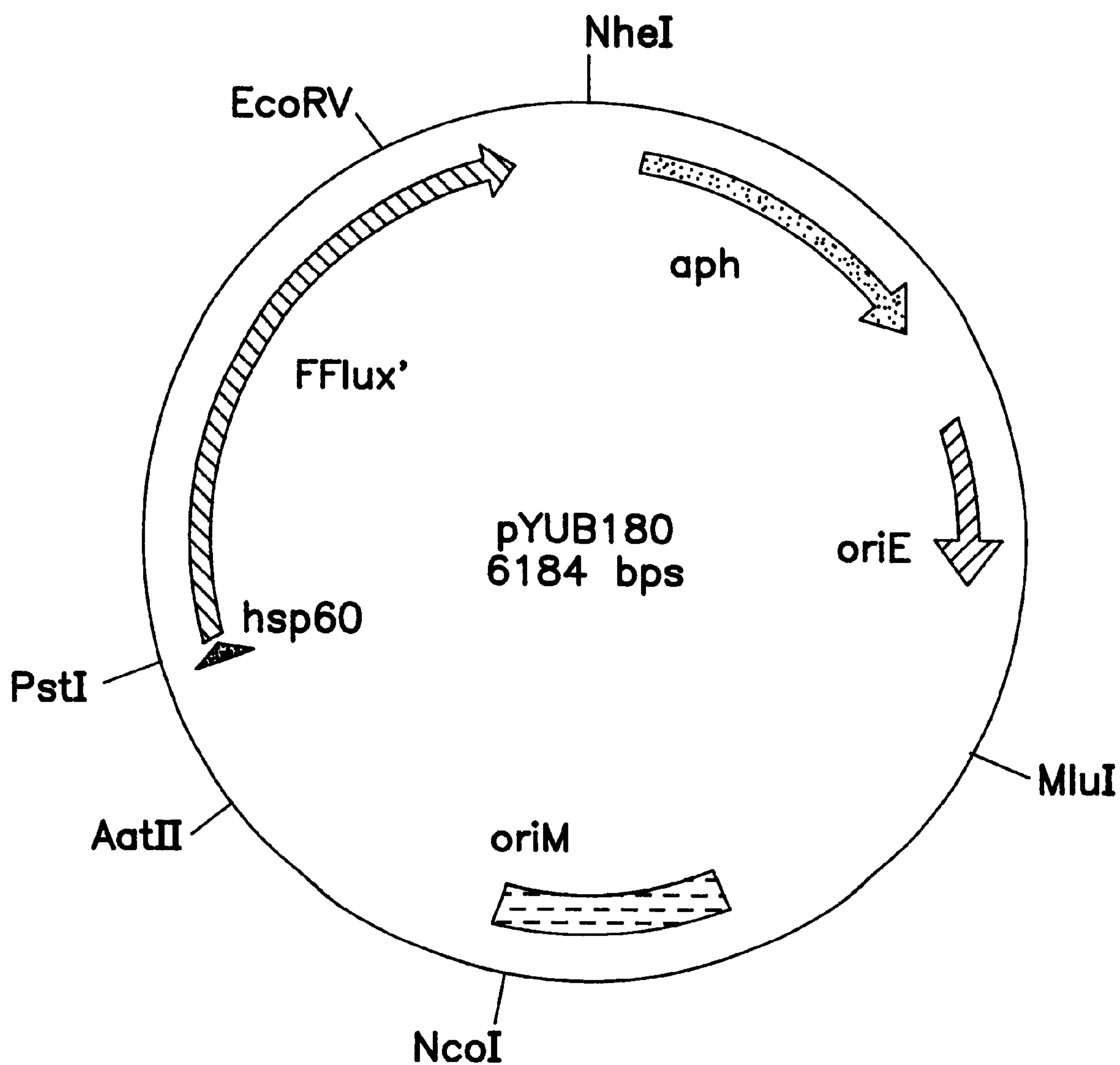
FIG. 2 represents a luciferase shuttle plasmid pYUB180 wherein reporter gene FFlux is fused to the BCG hsp60 promoter.

The FFlux gene was cloned into pMV261 downstream from the hsp60 promoter in plasmid pYUB180 (see FIG. 2), which plasmid was shown to express the FFlux gene in *M. smegmatis*, BCG and *M. tuberculosis* H37Ra. The expression of the FFlux gene was detected by observing luminescence of mycobacterial clones containing the cloned gene in the dark room, and verified use in photographic film. This demonstrated that the luciferase was expressed in the mycobacteria, and that luciferin, the substrate used, was able to penetrate mycobacterial cell walls and yield photons expressed by the mycobacteria.

Detection of Photons In Mycobacterial Cells Expressing FFlux

Figure 3:
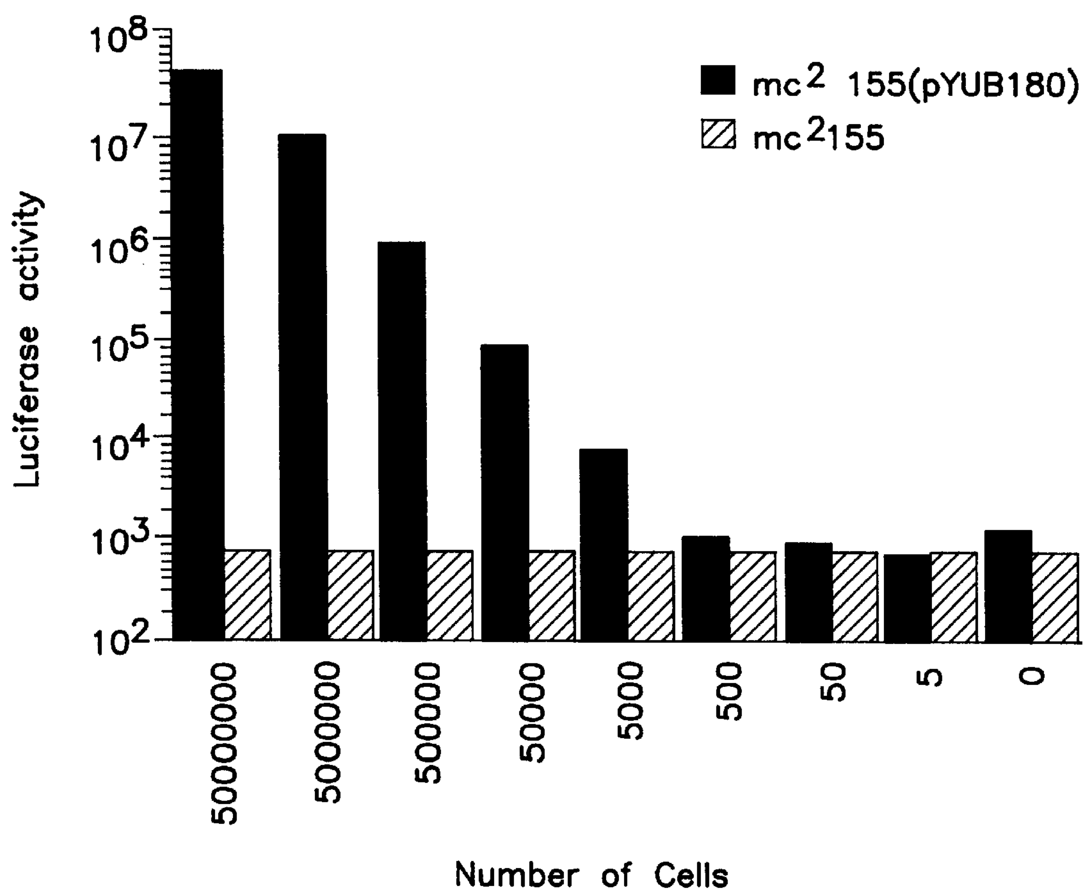
FIG. 3 represents the amount of luciferase activity of *M. smegmatis* which contains the pYUB180 shuttle plasmid and the FFlux gene.

The expression of FFlux from the plasmid pYUB180 in *M. smegmatis* provided a model with which to determine a minimal number of individual cells detectable with the luciferase assay. *M. smegmatis* containing pYUB180 were grown in the presence of kanamycin to ensure that every cell contained the plasmid. The cells were diluted 10-fold serially and the amount of luciferase activity was determined using a luminometer. FIG. 3 shows that the amount of luciferase activity from $5\times10^7$ cells approached $10^8$ luciferase units, though at this level of activity the luminometer was unable to yield an accurate measurement. However, the activity decreased in a linear manner down to 1200 units for 500 cells. Hence, 5000 cells expressing the FFlux gene can be clearly discerned above the background measurement, which approaches the number of cells that one would expect to observe in clinical samples.

Demonstration of Luciferin Uptake by Mycobacteria

Figure 12:
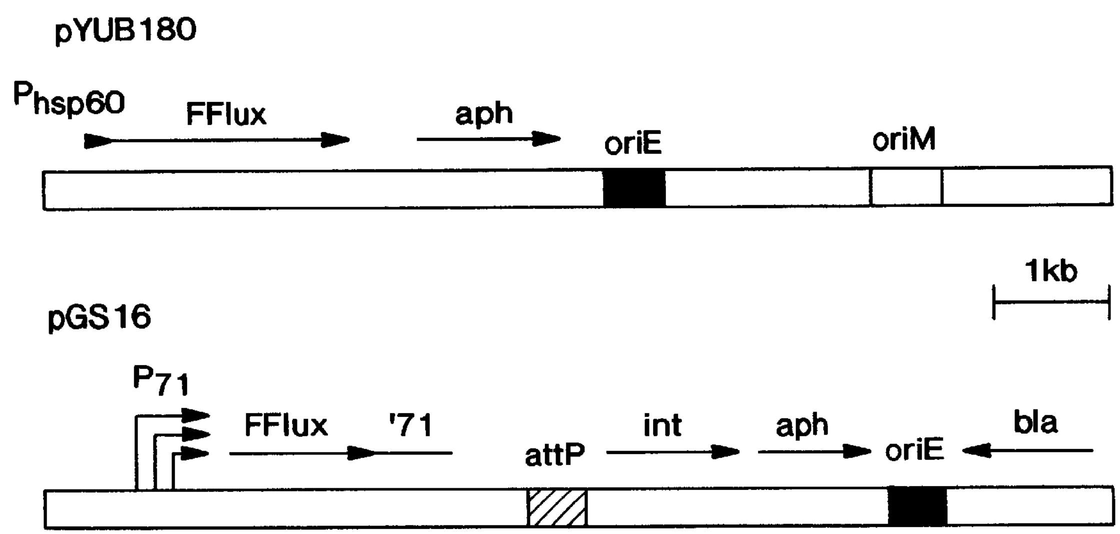
FIG. 12 represents a schematic diagram of the extrachromosomal plasmid pYUB180 and the integration plasmid pGS16.

In order to ascertain whether the substrate luciferin could be transported across the intact mycobacterial cell wall, the firefly luciferase (FFlux) gene was cloned downstream of the hsp60 promoter in a mycobacterial extrachromosomal plasmid, and was also cloned downstream of the gene 71 promoter of the mycobacteriophage L5 in a mycobacterial integrating vector. FIG. 12 shows a schematic diagram of the extrachromosomal plasmid pYUB180 and the integration plasmid pGS16.

Figure 13:
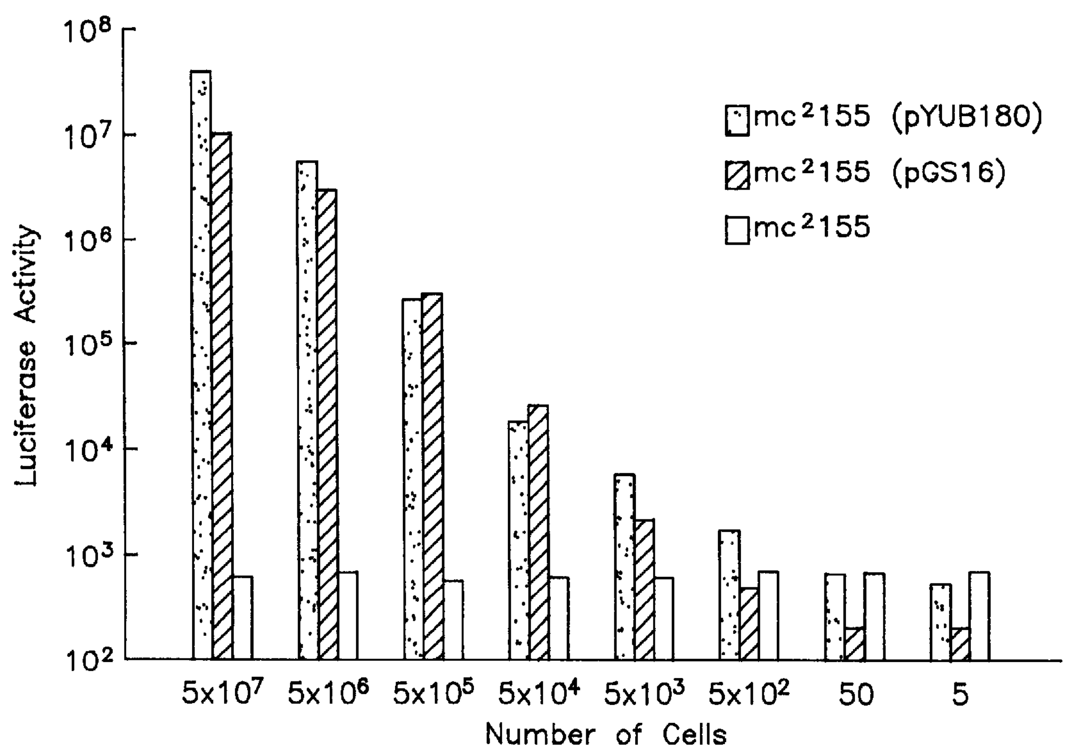
FIG. 13 represents the expression of luciferase by *M. smegmatis* after plasmids pYUB180 and pGS16 were electroporated therein.

Both of the luciferase constructs were electroporated into the *M. smegmatis* strain $mc^2155$. $Kan^r$ transformants were grown to a density of approximately $5\times10^8$ cells/ml and 10-fold serial dilutions were prepared. 100 μsamples were mixed with 250 μl of 0.1 M Na citrate, pH5 in a 13×75 mM polystyrene tube. This mixture was placed in the monolight 2010 luminometer (Analytical Luminescence Laboratory, San Diego, Calif.) and 100 μl of 1 mM luciferin (Sigma, St. Louis, Mo.) was injected into the tube and the luciferase activity was measured as relative light units. As shown in FIG. 13, upon the addition of luciferin, luciferase activity was readily measured from intact mycobacterial cells infected with both the extrachromosomal and the integrating vectors. Serial dilutions indicated that it was possible to detect as few as 500 to 5,000 *M. smegmatis* cells expressing firefly luciferase, thereby establishing that the luciferase-luciferin system could be developed as a sensitive reporter system for ATP in mycobacteria.

Distinguishing Drug-Resistant Mycobacteria From Drug-Sensitive Mycobacteria Using Luciferase Activity Since Firefly luciferase activity requires ATP, and ATP is produced only by living cells which are metabolically active, luciferase is a powerful indicator of the metabolic abilities of a bacterial cell. Since anti-tuberculosis drugs are likely to significantly decrease the metabolic activity of a cell, the measurement of luciferase activity should provide a sensitive means of distinguishing drug-resistant mycobacteria from drug-sensitive mycobacteria.

First, the kinetics of the production of luciferase activity of *M. smegmatis* containing pYUB180 following the addition of streptomycin, isoniazid, ethambutol, rifampicin, ciprofloxacin, novobiocin or cyanide, added at levels that inhibit the growth of *M. smegmatis* in plate assays, was measured.

As shown in FIG. 4, Panel A, the levels of luciferase production were 100 to 1000 times less at eight hours after the addition of the drugs compared to the untreated control.

Next, this approach was used to distinguish drug-resistant from drug-sensitive mycobacteria. The pYUB180 deposit was transformed into streptomycin-resistant or novobiocin-resistant *M. smegmatis* mutants. Photon production by the drug-sensitive parent was compared to the streptomycin-resistant or novobiocin-resistant mutants. The drug-resistant mutants continued to produce luciferase activity levels comparable to the untreated patent in the presence of the appropriate antibiotic. In addition, the drug-resistant mutants produced 100 to 1000 times more luciferase activity than the drug-sensitive parent (see FIG. 4, Panels B and C). Hence, a luciferase-based assay may be used to determine mycobacterial drug susceptibility.

Figure 5A:
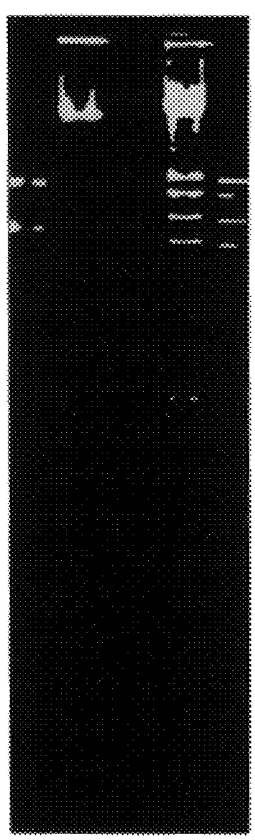
FIG. 5 represents shuttle plasmid phAE39 wherein the reported gene is FFlux, the promoter is hsp60, the phage is TM4 and the cosmid is pYUB216.
Figure 5B:
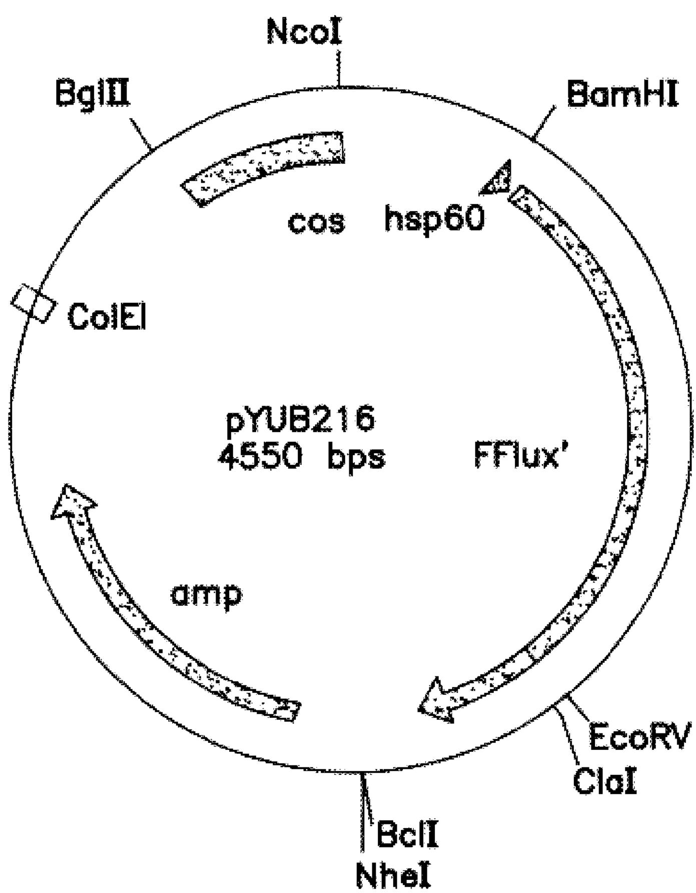

Construction of TM4 Reporter Mycobacteriophages (phAE39, phAE37 and phAE40) and Detection of Photons Following TM4::lux Infection The first vectors developed to introduce recombinant DNA into mycobacteria were shuttle phasmid phage vectors. Shuttle phasmids have the ability to replicate in *E. coli* as cosmids and then replicate in mycobacteria as phages. Shuttle phasmids of TM4 which contained the FFlux and lacz genes transcribed from hsp60 and L1 promoters, respectively, were constructed (see FIG. 5).

Figure 6:
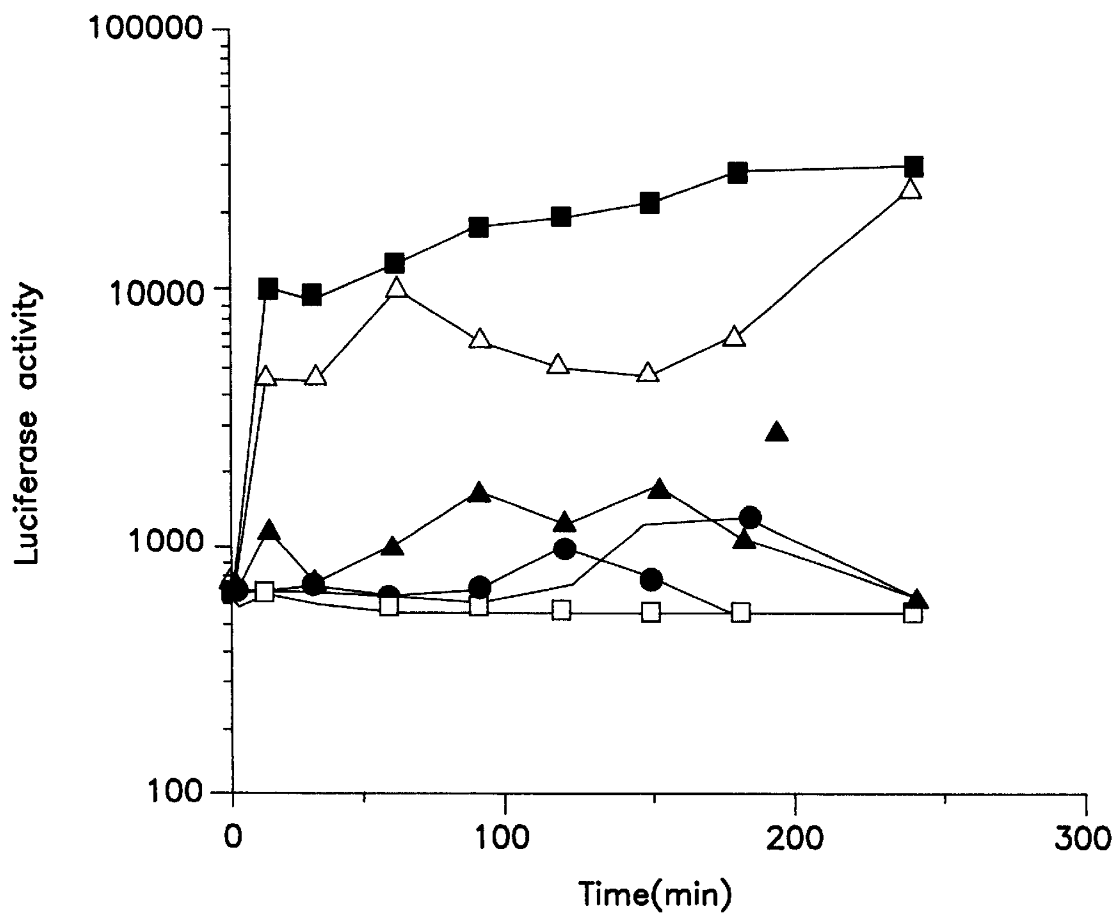
FIG. 6 represents luciferase activity of *M. smegmatis* cells infected with shuttle phasmids phAE39.
Figure 7:
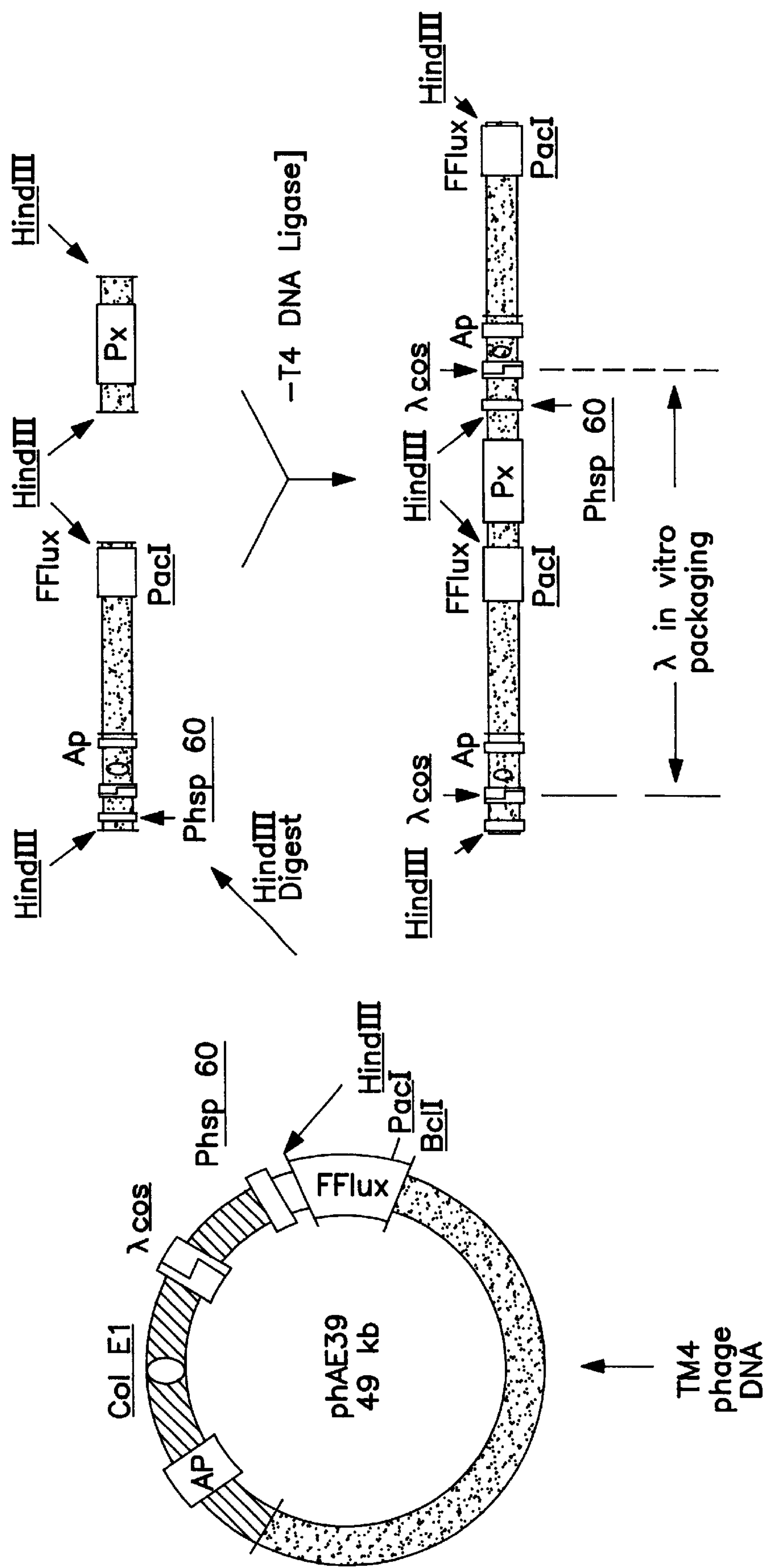
FIG. 7 represents a flow chart for cloning different promoters into TM4::lux shuttle phasmid phAE39.

A deposit of the shuttle phasmid (reporter mycobacteriophage) phAE39 which contains mycobacteriophage TM4, cosmid pYUB216, reporter gene FFlux and promoter hsp60, was made with the American Type Culture Collection on Jan. 15, 1992 and catalogued as ATCC No. 75183. When the TM4::lux shuttle phasmid phAE39 was mixed with *M. smegmatis* cells, luciferase activity could be detected within 15 minutes of incubation, and continued to increase slightly over the next 4 hours (see FIG. 6). These results show that the TM4::lux mycobacteriophage is capable of introducing the FFlux gene into mycobacterial cells, and that the FFlux gene can be expressed in mycobacteriophage-infected cells. FIG. 7 represents a flow chart for cloning different promoters into the TM4:: lux shuttle phasmid phAE39.

A deposit of the shuttle phasmid (reporter mycobacteriophage) phAE37 which contains mycobacteriophage TM4, cosmid pYUB216, reporter gene lacZ and promoter L1, was made with the American Type Culture Collection on Feb. 10, 1992 and catalogued as ATCC No. 75204. The TM4::lacZ mycobacteriophage formed bright blue plaques when plated on media containing X-gal.

Figure 8:
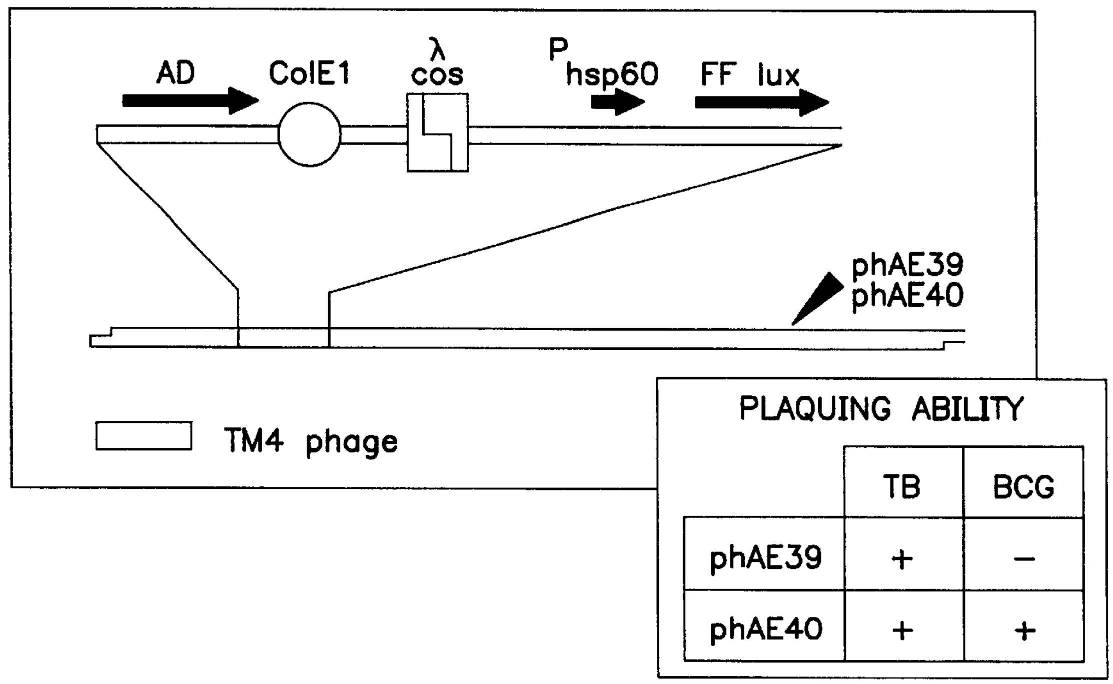
FIG. 8 represents a schematic diagram of the luciferase reporter mycobacteriophages phAE39 and phAE40.
Figure 9:
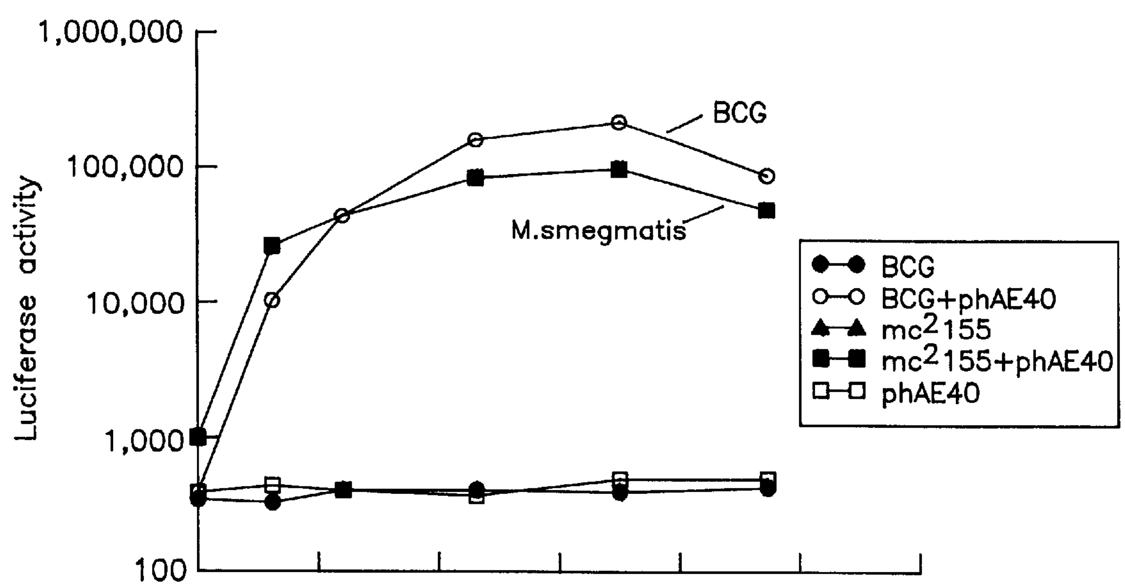
FIG. 9 represents the production of light (photons) by mycobacteria following infection with the luciferase reporter phage phAE40.

A mutant of the shuttle phasmid phAE39, designated phAE40, was isolated. As discussed hereinabove, in order to produce shuttle phasmid phAE39, *E. coli* cosmid pYUB216 was inserted into a non-essential region of the mycobacteriophage TM4. The pYUB216 cosmid contained FFlux in a transcriptional fusion with the hsp60 promoter of BCG, a ColE1 origin and an ampicillin-resistant gene (AP) for replication and selection in *E. coli*, and a bacteriophage lambda cos sequence as well as a unique Bc/1 site. The phAE39 shuttle phasmid was constructed with Bc/1-digested pYUB216 being ligated to Sau3A-partially digested TM4 DNA. As shown in FIG. 8, the shuttle phasmid phAE39 readily forms plaques of *M. tuberculosis*, but does not efficiently plaque on BCG. A spontaneous host range mutant of phAE39 was isolated at a frequency of $10^{-6}$ to $10^{-7}$, and designated phAE40. Mutant shuttle phasmid phAE40 was found to be capable of infecting BCG vaccine strains, in addition to being capable of infecting *M. smegmatis* and *M. tuberculosis* strains. The shuttle phasmid phAE40 was deposited with the American Type Culture Collection on Apr. 29, 1993 and catalogued as ATCC No. 25457.

In order to test whether the phAE39 and phAE40 reporter mycobacteriophages were capable of eliciting the production of light following infection of mycobacteria, the reporter mycobacteriophages were mixed with *M. smegmatis* cells and then exposed at different times to luciferin. In order to perform this, high titers of phAE40 were prepared as described above for TM4 phages. Both *M. smegmatis*, $mc^2155$ cells and BCG-Pasteur cells were grown in roller bottles to approximately $5 \times 10^7$ cells per ml in M-ADC-TW broth at 37° C. Either the *M. smegmatis* or the BCG cells were harvested by centrifugation and washed two times in M-ADC broth, containing no tween. The resulting pellet was resuspended in the original volume of M-ADC broth. The cells were then diluted into fresh M-ADC broth and allowed to incubate overnight standing at 37° C. Tween-80 appeared to remove the receptors, and it was determined that the optimal activities were achieved if the cells were given a chance to grow in the absence of tween. This may have allowed the regeneration of phage receptors. Next, 1 ml of washed cells (approximately $5 \times 10^7$ cells) was mixed with 0.1 ml phAE40 particles ($5 \times 10^8$ pfu/ml) that had been concentrated on CsCl gradients to achieve a multiplicity of infection of 10. The cells phage mixture was incubated at 37° C. Beginning at the time of the addition of the phAE40, 0.1 ml samples were removed. Luciferase activity was measured as described in FIG. 13. Light signals were detected within minutes following infection using a luminometer and increased 1,000 fold within 2 hours. The rapid kinetics of light production allowed for the testing of the simple hypothesis that one reason slow-growing mycobacteria, such as BCG and *M. tuberculosis*, have generation times 10-fold longer than other mycobacteria is the consequence of a generalized slow rate of transcription or translation. The observation that the kinetics of light production following infection of BCG with the reporter mycobacteriophages is almost identical to that of *M. smegmatis*, thereby suggesting that the slow growth of slow growing mycobacteria is unlikely to be attributable to slower rates of metabolic processes, but rather is the result of a highly regulated event, such as the initiation of chromosome replication or cell division.

Figure 10A:
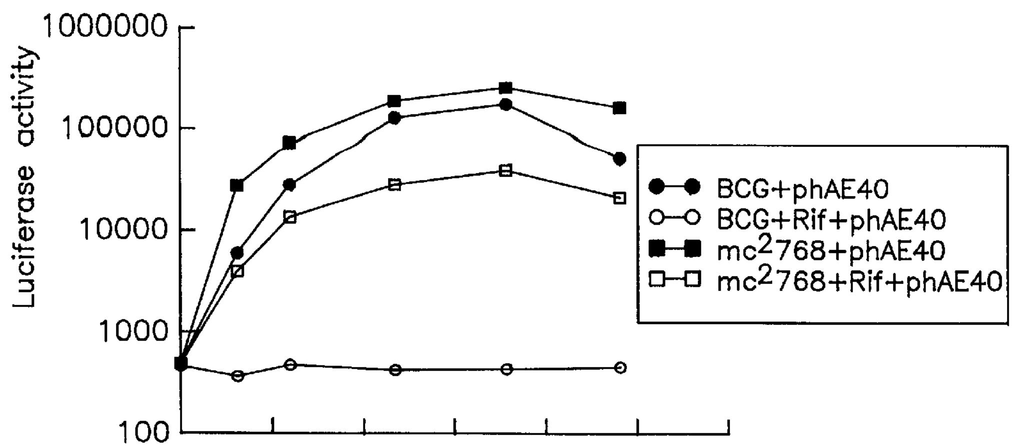
FIG. 10 represents a comparison of the kinetics of light production following phage infection of drug-sensitive BCG cells to drug-resistant BCG mutant cells.
Figure 10B:
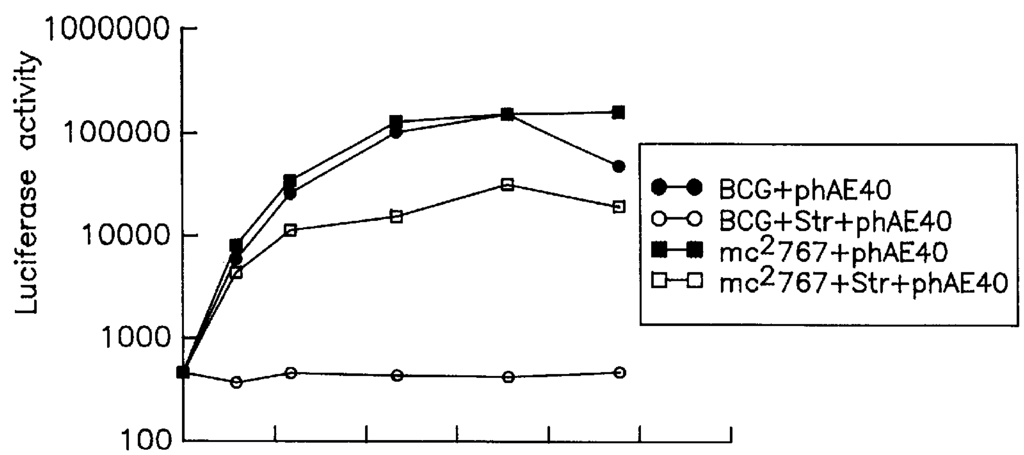
Figure 10C:
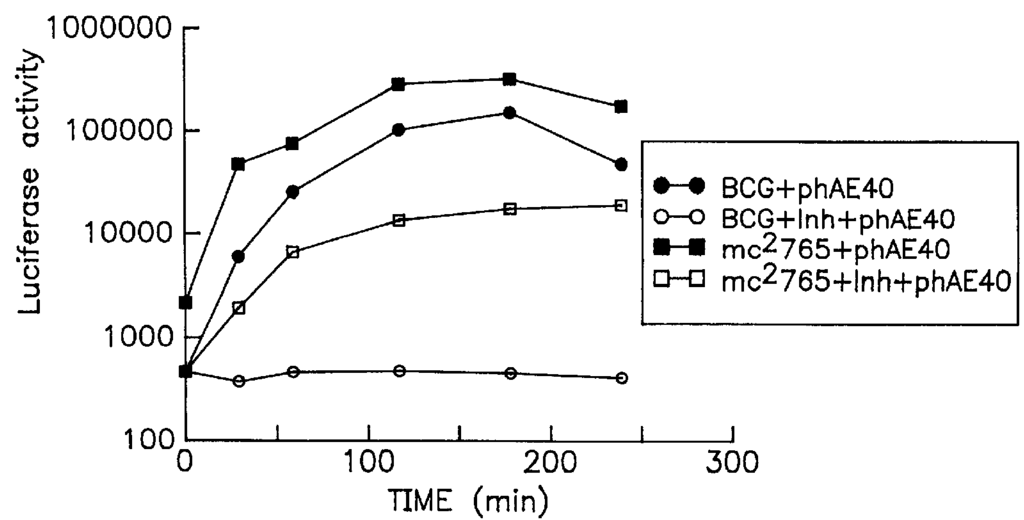

Since it was determined that the phAE39 and phAE40 reporter mycobacteriophages were able to elicit the production of light following infection of mycobacteria, they were used to distinguish between drug-resistant and drug-sensitive organisms. In order to perform this, mutants of BCG were selected that were resistant to streptomycin, isoniazid and rifampicin. Spontaneous mutants of BCG-Pasteur were isolated on Middlebrook 7H10 agar containing either 50 μg/ml rifampicin, 250 μg/ml streptomycin or 50 μg/ml isoniazid. The rifampicin-, streptomycin-, or isoniazid-resistant mutants were purified and designated $mc^2768$, $mc^2767$ and $mc^2765$, respectively. All three mutants and the BCG parent were grown to midlog phase, harvested and washed. As shown in the top panel of FIG. 10, the $mc^2768$ cells and the BCG cells were incubated standing at 37° C. in the presence or absence of rifampicin (50 μg/ml) for 24 hours. A 0.5 ml sample (approximately $5\times10^7$ viable cells) was mixed with 0.1 ml ($5\times10^8$ pfu) of phAE40 particles and luciferase activity was determined. The samples were removed and luciferase activity was measured. As shown in the middle panel of FIG. 10, the $mc^2767$ cells and the BCG cells were incubated standing at 37° C. in the presence or absence of streptomycin (250 μg/ml) for 24 hours. A reporter assay was performed as described above. As shown in the bottom panel of FIG. 10, the $mc^2765$ cells and the BCG cells were incubated standing at 37° C. in the presence or absence of isoniazid (50 μg/ml) for 24 hours. The reporter assay was performed as described above. As shown in FIG. 10, when wild-type BCG and the mutants were cultured for 24 hours with the antibiotics, the parental strain (wild-type BCG) failed to produce any signal, whereas light was produced by the drug-resistant mutants.

Next, the luciferase reporter phage assay was tested on clinically-derived *M. tuberculosis* strains, which were both singly and multiply drug-resistant. In order to perform this, the following *M. tuberculosis* strains were grown in a biological safety level 3 containment facility: (i) the virulent drug-sensitive *M. tuberculosis* Erdman strain; (ii) strain 92-2025, a singly isoniazid-resistant strain; and (iii) an MDR strain of tuberculosis that has been shown to be resistant to rifampicin, streptomycin, isoniazid, ethambutol and ethionamide and the cause of several nosocomial outbreaks in New York City. The Erdman strain was subcultured from the starter culture by inoculation of 0.4 ml into 20 ml of Middlebrook 7H9 broth containing OADC enrichment (Difco Laboratories, Detroit, MI) plus 0.5 Tween-80 (M-OADC-TW broth). The 92-2025 and the MDR strains, which grow more slowly than the Erdman strain, were subcultured by inoculation of 2 ml into 20 ml M-OADC-TW broth.

All three cultures were grown standing at 37° C. for 7 to 8 days. The cells were washed and resuspended in 0.5× the original volume. Washed cells (0.2 ml) were inoculated into 0.7 ml of M-OADC broth and incubated in 13×100 mm polypropylene tubes in a heating block in a Biohazard hood for 48 hours. Rifampicin, streptomycin, or isoniazid were added to final concentrations of 2 μg/ml, 0 μg/ml, and 1 μg/ml, respectively. After 48 hours of incubation, 0.1 ml of phAE40 particles ($1\times10^{11}$ particles) were added to attain a multiplicity of infection of 1000. Samples of 100 μl were removed at 1, 3 and 5 hours after addition of the phage and were mixed with 250 μl of 0.1 M sodium citrate (pH 5) in a Lumacuvette (Lumac, BV, Netherlands). One hundred microliters of 1 mM luciferin were added, and the Lumacuvette was plugged with cotton. The tube was placed in a Lumac Biocounter (M1500P), and readings were recorded as described above. (The Lumac Biocounter had dimensions that permit it to fit in a standard biohazard hood.) The light production followed kinetics similar to the BCG experiments, and the readings at 3 and 5 hours differed by no more than twofold. The results at 3 hours are shown for the Erdman (A), 92-2025 (B), and the MDR (C) *M. tuberculosis* strains.

Figure 11A:
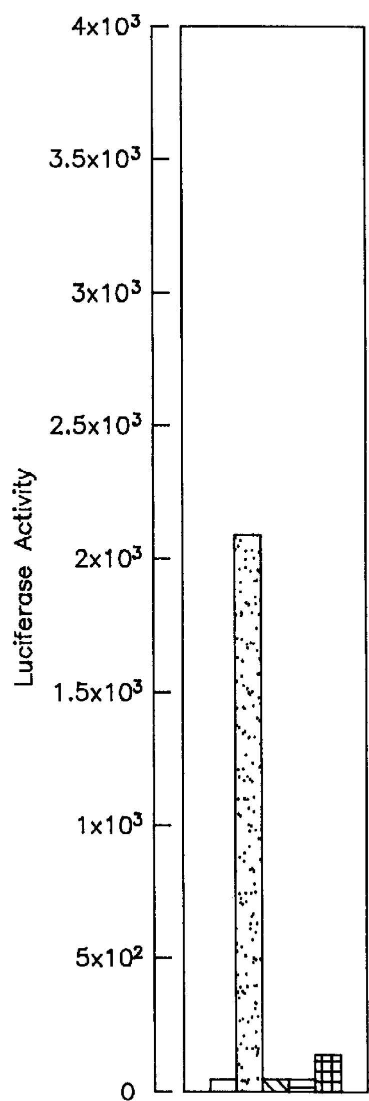
FIG. 11 represents a comparison of drug-sensitive *M. tuberculosis* and drug-resistant *M. tuberculosis* using the luciferase reporter phage assay.
Figure 11B:
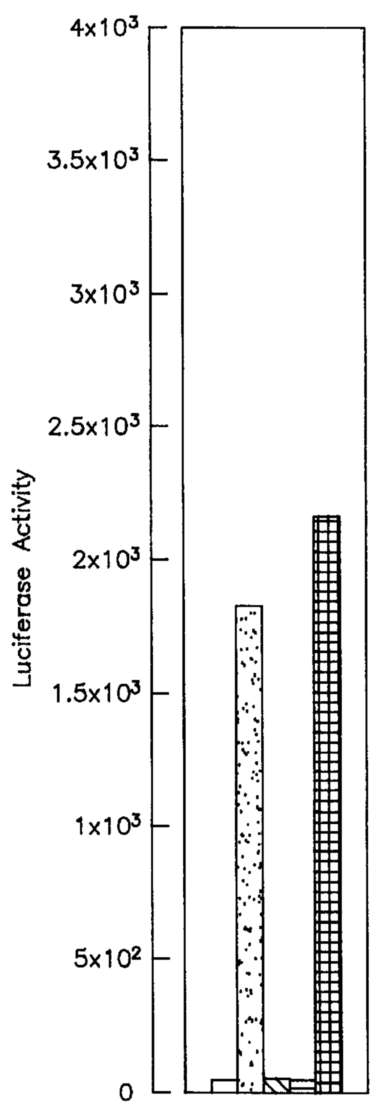
Figure 11C:
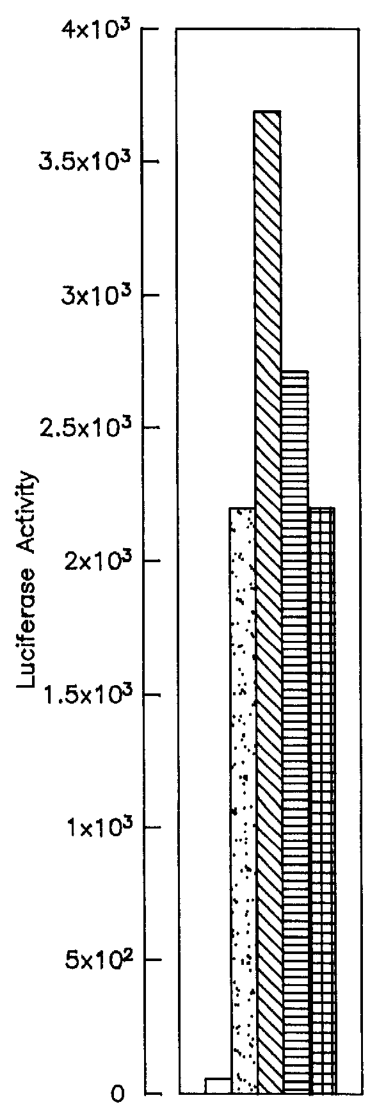

A repeated experiment gave similar results, with the samples cultured in the absence of drug exhibiting an 80-fold greater luminescence than the cells cultured with rifampicin or streptomycin and greater than 10-fold luminescence relative to those cultured with isoniazid at 3 and 5 hours. Open bars represent cells alone; filled bars represent cells plus LRP; diagonal lines represent cells plus rifampicin plus LRP; cross-hatching represents cells plus streptomycin plus LRP; squares represents cells plus isoniazid. As shown in FIG. 11, the luciferase reporter phages were capable of rapidly revealing the patterns of drug-susceptibility or resistance of *M. tuberculosis* strains.

Construction of L5 Reporter Mycobacteriophages (phGS1 and phGS5)

In order to construct L5::FFlux phages, a plasmid (pGS12) was constructed in which a DNA segment of the L5 genome was inserted into the *E. coli*-mycobacterial shuttle plasmid pMD31. pMD31 is described by Donnelly-Wu et al. in "Superinfection Immunity of Mycobacteriophage L5: Applications for Genetic Transformation of Mycobacteria", *Molecular Microbiology*, Vol. 7, No. 3, pages 407–417 (1993). This DNA segment contained the tRNA gene cluster from L5 as described by Hatfull et al. in "DNA Sequence, Structure and Gene Expression of Mycobacteriophage L5: A Phage System for Mycobacterial Genetics", *Molecular Microbiology*, Vol. 7, No. 3, pages 395–405 (1993). Next, this plasmid was further manipulated by insertion of a segment of DNA containing the FFlux gene between the second and third tRNA, to produce pGS24. The resulting plasmid DNA was introduced into *M. smegmatis* by electroporation, and an L5 lysate was prepared by growth of L5 phage on this plasmid-containing strain.

Individual phages were screened by hybridization using an FFlux probe and filters containing $10^6$–$10^7$ plaques. Several positive plaques were identified and two were purified and characterized. These two phages were named phGS1 and phGS5.

Construction of Plasmids pGS11, pGS12, pGS22 and pGS24

Plasmids PGS11, pGS12 and pGS22 were constructed as described below and then used to construct plasmid pGS24.

Figure 14:
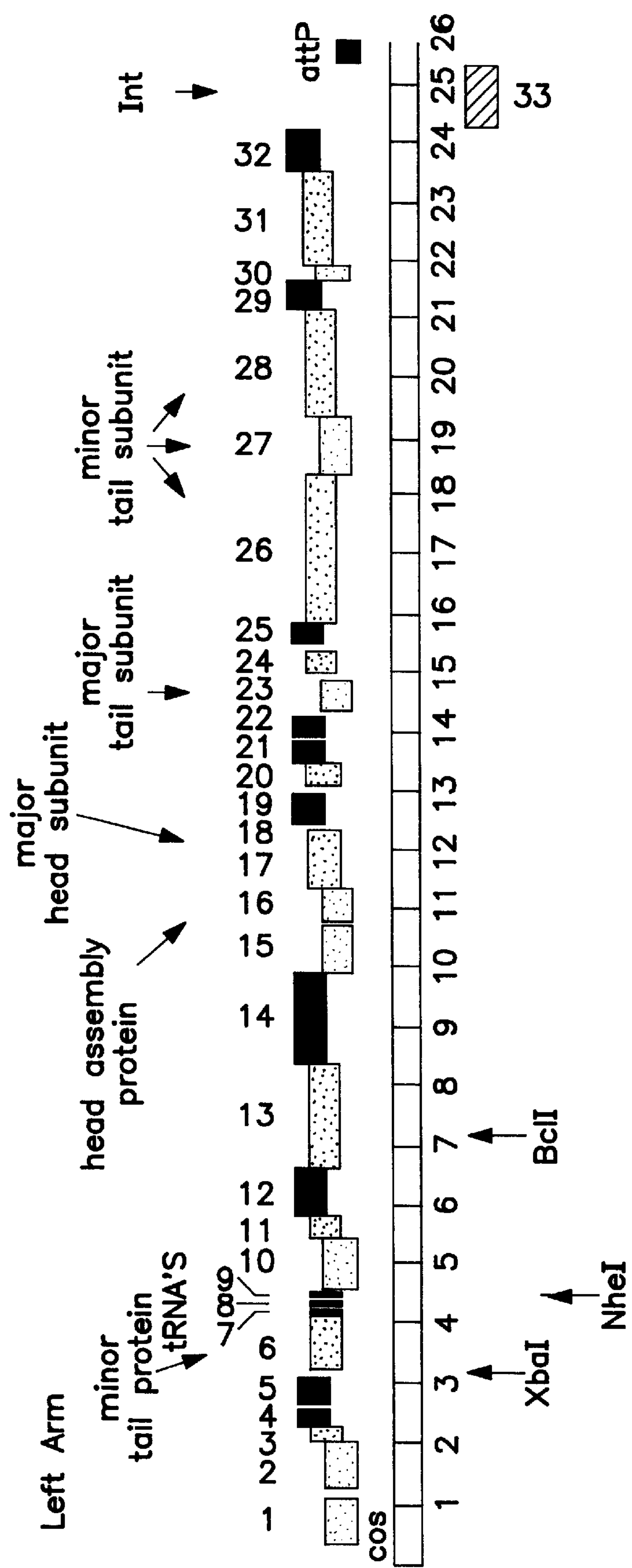
FIG. 14 represents a DNA fragment of the L5 segment defined by the coordinates 3,150-7,143 after cleaving with Xba I and Bcl I.
Figure 15:
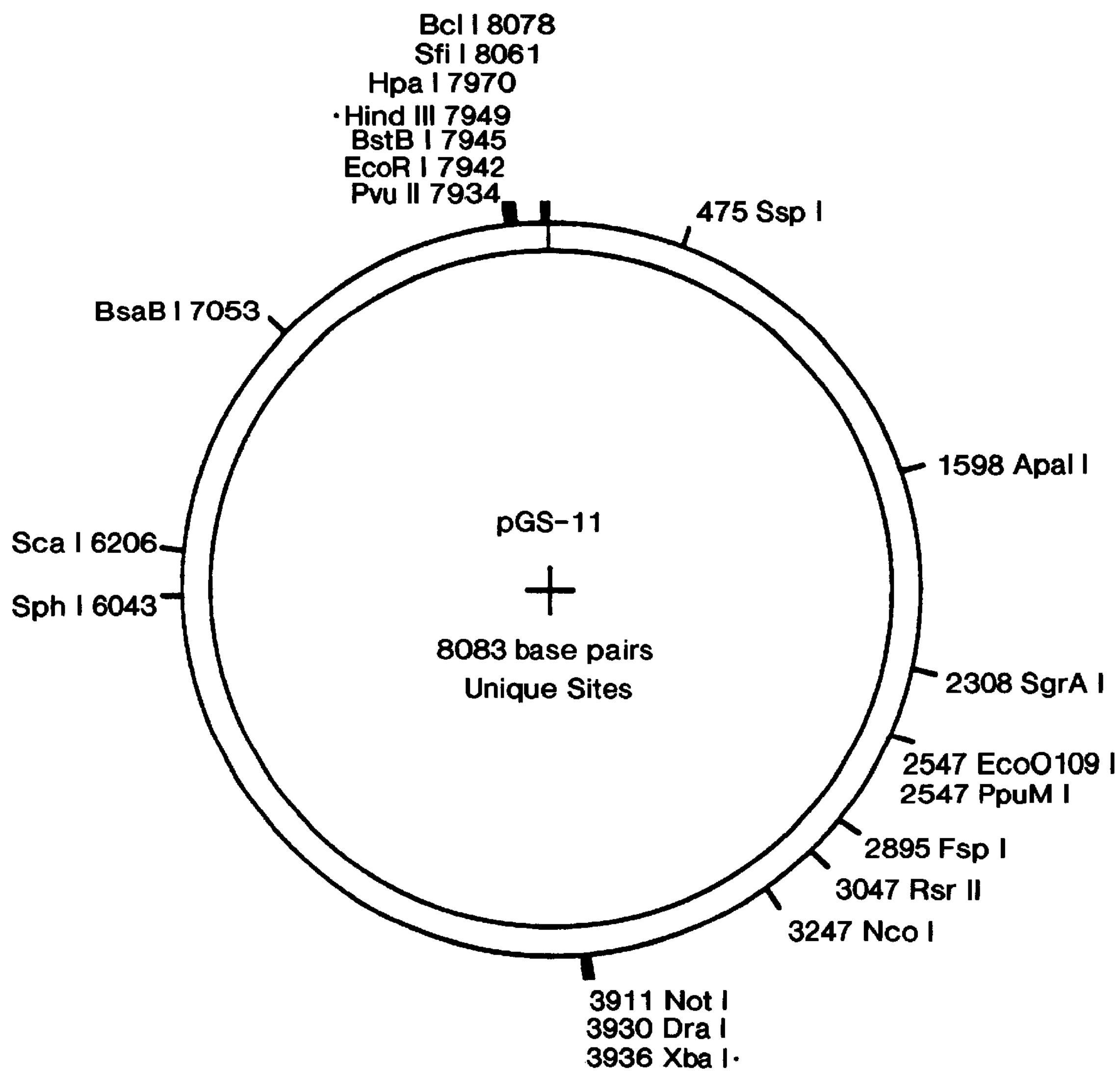
FIG. 15 represents the DNA fragment of L5 after insertion into plasmid pMV261lacZ and cleaving with Xba I and BAMHI to produce plasmid pGS11.

L5 DNA was cleaved with Xba I and Bcl I and the 3,993 bp fragment was purified. This DNA fragment represents the L5 segment defined by the coordinates 3,150-7,143. FIG. 14 is a segment of L5 DNA used for FFlux insertion which shows the left arm of the L5 genome with genes 1-33 indicated. The segment of L5 taken to make FFlux inserts is between the Xba I and Bcl I sites indicated. The Nhe I site that defines the position of insertion of FFlux is shown. This DNA fragment was inserted into plasmid pMV261lacZ (see Stover et al., *Nature*, Vol. 351, pp. 456–460, 1991) cleaved with Xba I and Bam HI to produce plasmid pGS11 (see FIG. 15). FIG. 15 is a map of plasmid pGS11 which contains the Xba I-Bcl I segment of L5 inserted into pMV261lacZ. The Bcl I end was inserted into the Bam HI site of the vector and both the Bcl I and Bam HI sites were destroyed. The Hind III and Xba I sites that were used to construct pGS12 are indicated.

Figure 16:
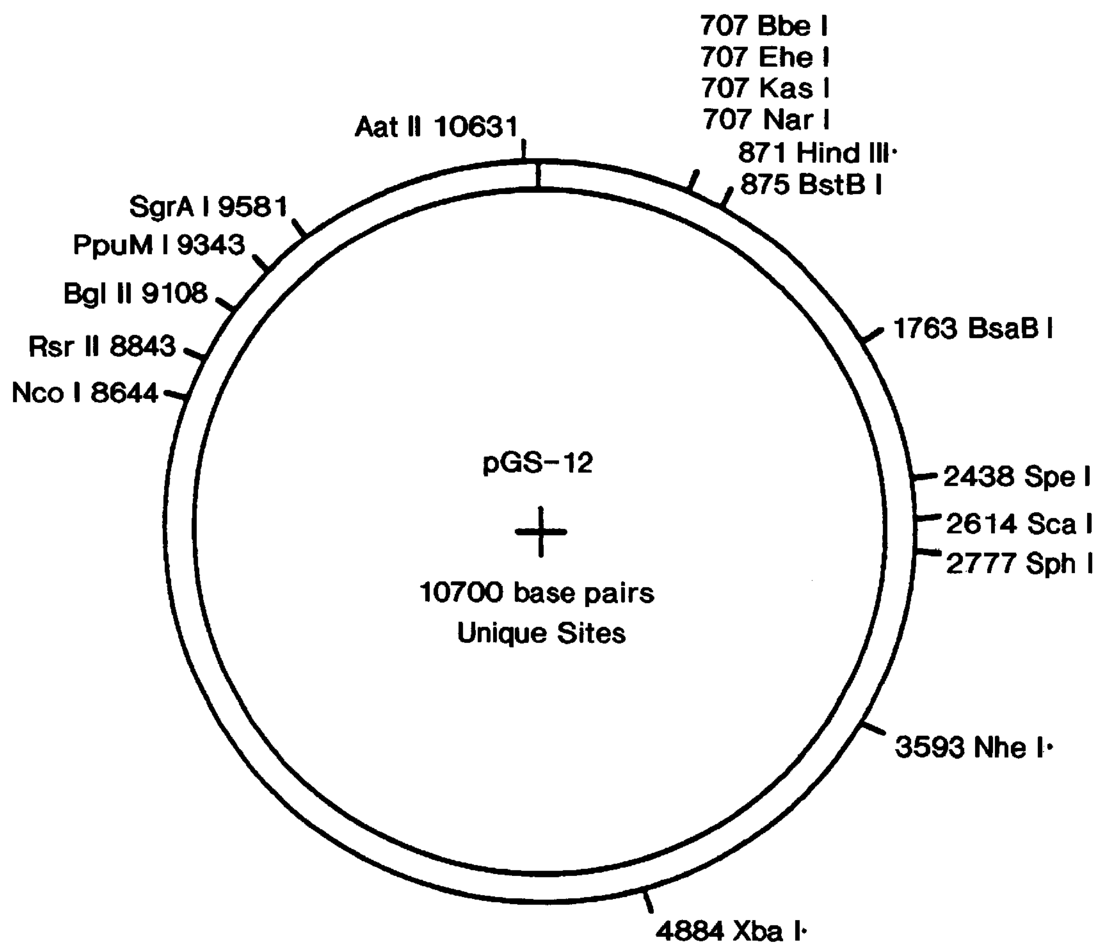
FIG. 16 represents plasmid pGS12 which was produced by cleaving pGS11 DNA with Xba I and Hind III, and inserting fragment 4,013 bp into plasmid pMD31.

Plasmid pGS11 DNA was cleaved with Xba I and Hind III and the 4,013 bp fragment was purified and inserted into plasmid pMD31 (Donnelly-Wu et al., 1993) cleaved with Xba I and Hind III. This plasmid was named pGS12. FIG. 16 is a map of plasmid pGS12 showing the location of the Xba I and Hind III sites used to insert the Xba I-Hind III piece from pGS11 into pMD31. The unique Nhe I site used for the insertion of FFlux is also shown. Plasmid pGS12 contains a unique Nhe I restriction site which corresponds to the Nhe I site at position 4,441 in the L5 genome which is located between the tRNA-trp and tRNA-gln genes (genes 8 and 9).

Figure 17:
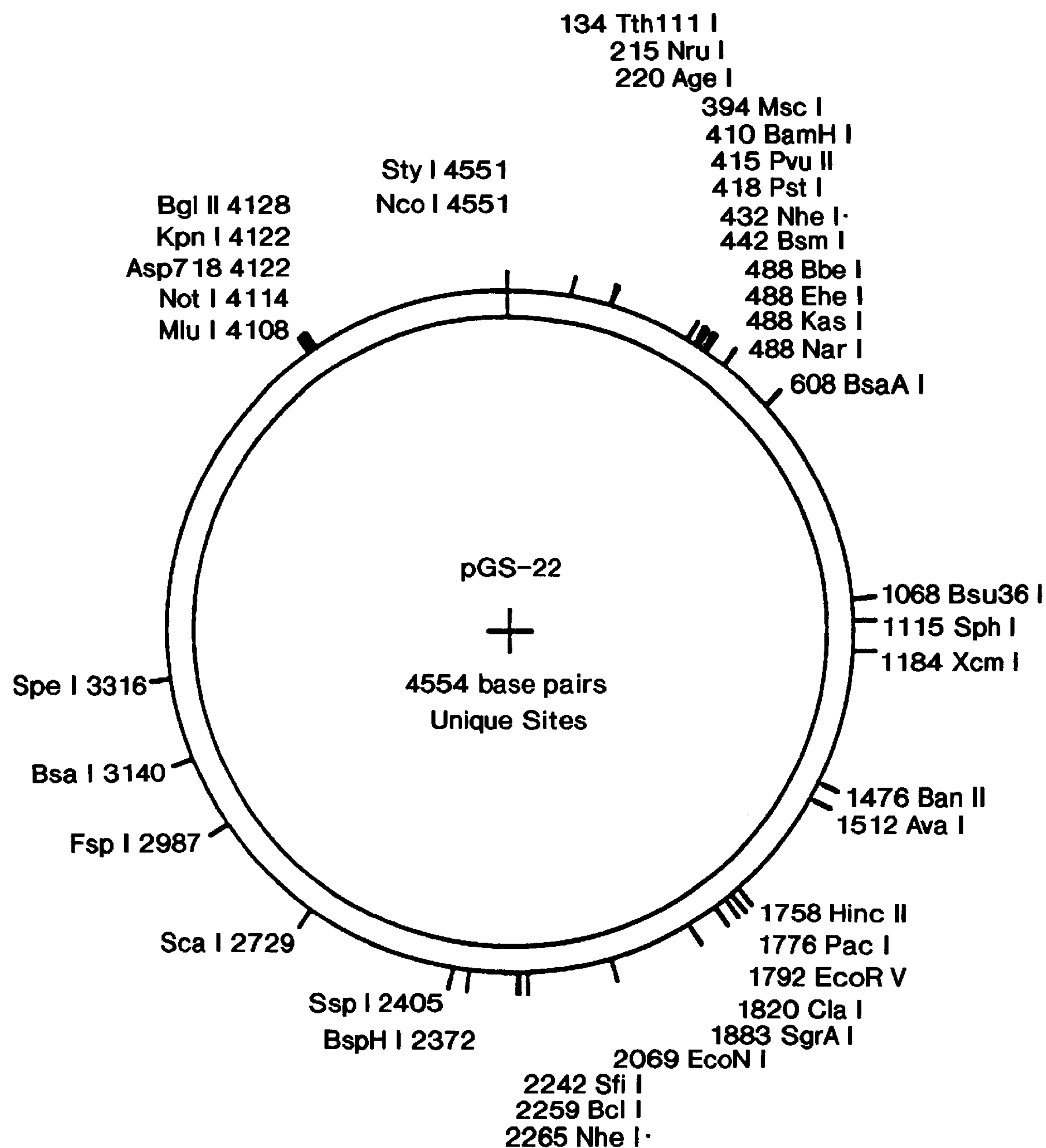
FIG. 17 represents plasmid pGS22, which was produced by cutting plasmid pYUB216 with Hind III and converting the sticky ends to blunt ends by Klenow enzyme and dNTP's.
Figure 18:
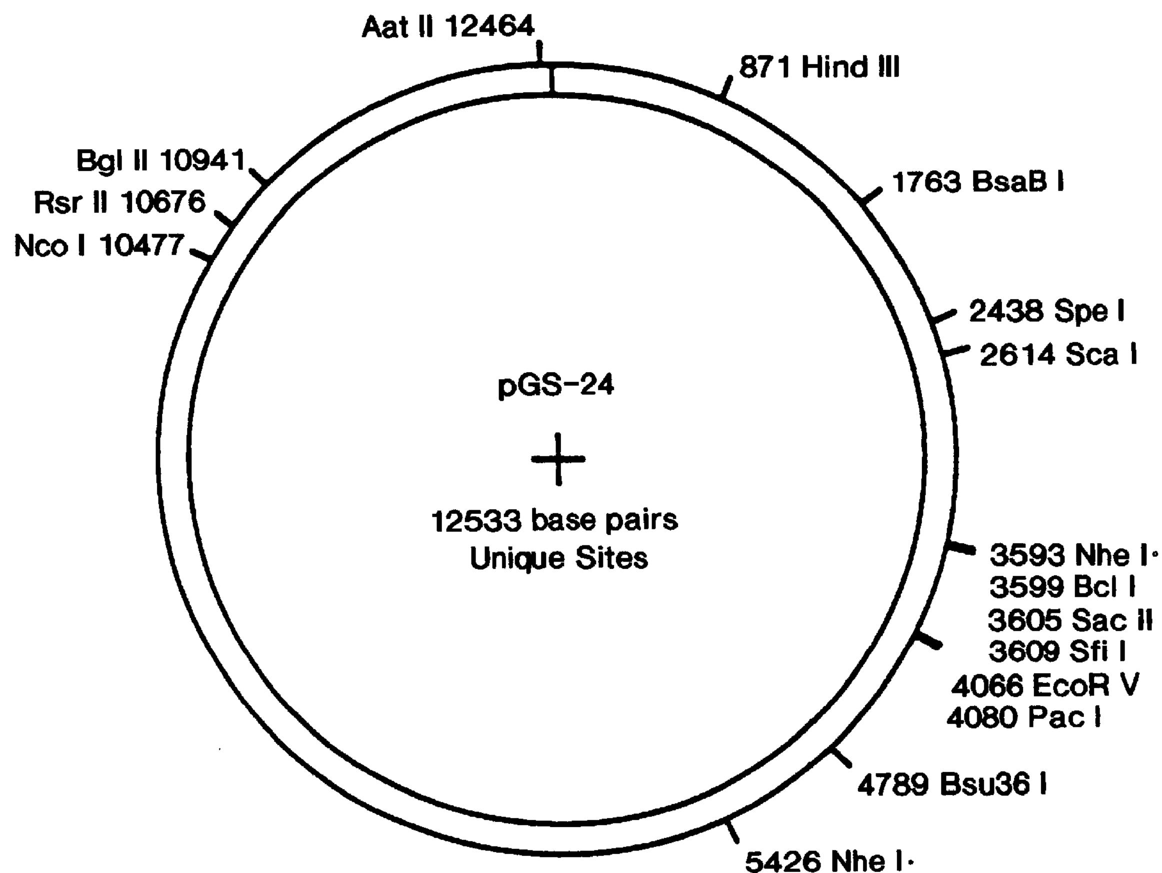
FIG. 18 represents plasmid pGS24, which was produced by inserting plasmid pGS22 into the NHE I site of pGS12 plasmid.

Plasmid pYUB216 was cut with Hind III, the sticky ends converted to blunt ends by Klenow enzyme and dNTP's and the DNA religated. The resulting plasmid was named pGS22. FIG. 17 is a map of plasmid pGS22 which shows the two Nhe I sites that flank the FFlux gene. This procedure was followed to generate an additional Nhe I site upstream of the FFlux gene in pYUB216.

pGS12 was digested with Nhe I. pGS22 was also digested with Nhe I which produces a fragment of approximately 2.4 kb. The DNA's were mixed, ligated and a recombinant recovered in which the Nhe I fragment derived from pGS22 was inserted into the Nhe I site of pGS12. This plasmid was named pGS24. FIG. 18 is a map of plasmid pGS24 which contains the Nhe I FFlux DNA fragment inserted into the unique Nhe I site of pGS12. The two Nhe I sites are indicated. The orientation of the inserted DNA was determined by restriction enzyme digestion and found to be in the appropriate orientation for FFlux to be expressed from the same DNA strand as the L5 tRNA's. pGS24 is thus a *E. coli*-mycobacterial shuttle plasmid that contains the FFlux gene flanked upstream by approximately 1,291 bp of L5 DNA and downstream by approximately 2,702 bp L5 DNA.

Construction of phGS1 and phGS5

Figure 19:
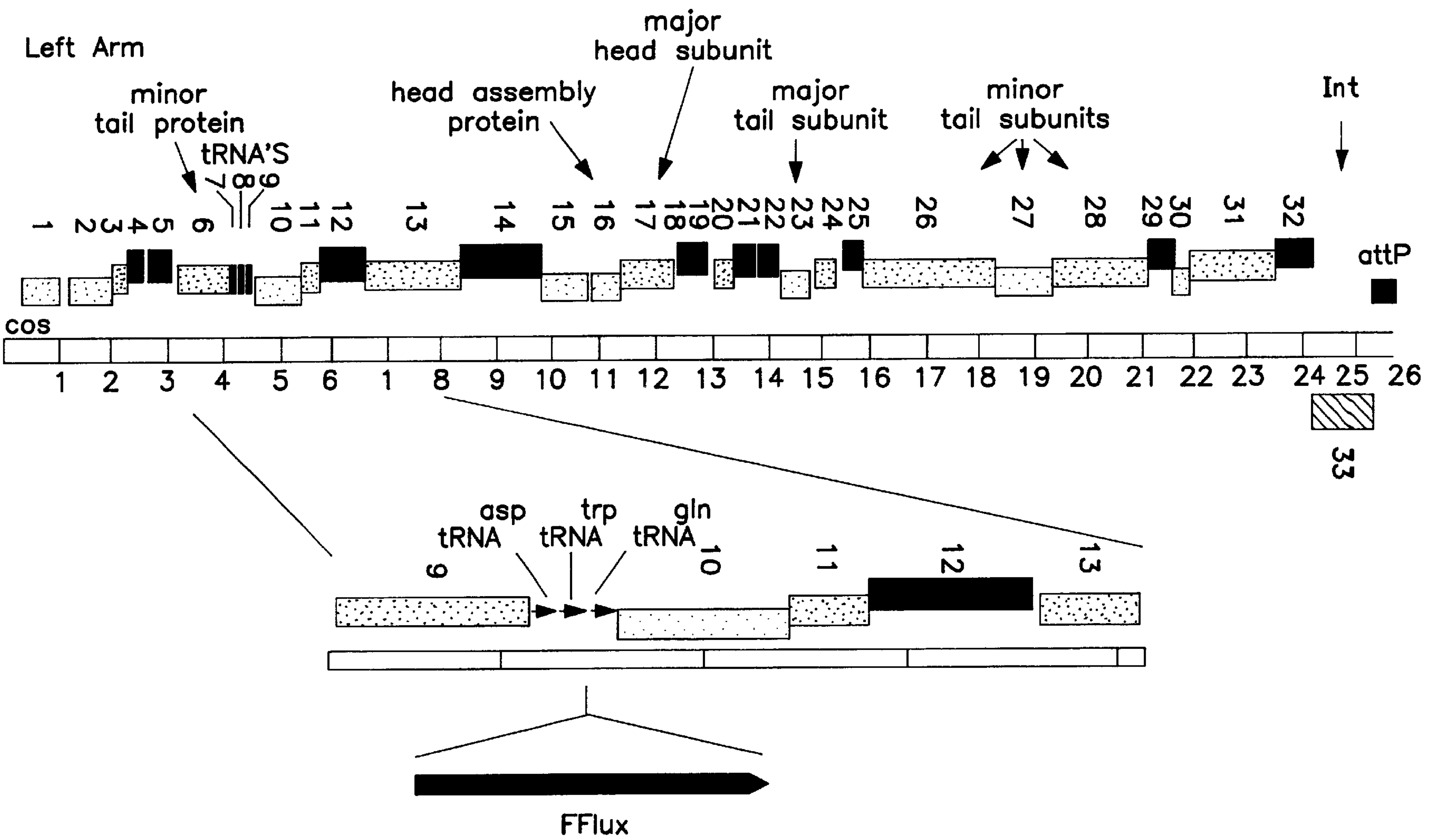
FIG. 19 represents a double crossover event between plasmid pGS24 and L5.

Having constructed a plasmid containing FFlux flanked by L5 DNA, FFlux was inserted onto the L5 genome by a double crossover event between plasmid pGS24 and L5. This was achieved by growth of an L5 lysate on *M. smegmatis* carrying plasmid pGS24 and searching among the progeny for FFlux-containing phage by hybridization. FIG. 19 shows the strategy for recombination between pGS24 and L5. Specifically, the upper part of the figure shows the left arm of L5 and the position of genes 1-33. The lower part shows the segment of L5 DNA present in pGS24 and the location of FFlux inserted between the tRNA-trp and tRNA-gln genes. It was hoped that by growth of L5 phage in cells containing plasmid pGS24 that progeny could be recovered in which the FFlux gene had been inserted into the L5 genome by homologous recombination within the common sequences to the left and right of FFlux in pGS24 and those in L5.

Plasmid pGS24 DNA was introduced into *M. smegmatis* $mc^2$-155 by electroporation, and transformants recovered by selection with kanamycin. A lysate of phage L5 was prepared by infection of approximately 0.5 ml late-log phage *M. smegmatis* cells containing plasmid pGS24 with approximately $10^6$ L5ts11 particles and incubation on solid media at 37° C. [L5ts11 is a poorly characterized temperature-sensitive mutant of L5]. The phages were harvested and shown to have a titer of approximately $10^{10}$ plaque forming particles/ml (pfu/ml).

Approximately $10^6$–$10^7$ phage articles were added to *M. smegmatis* $mc^2$-155 cells and plated onto large agar plates. After incubation, plaques were transferred to nitrocellulose filters and probed with radioactively labeled pYUB216 DNA. About 15 positive plaques were identified.

Several positive plaques were recovered from the agar plates purified through several rounds of plaque purification, checking with positive hybridization to the pYUB216 DNA probe at each stage. At the end of this procedure, two of the phages were chosen for further characterization. These phages were named phGS1 and phGS5.

Characterization of phGS1 and phGS5 DNA's

Phage DNA's were prepared from high titer stocks of phGS1 and phGS5 using standard methods. phGS1 and phGS5 DNA's were digested with several different restriction enzymes (including Bam HI, Nhe I, Bst E II, Asp718, Cla I, Bgl II) and the patterns observed compared with those obtained from wild-type L5, using agarose gel electrophoresis. Several differences were observed between phGS1 and phGS5 as compared to L5 DNA. Some of these changes were consistent with a double crossover recombination event inserting FFlux onto the L5 genome as anticipated. Other differences were consistent with deletion of some of the L5 DNA close to the right end of the genome.

Figure 20A:
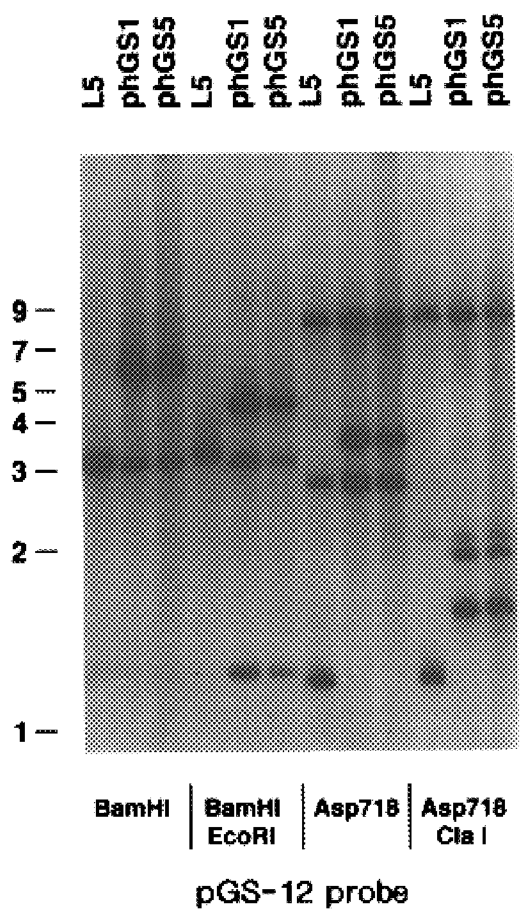
FIG. 20 represents hybridized bands detected by autoradiography.
Figure 20B:
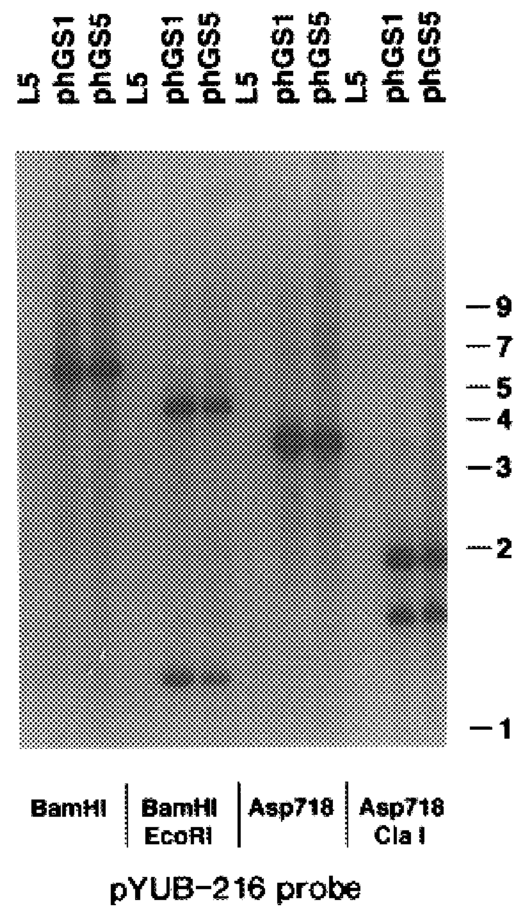

Confirmation of the structures of phGS1 and phGS5 was obtained by hybridization of Southern blots of the DNA's using a variety of DNA probes.

phGS1, phGS5 and L5 DNA's were digested with either Bam HI, Bam HI and EcoRI, Asp718 or Asp718 and ClaI. DNA fragments were separated by agarose gel electrophoresis and transferred to a nitrocellulose filter. This filter was probed with radiolabelled pGS12 DNA and the hybridizing bands detected by autoradiography. The results are shown in FIG. 20. FIG. 20 shows a Southern blot of the insertion of FFlux into L5. DNA purified from L5, phGS1 and phGS5 particles was cleaved with restriction enzymes as indicated and the fragments separated by agarose gel electrophoresis. The DNA fragments were transferred to a nitrocellulose filter and probed with radiolabelled pGS12 DNA (left panel). Following autoradiography, the filter was stripped and probed with radiolabelled pYUB216 DNA (right panel). These data conclusively demonstrate that FFlux is inserted into the L5 genome in a corresponding location to that in pGS24 as would be expected from a pair of homologous recombination events in the common flanking sequences. A map of the expected DNA fragments is shown in FIG. 21.

FIG. 21A maps show the expected restriction products from FFlux insertion—Bam HI. The location of the L5 probe (from pGS12) used for hybridization is shown (labeled 'probe'). This probe is expected to hybridize to two comigrating Bam HI fragments (3.010 bp and 3,104 bp) in wild-type L5 DNA (shown as 'labeled BAM HI fragments' in the top part of the figure). The lower part of the figure shows the anticipated structure of the FFlux insertion and the expected fragments resulting from digestion with either Bam HI or BAM HI+EcoRI that hybridize with the probe. These are 3,010 bp and 4,937 bp fragments from Bam HI digestion and 3,010 bp, 1,183 bp and 3,754 bp fragments from Bam HI and EcoRI digestion. The location of the FFlux probe derived from pYUB216 is indicated in the lower part of the figure. It is expected to hybridize to the 4,937 bp Bam HI fragment, and the 1,183 bp and 3,754 bp Bam HI/EcoRI fragments in the recombinants, but not to L5 at all. The data shown in FIG. 21 agree well with these predictions.

FIG. 21B maps show the expected restriction products from FFlux insertion—Asp718/Cla I. The pGS12 probe is anticipated to hybridize to 2,690 bp, 1,148 bp and 8,078 bp fragments resulting from Asp718 digestion of L5 and 2,690 bp, 2,981 bp and 8,078 bp from the FFlux recombinants. This probe is also expected to hybridize to 645 bp, 1,148 bp and 8,078 bp L5 fragments from Asp718+Cla I digestion and 645 bp, 1,078 bp and 8,078 bp fragments from this digestion of the FFlux recombinants. Note that the 1,078 bp fragment migrates as a fragment of approximately 1.5 kb which reflects the difference between the DNA strider generated maps and empirically-determined maps. The FFlux probe in pYUB216 hybridizes to the 2,981 bp Asp718 fragments and the 1,903 bp and 1,078 bp fragments from Asp718—Cla I digestion's of the recombinant phage.

Digestion of phGS1 and phGS5 DNA with Bam HI indicated that neither contained the largest Bam HI fragment (7.711 bp). The coordinates of the Bam HI sites that yield this fragment in wild-type L5 are 43,933 and 51,644. phGS1 and phGS5 thus appear to have lost a segment of L5 DNA close to the right end of the genome. Since the adjacent Bam HI fragments appear to be intact, it seemed probable that both Bam HI sites were present in phGS1 and phGS5 and that segments within the 7.711 bp Bam HI fragment were deleted. It was also not clear whether phGS1 and phGS5 were identical in this respect.

Hybridization of a specific L5 DNA probe derived from the 7.711 bp Bam HI fragment to a Southern blot of digested DNA's showed that phGS1 and phGS5 contain deletions of different sizes. phGS1 contained a new hybridizing fragment of approximately 3.4 kb indicating that 4.3 kb of DNA internal to the 7.7 kb Bam HI fragment had been deleted. phGS5 contained a new hybridizing fragment of 5.3 kb indicating that 2.4 kb of DNA internal to the 7.7 kb Bam HI fragment had been deleted.

Figure 22:
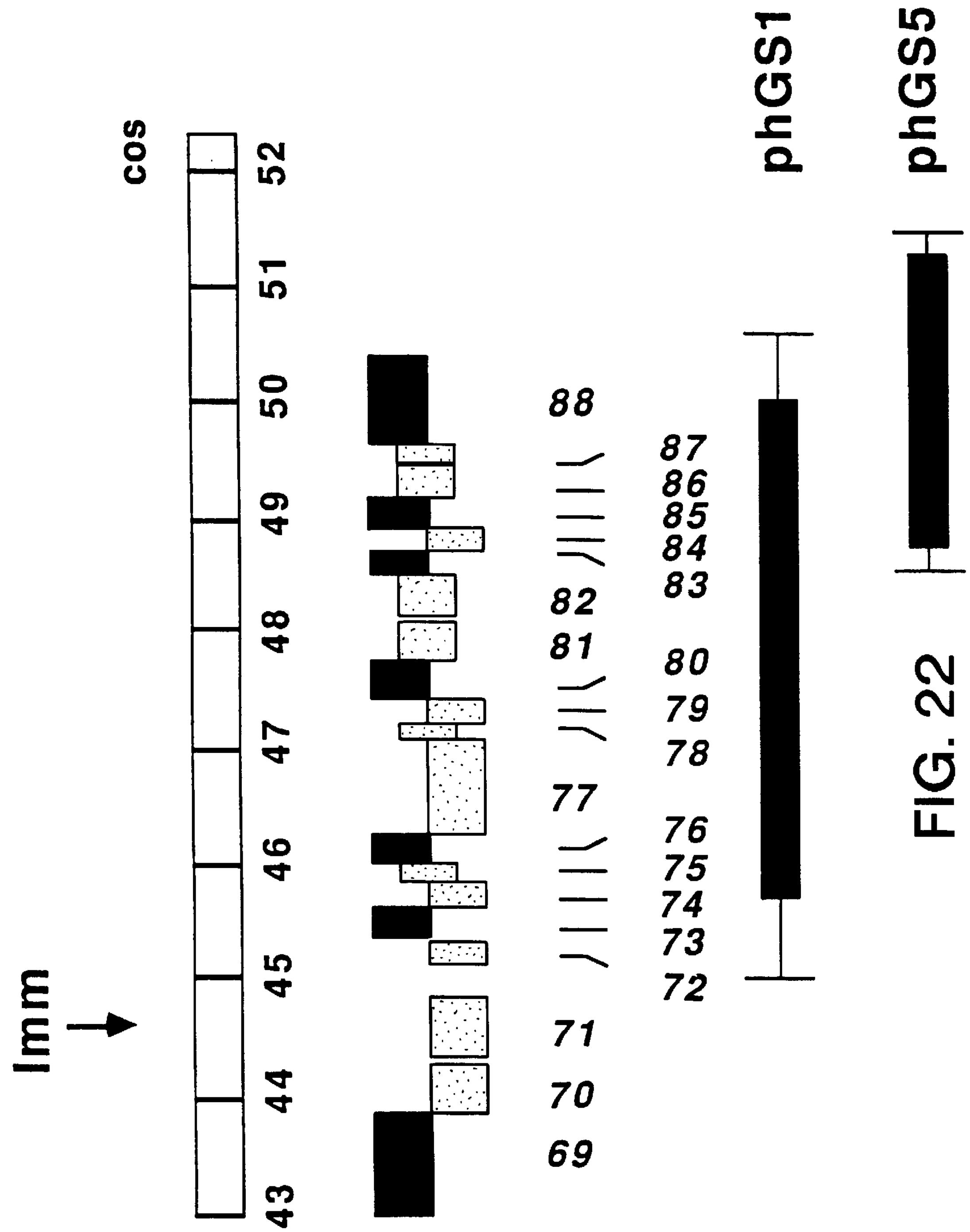
FIG. 22 represents restriction enzyme mapping and Southern blot hybridization for phGS1 and phGS5.

The exact end points of the deletions in phGS1 and phGS5 have not yet been determined. However, approximate end points were determined through a combination of restriction enzyme mapping and Southern blot hybridization as shown in FIG. 22. FIG. 22 map shows deleted regions in phGS1 and phGS5. phGS1 and phGS5 DNA's were found to contain deletions of L5 DNA in the right arm close to the right end of the genome. The location of these deletions was determined by a series of restriction enzyme digestions and Southern blot hybridizations and the approximate locations are shown here. The dark box represents the deleted portions and the limits of the positions are defined by the vertical lines. phGS1 contains a deletion of approximately 4.3 kb DNA and phGS5 contains a deletion of approximately 2.4 kb DNA.

For phGS1, the left end point appears to be to the right of the Bgl II site located at position 44,803 (wild-type L5 coordinates); the right end point is to the right of the BstE II site at 49,588 and to the left of the Bgl II site at 50,716. For phGS5, the left end point is to the right of the Sca I site at 47,559 and to the left of the Asp718 site at 48,750; the right end point is to the right of the Bgl II site at 50,716 and to the left of the Mse I site at 51,344.

Plasmids phGS1 and phGS5 were deposited on Apr. 27, 1993 with the American Type Culture Collection, Rockville, Md., and catalogued as ATCC Nos. 70454 and 70423, respectively.

Construction of other phGS1 and phGS5 Derivatives

In order to fully evaluate the behaviors of the L5::FFlux recombinants, several additional derivatives were isolated.

Isolation of phGS1$^{ts+}$ and phGS5$^{ts+}$:

It should be noted phGS1 and phGS5 are both derivatives of L5ts11. L5ts11 was chosen because some preliminary data indicated the temperature-sensitive mutation may lie within the region of DNA represented in pGS12. However, both phGS1 and phGS5 are still temperature-sensitive and fail to grow at 42° C. Temperature-resistant derivatives were isolated from phGS1 and phGS5 by plating approximately $10^6$ particles at 42° C. and recovering a derivative that was now competent to grow normally at 42° C. These were named phGS1$^{ts+}$ and phGS5$^{ts+}$, respectively. It is likely that these are simply derivatives of phGS1 and phGS5 that have resulted from the initial temperature-sensitive mutation in L5ts11. Phages phGS1$^{ts+}$ and phGS5$^{ts+}$ behave similarly to their direct parents in all respects except that they are competent to grow at high temperatures.

Isolation of phGS5$^{ts+}$cpm1, phGS5$^{ts+}$cpm2 phGS5$^{ts+}$cpm3, phGS5$^{ts+}$cpm4, and phGS5$^{ts+}$cpm5.

Several clear plaque mutants of phGS5$^{ts+}$ were isolated that are unable to form lysogens. These were isolated by plating various numbers of phage particles on *M. smegmatis* cells at 42° C. and looking for clear plaque versions. We have shown previously that these mutants arise at a frequency of $10^{-3}$–$10^{-4}$ (Donnelly-Wu et al., 1993). Five separate mutants were isolated and named phGS5$^{ts+}$cpm1, phGS5$^{ts+}$cpm2, phGS5$^{ts+}$cpm3, phGS5$^{ts+}$cpm4, and phGS5$^{ts+}$cpm5.

Isolation of phGS1 and phGS5 Lysogens of *M. smegmatis* phGS1 and phGS5 lysogens of *M. smegmatis* mc$^2$-155 were generated using standard methods. The phage lysates were used to infect *M. smegmatis* mc$^2$-155. Cells were then recovered from the infected area and purified by plating for isolated colonies. One lysogenic isolate was prepared from each phage and shown to confer immunity to superinfection by L5, a known property of L5 lysogens (Donnelly-Wu et al., 1993). These were named *M. smegmatis* mc$^2$-155 (phGS1) and *M. smegmatis* mc$^2$-155(phGS5).

Luciferase Activity of Plasmids and Lysogens

It was anticipated that plasmid pGS24 would have little or no luciferase activity in *M. smegmatis* mc$^2$-155. Likewise, it was not anticipated that *M. smegmatis* mc$^2$-155(phGS1) and *M. smegmatis* mc$^2$-155(phGS5) lysogens would have much luciferase activity. This view was arrived at via the assumption that transcriptional promoters for expression of the L5 genes 1–32 probably resided between genes 88 and 1. These promoters would thus have been removed from plasmid pGS24 and were expected to be inactive in the lysogenic state.

Figure 23:
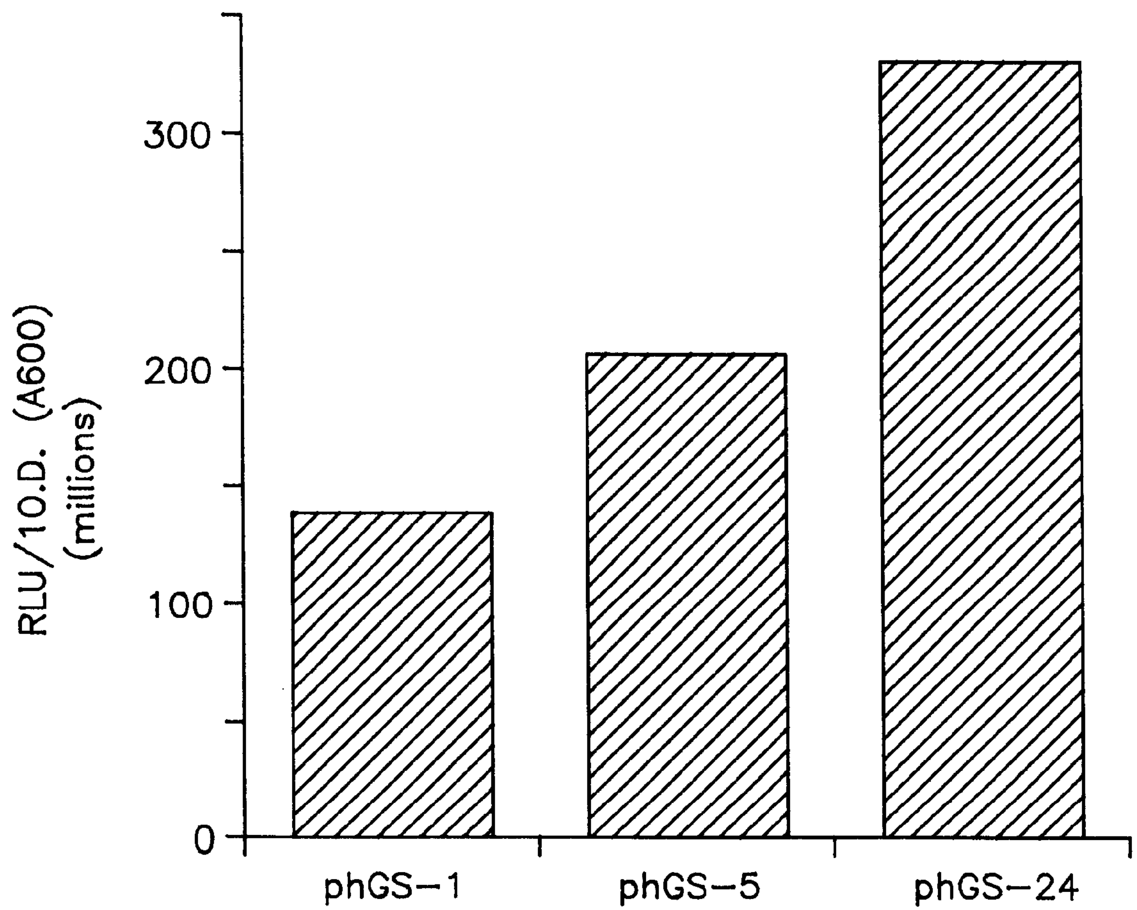
FIG. 23 represents determination of the luciferase activity of pGS24, phGS1 and phGS5.

Determination of the luciferase activity of pGS24 and the lysogens indicated that these assumptions were incorrect. FIG. 23 shows luciferase activity of pGS24 and phGS1 and phGS5 lysogens. Cultures of either *M. smegmatis* mc$^2$-155 lysogens of phGS1 or phGS5 or *M. smegmatis* mc$^2$-155 carrying pGS24 were grown to early log phase and the optical density (O.D.) determined at $A_{600}$. A portion (10–20 $\mu$l) was removed and FFlux activity determined in a Luminometer (Analytical Luminescence Monolight 2010) using luciferin as a substrate. The activities shown are normalized for 1.0 O.D. unit for 1 ml culture.

As shown in FIG. 23, lysogens of phGS1 and phGS5 and pGS24 all have considerable amounts of luciferase activity. There is a small difference between the activities of phGS1 and phGS5 which is probably not significant.

Luciferase Activity Following Infection of *M. smegmatis* mc$^2$-155

Luciferase activity was determined following liquid infection of *M. smegmatis* mc$^2$-155 with phGS1 and phGS5.

Figure 24:
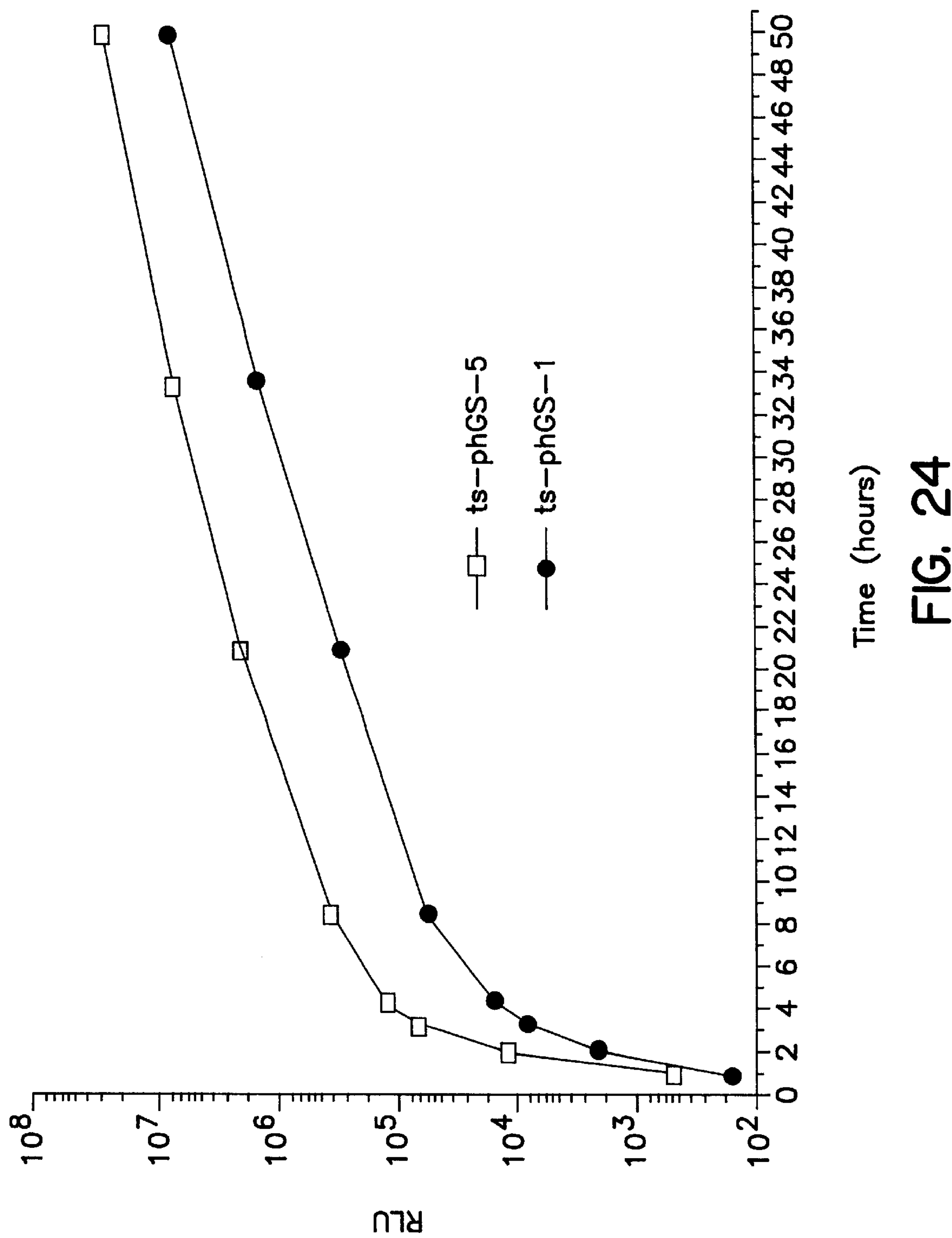
FIG. 24 represents luciferase activity as determined after liquid infection of *M. smegmatis* $mc^2155$ with phGS1 and phGS5.

FIG. 24 shows luciferase activity following infection of *M. smegmatis* with phGS1 and phGS5. phGS1 or phGS5 (approximately $4\times10^7$ pfu) were added to an early log phase culture of *M. smegmatis* $mc^2$-155 (O.D. $A_{600}$=0.1) incubated at 30° C. and 50 $\mu$l samples removed for FFlux activity determination at various times. The absolute relative light units (RLU) obtained are shown at each time point. As shown in FIG. 24, activity increased sharply for four hours and then increased less rapidly for as long as the experiment was pursued, up to about 50 hours. phGS1 consistently produced less activity than phGS5 in this assay. These phages are extremely active in FFlux activity, and phGS5 produced almost $10^7$ relative light units (RLU) after 50 hours. The background in this assay (for example if phages are omitted) is routinely between 180 and 200 RLU's.

Efficient Light Production Requires the Formation of Lysogens

Figure 25:
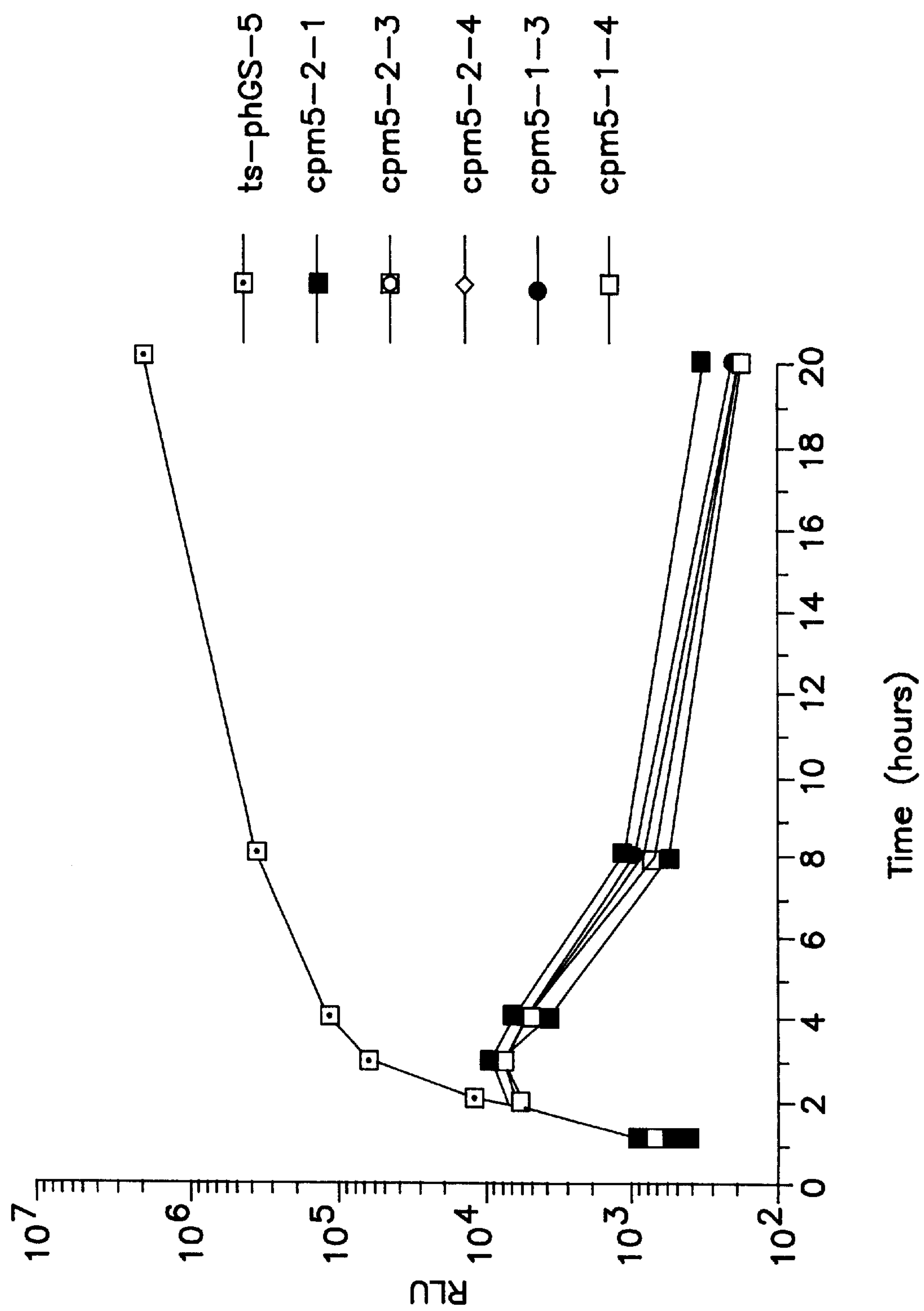
FIG. 25 represents a comparison of luciferase activity of phGS5 with clear plaque mutant derivatives that are not competent to form lysogens.

Since light production increases over a long period of time after phGS1 and phGS5 infection, it was reasoned that this could result from formation and growth of stable lysogens. It was shown above phGS1 and phGS5 strongly express FFlux in the lysogenic state. This hypothesis was tested by comparing the activity of phGS5 with clear plaque mutant derivatives that are not competent to form lysogens. The data are shown in FIG. 25. It was apparent that where the activity of phGS5 continued with time, the clear plaque mutant derivatives rose to a maximum activity after about three hours and then declined to a background level. The difference in activity of phGS5 and the clear plaque mutants was greater than $10^4$-fold at 20 hours after infection.

Comparison of L5::FFlux and TM4::FFlux Phases

Figure 26:
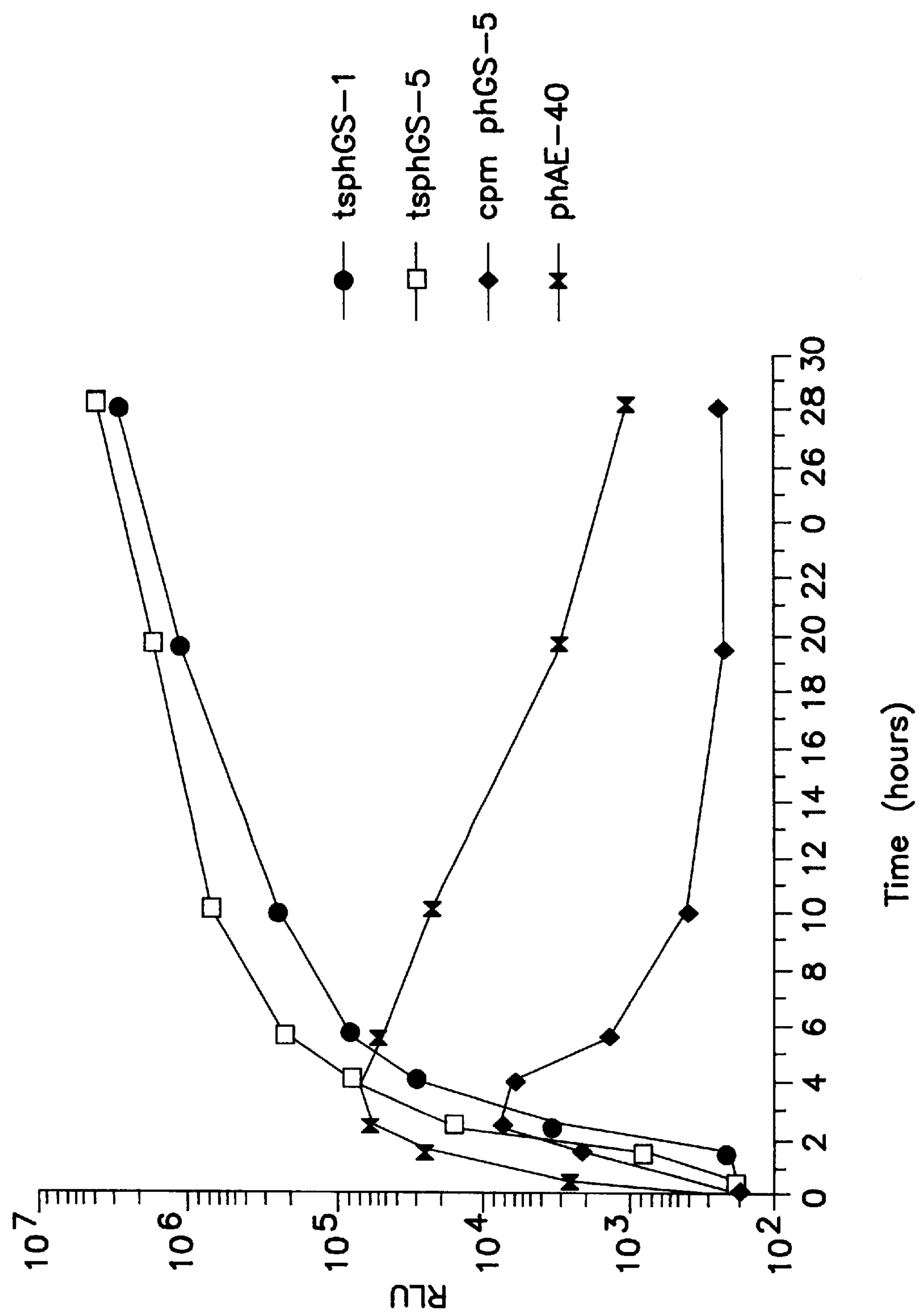
FIG. 26 represents the activity of phAE40 and the L5::FFlux phages following infection with *M. smegmatis* $mc^2155$.

The activity of phages phAE40 and the L5::FFlux phages were compared following infection of *M. smegmatis* $mc^2$-155 (see FIG. 26). The activity of phAE40 had characteristics similar to that of the clear plaque mutants of phGS5 although the maximum activity was greater. However, at all points after 4 hours, the phGS5 and phGS1 phage had substantially greater activity.

Sensitivity of the phGS5 Phage

It was apparent that phGS5 has the greatest potential of all of the luciferase reporter phages constructed to detect small numbers of mycobacterial cells. To evaluate its sensitivity, serial dilutions of a culture of *M. Smegmatis* $mc^2$-155 was prepared, infected with phGS5 and then FFlux activity 20 hours after infection was determined. Two different concentrations of phGS5 phage were used. A culture of *M. smegmatis* $mc^2$-155 (O.D. $A_{600}$=0.1) was diluted by serial 10-fold dilution. 100 $\mu$l portions were infected with either $4\times10^7$ pfu or $4\times10^5$ pfu phGS5 as indicated. After 20 hours incubation at 30° C., 50 $\mu$l samples were removed for measuring FFlux activity. Assuming that a culture of *M. smegmatis* $mc^2$-155 with an O.D. $A_{600}$=0.1 contains approximately $10^8$ bacteria/ml, this experiment demonstrates that approximately 5,000 cells of *M. smegmatis* can be readily detected in this assay.

Figure 27:
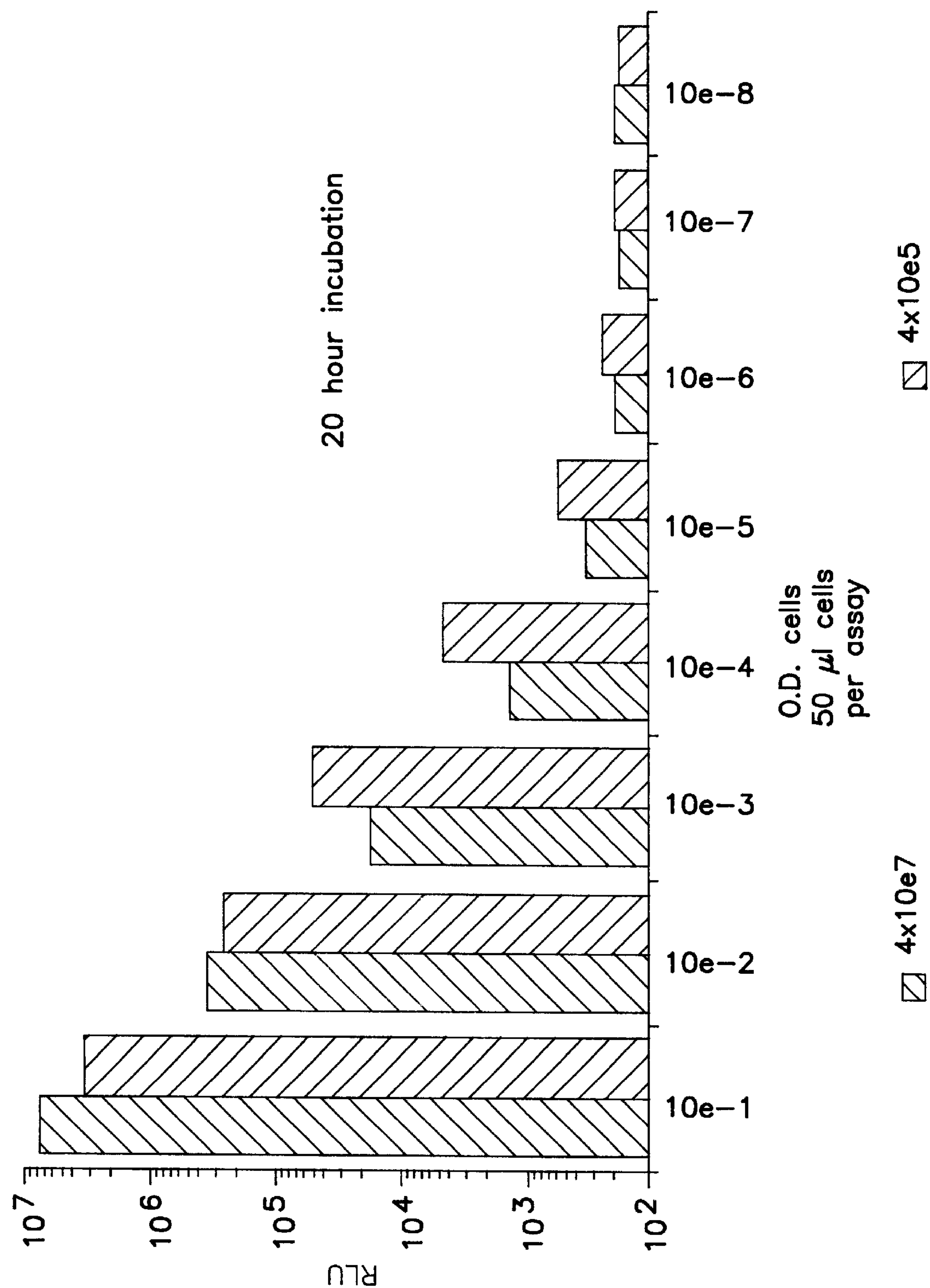
FIG. 27 represents the sensitivity of phage phGS5 after infecting *M. smegmatis* mc$^{2}$155.

The results are shown in FIG. 27. These data demonstrate that a 50 pl culture with an O.D. ~0.0001 (equivalent to approximately 5,000 bacterial cells) infected with $4\times10^5$ pfu phGS5 produced a signal (4,000 RLU) more than 10-fold greater than in a culture containing no mycobacteria (180–200 RLU). A culture containing approximately 500 cells produced a signal (approximately 600 RLU) infected with a similar titer of phage gave a signal 2-fold greater than background. It was concluded that phGS5 offers exquisite sensitivity for the detection of small numbers of *M. smegmatis* cells.

Further Evaluation of Sensitivity of L5::FFlux Phages

Figure 28A:
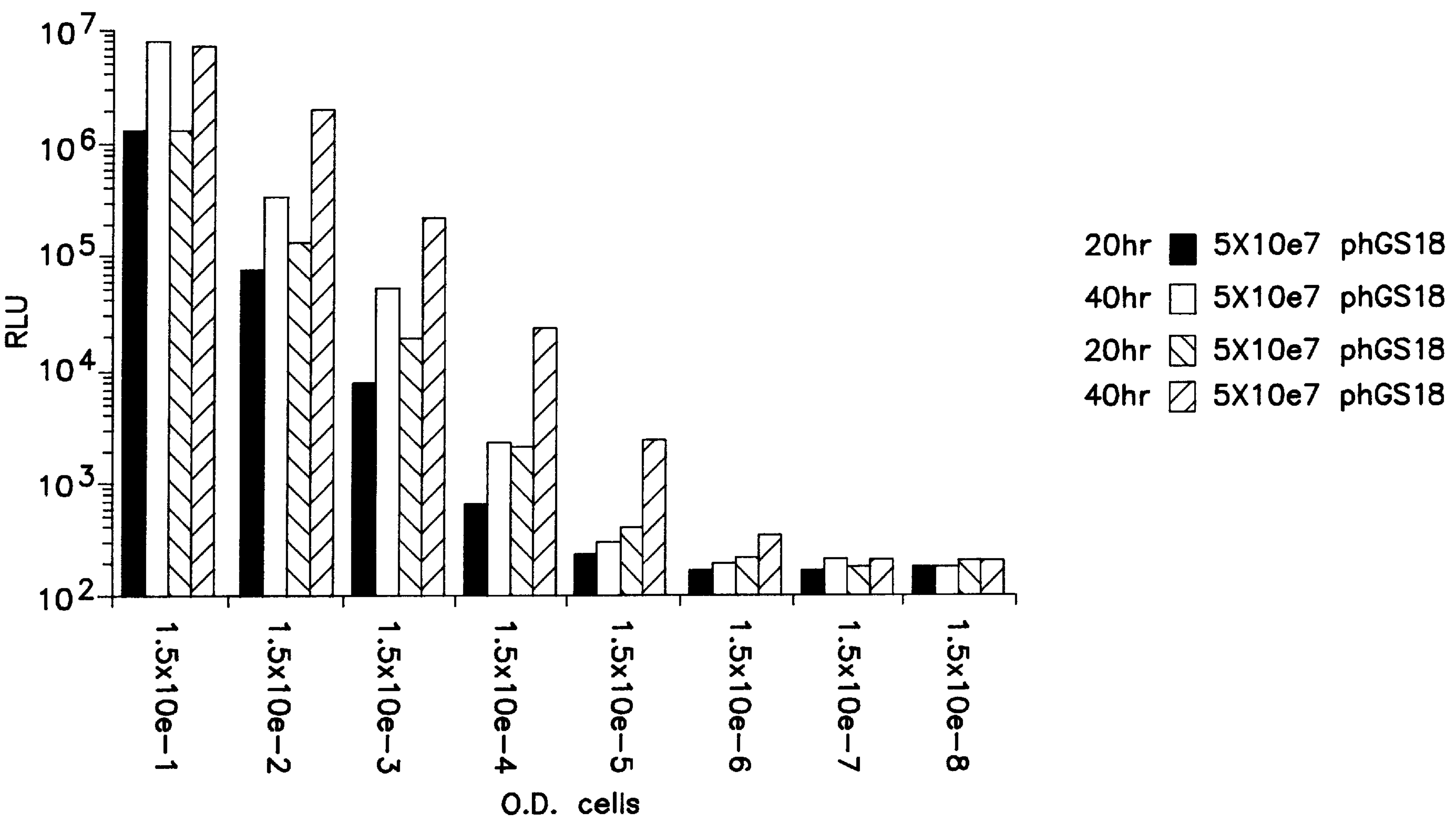
FIG. 28A represents the detection of luciferase activity after liquid infection of serial dilutions of *M. smegmatis* with phGS18.

An experiment similar to that described in FIG. 27 was performed to measure for light production (RLU) at both 20 hours and 40 hours after the addition of phage phGS18. Aliquots were plated onto agar for viable colony counts from several samples either before or after phage infection. Infections were done in duplicate and average numbers are shown in FIG. 28A.

10 $\mu$l aliquots were removed from samples either immediately prior to addition of phage (T=0), or 20 hours (T=20) or 40 hours (T=40) following addition of phage. Each row shows viable colony forming units present in a 50 $\mu$l sample for a given size of phage (either $5\times10^7$ or $5\times10^7$pfu) and starting cell innoculum. FIG. 28B shows the light produced (RLU) for each sample and the calculated light per colony forming unit (RLA/Cell) at both 20 hours and 40 hours. These numbers correlate to FIG. 28A such that the sample shown as 1.5x10e-5 in FIG. 28A contained a starting innoculum of an estimated 69 colony forming units and when infected with $5\times10^5$ phage yielded a signal of 2,229 RLU after 40 hours at 30° C. This illustrates the exquisite sensitivity of these reporter phages and the use of lysogeny to amplify the signal.

Infection of an L5 Lysoqen

Figure 29:
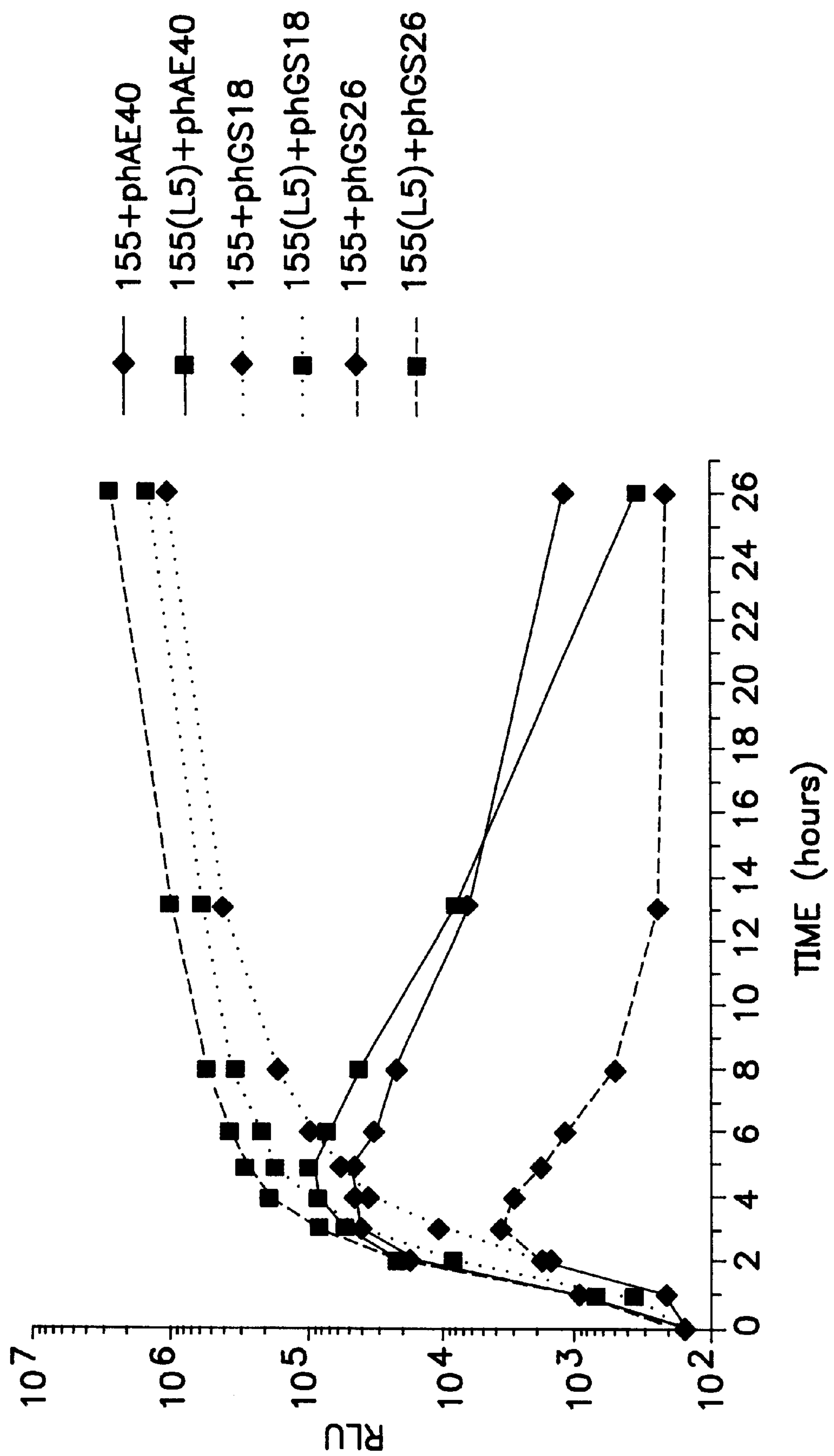
FIG. 29 represents the result of liquid infection of nonlysogen and lysogen strains of *M. smegmatis* with phAE40, phGS18 and phGS26.

To evaluate the influence of lysogeny of the host, light production following infection of an *M. smegmatis* L5 lysogen [155(L5)] with a non-lysogen (155) was compared. FIG. 29 shows the data from a similar experiment using phAE40 which was expected to be unaffected by L5 lysogeny. Interestingly, it was observed that infection of an L5 lysogen [155(L5)] with phGS18 produced at least as much light (RLU) as from infection of a non-lysogen and is actually consistently 2–5 fold higher. Given this observation, it was predicted that the clear plaque mutant phGS26 would give extended light production after infection of an L5 lysogen, in contrast to the characteristic pattern observed in a non-lysogen (see also FIG. 25). FIG. 29 shows this to be exactly what was observed. In addition, FIG. 29 shows that L5 lysogeny has no effect on phAE40 infection. It was concluded that the potential problem of naturally occurring lysogens of *M. tuberculosis* does not present a significant one in this assay.

Each L5::FFlux phage constructed to date is listed in FIG. 30 along with any alternative or previous designation, whether or not it has been characterized further, a brief description and the date of isolation. Note that of the initial phage derivatives, only phGS1 and phGS5 have been characterized further with respect to the point of insertion of FFlux and approximate location of deletions in the right arm of the phage genome. The $ts^+$ derivatives and clear plaque mutant derivatives have not been fully characterized with respect to their specific differences from their phGS1 or phGS5 precursors.

Other Methods of Constructing L5 Reporter Mycobacteriophages

The use of the shuttle phasmid approach starting with L5 deletion derivatives, in which the size of the genome has been reduced, should be further explored in determining strategies for the construction of recombinant L5 mycobacteriophages. Initially, the largest gene 71 deletion available could be used, or deletions of the gene 72–88 region similar to those described for phGS1 and phGS5 as described in FIG. 22 could be used. Another approach would be to attempt to introduce genes by homologous recombination with plasmids. Still another approach would be to transpose lux genes onto L5 using either the mini-Mu in vitro transposition system or a mycobacterial transposon such as IS1096.

Recombining reporter genes from additional recombinant plasmids onto L5 using a double recombination event may be performed. This involves first constructing a recombinant plasmid that carries a reporter gene (lacZ may be more suitable) inserted into gene 71 such that both the upstream and downstream parts of gene 71 are present. Advantages of this approach are that lacz can be easily detected in agar media, that gene 71 is not an essential gene, and that lacZ is efficiently expressed from a promoter immediately upstream of gene 71. An L5 mycobacteriophage lysate may be prepared by growth of the plasmid-containing strain and recombinant mycobacteriophage progeny identified by plating the lysate on wild-type *M. smegmatis* for individual plaques on agar containing the indicator X-gal. Alternatively, recombinant phage derivatives could be identified by hybridization.

This recombination approach may be expanded to introduce other gene or DNA segments of the L5 genome. For example, it should be possible to add luciferase genes from FFlux in an identical manner, provided that packaging limits are not exceeded. In addition, inclusion of polylinker containing restriction enzyme sites unique for L5 would open the way for construction of L5 recombinants in vitro. Similar genetic strategies may be used to systematically reduce the size of the L5 genome by deletion of non-essential sequences.

Transposition offers an alternative method for the construction of reporter mycobacteriophages. A transposition system which is available is the mini-Mu in vitro transposition system. This is a defined biochemical reaction in which a mini-Mu transposon carrying the desired gene is transposed onto the phage genome using purified MuA and MuB proteins. Similar transposition experiments have been tried with L5, but few L5 mini-Mu derivatives have been isolated. It is possible that this is due to the relatively large size of the transposon used. It is necessary to first construct a small Mu transposon which contains the reporter gene, a promoter and the two Mu in order for these experiments to be successful.

Development of L5 in vivo and in vitro Packaging Systems

λ cosmids and packaging systems provide the efficiency of mycobacteriophage infection with the ability to inject large segments of non-mycobacteriophage DNA. Analogous mycobacterial systems would overcome packaging constraints encountered with recombinant mycobacteriophage genomes and allow the introduction of multiple copies or types of reporter genes into mycobacteria, potentially enhancing the sensitivity of the assay. In addition, they would help overcome any problems with host synthesis inhibition.

The development of L5 cosmids and packaging systems is dependent on the finding that the L5 genome contains cohesive termini. The λ paradigm suggests that a relatively small region of DNA (approximately 500 bp) around the cos site (in the ligated form) is necessary to promote packaging. The first series of experiments with L5 would therefore be to identify the segment of the genome required for packaging by constructing a series of plasmids containing the L5 cos site and surrounding sequences. Cos activity may be determined by preparation of an L5 lysate on plasmid-containing *M. smegmatis* strains, followed by the identification of antibiotic-resistant transductants in the lysate, by transduction of *M. smegmatis*. This assay assumes that plasmid multimers of a total size of approximately 50 kb are present in the cell and will be packaged. Although the presence of such multimers has not been demonstrated directly, they are likely to be generated by the homologous recombination system of *M. smegmatis*. If this assay should fail, cosmid vectors which contain both L5 λ cos sites may be constructed. Insertion of 40–45 kb of DNA (as in the construction of cosmid libraries) followed by λ packaging in vitro and infection with *E. coli* will generate 50 kb sized molecules containing L5 cos site. These should be isolated from *E. coli* and introduced by electroporation into *M. smegmatis*. Assuming that one of these approaches is successful, it would then be possible to define a small segment of L5 DNA required for packaging.

The construction of in vivo cosmid packaging systems is a particularly attractive idea since it has proven very useful in *E. coli*. Thermoinducible lysogens of L5 may be suitable for in vivo packaging of L5 cosmids without further modification, since prophage excision may be a temperature-sensitive event. Efficient packaging of extrachromosomal cosmids present in the lysogen may be achieved by simple induction and growth at 42° C.

It is possible that some process other than excision is temperature-sensitive in lysogen induction. If so, it will be necessary to further debilitate the prophage in order to prevent DNA packaging of the prophage. There are a variety of ways to accomplish this. For example, the excise gene itself could be deleted (using a recombination strategy similar to that described above) such as to prevent excision. Another approach is to damage the cohesive termini (by exonucleolytic digestion) of an L5 thermoinducible derivative and construct a defective lysogen. A combination of approaches may be desirable, since even if prophage excision is a temperature-sensitive process, the destruction of cos might effectively reduce the background of spontaneous mycobacteriophage release.

Construction of in vitro packaging systems will follow similar lines. Extracts may be prepared from thermoinducible strains with non-packagable prophages and assessed for their ability to package exogenously added L5 cosmid or mycobacteriophage DNA. Optimization of conditions should follow both empirical biochemical approaches and the well-established λ systems. For example, it may be necessary to supplement the extracts with purified mycobacteriophage products such as the terminase or the tape-measure analogues (genes A/Nu and H of λ respectively), neither of which have yet been identified.

Construction of Novel Shuttle Phasmids From Any Mycobacteriophage

Although mycobacteriophages L5 and TM4 can be used in the development of diagnostic luciferase and β-galactosidase shuttle phasmids, there may be other mycobacteriophages, such as the mycobacteriophage DS6A which only infects BCG and *M. tuberculosis* strains, that might prove to have a more useful host range for clinical isolates. Diagnostic luciferase mycobacteriophages from these other mycobacteriophages may be developed by using the shuttle phasmid methodology described herein that has been proven successful for constructing mycobacteriophage vectors from both TM4 and phage L1.

Isolate Mycobacteriophage L5 and TM4 Mutants to Infect the Maximum Number of Clinical Isolates For the diagnostic luciferase mycobacteriophage system to have maximal use in the clinical laboratory, it will be essential that to develop a set of diagnostic mycobacteriophages that can efficiently infect any clinical isolate and possibly distinguish *M. tuberculosis* from *M. avium* and BCG. Both mycobacteriophages TM4 and L5 appear to have the ability to infect a large number of *M. tuberculosis* isolates. TM4 is very closely related to phage 33D, a mycobacteriophage that has been found not to infect every *M. tuberculosis* isolate used to define the mycobacteriophage typing schemes for *M. tuberculosis* isolates. However, this mycobacteriophage does not infect BCG. TM4 has been found to be almost identical by DNA hybridization and restriction analysis to 33D, and it shares the host-specificity with 33D in that it infects *M. tuberculosis*, but fails to infect BCG. Mycobacteriophage L5 appears to share the same receptor as mycobacteriophage D29 which receptor has been previously shown to infect a very large number of *M. tuberculosis* isolates. L5, unlike 33D or TM4, infects all three morphotypes of *M. avium* including a wide range of serovariants.

If L5 or TM4 are found not to infect certain *M. tuberculosis* isolates, it may be possible to isolate mutants of these mycobacteriophages which plaque on the particular isolate. The inability to plaque on a particular isolate could result from the lack of a mycobacteriophage receptor or be the result of lysogenization of the isolate with a homoimmune phage. Phage mutants with altered host range specificities or mutants which no longer bind a repressor (equivalent to virulent mutant of λ) have been isolated in other systems. Variants of TM4 which can efficiently infect BCG have been isolated at frequencies of $10^7$. Previous work has demonstrated that 33D, similarly to TM4, cannot adsorb to BCG cells. Host-range variants of TM4 which not only plaque BCG, but also still plaque *M. tuberculosis* have been isolated. Similar strategies for *M. tuberculosis* isolates which are uninfected by L5 or TM4 may be used.

Detecting the Presence of *M. tuberculosis* in Clinical Samples

The combined sensitivities of luciferase and mycobacteriophage infections should permit the detection of previously undetectable levels of *M. tuberculosis* cells in sputum, blood samples, or cerebral spinal fluid. A number of preliminary studies to optimize the detection of *M. tuberculosis* cells in a variety of body samples will be performed.

Detecting *M. tuberculosis* Grown In Primary Human Macrophages and Macrophage Cell Lines As a model system for optimizing detection of *M. tuberculosis* in infected monocytes and macrophages, primary human monocytes which have been purified by adherence for 1 hour or primary macrophages which have been cultured for 6 days in microwells will be infected with *M. tuberculosis* H37Ra at varying multiplicities. The number of cells initially infected will be determined microscopically, and then at various periods of time from 2 hours to 30 days, the cells will by lysed by non-ionic detergent NP40 which has no effect on viability of mycobacteria, concentrated by centrifugation, plated for viable organisms and infected with the luciferase plasmids. Quantitative studies at different moi's and with varying numbers of infected cells will indicate how few bacilli/cell and bacilli/specimen can be detected.

The inability of *M. tuberculosis* cells isolated from macrophages to be infected with diagnostic shuttle phasmids could result from either the absence of the expression of the mycobacteriophage-receptor or the masking of the receptor with a membrane from a phagosome of the macrophage. The level of expression of phage receptors may be regulated by the environment in which the host cell is grown. For example, the λ repressor of *E. coli* is induced by maltose and repressed by glucose. Studies to identify the receptors for mycobacteriophage L5 have been initiated. Similar studies for mycobacteriophage TM4 will also be performed. By identifying the genes encoding the receptor, it is possible to assay gene repression of the mycobacteriophage receptor of *M. tuberculosis* cells when grown in macrophages by hybridization for the MRNA synthesis. If the receptor is not expressed in macrophages, it may be necessary to use a mycobacteriophage which recognizes a receptor that is constitutively expressed.

If the receptor is masked by a membrane of the macrophage, the cells isolated from macrophages may be treated with a variety of different detergents to find a treatment that would allow infection of the *M. tuberculosis* cells with the mycobacteriophages. Again, it may be necessary to cultivate the detergent-treated macrophages in broth for a few generations to gain expression of the receptors. The assays to determine the infectability of macrophages from mycobacteria include not only the luciferase assay for the TM4::lux mycobacteriophages, but also infectious centers assays in which free mycobacteriophages are removed and mycobacteriophage-producing cells are scored by a mixed plating on a lawn of *M. smegmatis*. This assay would be useful since infectability can be scored even if there are insufficient *M. tuberculosis* cells to form a bacterial lawn. It is important to re-evaluate the host range specificities of all of the mycobacteriophages in this assay. Free mycobacteriophages can simply be removed through the use of specific anti-mycobacteriophage antibodies.

Detecting *M. tuberculosis* in Sputum Samples

Sputum from a patient infected with *M. tuberculosis* contains a mixture of mucopolysaccharide, free *M. tuberculosis* cells, macrophages containing *M. tuberculosis* cells and a variety of cellular debris. Sputum samples from patients thought to have pulmonary tuberculosis may be used for a study in which various numbers of *M. tuberculosis* cells are added to sputum samples found to have no or few organisms by acid-fast staining. A variety of methods can be used to treat sputum samples so as to liquify the mucous and decontaminate the specimen under conditions in which all bacteria other than mycobacteria are killed. Because of the specificity of the phasmids, decontamination may not be as important as preserving the mycobacteriophage receptors. Nonetheless, the sputum samples may be treated initially with 2% w/v NaOH for 30 minutes at 37° C. or with 0.5% N-acetyl cysteine +1% NaOH. Alternatively, the sample may be treated with a variety of hydrolytic enzymes, such as collagenase, to help dissolve the sputum sample. If mycobacteriophage receptors are carbohydrates possibly sensitive to these conditions, other conditions may be utilized or the cells will be cultured 3–16 hours to allow recovery of infectivity before mycobacteriophage infection.

Detecting Mycobacteria In Blood Samples

Tuberculosis has been known to have a bacteremia. If the sensitivity necessary to detect 100 to 200 *M. tuberculosis* cells in a ml of sample can be obtained, levels of bacteremia in tuberculosis patients which were not previously observable may be observed. White cells should be purified over Ficoil-hypaque and lysed with 2% NP40, 1% SDS or freeze-thawing in the presence of DNAse to liberate intracellular mycobacteria. The pellet should then be infected with the diagnostic luciferase mycobacteriophage, or if only few organisms are present they can be concentrated by filtration onto filters, and filter areas cut out and infected.

Assuring Specificity On a Variety of Clinical Isolates and Species; Assessment of False Positives and Negatives The luciferase assay may be optimized such that positive correlations of *M. tuberculosis* infections as indicated in the clinical lab may be obtained. The recombinant mycobacteriophages may be tested to ascertain the range of specificity that they have for other mycobacteria, and for the closely related genera Norcardia, Corynebacterium, and Actinomycetes strains. These strains may be obtained from the ATCC. A number of blinded tests including negative controls, *M. tuberculosis*-infected patients, samples from patients infected with *M. avium*, and samples infected with other non-mycobacterial pathogens may be performed to ascertain the range of specificity.

The ability to rapidly assess the susceptibilities of *M. tuberculosis* isolates to isoniazid, ethambutol, rifampicin, pyrazinamide and other antibiotics will have a major impact on the treatment of tuberculosis patients. After the isolation of *M. tuberculosis* cells from a sputum sample, which may take several weeks, the assessment of drug-susceptibilities may take an additional 2 to 9 weeks. Diagnostic reporter mycobacteriophages may allow for evaluations of drug-susceptibilities at the time a sputum sample is collected. Alternatively, this approach would shorten the time necessary to assess drug-susceptibilities of purified *M. tuberculosis* colonies grown up from clinical samples.

Luciferase Assays for *M. tuberculosis* Cells in the Presence of Drugs

The results of the experiments suggest that by using luciferase as an indicator for the metabolic ability of the cell, it may be possible to define conditions which will enable us to distinguish drug-resistant mycobacteria from drug-sensitive mycobacteria. To test this hypothesis, isolated mutants of *M. tuberculosis* H37Ra which are resistant to isoniazid, rifampicin, ethambutol, or pyrazinamide would be used to generate a set of cogenic mutants. These independent mutants and the parent strains would be transformed with pYUB180. Luciferase activity will be assessed in the presence and absence of drugs in order to determine the optimal conditions for distinguishing between drug-resistant and drug-sensitive cells. It is quite possible that the window of time to observe differences for different drugs could vary and require different incubation times for each drug.

The choice of the promoter for expressing luciferase may provide a needed parameter to more readily assess drug action. For example, in the case of *E. coli*, gyrase promoters are greatly stimulated in the presence of gyrase inhibitors.

Clinical isolates of *M. tuberculosis* may be transformed with PYUB180 and tested for luciferase activity in the presence and absence of drugs. The luciferase assays with mycobacteriophage infections with lux mycobacteriophages on in vitro-grown *M. tuberculosis* cells will first be optimized, and then extended to *M. tuberculosis* cells grown in macrophages or isolated from sputum samples.

Critical Assessment of Drug-Susceptibility Testing

As for the detection of *M. tuberculosis* from clinical samples, the luciferase assay may be optimized so that the drug-susceptibility patterns for any clinical isolate may be obtained. It may be possible to add diagnostic mycobacteriophages to a single clinical specimen, aliquot the mixture into various tubes and add antibiotic drugs. Thus every experiment would have an internal control and each drug-treated sample could be compared to an untreated control. The critical parameter to conclude drug-resistance or sensitivity lies in the comparison.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

What is claimed is:

1. A method for screening for drugs which inhibit the growth of mycobacterial lysogens comprising:

(a) incubating mycobacterial lysogens in the presence of a drug, wherein the mycobacterial lysogens are capable of expressing a reporter molecule and wherein the mycobacterial lysogens are formed by incubating mycobacteria with a temperate mycobacteriophage specific for the mycobacteria, the mycobacteriophage containing in its genome DNA encoding the reporter molecule and a transcriptional promoter which controls transcription of the reporter molecule DNA; and (b) assessing the effect the drug has on the growth of the mycobacterial lysogens.

2. The method of claim 1, wherein the reporter molecule is luciferase.

3. The method of claim 2, wherein the luciferase is Firefly luciferase, *Vibrio fisceri* luciferase, or *Xenorhabdus luminescens* luciferase.

4. The method of claim 1, wherein the reporter molecule is β-galactosidase.

5. The method of claim 1, wherein the mycobacteria are *Mycobacterium smegmatis*.

6. The method of claim 1, wherein the mycobacteria are *Mycobacterium tuberculosis*.

7. The method of claim 1, wherein the mycobacteria are *Mycobacterium avium*.

8. The method of claim 1, wherein the mycobacteria are BCG.

* * * * *